United States Patent
Lundquist et al.

(10) Patent No.: US 6,329,574 B1
(45) Date of Patent: Dec. 11, 2001

(54) HIGH LYSINE FERTILE TRANSGENIC CORN PLANTS

(75) Inventors: Ronald C. Lundquist, Minnetonka, MN (US); David A. Walters, Groton, CT (US); Julie A. Kirihara, Bloomington, MN (US)

(73) Assignee: Dekalb Genetics Corporation, DeKalb, IL (US)

( * ) Notice: Subject to any disclaimer, the term of this patent is extended or adjusted under 35 U.S.C. 154(b) by 0 days.

(21) Appl. No.: 09/122,399

(22) Filed: Jul. 24, 1998

Related U.S. Application Data

(60) Division of application No. 08/440,646, filed on May 15, 1995, which is a division of application No. 08/112,245, filed on Aug. 25, 1993, which is a continuation-in-part of application No. 07/636,089, filed on Dec. 28, 1990, now abandoned, which is a continuation-in-part of application No. 07/508,045, filed on Apr. 11, 1990, now Pat. No. 5,484,956, which is a continuation-in-part of application No. 07/467,983, filed on Jan. 22, 1990, now abandoned.

(51) Int. Cl.[7] .............................. C12N 15/00; A01H 1/06; A01H 4/00
(52) U.S. Cl. ................................. 800/300.1; 800/320.1; 800/278; 800/287; 800/288; 800/293
(58) Field of Search ................................ 800/320.1, 278, 800/288, 287, 284, 292, 293, 300.1

(56) References Cited

U.S. PATENT DOCUMENTS

| | | | |
|---|---|---|---|
| 4,370,160 | 1/1983 | Ziemelis | 71/117 |
| 4,399,216 | 8/1983 | Axel et al. | 435/6 |
| 4,520,113 | 5/1985 | Gallo et al. | 436/504 |
| 4,535,060 | 8/1985 | Comai | 435/172.3 |
| 4,536,475 | 8/1985 | Anderson | 435/172.3 |
| 4,559,301 | 12/1985 | Turner et al. | 435/76 |
| 4,559,302 | 12/1985 | Ingolia | 435/172.3 |
| 4,581,847 | 4/1986 | Hibberd et al. | 47/58 |
| 4,634,665 | 1/1987 | Axel et al. | 435/68 |
| 4,642,411 | 2/1987 | Hibberd et al. | 800/1 |
| 4,665,030 | 5/1987 | Close | 435/240 |
| 4,666,844 | 5/1987 | Cheng | 435/240 |
| 4,683,202 | 7/1987 | Mullis | 435/91 |
| 4,708,818 | 11/1987 | Montagnier et al. | 435/5 |
| 4,727,028 | 2/1988 | Santerre et al. | 435/240.2 |
| 4,743,548 | 5/1988 | Crossway et al. | 435/172.3 |
| 4,761,373 | 8/1988 | Anderson et al. | 435/172.3 |
| 4,806,483 | 2/1989 | Wang | 435/240.49 |
| 4,885,357 | 12/1989 | Larkins et al. | 530/373 |
| 4,886,878 | 12/1989 | Larkins et al. | 536/26 |
| 4,940,835 | 7/1990 | Shah et al. | 800/205 |
| 4,945,050 | 7/1990 | Sanford et al. | 435/172.1 |
| 4,956,282 | 9/1990 | Goodman et al. | 435/69.51 |
| 4,971,908 | 11/1990 | Kishore et al. | 435/172.1 |
| 5,001,060 | 3/1991 | Peacock et al. | 435/172.3 |
| 5,004,863 | 4/1991 | Umbeck | 800/205 |
| 5,013,658 | 5/1991 | Dooner et al. | 435/172.3 |
| 5,015,580 | 5/1991 | Christou et al. | 435/172.3 |
| 5,034,322 | 7/1991 | Rogers et al. | 435/172.3 |
| 5,036,006 | 7/1991 | Sanford et al. | 435/170.1 |
| 5,049,500 | 9/1991 | Arnizen et al. | 435/172.3 |
| 5,077,399 | 12/1991 | Brauer et al. | 536/27 |
| 5,082,767 | 1/1992 | Hatfield et al. | 435/6 |
| 5,094,945 | 3/1992 | Comai | 435/172.3 |
| 5,097,093 | 3/1992 | Vandeventer et al. | 800/200 |
| 5,110,732 | 5/1992 | Benfey et al. | 435/172.3 |
| 5,134,074 | 7/1992 | Gordon et al. | 435/240.4 |
| 5,145,777 | 9/1992 | Goodman et al. | 435/172.3 |
| 5,164,310 | 11/1992 | Smith et al. | 435/172.3 |
| 5,177,010 | 1/1993 | Goldman et al. | 435/172.2 |
| 5,187,073 | 2/1993 | Goldman et al. | 435/172.3 |
| 5,187,267 | 2/1993 | Comai et al. | 536/23.1 |
| 5,188,642 | 2/1993 | Shah et al. | 47/58 |
| 5,188,958 | 2/1993 | Moloney et al. | 435/240.4 |
| 5,196,342 | 3/1993 | Donovan | 435/320.1 |
| 5,215,912 | 6/1993 | Hoffman et al. | 435/240.4 |
| 5,231,020 | 7/1993 | Jorgensen et al. | 435/172.3 |
| 5,240,841 | 8/1993 | Johnston et al. | 435/172.3 |

(List continued on next page.)

FOREIGN PATENT DOCUMENTS

| | | | |
|---|---|---|---|
| 80893/87 | 12/1988 | (AU) | C12N/15/00 |
| 2064761 | 2/1991 | (CA) | C12N/15/82 |
| 2 032 443 | 6/1991 | (CA) | C12N/15/87 |

(List continued on next page.)

OTHER PUBLICATIONS

Armstrong, C.L., et al., "Genetic and Cytogenetic Variation in Plants Regenerated from Organogenic and Friable, Embryogenic Tissue Cultures in Maize", *Biol. Abstracts*, 85, Abstract No. 117662, p. 22 (1988).

Raineri, D.M., et al., "VirA, the Plant–Signal Receptor, is Responsible for the Ti Plasmid–Specific Transfer of DNA to Maize by Agrobacterium", *Proc. Natl. Acad. Sci. USA*, 90, 3549–3553 (Apr. 1993).

Van den Broeck, G., et al., "Targeting of a Foreign Protein to Chloroplasts by Fusion to the Transit Peptide from the Small Subunit of Ribulose 1,5–bisphosphate Carboxylase", *Nature*, 313, 358–363 (Jan. 31, 1985).

(List continued on next page.)

*Primary Examiner*—Gary Benzion
(74) *Attorney, Agent, or Firm*—Schwegman, Lundberg, Woessner & Kluth, P.A.

(57) ABSTRACT

This invention relates to a reproducible system for the production of stable, genetically transformed maize cells, and to methods of selecting cells that have been transformed. One method of selection disclosed employs the *Streptomyces bar* gene introduced by microprojectile bombardment into embryogenic maize cells which were grown in suspension cultures, followed by exposure to the herbicide bialaphos. The methods of achieving stablefs transformation disclosed herein include tissue culture methods and media, methods for the bombardment of recipient cells with the desired transforming DNA, and methods of growing fertile plants from the transformed cells. This invention also relates to the transformed cells and seeds and to the fertile plants grown from the transformed cells and to their pollen.

41 Claims, 52 Drawing Sheets

U.S. PATENT DOCUMENTS

| | | | |
|---|---|---|---|
| 5,250,515 | 10/1993 | Fuchs et al. | 514/12 |
| 5,254,799 | 10/1993 | De Greve et al. | 800/205 |
| 5,258,300 | 11/1993 | Glassman et al. | 435/240 |
| 5,268,463 | 12/1993 | Jefferson | 536/23.7 |
| 5,272,072 | 12/1993 | Kaneko et al. | 435/172.3 |
| 5,273,894 | 12/1993 | Strauch et al. | 435/129 |
| 5,276,268 | 1/1994 | Strauch et al. | 800/205 |
| 5,278,325 | 1/1994 | Strop et al. | 554/12 |
| 5,290,924 | 3/1994 | Last et al. | 536/24.1 |
| 5,302,523 | 4/1994 | Coffee et al. | 435/172.1 |
| 5,310,667 | 5/1994 | Eichholtz et al. | 435/172.3 |
| 5,350,689 | 9/1994 | Shillito et al. | 435/240.47 |
| 5,352,605 | 10/1994 | Fraley et al. | 435/240.4 |
| 5,367,110 | 11/1994 | Galili et al. | 800/205 |
| 5,371,003 | 12/1994 | Murry et al. | 435/172.3 |
| 5,371,015 | 12/1994 | Sanford et al. | 435/287 |
| 5,380,831 | 1/1995 | Adang et al. | 536/23.71 |
| 5,384,253 | 1/1995 | Krzyzek et al. | 435/172.3 |
| 5,405,765 | 4/1995 | Vasil et al. | 435/172 |
| 5,422,254 | 6/1995 | Londesborough et al. | 435/97 |
| 5,436,389 | 7/1995 | Pfund | 800/200 |
| 5,436,393 | 7/1995 | Rocha-Sosa et al. | 800/205 |
| 5,451,513 | 9/1995 | Maliga et al. | 438/172.3 |
| 5,464,763 | 11/1995 | Schilperoort et al. | 435/172.3 |
| 5,472,869 | 12/1995 | Krzyzek et al. | 435/240.4 |
| 5,484,956 | 1/1996 | Lundquist et al. | 800/205 |
| 5,489,520 | 2/1996 | Adams et al. | 435/172.3 |
| 5,491,288 | 2/1996 | Chaubet et al. | 800/205 |
| 5,495,071 | 2/1996 | Fischhoff et al. | 800/205 |
| 5,500,365 | 3/1996 | Fischhoff et al. | 435/240.4 |
| 5,508,468 | 4/1996 | Lundquist et al. | 800/205 |
| 5,538,877 | 7/1996 | Lundquist et al. | 435/172.3 |
| 5,538,880 | 7/1996 | Lundquist et al. | 435/172.3 |
| 5,545,545 | 8/1996 | Gengenbach et al. | 435/172.3 |
| 5,550,318 | 8/1996 | Adams et al. | 800/205 |
| 5,554,798 | 9/1996 | Lundquist et al. | 800/205 |
| 5,561,236 | 10/1996 | Leemans et al. | 800/205 |
| 5,563,324 | 10/1996 | Tarczynski et al. | 800/205 |
| 5,565,347 | 10/1996 | Fillatti et al. | 435/172.3 |
| 5,567,600 | 10/1996 | Adang et al. | 536/23.71 |
| 5,567,862 | 10/1996 | Adang et al. | 800/205 |
| 5,576,203 | 11/1996 | Hoffman | 435/172.3 |
| 5,578,702 | 11/1996 | Adang et al. | 530/350 |
| 5,580,716 | 12/1996 | Johnston et al. | 435/5 |
| 5,589,615 | 12/1996 | De Clercq et al. | 800/205 |
| 5,589,616 | 12/1996 | Hoffman | 800/205 |
| 5,593,963 | 1/1997 | Van Ooijen et al. | 514/12 |
| 5,595,733 | 1/1997 | Carswell et al. | 424/93.21 |
| 5,596,131 | 1/1997 | Horn et al. | 800/205 |
| 5,623,067 | 4/1997 | Vanderkerckhove et al. | 536/24.1 |
| 5,625,136 | 4/1997 | Koziel et al. | 800/205 |
| 5,641,664 | 6/1997 | D'Halluin et al. | 435/172.3 |
| 5,641,876 | 6/1997 | McElroy et al. | 536/24.1 |
| 5,677,474 | 10/1997 | Rogers | 800/205 |
| 5,693,507 | 12/1997 | Daniell et al. | 435/172.3 |
| 5,743,477 | 4/1998 | Walsh et al. | 424/94.6 |
| 5,773,691 | 6/1998 | Falco et al. | 800/205 |
| 5,780,708 | 7/1998 | Lundquist et al. | 800/205 |
| 5,874,265 | 2/1999 | Adams et al. | 435/172.3 |
| 5,886,244 | 3/1999 | Tomes et al. | 800/293 |
| 5,919,675 | 7/1999 | Adams et al. | 435/172.3 |
| 5,969,213 | 10/1999 | Adams et al. | 800/205 |
| 5,990,387 | 11/1999 | Tomes et al. | 800/293 |
| 5,990,390 | 11/1999 | Lundquist et al. | 800/302 |
| 6,013,863 | 1/2000 | Lundquist et al. | 800/293 |
| 6,020,539 | 2/2000 | Goldman et al. | 800/294 |
| 6,022,846 | 2/2000 | Van Ooijen et al. | 512/5 |
| 6,025,545 | 2/2000 | Lundquist et al. | 800/293 |

FOREIGN PATENT DOCUMENTS

| | | | |
|---|---|---|---|
| 37 38 874 | 11/1988 | (DE) | A01H/1/06 |
| 40 13 099 | 10/1991 | (DE) | C12N/15/82 |
| 0 131 623 | 1/1984 | (EP) | C12N/15/11 |
| 0 126 537 | 11/1984 | (EP) | A61K/9/52 |
| 0 141 373 | 5/1985 | (EP) | A01G/7/00 |
| 0 142 924 | 5/1985 | (EP) | C12N/15/00 |
| 0 154 204 | 9/1985 | (EP) | C12N/15/00 |
| 0 160 390 | 11/1985 | (EP) | A01H/15/00 |
| 0 174 791 | 3/1986 | (EP) | C12N/15/00 |
| 0 189 707 | 8/1986 | (EP) | C12N/15/00 |
| 0 193 259 | 9/1986 | (EP) | C12N/15/00 |
| 0 202 668 | 11/1986 | (EP) | C12N/5/02 |
| 0 204 549 | 12/1986 | (EP) | C12N/15/00 |
| 0 242 236 | 10/1987 | (EP) | C12N/15/00 |
| 0 242 246 | 10/1987 | (EP) | C12N/15/00 |
| 0 299 552 | 1/1988 | (EP) | C12N/15/00 |
| 0 257 472 | 3/1988 | (EP) | C12N/15/00 |
| 0 262 971 | 4/1988 | (EP) | A01H/1/02 |
| 0 269 601 | 6/1988 | (EP) | C12N/15/00 |
| 0 270 356 | 6/1988 | (EP) | C12N/15/00 |
| 0 271 408 | 6/1988 | (EP) | C12N/15/00 |
| 0 275 069 | 7/1988 | (EP) | C12N/15/00 |
| 0 280 400 | 8/1988 | (EP) | A01C/1/06 |
| 0 282 164 | 9/1988 | (EP) | C12N/5/00 |
| 0 289 479 | 11/1988 | (EP) | C12N/15/00 |
| 0 290 395 | 11/1988 | (EP) | C12N/15/00 |
| 0 292 435 | 11/1988 | (EP) | C12N/15/00 |
| 0 301 749 | 2/1989 | (EP) | C12N/15/00 |
| 0 331 083 | 9/1989 | (EP) | C12N/15/00 |
| 0 331 855 | 9/1989 | (EP) | C12M/3/00 |
| 0 334 539 | 9/1989 | (EP) | C12N/15/00 |
| 0 335 528 | 10/1989 | (EP) | C12N/15/00 |
| 0 348 348 | 12/1989 | (EP) | A01N/65/00 |
| 0 353 908 | 2/1990 | (EP) | C12N/15/29 |
| 0 359 472 | 3/1990 | (EP) | C12N/15/32 |
| 0 359 617 | 3/1990 | (EP) | C12N/15/53 |
| 0 360 750 | 3/1990 | (EP) | C12N/15/29 |
| 0 408 403 | 5/1990 | (EP) | C12N/15/32 |
| 0 385 962 | 9/1990 | (EP) | C12N/15/82 |
| 0 420 358 | 4/1991 | (EP) | C12N/15/55 |
| 0 424 047 | 4/1991 | (EP) | C12N/15/87 |
| 0 459 643 | 5/1991 | (EP) | C12N/15/82 |
| 0 442 174 | 8/1991 | (EP) | C12N/15/82 |
| 0 442 175 | 8/1991 | (EP) | A01H/1/02 |
| 0 452 269 | 11/1991 | (EP) | C12N/15/82 |
| 0 469 273 | 2/1992 | (EP) | C12N/15/82 |
| 0 485 970 | 5/1992 | (EP) | C12N/15/82 |
| 2 661 421 | 10/1991 | (FR) | C12N/15/09 |
| 2 159 173 | 11/1985 | (GB) | C12N/15/00 |
| 61-134343 | 6/1986 | (JP) | . |
| 8801444 | 1/1990 | (NL) | C12N/15/87 |
| 85/01856 | 5/1985 | (WO) | A01B/76/00 |
| 85/02972 | 7/1985 | (WO) | A01C/1/06 |
| 85/02973 | 7/1985 | (WO) | A01J/7/00 |
| 86/01536 | 3/1986 | (WO) | C12P/15/00 |
| 86/03776 | 7/1986 | (WO) | C12N/15/00 |
| 87/04181 | 7/1987 | (WO) | C12N/1/00 |
| 87/05629 | 9/1987 | (WO) | C12N/15/00 |
| 88/08034 | 10/1988 | (WO) | C12P/21/00 |
| 89/04371 | 5/1989 | (WO) | C12P/21/00 |
| 89/10396 | 11/1989 | (WO) | C12N/5/00 |
| 89/11789 | 12/1989 | (WO) | A01H/1/00 |
| 89/12102 | 12/1989 | (WO) | C12N/15/00 |
| 90/01551 | 2/1990 | (WO) | C12N/15/82 |
| 90/01869 | 3/1990 | (WO) | A01H/1/04 |
| 90/02801 | 3/1990 | (WO) | C12N/15/32 |
| 90/10691 | 9/1990 | (WO) | C12N/5/00 |
| 90/10725 | 9/1990 | (WO) | C23C/16/00 |
| 91/02071 | 2/1991 | (WO) | C12N/15/82 |
| 91/04270 | 4/1991 | (WO) | C07K/13/00 |

| | | | | |
|---|---|---|---|---|
| 91/04323 | 4/1991 | (WO) | ............................. | C12N/9/10 |
| 91/10725 | 7/1991 | (WO) | ............................. | C12N/5/00 |
| 91/16432 | 10/1991 | (WO) | ............................ | C12N/15/31 |
| 92/06205 | 4/1992 | (WO) | ............................ | C12N/15/82 |
| 92/09696 | 6/1992 | (WO) | ............................ | C12N/15/82 |
| 92/12250 | 7/1992 | (WO) | ............................ | C12N/15/82 |
| 92/14822 | 9/1992 | (WO) | ............................ | C12N/15/29 |
| 92/17580 | 10/1992 | (WO) | ............................. | C12N/5/10 |
| 92/19731 | 11/1992 | (WO) | ............................ | C12N/15/00 |
| 93/06220 | 4/1993 | (WO) | ............................ | C12N/15/82 |
| 93/07278 | 4/1993 | (WO) | ............................ | C12N/15/82 |
| 93/08682 | 5/1993 | (WO) | ............................. | A01H/1/00 |
| 93/09237 | 5/1993 | (WO) | ............................ | C12N/15/82 |
| 93/14210 | 7/1993 | (WO) | ............................ | C12N/15/82 |

OTHER PUBLICATIONS

International Search Report, PCT/US 90/09699, mailed Aug. 16, 1991.
International Search Report, PCT/US 90/04462, mailed Jan. 15, 1991.
International Search Report, PCT/US 97/00978, mailed Jul. 22, 1997.
International Search Report, PCT/US 97/00983, mailed Jun. 12, 1997.
"BioTechnica Applies for Field Test of Genetically Engineered Corn", *Genetic Technology News*, 10 (Mar. 1990).
"Bullets Transform Plant Cells", *Agricell Report*, 9, 5, (Jul. 1987).
In: *Handbook of Fine Chemicals*, Catalog, Aldrich Chemical Co., p. 508, (1988).
"Chipping Away At Old Weed Enemies", *Prairie Farmer*, 162, 34, (Feb. 20, 1990).
"Corn Transformers Multiply", *Bio/Technology*, 8, 490, (Jun. 1990).
"Cornell U. Gene Gun Hits Biotech Bullseye", *Agriculture Technology*, p. 13.
"Dalapon", *Merck Index*, 11th Edition, S. Budavae, (ed.), Merck and Co., p. 405–406, (1989).
"Dekalb Researchers Produce Fertile Corn Plants with Foreign Genes", *AGRI Newsletter*, (Oct.–Nov. 1990).
"Gene Guns Succeed in Altering Corn", *Biotechnology News*, 2, (Apr. 1990).
"Genetic Engineering Advance Announced for Corn Plants", *Investor's Daily*, (Apr. 19, 1990).
"Genetically Engineered Corn: Breakthrough Brings Market Closer", *Genetic Technology News*, 8–11, (Oct. 1990).
Office Action, U.S. Ser. No. 06/880,271, Goldman et al., dated May 30, 1989.
Office Action, U.S. Ser. No. 06/880,271, Goldman et al., dated Mar. 8, 1990.
Patent Search of Japanese Patent No. 61–134,343 (Issued Jun. 21, 1986).
Patent Family Record for Australia Patent 80893/87 (Issued Dec. 5, 1988).
"Plant Science Research, Inc., Achieves Successful Transformation of Corn", *Genetic Engineering News*, 10, 3, (Mar. 1990).
"Shotgunning DNA into Cells", *Genetic Engineering News*, (Jul.–Aug. 1987).
"Sticky Ends", *Genetic Engineering News*, 10, 1, (May 1990).
"Teams from USDA/Monsanto and DeKalb Genetically Engineer Corn", *Genetic Technology News*, 10, (May 1990).
"Two Teams Succeed in Putting Foreign Genes in Corn Plants", *Genetic Engineering Letter*, 10, 3, (Apr. 24, 1990).

"USDA Approves Field Test for BioTechnica's Genetically Engineered Corn", *Genetic Technology News*, 10, 6, (Jul. 1990).
"USDA Approves More Field Tests", *Genetic Technology News*, 11, 12, (Jul. 1991).
Adang, M.J., et al., "Characterized Full–Length and Truncated Plasmid Clones of the Crystal Protein of *Bacillus thuringiensis* subsp. *kurstaki* HD–73 and Their Toxicity to *Manduca sexta*", *Gene*, 36, 289–300, (1985).
Ahokas, H., "Electrophoretic Transfection of Cereal Grains with Exogenous Nucleic Acid", Abstracts, Soc. Biochem. Biophys. Microbio. Fen., Biotieteen Paivat (Bioscience Days), Technical University of Helsinki, Espoo, Finland, p. 2, (1989).
Ahokas, H., "Transfection of Germinating Barley Seed Electrophoretically with Exogenous DNA", *Theor. Appl. Genet.*, 77, 469–472, (1989).
Akella, V., et al., "Expression in Cowpea Seedings of Chimeric Transgenes after Electroporation into Seed Derived Embryos", *Plant Cell Rep.*, 12, 110–117, (1993).
Altenbach, S.B., et al., "Cloning and Sequence Analysis of a cDNA Encoding a Brazil Nut Protein Exceptionally Rich in Methionine", *Plant Mol. Biol.*, 8, 239–250, (1987).
Altenbach, S.B., et al., "Enhancement of the Methionine Content of Seed Proteins by the Expression of a Chimeric Gene Encoding a Methionine–Rich Protein in Transgenic Plants", *Plant Mol. Biol.*, 13, 513–522, (1989).
Ampe, C., et al., "The Amino–Acid Sequence of the 2S Sulphur–Rich from Seed of Brazil Nut (*Bertholletia excelsa* H.B.K.)", *Eur. J. Biochem.*, 159, 597–604, (1986).
Andrews, D.L., et al., "Characterization of the Lipid Acyl Hydrolase Activity of the Major Potato (*Solanum tuberosum*) Tuber Protein, Patatin, by Cloning and Abundant Expression in a Baculovirus Vector", *Biochem. J.*, 252, 199–206, (1988).
Armstrong, C.L., et al., "Establishment and Maintenance of Friable, Embryogenic Maize Callus and the Involvement of L–Proline", *Planta*, 164, 207–214, (1985).
Armstrong, C.L., et al., "Genetic and Cytogenetic Variation in Plants Regenerated from Organogenic and Friable, Embryogenic Tissue Cultures in Maize", *Crop Science*, 28, 363–369, (1988).
Atanassova, R., et al., "A 126 bp Fragment of a Plant Histone Gene Promoter Confers Preferential Expression in Meristems of Transgenic Arabidopsis", *The Plant Journal*, 2, 291–300, (1992).
Aves, K., et al., "Transformation of an Elite Maize Inbred Through Microprojectile Bombardment of Regenerable Embryonic Callus", *In Vitro Cell. Develop Bio.*, 28A, Abstract No. P–1134, p. 124A, (1992).
Barker, R.F., et al., "Nucleotide Sequence of the T–DNA Region from the *Agrobacterium tumefaciens* Octopine Ti Plasmid pTi15955", *Plant Mol. Biol.* 2, 335–350, (1983).
Beerman, F., et al., "Tyrosinase as a Marker for Transgenic Mice", *Nuc. Acids. Res.*, 19, 958, (1991).
Belanger, F.C., et al., "Molecular Basis for Allelic Polymorphism of the Maize Globulin–1 Gene", *Genetics*, 129, 863–872, (1991).
Benner, M.S., et al., "Genetic Analysis of Methionine–Rich Storage Protein Accumulation in Maize", *Theor. Appl. Genet.*, 78, 761–767, (1989).
Bevan, M., et al., "A Chimaeric Antibiotic Resistance Gene as a Selectable Marker for Plant Cell Transformation", *Nature*, 304, 184–187, (1983).

Bevan, M., et al., "Structure and Transcription of the Nopaline Synthase Gene Region of T–DNA", *Nuc. Acids Res.*, 11, 369–385, (1983).

Binns, A.N., et al., "Agrobacterium–Mediated Gene Delivery and the Biology of Host Range Limitations", *Physiologia Plantarum*, 79, 135–139, (1990).

Bishop, J.E., "Two Teams Plane Genes into Corn", *The Wall Street Journal*, B1, (Apr. 1990).

Booy, G., et al., "Attempted Pollen–Mediated Transformation of Maize", *J. Plant Physiol.*, 135, 319–324, (1989).

Botterman, J., et al., "Engineering Herbicide Resistance in Plants", *Trends in Genetics*, 4, 219–222, (Aug. 1988).

Boulton, M.I., et al., "Specificity of Agrobacterium–Mediated Delivery of Maize Streak Virus DNA to Members of the Gramineae", *Plant Mol. Biol.*, 12, 31–40, (1989).

Boyer, J.S., "Water Deficits and Photosynthesis", In: *Water Deficits and Plant Growth*, vol. IV, Kozlowski, T.T., (ed.), Academic Press, New York, pp. 153–190, (1976).

Brignon, P., et al., "Nuclease Sensitivity and Functional Analysis of a Maize Histone H3 Gene Promoter", *Plant Molecular Biology*, 22, 1007–1015, (1993).

Brill, W.J., "Agricultural Microbiology", *Scientific American*, 245, 199–215, (Sep. 1981).

Brunke, K.J., et al., "Insect Control with Genetically Engineered Crops", *Trends in Biotechnology*, 9, 197–200, (1991).

Buchanan–Wollaston, V., et al., "Detoxification of the Herbicide Dalapon by Transformed Plants", *J. Cell. Biochem.*, 13D, Abstract No. M503, p. 330, (1989).

Caligiuri, M.G., et al., "Identification of Amino Acid Residues Involved in Feedback Regulation of the Anthranilate Synthase Complex from *Salmonella typhimurium*", *J. Biol. Chem.*, 266, 8328–8335, (May 5, 1991).

Callis, J., et al., "Introns Increase Gene Expression in Cultured Maize Cells", *Genes and Development*, 1, 1183–1200, (1987).

Cao, J., et al., "Transformation of Rice and Maize Using the Biolistic Process", In: *Plant Gene Transfer*, Lamb, C.J., et al., (eds.), Wiley–Liss, Inc., New York, pp. 21–33, (1990).

Carpita, N.C., "The Biochemistry of "Growing" Cell Walls", In: *Physiology of Cell Expansion During Plant Growth*, Cosgrove, D.J. et al, (eds.), Am. Soc. Plant Physiol., p. 28–100, (1987).

Chan, M., et al., "Agrobacterium–Mediated Production of Transgenic Rice Plants Expressing a Chimeric α–Amylase Promoter/β–Glucuronidase Gene", *Plant Mol. Biol.*, 22, 491–506, (1993).

Chandler, V.L., et al., "Two Regulatory Genes of the Maize Anthocyanin Pathway are Homologous: Isolation of a B Utilizing R Genomic Sequences", *The Plant Cell*, 1, 1175–1183, (1989).

Charest, P.J., et al., "Factors Affecting the Use of Chloramphenicol Acetyltransferase as a Marker for Brassica Genetic Transformation", *Plant Cell Reports*, 7, 628–631, (1989).

Chasan, R., "Transforming Maize Transformation", *The Plant Cell*, 4, 1463–1464, (1992).

Chourey, P.S., et al., "Callus Formation from Protoplasts of a Maize Cell Culture", *Theor. Appl. Genet.*, 59, 341–344, (1981).

Christou, P., et al., "Cotransformation Frequencies of Foreign Genes in Soybean Cell Cultures", *Theor. Appl. Genet.*, 79, 337–341, (1990).

Christou, P., et al., "Genetic Transformation of Crop Plants Using Microprojectile Bombardment", *The Plant Journal*, 2, 275–281, (1992).

Christou, P., et al., "Opine Synthesis in Wild–Type Plant Tissue", *Plant Physiol.*, 82, 218–221, (1986).

Christou, P., et al., "Soybean Genetic Engineering—Commercial Production of Transgenic Plants", *Trends in Biotechnology*, 8, 145–151, (1990).

Christou, P., et al., "Stable Transformation of Soybean Callus by DNA–Coated Gold Particles", *Plant Physiol.*, 87, 671–674, (1988).

Chu, C., et al., "Establishment of an Efficient Medium for Another Culture of Rice Through Comparative Experiments on the Nitrogen Sources", *Scientia Sinica*, 18, 659–668, (Sep.–Oct. 1975).

Clark, B., "Biotech Advance in Corn: Gunslinging Researchers Fire Marker Genes into Corn", *AG Consultant*, 46, 12, (Jul. 1990).

Cocking, F., et al., "Gene Transfer in Cereals", *Science*, 236, 1259–1262, (1987).

Coe, E., et al., "The Genetics of Corn", In: *Corn and Corn Improvement*, 3rd Edition, Sprague, G.F., et al., (eds.), American Society of Agronomy, Inc., Madison, WI, 81–258, (1988).

Comai, L., et al., "Expression in Plants of a Mutant aroA Gene from *Salmonella typhimurium* Confers Tolerance to Glyphosate", *Nature*, 317, 741–744, (Oct. 1985).

Creissen, G., et al., "Agrobacterium– and Microprojectile–Mediated Viral DNA Delivery into Barley Microspore–Derived Cultures", *Plant Cell Reports*, 8, 680–683, (Apr. 1990).

Crossway, A., et al., "Integration of Foreign DNA Following Microinjection of Tobacco Mesophyll Protoplasts", *Mol. Gen. Genet.*, 202, 179–185, (1986).

D'Halluin, K., et al., "Transgenic Maize Plants by Tissue Electroporation", *The Plant Cell*, 4, 1495–1505, (Dec. 1992).

Darvill, A., et al., "The Primary Cell Walls of Flowering Plants", In: *The Plant Cell*, vol. 1 of "The Biochemistry of Plants" Series, Tolbert, N.E., (ed.), Academic Press, New York, pp. 91–162, (1980).

Datta, S.K., et al., "Genetically Engineered Fertile Indica–Rice Recovered from Protoplasts", *Bio/Technology*, 8, 736–740, (Aug. 1990).

Dauce–Le Reverend, B., et al., "Improvement of *Escherichia coli* Strains Overproducing Lysine Using Recombinant DNA Techniques", *European J. Appl. Microbiol. Biotechnol.*, 15, 227–231, (1982).

De Block, M., et al., "Engineering Herbicide Resistance on Plants by Expression of a Detoxifying Enzyme", *EMBO J.*, 6, 2513–2518, (1987).

De Greef, W., et al., "Evaluation of Herbicide Resistance in Transgenic Crops under Field Conditions", *Bio/Technology*, 7, 61–64, (1989).

Dekeyser, R.A., et al., "Evaluation of Selectable Markers for Rice Transformation", *Plant Physiol.*, 90, 217–223, (1989).

Dekeyser, R.A., et al., "Transient Gene Expression in Intact and Organized Rice Tissues", *The Plant Cell*, 2, 591–602, (Jul. 1990).

DeWald, et al., "Plant Regeneration from Inbred Maize Suspensions", VIIth International Congress on Plant Tissue and Cell Culture, Amsterdam, The Netherlands, Abstract No. A1–36, p. 12, (Jun. 24–29, 1990).

DeWet, J.J., et al., "Exogenous Gene Transfer in Maize (*Zea mays*) using DNA–treated Pollen", In: *The Experimental Manipulation of Ovule Tissues*, Chapman, G.P., et al., (eds.), Longman, New York, pp. 197–209, (1985).

DeWet, J.R., et al., "Cloning of Firefly Luciferase cDNA and the Expression of Active Luciferase in *Escherichia coli*", *Proc. Nat. Acad. Sci. USA*, 82, 7870–7873, (1985).

Donn, G., et al., "Stable Transformation of Maize with a Chimaeric, Modified Phosphinothricin–Acetyltransferase Gene from *Streptomyces viridochromogenes*", Abstracts, VIIth International Congress on Plant Tissue Cell Culture, Amsterdam, The Netherlands, Abstract No. A2–38, p. 53, (Jun. 24–29, 1990).

Dupuis, I., et al., "Gene Transfer to Maize Male Reproductive Structure by Particle Bombardment of Tassel Primordia", *Plant Cell Rep.*, 12, 607, (1993).

Dure III, L., et al., "Common Amino Acid Sequence Domains Among the LEA Proteins of Higher Plants", *Plant Molecular Biology*, 12, 475–486, (1989).

Ellis, J.G., et al., "Does the OCS–Element Occur as a Functional Component of the Promotors of Plant Genes", *The Plant Journal*, 4, 433–443, (1993).

European Patent Office, Notice Regarding Publication of Bibliographic Data for European Patent No. 0 485 506 (1992).

Evans, D.A., et al., "Somaclonal Variation—Genetic Basis and Breeding Applications", *Trends Genet.*, 5, 46–50, (1989).

Fennel, A., et al., "Electroporation and PEG Delivery of DNA into Maize Microspores", *Plant Cell Reports*, 11, 567–570, (1992).

Fitzpatrick, T., "Pleiotrophic Gene Found in Barley Plant", *Genetic Engineering News*, 13, 1, (1993).

Flavell, R., et al., "Prospects for Transforming Monocot Crop Plants", *Nature*, 307, 108–109, (Jan. 12, 1984).

Fransz, P., et al., "Cytodifferentiation During Callus Initiation and Somatic Embryogenesis in *Zea mays* L.", Ph.D. Thesis, University of Wageningen Press, The Netherlands, (1988).

Freeling, J.C., et al., "Developmental Potentials of Maize Tissue Cultures", *Maydica*, XXI, 97–112, (Jul. 1977).

Freiberg, B., "More Researchers Discover Corn Transformation Technology", *AG Biotechnology News*, p. 26, (1990).

Fromm, M.E., et al., "Expression of Genes Transfected into Monocot and Dicot Plant Cells by Electroporation", *Proc. Nat. Acad. Sci. USA*, 82, 5824–5828, (1985).

Fromm, M.E., et al., "Inheritance and Expression of Chimeric Genes in the Progeny of Transgenic Maize Plants", *Bio/Technology*, 8, 833–839, (1990).

Fromm, M.E., et al., "Stable Transformation of Maize after Gene Transfer by Electroporation", *Nature*, 319, 791–793, (1986).

Fry, S.C., "Introduction to the Growing Cell Wall", In: *The Growing Plant Cell Wall: Chemical and Metabolic Analysis*, Longman Scientific and Technical, New York, pp. 1–5, 102–109, (1988).

Geiser, M., et al., "The Hypervariable Region on the Genes Coding for Entomophatogenic Crystal Proteins of *Bacillus thuringiensis*: Nucleotide Sequence of the kurhd1 gene of subsp. *kurstaki* HDI", *Gene*, 48, 109–118, (1986).

Goodman, R.M., et al., "Gene Transfer in Crop Improvement", *Science*, 236, 48–54, (Apr. 3, 1987).

Gordon–Kamm, W.J., et al., "Stable Transformation of Embryonic Maize Cultures by Microprojectile Bombardment", *J. Cellular Biochem.*, 13D, Abstract No. M122, p. 259, (1989).

Gordon–Kamm, W.J., et al., "Transformation of Maize Cells and Regeneration of Fertile Transgenic Plants", *The Plant Cell*, 2, 603–618, (Jul. 1990).

Gould, J., et al., "Transformation of the Graminae by *Agrobacterium tumefaciens*", Program and Abstracts, International Society for Plant Molecular Biology, Third International Congress, Tucson, AZ, Abstract No. 1277, (Oct. 6–11, 1991).

Gould, J., et al., "Transformation of *Zea mays* L. Using *Agrobacterium tumefaciens* and the Shoot Apex", *Plant Physiology*, 95, 426–434, (1991).

Gould, O., et al., "Shoot Tip Culture as a Potential Transformation System", Abstracts, Beltwide Cotton Production Research Conferences, New Orleans, LA, p. 91, (1988).

Graves, A., et al., "The Transformation of *Zea mays* Seedlings with *Agrobacterium tumefaciens*", *Plant Mol. Biol.*, 7, 43–50, (1986).

Green, C., et al., "Plant Regeneration in Tissue Cultures of Maize", *Crop Sci.*, 15, 417–421, (1975).

Green, C., et al., "Somatic Cell Genetic Systems in Corn", In: *Advances in Gene Technology: Molecular Genetics of Plants and Animals*, Academic Press, Inc., pp. 147–157, (1983).

Green, C.E., et al., "Plant Regeneration in Tissue Cultures of Maize", In: *Maize for Biological Research*, Sheridan, W.F., (ed.), Plant Molecular Biology Association, Charlottesville, VA, pp. 367–372, (1982).

Grimsley, N., et al., "DNA Transfer from Agrobacterium to *Zea mays* or Brassica by Agroinfection is Dependent on Bacterial Virulence Functions", *Mol. Gen. Genet.*, 217, 309–316, (1989).

Gritz, L., et al., "Plasmid–Encoded Hygromycin B Resistance: The Sequence of Hygromycin B Phosphotransferase Gene and Its Expression in *Escherichia coli* and *Saccharomyces cerevisiae*", *Gene*, 25, 179–188, (1983).

Guerineau, F., et al., "Sulfonamide Resistance Gene for Plant Transformation", *Plant Molecular Biology*, 15, 127–136, (1990).

Guilley, H., et al., "Transcription of Cauliflower Mosaic Virus DNA: Detection of Promoter Sequences, and Characterization of Transcripts", *Cell*, 30, 763–773, (Oct. 1982).

Gunset, G., "Corn Farmers See Economic, Environment Gold in Designer Genes", *Chicago Tribune*, (Jan. 21, 1991).

Gunset, G., "Genetic Advance May Transform Corn", *Chicago Tribune*, (Apr. 19, 1990).

Hallauer, A.R., et al., "Corn Breeding", In: *Corn and Corn Improvement*, 3rd Edition, Sprague, G.F., et al., (eds.), American Society of Agronomy, Inc., Madison, WI, pp. 463–564, (1988).

Haughn, G.W., "Transformation with a Mutant Arabidopsis Acetolactate Synthase Gene Renders Tobacco Resistant to Sulfonylurea Herbicides", *Mol. Gen. Genet.*, 211, 266–271, (1988).

Hauptmann, R.M., et al., "Evaluation of Selectable Markers for Obtaining Stable Transformants on the Gramineae", *Plant Physiol.*, 86, 602–606, (1988).

Herrera–Estrella, L., et al., "Use of Reporter Genes to Study Gene Expression in Plant Cells", In: *Plant Molecular Biology Manual B1*, Kluwer Academic Publishers, Dordrecht, Belgium, pp. 1–22, (1988).

Hoffman, L.M., et al., "A Modified Storage Protein is Synthesized, Processed, and Degraded in the Seeds of Transgenic Plants", *Plant Mol. Biol.*, 11, 717–729, (1988).

Hoffman, L.M., et al., "Synthesis and Protein Body Deposition of Maize 15–kd Zein in Transgenic Tobacco Seeds", *EMBO J.*, 6, 3213–3221, (1987).

Hofte, H., et al., "Insecticidal Crystal Proteins of *Bacillus thuringiensis*", *Microbiol. Rev.*, 53, 242–255, (Jun. 1989).

Hong, B., et al., "Developmental and Organ–Specific Expression of an ABA– and Stress–Induced Protein in Barley", *Plant Mol. Biol.*, 18, 663–673, (1992).

Hooykaas–Van Slogteren, G.S., et al., "Expression of Ti Plasmid Genes in Monocotyledonous Plants Infected with *Agrobacterium tumefaciens*", *Nature*, 311, 763–764, (Oct. 25, 1984).

Hooykaas, P.J., "Transformation of Plant Cell via Agrobacterium", *Plant Mol. Biol.*, 13, 327–336, (1989).

Horn, M., et al., "Transgenic Plants of Orchardgrass (*Dactylis glomerata* L.) from Protoplasts", *Chem. Abstracts*, 110, Abstract No. 89869a, 208, (1989).

Horn, M., et al., "Transgenic Plants of Orchardgrass (*Dactylis glomerata* L.) from Protoplasts", *Plant Cell Reports*, 7, 469–472, (1988).

Howe, A., et al., "Development of Glyphosphate as a Selectable Marker for the Production of Fertile Transgenic Corn Plants", *In Vitro Cell. Develop. Biol.*, 28A, Abstract No. P–1136, (Jul.–Aug. 1992).

Huang, Y., et al., "Factors Influencing Stable Transformation of Maize Protoplasts by Electroporation", *Plant Cell, Tissue and Organ Culture*, 18, 281, (1989).

Imbrie–Milligan, C., et al., "Microcallus Growth from Maize Protoplasts", *Planta*, 171, 58–64, (1987).

International Society for Plant Molecular Biology, *Program and Abstracts, Molecular Biology of Plant Growth and Development*, Tucson, Arizona, (Oct. 6–11, 1991).

Jahne, A., et al., "Regeneration of Fertile Plants from Protoplasts Derived from Embryogenic Cell Suspensions of Barley (*Hordeum vulgare* L.)", *Plant Cell Rep.*, 10, 1–6, (1991).

Jayne, S., et al., "Analysis of Elite Transgenic Maize Plants Produced by Microprojectile Bombardment", *Program and Abstracts, International Society for Plant Molecular Biology, Third International Congress*, Tucson, AZ, Abstract No. 338, (Oct. 6–11, 1991).

Jaynes, J.M., et al., "Plant Protein Improvement by Genetic Engineering: Use of Synthetic Genes", *Trends in Biotechnology*, 4, 314–320, (Dec. 1986).

Jefferson, R.A., "Assaying Chimeric Genes in Plants: The GUS Gene Fusion System", *Plant Mol. Biol. Rep.*, 5, 387–405, (1987).

Jefferson, R.A., et al., "Beta–Glucuronidase from *Escherichia coli* as a Gene–Fusion Marker", *Proc. Nat. Acad. Sci. USA*, 83, 8447–8451, (1986).

Jefferson, R.A., et al., "GUS Fusions: Beta–Glucuronidase as a Sensitive and Versatile Gene Fusion Marker in Higher Plants", *EMBO J.*, 6, 3901–3907, (1987).

Johri, M.M., et al., "Genetic Approaches to Meristem Organization", In: *Maize for Biological Research*, W. F. Sheridan, (ed.), Plant Molecular Biology Association, Charlottesville, VA, pp. 301–310, (1982).

Jones, H., et al., "Recent Advances in Plant Electroporation", *Oxford Surveys of Plant Molecular and Cell Biology*, 4, 347–357, (1987).

Jones, H., et al., "Transient Gene Expression in Electroporated Solanum Protoplasts", *Plant Mol. Biol.*, 13, 503–511, (1989).

Kaeppler, H.F., et al., "Silicon Carbide Fiber–Mediated DNA Delivery into Plant Cells", *Plant Cell Rep.*, 9, 415–418, (1990).

Kamo, K., et al., "Establishment and Characterization of Long–Term Embryonic Maize Callus and Cell Suspension Cultures", *Plant Sci.*, 45, 111–117, (1986).

Kamo, K., et al., "Regeneration of *Zea mays* L. from Embryogenic Callus", *Bot. Gaz.*, 146, 327–334, (1985).

Kao, K.N., et al., "Nutritional Requirements for Growth of *Vicia hajastana* Cells and Protoplasts at a Very Low Population Density in Liquid Media", *Planta*, 126, 105–110, (1978).

Kartha, K., et al., "Transient Expression of Chloramphenicol Acetyl Transferase (CAT) Gene in Barley Cell Cultures and Immature Embryos Through Microprojectile Bombardment", *Plant Cell. Rep.*, 8, 429–432, (1989).

Kay, R., et al., "Duplication of CaMV 35S Promoter Sequences Creates a Strong Enhancer for Plant Genes", *Science*, 236, 1299–1302, (Jun. 5, 1987).

Kirihara, J., et al., "Differential Expression of a Gene for a Methionine–Rich Storage Protein in Maize", *Mol. Gen. Genet.*, 211, 477–484, (1988).

Kirihara, J., et al., "Isolation and Sequence of a Gene Encoding a Methionine–Rich 10–kDa Zein Protein from Maize", *Gene*, 71, 359–370, (1988).

Klein, T.M., et al., "Factors Influencing Gene Delivery into *Zea mays* Cells by High Velocity Microprojectiles", *Bio/Technology*, 6, 559–563, (1988).

Klein, T.M., et al., "Genetic Transformation of Maize Cells by Particle Bombardment", *Plant Physiology*, 91, 440–444, (1989).

Klein, T.M., et al., "High–Velocity Microprojectiles for Delivering Nucleic Acids into Living Cells", *Nature*, 327, 70–73, (1987).

Klein, T.M., et al., "Regulation of Anthocyanin Biosynthetic Genes Introduced into Intact Maize Tissues by Microprojectiles", *Pro. Nat. Acad. Sci. USA*, 86, 6681–6685, (Sep. 1989).

Klein, T.M., et al., "Transfer of Foreign Genes into Intact Maize Cells with High–Velocity Microprojectiles", *Proc. Nat. Acad. Sci. USA*, 85, 4305–4309, (1988).

Kozak, M., "Compilation and Analysis of Sequences from the Translational Start Site in Eukaryotic mRNAs", *Nuc. Acids Res.*, 12, 857–872, (1984).

Kozak, M., "Point Mutations Define a Sequence Flanking the AUG Initiator Codon that Modulates Translation by Eukaryotic Ribosomes", *Cell*, 44, 283–292, (1986).

Koziel, M.G., et al., "Field Performance of Elite Transgenic Maize Plants Expressing as Insecticidal Protein Derived from *Bacillus thuringiensis*", *Bio/Technol.*, 11, 194–200, (1993).

Kreitlow, B., "Genetic Engineering 'Breakthrough' Disputed", *Cedar Rapids Gazette*, (Apr. 20, 1990).

Kriz, A.L., et al., "Characterization of the Maize Globulin–2 Gene and Analysis of Two Null Alleles", *Biochemical Genetics*, 29, 241–254, (1991).

Kuhlemeier, C., et al., "Regulation of Gene Expression in Higher Plants", *Ann. Rev. Plant Physiol.*, 38, 234–239, (1987).

Langridge, P., et al., "Transformation of Cereals via Agrobacterium and the Pollen Pathway: A Critical Assessment", *The Plant Journal*, 2, 613–638, (1992).

Lazzeri, P., et al., "In Vitro Genetic Manipulation of Cereals and Grasses", *Adv. Cell Culture*, 6, 291–293, (1988).

Lee, J.S., et al., "Gene Transfer into Intact Cells of Tobacco by Electroporation", *Korean J. Genetics*, 11, 65–72, (1989).

Leemans, J., "Genetic Engineering for Fertility Control", Keystone Symposium on Crop Improvement via Biotechnology: An International Perspective, Abstract No. Y016, (Apr. 10–26, 1992).

Lemaux, P.G., et al., "Selection of Stable Transformants from Maize Suspension Cultures Using the Herbicide Bialphos", *J. Cell. Biochem.*, 14e, Abstract R230, 304, (Mar. 31, 1990).

Levitt, J., "Growth Regulators", In: *Introduction to Plant Physiology*, The C.V. Mosby Company, St. Louis, MO, p. 241, (1969).

Li, B.J., et al., "Introduction of Foreign Genes into the Seed Embryo Cells of Rice by Electroinjection and the Regeneration of Transgenic Rice Plants", *Science in China*, 34, 925–931, (1991).

Li, X.Q., et al., "GUS Expression in Rice Tissue Using Agrobacterium–Mediated Transformation", *Program and Abstracts, International Society for Plant Molecular Biology, Third International Congress*, Tucson, AZ, Abstract No. 385 (Oct. 6–11, 1991).

Lindsey, K., et al., "Electroporation of Cells", *Physiol. Plant.*, 79, 168–172, (1990).

Lindsey, K., et al., "Stable Transformation of Sugarbeet Protoplasts by Electroporation", *Plant Cell Rep.*, 8, 71–74, (1989).

Lindsey, K., et al., "The Permeability of Electroporated Cells and Protoplasts of Sugar Beet", *Planta*, 172, 346–355, (1987).

Lindsey, K., et al., "Transient Gene Expression in Electroporated Protoplasts and Intact Cells of Sugar Beet", *Plant Mol. Biol.*, 10, 43–52, (1987).

Looker, D., "Dekalb Claims Success in Effort to Alter Genetic Makeup of Corn", *Des Moines Register*, (Apr. 19, 1990).

Lorz, H., et al., "Advances in Tissue Cultures and Progress Towards Genetic Transformation of Cereals", *Plant Breeding*, 100, 1–25, (1988).

Ludwig, S., et al., "A Regulatory Gene as a Novel Visible Marker for Maize Transformation", *Science*, 247, 449–450, (1990).

Ludwig, S., et al., "High Frequency Callus Formation from Maize Protoplasts", *Theor. Appl. Genet.*, 71, 344–350, (1985).

Ludwig, S., et al., "Lc, a Member of the Maize R Gene Family Responsible for Tissue–Specific Anthocyanin Production, Encodes a Protein Similar to Transcriptional Activators and Contains the myc–Homology Region", *Proc. Natl. Acad. Sci. USA*, 86, 7092–7096, (1989).

Ludwig, S., et al., "Maize R Gene Family: Tissue–Specific Helix–Loop–Helix Proteins", *Cell*, 62, 849–851, (1990).

Lutcke, H., et al., "Selection of AUG Initiation Codons Differs in Plants and Animals", *EMBO J.*, 6, 43–48, (1987).

Maas, C., et al., "A Highly Optimized Monocot Expression Cassette: Application for Barley Transformation and Barley Virus Research", *Program and Abstracts, International Society for Plant Molecular Biology, Third International Congress*, Tucson, AZ, Abstract No. 386, (Oct. 6–11, 1991).

Maddock, S.E., et al., "Expression in Maize Plants of Wheat Germ Agglutinin, a Novel Source of Insect Resistance", *Program and Abstracts, International Society for Plant Molecular Biology, Third International Congress*, Tucson, AZ, Abstract No. 372, (Oct. 6–11, 1991).

Mariani, C., et al., "Engineered Male Sterility in Plants", *Symposia of the Society for Experimental Biology, Number XLV*, Proceedings of a Meeting Held at the University of Glasgow, Scotland, 271–279, (1991).

Masumura, T., et al., "cDNA Cloning of an mRNA Encoding a Sulfur–Rich 10 kDa Prolamin Polypeptide in Rice Seeds", *Plant Mol. Biol.*, 12, 123–130, (1989).

McCabe, D.E., et al., "Stable Transformation of Soybean (*Glycine max*) by Particle Acceleration", *Bio/Technology*, 6, 923–926, (Aug. 1988).

McCue, K.F., et al., "Drought and Salt Tolerance: Towards Understanding and Application", *TIBTECH*, 8, 358–362, (Dec. 1990).

McDaniel, C., et al., "Cell–Lineage Patterns in the Shoot Apical Meristem of the Germinating Maize Embryo", *Planta*, 175, 13–22, (1988).

Meadows, C., et al., "Characterization of Cells and Protoplasts of the B73 Maize Cell Line", *Plant Sci. Lett.*, 28, 337–348, (1982–1983).

Mendel, R., et al., "Delivery of Foreign Genes to Intact Barley Cell by High–Velocity Microprojectiles", *Theor. Appl. Genet.*, 78, 31–34, (1989).

Messing, J., "Corn Storage Protein: A Molecular Genetic Model", Division of Energy BioSciences—Summaries of FY 1990 Activities, Abstract No. 135, p. 70, (1990).

Milborrow, B.V., "Abscisic Acid and Other Hormones", In: *The Physiology and Biochemistry of Drought Resistance in Plants*, Paleg, L.G., et al., (eds.), Academic Press, New York, pp 347–388, (1981).

Moffat, A.S., "Corn Transformed", *Science*, 249, 630, (Aug. 10, 1990).

Morikawa, H., et al., "Gene Transfer into Intact Plant Cells by Electroporation Through Cell Walls and Membranes", *Gene*, 41, 121–124, (1986).

Morocz, S., et al., "An Improved System to Obtain Fertile Regenerants via Maize Protoplasts Isolated From a Highly Embryogenic Suspension Culture", *Theor. Appl. Genet.*, 80, 721–726, (1990).

Morocz, S., et al., "Two Approaches to Rendering *Zea mays* L. Applicable to Tissue Culture Manipulations", *Abstracts, VIIth International Congress on Plant Tissue and Cell Culture*, A1–102, Amsterdam, The Netherlands, Abstract No. 209, p. 190, (1990).

Murakami, T., et al., "The Bialaphos Biosynthetic Genes of *Streptomyces hygroscopicus*: Molecular Cloning and Characterization of the Gene Cluster", *Mol. Gen. Genet.*, 205, 42–50, (1986).

Murashige, T., et al., "A Revised Medium for Rapid Growth and Bio Assays with Tobacco Tissue Cultures", *Physiol. Plant.*, 15, 473–497, (1962).

Murphy, H.L., "New Dekalb–Pfizer Seed Chief to Harvest R & D Breakthroughs", *Crains's Business Weekly*, 38–39, (1990).

Murray, E.E., et al., "Codon Usage in Plant Genes", *Nuc. Acids Res.*, 17, 477–498, (1989).

Murry, L.E., et al., "Transgenic Corn Plants Expressing MDMV Strain B Coat Protein are Resistant to Mixed Infections of Maize Dwarf Mosaic Virus and Maize Chlorotic Motle Virus", *Bio/Technology*, 11, 1559–1564, (1993).

Nelson, R.S., "Virus Tolerance, Plant Growth and Field Performance of Transgenic Tomato Plants Expressing Coat Protein from Tobacco Mosaic Virus", *Bio/Technology*, 6, 403–409, (Apr. 1988).

Nelson, T., "New Horses for Monocot Gene Jockeys", *The Plant Cell*, 2, 589, (1990).

Neuffer, M.G., "Growing Maize for Genetic Purposes", In: *Maize for Biological Research*, Sheridan, W.F., (ed.), Plant Molecular Biology Association, Charlottesville, VA, p. 19–30, (1988).

Niyogi, K.K., et al., "Suppressors of trp I Fluorescence Identify a New Arabidopsis Gene, TRP4, Encoding the Anthranilate Synthase β Gene", *The Plant Cell*, 5, 1011–1027, (1993).

Niyogi, K.K., et al., "Two Anthranilate Synthase Genes in Arabidopsis: Defense–Related Regulation of the Tryptophan Pathway", *The Plant Cell*, 4, 721–733, (1992).

Odell, J., et al., "Identification of DNA Sequences Required for Activity of the Cauliflower Mosaic Virus 35S Promoter", *Nature*, 313, 810–811, (1985).

Ohta, Y., et al., "Gene Manifestation of Exogenous DNA Applied to Self–Propagating Stigma (Gene Action Revealed in the $M_1$ and $M_2$ Generations from Self–Pollination Applying Exogenous DNA)", *Jap. J. Breed.*, 30, 184–185, (1980).

Ohta, Y., et al., "High–Efficiency Genetic Transformation of Maize by a Mixture of Pollen and Exogenous DNA", *Proc. Nat. Acad. Sci. USA*, 83, 715–719, (1986).

Omirullen, S., et al., "Activity of a Chimeric Promoter with the Doubled CaMV 35S Enhancer in Protoplast–Derived Cells and Transgenic Plants in Maize", *Plant Mol. Biol.*, 21, 415–428, (1993).

Ozias–Akins, P., et al., "In Vitro Regeneration and Genetic Manipulation of Grasses", *Physiol. Plant.*, 73, 565–569, (1988).

Ozias–Akins, P., et al., "Progress and Limitations in the Culture of Cereal Protoplasts", *Trends in Biotechnology*, 2, 119–123, (1984).

Park, S.H., et al., "Selection of Maize Transformants form Shoot Apex Cultures Cocultivated with Agrobacterium Containing the Bar Gene", *In Vitro Cell Develop. Biol.*, 29A, Abstract No. P–1102, 85, (1993).

Parker, W.B., et al., "Selection and Characterization of Sethoxydim–Tolerant Maize Tissue Cultures", *Plant Physiol.*, 92, 1220–1225, (1990).

Paszkowski, J., et al., "Direct Gene Transfer to Plants", *The EMBO Journal*, 3, 2717–2722, (1984).

Pederson, K., et al., "Sequence Analysis and Characterization of a Maize Gene Encoding a High–Sulfur Zein Protein of $M_r$ 15,000", *J. Biol. Chem.*, 261, 6279–6284, (1986).

Perl, A., et al., "Bacterial Dihydrodipicolinate Synthase and Desensitized Aspartate Kinase: Two Novel Selectable Markers for Plant Transformation", *Bio/Technol.*, 11, 715–718, (1993).

Perlack, F.J., et al., "Modification of the Coding Sequence Enhances Plant Expression of Insect Control Protein Genes", *Proc. Nat. Acad. Sci. USA*, 88, 3324–3328, (1991).

Phillips, R.L., et al., "Cell/Tissue Culture and In Vitro Manipulation", In: *Corn and Corn Improvement*, 3rd Edition, Sprague, G.F., et al, (eds.), American Society of Agronomy, Inc., Madison, WI, 345–387, (1988).

Phillips, R.L., et al., "Elevated Protein–Bound Methionine in Seeds of a Maize Line Resistant to Lysine Plus Threonine", *Cereal Chem.*, 62, 213–218, (1985).

Piatkowski, D., et al., "Characterization of Five Abscisic Acid–Responsive cDNA Clones Isolated from the Desiccation–Tolerant Plant *Craterostigma plantagineum* and Their Relationship to Other Water–Stress Genes", *Plant Physiology*, 94, 1682–1688, (Jun. 1990).

Poehlman, J.M., "Backcross Breeding", In: *Breeding Field Crops*, 3rd Edition, AVI Publishing Company, Inc., Westport, CT, 203–206, (1988).

Poehlman, J.M., "Breeding Corn (Maize)", In: *Breeding Field Crops, 3rd Edition*, AVI Publishing Co., Westport, CT, p. 469–470, 477–481, (1988).

Potrykus, I., "Gene Transfer to Cereals: An Assessment", *Bio/Technology*, 8, 535–542, (Jun. 1990).

Potrykus, I., "Gene Transfer to Cereals: An Assessment", *Trends in Biotechnology*, 7, 269–273, (Oct. 1989).

Potrykus, I., "Gene Transfer to Plants: Assessment and Perspectives", *Physiol. Plant.*, 79, 125–134, (1990).

Potrykus, I., et al., "Callus Formation from Cell Culture Protoplasts of Corn (*Zea mays* L.)", *Theor. Appl. Genet.*, 54, 209–214, (1979).

Potrykus, I., et al., "Callus Formation from Stem Protoplasts of Corn (*Zea mays* L.)", *Mol. Gen. Genet.*, 156, 347–350, (1977).

Potrykus, I., et al., "Direct Gene Transfer to Cells of a Graminaceous Monocot", *Mol. Gen. Genet.*, 199, 183–188, (1985).

Potter, H., et al., "Enhancer–Dependent Expression of Human Kappa Immunoglobulin Genes Introduced into Mouse Pre–B Lymphocytes by Electroporation", *Proc. Nat. Acad. Sci. USA*, 81, 7161–7165, (1984).

Prioli, L.M., et al., "Plant Regeneration and Recovery of Fertile Plants from Protoplasts of Maize (*Zea mays* L)", *Bio/Technology*, 7, 589–594, (Jun. 1989).

Puite, K.J., et al., "Electrofusion a Simple and Reproducible Technique in Somatic Hybridization of *Nicotiana plumbaginifolia* mutants", *Plant Cell Rep.*, 4, 274–276, (1985).

Ranch, J.P., et al., "Expression of 5–Methyltryptophan Resistance in Plants Regenerated from Resistant Cell Lines of *Datura innoxia*", *Plant Physiol.*, 71, 136–140, (1983).

Rathinasabapathi, B., et al., "Metabolic Engineering of Glycine Betaine Synthesis: Plant Betaine Aldehyde Dehydrogenases Lacking Typical Transit Peptides Are Targeted to Tobacco Chloroplasts Where They Confer Betaine Aldehyde Resistance", *Planta*, 193, pp. 155–162, (1994).

Rhodes, C.A., "Corn: From Protoplasts to Fertile Plants", *Bio/Technology*, 7, 548, (Jun. 1989).

Rhodes, C.A., et al., "Genetically Transformed Maize Plants from Protoplasts", *Science*, 240, 204–207, (Apr. 1988).

Rhodes, C.A., et al., "Plant Regeneration from Protoplasts Isolated from Embryogenic Maize Cell Cultures", *Bio/Technology*, 6, 56–60, (Jan. 1988).

Richaud, F., et al., "Chromosomal Location and Nucleotide Sequence of the *Escherichia coli* dapA Gene", *Biol. Abstracts*, 82, Abstract No. 3396, p. 391, (1986).

Richaud, F., et al., "Chromosomal Location and Nucleotide Sequence of the *Escherichia coli* dapA Gene", *Journal of Bacteriology*, 166, 297–300, (Apr. 1986).

Robbins–Roth, C., et al., "They Make it Happen in Biotech", *Bioworld*, 30–36, (Nov.–Dec. 1990).

Robertson, D.S., "Loss of Mu Mutator Activity when Active Mu Systems are Transferred to Inbred Lines", *Maize Genetics Coop. Newsletter*, 60, 10, (1986).

Ross, M.C., et al., "Transient and Stable Transgenic Cells and Calli of Tobacco and Maize Following Microprojectile Bombardment", *J. Cell. Biochem.*, 13D, Abstract No. M149, p. 268, (1989).

Sahi, S.V., et al., "Metabolites in Maize Which Affect Virulence Induction in *Agrobacterium tumefaciens*", *Plant Physiol.*, Supplement, Abstract No. 514, p. 86, (1989).

Sanford, J.C., "Biolistic Plant Transformation", *Physiol. Plant.*, 79, 206–209, (1990).

Sanford, J.C., "The Biolistic Process", *Trends in Biotechnology*, 6, 299–302, (1988).

Sanford, J.C., et al., "Attempted Pollen–Mediated Plant Transformation Employing Genomic Donor DNA", *Theor. Appl. Genet.*, 69, 571–574, (1985).

Sanford, J.C., et al., "Delivery of Substances into Cells and Tissues Using a Particle Bombardment Process", *Particulate Sci. Technol.*, 5, 27–37, (1987).

Sass, J.E., "Morphology: Development of the Caryopsis", In: *Corn and Corn Improvement*, 2nd Edition, Sprague, G.F., (ed.), American Society of Agronomy, Inc., Madison, WI, p. 89, 98, (1977).

Schmidt, A., et al., "Media and Environmental Effects of Phenolics Production from Tobacco Cell Cultures", *Chem. Abstracts.*, 110, Abstract No. 230156z, p. 514, (1989).

Shen, W.H., et al., "Excision of a Transposible Element from a Viral Vector Introduced into Maize Plants by Agroinfection", *The Plant Journal*, 2, 35–42, (1992).

Shigekawa, K., et al., "Electroporation of Eukaryotes and Prokaryotes: A General Approach to the Introduction of Macromolecules into Cells", *BioTechniques*, 6, 742–751, (1988).

Shillito, R.D., et al., "High Efficiency Direct Gene Transfer to Plants", *Bio/Technology*, 3, 1099–1103, (1985).

Shillito, R.D., et al., "Regeneration of Fertile Plants from Protoplasts of Elite Inbred Maize", *Bio/Technology*, 7, 581–587, (Jun. 1989).

Shimamoto, K., et al., "Fertile Transgenic Rice Plants Regenerated from Transformed Protoplasts", *Nature*, 338, 274–278, (1989).

Shotwell, M.A., et al., "The Biochemistry and Molecular Biology of Seed Storage Proteins", In: *The Biochemistry of Plants*, vol. 15, Marcus, A., (ed.), Academic Press, Inc., San Diego, CA, pp. 297–345, (1989).

Smith, R., et al., "Shoot Apex Explant for Transformation", *Plant Physiol. (Suppl.)*, 86, Abstract No. 646, p. 108, (1988).

Soberon, X., et al., "Construction and Characterization of New Cloning Vehicles. IV. Deletion Derivatives of pBR322 and pBR325", *Gene*, 9, 287–305, (1980).

Somers, D.A., et al., "Fertile, Transgenic Oat Plants", *Bio/Technology*, 10, 1589–1594, (Dec. 1992).

Songstad, D.D., et al., "Transient Expression of GUS and Anthocyanin Constructs in Intact Maize Immature Embryos Following Electroporation", *Plant Cell Tissue and Organ Culture*, 33, 195–201, (1993).

Spencer, T.M., et al., "Bialphos Selection of Stable Transformations from Maize Cell Culture", *Theor. Appl. Genet.*, 79, 625–631, (May 1990).

Spencer, T.M., et al., "Fertile Transgenic Maize", Abstracts, 7th Annual Meeting of the Mid–Atlantic Plant Molecular Biology Society, University of Maryland, College Park, MD, p. 30, (Aug. 16–17, 1990).

Spencer, T.M., et al., "Segregation of Transgenes in Maize", *Plant Mol. Biol.*, 18, 201–210, (1992).

Spencer, T.M., et al., "Selection of Stable Transformants from Maize Suspension Cultures using the Herbicide Bialphos", Poster Presentation, FASEB Plant Gene Expression Conference, Copper Mountain, CO, (Aug. 8, 1989).

Sprague, G.M., et al., "Corn Breeding", In: *Corn and Corn Improvement*, Second Edition, Sprague, G.F., (ed.), American Society of Agronomy, Inc., Madison, WI, pp. 305, 320–323, (1977).

Steimel, D., "Corn Breeders Stalk Perfect Hybrid", *Rockford Register Star*, (Aug. 6, 1990).

Steimel, D., "New Gun Will Custom–Design Corn: Breeding Technique Expected by End of 90's Will Let Crop Grow Without Pesticides or Much Water", (Apr. 1990).

Sugiyama, M., et al., "Use of the Tyrosinase Gene from Streptomyces to Probe Promoter Sequences for *Escherichia coli*", *Plasmid*, 23, 237–241, (1990).

Suttie, J., et al., "Use of Different Selection Agents to Produce Maize Transformants of an Elite Genotype Using Microprojectile Bombardment", *Program and Abstracts, International Society for Plant Molecular Biology, 3rd International Congress*, Tucson, AZ, Abstract No. 426, (Oct. 6–11, 1991).

Tarczynski, M.C., et al., "Expression of a Bacterial mtlD Gene in Transgenic Tobacco Leads to Production and Accumulation of Mannitol", *Proc. Natl. Acad. Sci. USA*, 89, 2600–2604, (1992).

Tarczynski, M.C., et al., "Stress Protection of Transgenic Tobacco by Production of the Osmolyte Mannitol", *Science*, 259, 508–510, (1993).

Thompson, C.J., et al., "Characterization of the Herbicide–Resistance Gene bar from *Streptomyces hygroscopicus*", *EMBO Journal*, 6, 2519–2523, (1987).

Tomes, D.T., "Status of Corn Transformation", 26th Annual Corn Breeders School, Meeting Proceedings, University of Illinois, Champaign, IL, p. 7–8, (Feb. 26–27, 1990).

Tomes, D.T., et al., "Transgenic Tobacco Plants and Their Progeny Derived by Microprojectile Bombardment of Tobacco Leaves", *Plant Mol. Biol.*, 14, 261–268, (Feb. 1990).

Twell, D., et al., "Transient Expression of Chimeric Genes Delivered into Pollen by Microprojectile Bombardment", *Plant Physiol.*, 91, 1271–1274, (1989).

Ulian, E., et al., "Transformation of Plants via the Shoot Apex", *In Vitro Cell. Dev. Biol.*, 9, 951–954, (1988).

Usami, S., et al., "Absence in Monocotyledonous Plants of the Diffusible Plant Factors inducing T–DNA Circularization and vir Gene Expression in Agrobacterium", *Mol. Gen. Genet.*, 209, 221–226, (1987).

Vain, P., et al., "Osmotic Pretreatment Enhances Particle Bombardment–Mediated Transient and Stable Transformation of Maize", *Plant Cell Rep.*, 12, 84–88, (1993).

Vasil, I.K., "Transgenic Cereals Becoming a Reality", *Bio/Technology*, 8, 797, (Sep. 1990).

Vasil, I.K., et al., "Culture of Protoplasts Isolated from Embryogenic Cell Suspension Cultures of Sugarcane and Maize", *IAPTC Abstracts*, p. 443, (1986).

Vasil, V., et al., "Isolation and Maintenance of Embryogenic Cell Suspension Cultures of Gramineae", In: *Cell Culture and Somatic Cell Genetics of Plants*, vol. I, Academic Press, pp. 152–158, (1984).

Vasil, V., et al., "Plant Regeneration from Friable Embryonic Callus and Cell Suspension Cultures of *Zea mays* L.", *J. Plant Physiol.*, 124, 399–408, (1986).

Vasil, V., et al., "Regeneration of Plants from Embryogenic Suspension Culture Protoplasts of Wheat (*Triticum aestivum* L.)", *Bio/Technology*, 8, 429–434, (May 1990).

Walbot, V., et al., "Molecular Genetics of Corn", In: *Corn and Corn Improvement*, 3rd Edition, Sprague, G.F., et al., (eds.), American Society of Agronomy, Madison, WI, pp. 389–430, (1988).

Waldron, C., et al., "Resistance to Hygromycin B", *Plant Mol. Biol.*, 5, 103–108, (1985).

Walters, D.A., et al., "Transformation and Inheritance of Hygromycin Phosphotransferase Gene in Maize Plants", *Plant Mol. Biol.*, 18, 189–200, (1992).

Wan, Y., et al., "Maize Transformation and Regeneration of Transgenic Plants by Microprojectile Bombardment of Type I Callus", *Abstracts, 35th Annual Maize Genetics Conference*, St. Charles, IL, p. 5, (Mar. 18–21, 1993).

Wang, Y., et al., "Characterization of cis–Acting Elements Regulating Transcription from the Promoter of a Constitutively Active Rice Actin Gene", *Mol. Cell. Biol.*, 12, 3399–2406, (1992).

Wang, Y.C., et al., "Transient Expression of Foreign Genes in Rice, Wheat and Soybean Cells Following Particle Bombardment", *Plant Molecular Biology*, 11, 433–439, (1988).

Weising, K., et al., "Foreign Genes in Plants: Transfer, Structure, Expression and Applications", *Ann. Rev. Genet.*, 22, 421–478, (1988).

White, J., et al., "A Cassette Containing the bar Gene of *Streptomyces hygroscopicus*: a Selectable Marker for Plant Transformation", *Nuc. Acids Res.*, 18, 1062, (1989).

Whitely, H.R., et al., "The Molecular Biology of Parasporal Crystal Body Formation in *Bacillus thuringiensis*", *Ann. Rev. Microbiol.*, 40, 549–576, (1986).

Wong, E.Y., et al., "*Arabidopsis thaliana* Small Subunit Leader and Transit Peptide Enhance the Expression of *Bacillus thuringiensis* Proteins in Transgenic Plants", *Plant Mol. Biol.*, 20, 81–93, (1992).

Yamaguchi–Shinozaki, K., et al., "Molecular Cloning and Characterization of 9 cDNAs for Genes that are Responsive to Desiccation in *Arabidopsis thaliana*: Sequence Analysis of One cDNA Clone that Encodes a Putative Transmembrane Channel Protein", *Plant Cell Physiol.*, 33, 217–224, (1992).

Yang, H., et al., "Production of Kanamycin Resistant Rice Tissues Following DNA Uptake into Protoplasts", *Plant Cell Rep.*, 7, 421–425, (1988).

Yanisch–Perron, C., et al., "Improved M13 Phage Cloning Vectors and Host Strains: Nucleotide Sequences of the M13mp18 and pUC19 Vectors", *Gene*, 33, 103–119, (1985).

Yugari, Y., et al., "Coordinated End–Product Inhibition in Lysine Synthesis in *Escherichia coli*", *Biochem. Biophys. Acta*, 62, 612–614, (1962).

*Abstracts, 35th Annual Maize Genetics Conference*, St. Charles, IL, p. 5, 30, 45–46 (Mar. 18–21, 1993).

"Ciba–Geigy Joins Maize Transformers", *Agrow*, No. 118, 20, (Aug. 31, 1990).

"European Firm Devises Insect–Resistant Plants", *Agricultural Biotechnology News*, 1, 6, (Mar.–Apr. 1986).

European Patent Office, Decision T153/88 (Stahlwerke Peine–Salzgitter/Hot strip) Issued by Technical Board of Appeal 3.3.3 on Jan. 9, 1991 (Not Published in the Official Journal): English Translation from [1997] EPOR pp. 371 to pp. 378, 371–378, (1997).

"Herbicide–Resistant Corn", *Connecticut Academy of Science and Engineering*, Case Reports, 5, 6, (1990).

*In Vitro Cellular & Developmental Biology*, 21, Program Issue: Thirty–Sixth Annual Meeting of the Tissue Culture Association, New Orleans, LA, 88 p. (Mar. 1985).

*In Vitro Cellular & Developmental Biology*, 23, Program Issue: Thirty–Eighth Annual Meeting of the Tissue Culture Association, Washington, D.C., 93 p. (Mar. 1987).

*In Vitro Cellular & Developmental Biology*, 24, Program Issue: Thirty–Ninth Annual Meeting of the Tissue Culture Association, Las Vegas, NV, 92 p. (Mar. 1988).

*In Vitro Cellular & Developmental Biology*, 25, Program Issue: Fortieth Annual Meeting of the Tissue Culture Association, Orlando, Fl, 73 p. (Mar. 1989).

*In Vitro Cellular & Developmental Biology*, 26, Program Issue: Forty–First Annual Meeting of the Tissue Culture Association, Houston, TX, 88 p. (Mar. 1990).

*In Vitro Cellular & Developmental Biology*, 28, Program Issue: 1992 World Congress on Cell and Tissue Culture, Washington, D.C., ISSN 0883–8364 (Jun. 20–25, 1992).

"Keystone Crops", *Agricultural Genetics Report*, (Mar./Apr. 1990).

"Molecular Strategies for Crop Improvement", *Journal of Cellular Biochemistry*, Supplement 14e, List of Plenary and Poster Sessions, organized by Arntzen, C., et al., for The Keystone Conference on Molecular Strategies for Crop Plant Improvement, held at the 19th UCLA Symposia, 257, (1990).

"Monsanto, DeKalb Gunning for Insect–, Disease–Resistant Corn", *Biotechnology Newswatch*, 4–5, (May 7, 1990).

Pioneer Hi–Bred International, Inc., Application for Release in the Environment Under 7 CFR 340, Permit No. 92–022–03, No CBI Copy, entitled Corn Plants Genetically Engineered to Express Wheat Germ Agglutinin (WGA) Genes, In Order to Confer Resistance t, p. 11, (May 4, 1992).

Pioneer Hi–Bred International, Inc., Application Under 7 C.F.R. 340, Release of Genetically Engineered Corn Plants, Permit No. 92–174–02, No CBI, p. 8, (Nov. 3, 1992).

Pioneer Hi–Bred International, Inc., Application Under 7 C.F.R. 340, Release of Genetically Engineered Corn Plants, Permit No. 92–212–01, CBI–Deleted, p. 11, (Nov. 16, 1992).

Pioneer Hi–Bred International, Inc., Application Under 7 C.F.R. 340, Release of Genetically Engineered Corn Plants, Permit No. 92–330–01, CBI–Deleted, p. 13, (Apr. 13, 1993).

"Plant Science Produces Transformed Corn", *Chemical and Engineering News*, 7, (Jan. 29, 1990).

Abbe, E.C., et al., "The Growth of the Shoot Apex in Maize: Embryogeny", *American Journal of Botany*, 41, 285–293, (Apr. 1954).

Abe, K., et al., "Molecular Cloning of a Cysteine Proteinase Inhibitor of Rice (Oryzacystatin)", *The Journal of Biological Chemistry*, 262, 16793–16797, (Dec. 15, 1987).

Adang, M.J., et al., "Expression of a *Bacillus thuringiensis* Insecticidal Crystal Protein Gene in Tobacco Plants", *Molecular Strategies for Crop Protection*, Arntzen, C.J., et al. (eds.), Alan R. Liss, Inc., New York, 345–353, (1987).

Al–Feel, W., et al., "Cloning of the Yeast FAS3 Gene and Primary Structure of Yeast Acetyl–CoA Carboxylase", *Proc. Natl. Acad. Sci. USA*, 89, 4534–4538, (May 1992).

Anderson, J.M., et al., "The Encoded Primary Sequence of a Rice Seed ADP–glucose Pyrophosphorylase Subunit and Its Homology to the Bacterial Enzyme", *The Journal of Biological Chemistry*, 264, 12238–12242, (Jul. 25, 1989).

Anderson, P.C., et al., "Herbicide–Tolerant Mutants of Corn", *Genome*, 31, 994–999, (1989).

Angus, T.A., "Implications of Some Recent Studies of *Bacillus thuringiensis*—A Personal Purview", *Proceedings of the 4th International Colloquium on Insect Pathology*, College Park, MD, 183–189, (Aug. 25–28, 1970).

Armaleo, D., et al., "Biolistic Nuclear Transformation of *Saccharomyces cerevisiae* and Other Fungi", *Curr. Genet.*, 17, 97–103, (1990).

Armstrong, C.L., et al., "Development and Availability of Germplasm with High Type II Culture Formation Response", *Maize Genetics Cooperation Newsletter,* 65, 92–93, (Mar. 1, 1991).

Arondel, V., et al., "Map–Based Cloning of a Gene Controlling Omega–3 Fatty Acid Desaturation in Arabidopsis", *Science,* 258, 1353–1355, (Nov. 20, 1992).

Aronson, A.I., et al., *"Bacillus thuringiensis* and Related Insect Pathogens", *Microbiological Reviews,* 50, 1–24, (Mar. 1986).

Aronson, J.N., et al., "Toxic Trypsin Digest Fragment from the *Bacillus thuringiensis* Parasporal Protein", *Applied and Evnironmental Microbiology,* 53, 416–421, (Feb. 1987).

Bartels, D., et al., "An ABA and GA Modulated Gene Expressed in the Barley Embryo Encodes an Aldose Reductase Related Protein", *EMBO Journal,* 10, 1037–1043, (May 1991).

Bartley, G.E., et al., "Molecular Cloning and Expression in Photosynthetic Bacteria of a Soybean cDNA Coding for Phytoene Desaturase, an Enzyme of the Carotenoid Biosynthesis Pathway", *Proc. Natl. Acad. Sci. USA,* 88, 6532–6536, (Aug. 1991).

Barton, K.A., et al., *"Bacillus thuringiensis* δ–Endotoxin Expressed in Transgenic *Nicotiana tabacum* Provides Resistance to Lepidopteran Insects", *Plant Physiol.,* 85, 1103–1109, (1987).

Barton, K.A., et al., "Production of *Bacillus thuringiensis* Insecticidal Proteins in Plants", *Transgenic Plants,* vol. 1, Kung, S.–D., et al., (eds.), Academic Press, Inc., San Diego, CA, 297–315, (1993).

Birk, Y., et al., "Separation of a Tribolium–Protease Inhibitor from Soybeans on a Calcium Phosphate Column", *Biochem. Biophys. Acta,* 67, 326–328, (Feb. 12, 1963).

Bishop, D.H., et al., "Genetically Engineered Viral Insecticides—A Progress Report 1986–1989", *Pestic. Sci.,* 27, 173–189, (1989).

Bol, J.F., et al., "Plant Pathogenesis–Related Proteins Induced by Virus Infection", *Annu. Rev. Phytopathol.,* 28, 113–138, (1990).

Bowler, C., et al., "Superoxide Dismutase and Stress Tolerance", *Ann. Rev. Plant Physiol. Plant Mol. Biol.,* 43, 83–116, (1992).

Boylan–Pett, W., et al., "Effectiveness of *Bacillus thuringiensis*–Transgenic Potato Plants for Control of Colorado Potato Beetles, 1991", *Insecticide & Acaricide Tests: 1992,* 17, 124–125, (1992).

Boynton, J.E., et al., "Chloroplast Transformation in Chlamydomonas with High Velocity Microprojectiles", *Science,* 240, 1534–1537, (Jun. 10, 1988).

Bryant, J.A., "At Last: Transgenic Cereal Plants from Genetically Engineered Protoplasts", *Trends in Biotechnology,* 6, 291–292, (Dec. 1988).

Burgerjon, A., et al., "Industrial and International Standardization of Microbial Pesticides—I. *Bacillus thuringiensis", Entomophaga,* 22, 121–129, (1977).

Busvine, J.R., *A Critical Review of the Techniques for Testing Insecticides,* Table of Contents, Commonwealth Agricultural Bureaux, Slough, England, iii–xi, (1971).

Bytebier, B., et al., "T–DNA Organization in Tumor Cultures and Transgenic Plants of the Monocotyledon *Asparagus officinalis", Proc. Natl. Acad. Sci. USA,* 84, 5345–5349, (Aug. 1987).

Calabrese, D.M., et al., "A Comparison of Protein Crystal Subunit Sizes in *Bacillus thruingiensis", Canadian Journal of Microbiology,* 26, 1006–1010, (Aug. 1980).

Caplan, A., et al., "Introduction of Genetic Material into Plant Cells", *Science,* 222, 815–821, (Nov. 18, 1983).

Carozzi, N.B., et al., "Expression of a Chimeric CaMV 35S *Bacillus thuringiensis* Insecticidal Protein Gene in Transgenic Tobacco", *Plant Molecular Biology,* 20, 539–548, (1992).

Chaleff, R.S., "Induction, Maintenance, and Differentiation of Rice Callus Cultures on Ammonium as Sole Nitrogen Source", *Plant Cell Tissue Organ Culture,* 2, 29–37, (1983).

Christou, P., et al., "Inheritance and Expression of Foreign Genes in Transgenic Soybean Plants", *Proc. Natl. Acad. Sci. USA,* 86, 7500–7504, (Oct. 1989).

Christou, P., et al., "Production of Transgenic Rice (*Oryza sativa* L.) Plants from Agronomically Important Indica and Japonica Varieties via Electric Discharge Particle Acceleration of Exogenous DNA into Immature Zygotic Embryos", *Bio/technology,* 9, 957–962, (Oct. 1991).

Cooksey, K.E., "Purification of a Protein from *Bacillus thuringiensis* Toxic to Larvae of Lepidoptera", *Biochem. J.,* 106, 445–454, (1968).

De Block, M., et al., "Expression of Foreign Genes in Regenerated Plants and Their Progeny", *EMBO J.,* 3, 1681–1689, (1984).

De Block, M., et al., "The Use of Phosphinothricin Resistance as a Selectable Marker in Tobacco Protoplast Transformation", In: *Progress in Plant Protoplast Research,* Proceedings of the 7th International Protoplast Symposium, Wageningen, The Netherlands, Puite, K.J., et al., (eds.), Kluwer Academic Publishers, Dordrecht, 389–390, (Dec. 6–11, 1987).

Denecke, J., et al., "Quantification of Transient Expression Levels of Genes Transferred to Plant Protoplasts by Electroporation", *Progress in Plant Protoplast Research,* Puite, K.J., et al., (eds.), Proceedings of the 7th International Protoplast Symposium, Wageningen, The Netherlands, 337–338, (Dec. 6–11, 1987).

Denholm, I., et al., "Tactics for Managing Pesticide Resistance in Arthropods: Theory and Practice", *Annu. Rev. Entomol.,* 37, 91–112, (1992).

Depicker, A.G., et al., "A Negative Selection Scheme for Tobacco Protoplast–Derived Cells Expressing the T–DNA Gene 2", *Plant Cell Reports,* 7, 63–66, (1988).

Domoney, C., et al., "Cloning and Characterization of Complementary DNA for Convicilin, a Major Seed Storage Protein in *Pisum sativum* L.", *Planta,* 159, 446–453, (1983).

Duncan, D.R., et al., "The Production of Callus Capable of Plant Regeneration for Immature Embryos of Numerous *Zea Mays* Genotypes", *Planta,* 165, 322–332, (1985).

Dunder, E., et al., "High Frequency Transformation of Maize by Microprojectile Bombardment of Immature Embryos", *Abstracts, 35 Annual Maize Genetics Conference,* St. Charles, IL, Poster No. 16, p. 30 (Mar. 18–21, 1993).

Dunder, E., et al., "Transgenic Anthocyanin Color Phenotypes Produced in Callus, Plants and Progeny of Maize", *Abstracts, 35th Annual Maize Genetics Conference,* St. Charles, IL, Poster No. 15, p. 30 (Mar. 18–31, 1993).

Dunleavy, J.M., *"Curtobacterium plantarum* sp. nov. Is Ubiquitous in Plant Leaves and Is Seed Transmitted in Soybean and Corn", *International Journal of Systematic Bacteriology,* 39, 240–249, (Jul. 1989).

Dunn, G.M., et al., "Inheritance of Cyclic Hydroxamates in *Zea mays* L.", *Can. J. Plant Sci.,* 61, 583–593, (Jul. 1981).

Dybvig, K., et al, "Transposition of Gram–Positive Transposon Tn916 in *Acholeplasma laidlawii* and *Mycoplasma pulmonis*", *Science,* 235, 1392–1394, (Mar. 13, 1987).

Edallo, S., et al., "Chromosomal Variation and Frequency of Spontaneous Mutation Associated with in vitro Culture and Plant Regeneration in Maize", *Maydica,* 26, 39–56, (1981).

Fast, P.G., et al., "*Bacillus thuringiensis* δ–Endotoxin: Evidence that Toxin Acts at the Surface of Susceptible Cells", *Experientia,* 34, 762–763, (1978).

Faust, R.M., et al., "Bacteria and Their Toxins as Insecticides", In: *Microbial and Viral Pesticides,* Kurstak, E., (ed.), Marcel Dekker, Inc., New York, 75–208, (1982).

Finkle, B.J., et al., "Growth and Regeneration of Alfalfa Callus Lines After Freezing in Liquid Nitrogen", *Plant Science,* 42, 133–140, (1985).

Finney, D.J., In: *Probit Analysis: A Statistical Treatment of the Sigmoid Response Curve,* iii–ix, (1952).

Fischhoff, D.A., et al., "Insect Tolerant Transgenic Tomato Plants", *Bio/technology,* 5, 807–812, (1987).

Fisher, D.K., et al., "Starch Branching Enzyme II from Maize Endosperm", *Plant Physiol.,* 102, 1045–1046, (1993).

Fromm, M., et al., "Transient Expression and Stable Transformation of Maize Using Microprojectiles", In: *Plant Molecular Biology,* vol. 2, Herrmann, R.G., et al., (eds.), Plenum Press, New York, 219, (1991).

Fukuto, T.R., "Physiocochemical Aspects of Insecticidal Action", In: *Insecticidal Biochemistry and Physiology,* Wilkinson, C.F., (ed.), Plenum Press, New York, 397–428, (1976).

Gallagher, S., "Progress and Promise of the Particle Gun", *Ag Biotechnology News,* 6, 12–13, (Mar.–Apr. 1989).

Gallie, D.R., et al., "The 5'–leader Sequence of Tobacco Mosaic Virus RNA Enhances the Expression of Foreign Gene Transcripts in Vitro and in Vivo", *Nucleic Acids Research,* 15, 3257–3273, (1987).

Gatehouse, A.M.R., et al., "Assessment of the Antimetabolic Effects of Trypsin Inhibitors from Cowpea (*Vigna unguiculata*) and Other Legumes on Development of the Bruchid Beetle *Callosobruchus maculatus*", *J. Sci. Food Agric.,* 34, 345–350, (1983).

Genovesi, A.D., et al., "Embryogenesis in Callus Derived from Rice Microspores", *Plant Cell Reports,* 1, 257–260, (1982).

Georghiou, G.P., et al., "Factors Influencing the Evolution of Resistance", In: *Pesticide Resistance: Strategies and Tactics for Management,* Committee on Strategies for the Management of Pesticide Resistant Pest Populations, Board on Agriculture, National Research Council, National Academy Press, Washington, D.C., 157–169, (1986).

Gepts, P., et al., "Enhanced Available Methionine Concentration Associated with Higher Phaseolin Levels in Common Bean Seeds", *Theor. Appl. Genet.,* 69, 47–53, (1984).

Gerlach, W.L., "Genetic Engineering: Its Place in Plant Breeding", In: *Plant Breeding and Genetic Engineering,* Zakri, A.H., (ed.), Society for the Advancement of Breeding Researches in Asia and Oceania, Bangi, Malaysia, 269–277, (1988).

Goff, S.A., et al., "Transactivation of Anthocyanin Biosynthetic Genes Following Transfer of B Regulatory Genes into Maize Tissues", *EMBO Journal,* 9, 2517–2522, (1990).

Goldburg, R.J., et al., "Are B.T.K. Plants Really Safe to Eat?", *Bio/technology,* 8, 1011–1015, (Nov. 1990).

Goldfarb, B., et at., "Transient Expression of Microprojectile–Introduced DNA in Douglas–Fir", *J. Cell. Biochem.,* 13D, Abstract No. M121, p. 259 (1989).

Goldman, S.L., et al., "Transformation of *Zea mays* by *Agrobacterium tumefaciens:* Evidence for Stable Genetic Alterations", *Journal of Cellular Biochemistry,* 11B, Abstract No. F 202, p. 26, (1987).

Gordon, P.N., et al., "Plant Regeneration from Tissue Cultures of Maize", *Maize Genetics Cooperation Newsletter,* 51, 79–80, (Mar. 1, 1977).

Gordon–Kamm, W.J., et al., "Transformation of Maize Using Microprojectile Bombardment: An Update and Perspective", *In Vitro Cellular and Developmental Biology,* 27, 21–27, (Jan. 1991).

Green, C.E., "New Developments in Plant Tissue Culture and Plant Regeneration", In: *Basic Biology of New Developments in Biotechnology,* Hollaender, A., et al., (eds.), Plenum Press, New York, 195–209, (1983).

Green, C.E., "Somatic Embryogenesis and Plant Regeneration from the Friable Callus of *Zea mays*", *Proccedings of the 5th International Congress on Plant Tissue & Cell Culture,* Tokyo, Japan, 107–108, (1982).

Guerrero, F.D., et al., "Turgor–Responsive Gene Transcription and RNA Levels Increase Rapidly When Pea Shoots are Wilted. Sequence and Expression of Three Inducible Genes", *Plant Mol. Biol.,* 15, 11–26, (1990).

Gupta, A.S., et al., "Increased Resistance to Oxidative Stress in Transgenic Plants that Overexpress Chloroplastic Cu/Zn Superoxide Dismutase", *Proc. Natl. Acad. Sci. USA,* 90, 1629–1633, (Feb. 1993).

Haccius, B., "Question of Unicellular Origin of Non–Zygotic Embryos in Callus Cultures", *Phytomorphology,* 28, 74–81, (1978).

Hallborn, J., et al., "Xylitol Production By Recombinant *Saccharomyces Cerevisiae*", *Bio/Technology,* 9, 1090–1095, (Nov. 1991).

Harms, C.T., et al., "Regeneration of Plantlets from Callus Cultures of *Zea mays* L.", *Z. Ptlanzenzuchtg,* 77, 347–351, (1976).

Hartree, E.F., "Determination of Protein: A Modification of the Lowry Method that Gives a Linear Photometric Response", *Analytical Biochemistry,* 48, 422–427, (1972).

Harvey, W.R., et al., "Potassium Ion Transport ATPase in Insect Epithelia", *J. Exp. Biol.,* 106, 91–117, (1983).

Heimpel, A.M., et al., "Recent Advances in the Knowledge of Some Bacterial Pathogens of Insects", *Proceedings of the Tenth International Congress of Entomology,* vol. 4, 711–722, (1956).

Heimpel, A.M., et al., "The Site of Action of Crystalliferous Bacteria in Lepidoptera Larvae", *Journal of Insect Pathology,* 1, 152–170, (1959).

Hernalsteens, J.–P., et al., "An Agrobacterium–Transformed Cell Culture from the Monocot *Asparagus Officinalis*", *The EMBO Journal,* 3, 3039–3041, (Dec. 1984).

Hibberd, K.A., "Induction, Selection, and Characterization of Mutants in Maize Cell Cultures", In: *Cell Culture and Somatic Cell Genetics of Plants,* vol. 1, Vasil, I.K., (ed.), Academic Press, Inc., Orlando, FL, 571–576, (1984).

Hickle, L.A., et al., "Analytical Chemistry of *Bacillus thuringiensis:* An Overview", In: *Analytical Chemistry of Bacillus thuringiensis,* Hickle, L.A., et al., (eds.), Developed from a Symposium Sponsored by the Division of Agrochemicals at the 198th National Meeting of the American Chemical Society, Miami Beach, FL, vii–ix, 1–8, (Sep. 10–15, 1989).
Hilder, V.A., et al., "A Novel Mechanism of Insect Resistance Engineered into Tobacco", *Nature,* 330, 160–163, (Nov. 12, 1987).
Hodges, T.K., et al., "Genotype Specificity of Somatic Embryogenesis and Regeneration in Maize", *Bio/technology,* 4, 219–223, (Mar. 1986).
Hodges, T.K., et al., "Regeneration of Maize", In: *Biotechnology in Plant Science,* Zaitlin, M., et al., (ed.), Academic Press, Inc., Orlando, FL, 15–33, (1985).
Hoekema, A., et al., "Codon Replacement in the PGK1 Gene of *Saccharomyces cerevisiae:* Experimental Approach to Study the Role of Biased Codon Usage in Gene Expression", *Molecular and Cellular Biology,* 7, 2914–2924, (Aug. 1987).
Hofmann, C., et al., "Binding of the Delta Endotoxin from *Bacillus thuringiensis* to Brush–Border Membrane Vesicles of the Cabbage Butterfly (*Pieris Brassicae*)", *Eur. J. Biochem.,* 173, 85–91, (1988).
Hofmann, C., et al., "Specificity of *Bacillus thuringiensis* δ–Endotoxins is Correlated with the Presence of High–Affinity Binding Sites in the Brush Border Membrane of Target Insect Midguts", *Proc. Natl. Acad. Sci. USA,* 85, 7844–7848, (Nov. 1988).
Höfte, H., et al., "Monoclonal Antibody Analysis and Insecticidal Spectrum of Three Types of Lepidopteran–Specific Insecticidal Crystal Proteins of *Bacillus thuringiensis", Applied and Environmental Microbiology,* 54, 2010–2017, (Aug. 1988).
Höfte, H., et al., "Structural and Functional Analysis of a Cloned Delta Endotoxin of *Bacillus thuringiensis berliner* 1715", *Eur. J. Biochem.,* 161, 273–280, (1986).
Hollingworth, R.M., "The Biochemical and Physiological Basis of Selective Toxicity", In: *Insecticidal Biochemistry and Physiology,* Wilkinson, C.F., (ed.), Plenum Press, New York, 431–506, (1976).
Hong, B., et al., "Cloning and Characterization of cDNA Encoding a mRNA Rapidly–Induced by ABA in Barley Aleurone Layers", *Plant Molecular Biology,* 11, 495–506, (1988).
Horsch, R.B., et al., "A Simple and General Method for Transferring Genes into Plants", *Science,* 227, 1229–1231, (Mar. 8, 1985).
Hu, N.T., et al., "Primary Structure of a Genomic Zein Sequence of Maize", *The EMBO Journal,* 1, 1337–1342, (1982).
Huber, H.E., et al., "*Bacillus thuringiensis* δ–Endotoxin: Composition and Activation", In: *Pathogenesis of Invertebrate Microbial Diseases,* Davidson, E.W., (ed.), Allanheld, Osmun & Co. Publishers, Inc., Totowa, NJ, 209–234, (1981).
Huber–Lukac, M., et al., "Characterization of Monoclonal Antibodies to a Crystal Protein of *Bacillus thuringiensis* subsp. *kurstaki", Infection and Immunity,* 54, 228–232, (Oct. 1986).
Imbrie–Milligan, C.W., et al., "Microcallus Formation from Maize Protoplasts Prepared from Embryogenic Callus", *Planta,* 168, 395–401, (1986).
Jarrett, P., "Potency Factors in the delta–Endotoxin of *Bacillus thuringiensis* var. *aizawi* and the Significance of Plasmids in their Control", *Journal of Applied Bacteriology,* 58, 437–448, (1985).
Jaworski, J.G., et al., "A Cerulenin Insensitive Short Chain 3–Ketoacyl–Acyl Carrier Protein Synthase in *Spinacia oleracea* Leaves", *Plant Physiol.,* 90, 41–44, (1989).
Johnson, D.E., "Toxicity of *Bacillus thuringiensis* Entomocidal Protein Toward Cultured Insect Tissue", *Journal of Invertebrate Pathology,* 38, 94–101, (1981).
Josefsson, L.G., et al., "Structure of a Gene Encoding the 1.7 S Storage Protein, Napin, from *Brassica napus", The Journal of Biological Chemistry,* 262, 12196–12201, (Sep. 5, 1987).
Kaasen, I., et al., "Molecular Cloning and Physical Mapping of the otsBA Genes, Which Encode the Osmoregulatory Trehalose Pathway of *Escherichia coli:* Evidence that Transcription is Activated by KatF (AppR)", *Journal of Bacteriology,* 174, 889–898, (Feb. 1992).
Kim, C.S., et al., "Improvement of Nutritional Value and Functional Properties of Soybean Glycinin by Protein Engineering", *Protein Engineering,* 3, 725–731, (1990).
King, P., et al., "Maize", In: *Handbook of Plant Cell Culture,* vol. 2, Sharp, W.R., et al., (eds.), Macmillan Publishing Company, New York, 69–91, (1984).
Klein, T.M., et al., "Advances in Direct Gene Transfer into Cereals", In: *Genetic Engineering: Principles and Methods,* vol. 11, Setlow, J.K., (ed.), Plenum Publishing Corp., New York, 13–31, (1989).
Klein, T.M., et al., "Genetic Transformation of Maize Cell by Particle Bombardment and the Influence of Methylation on Foreign Gene Expression", In: *Gene Manipulation in Plant Improvement II,* Gustafson, J.P., (ed.), Plenum Press, NY, pp. 265–266, (1990).
Klein, T.M., et al., "Particle Bombardment: A Universal Approach for Gene Transfer to Cells and Tissues", *Current Opinion in Biotechnology,* 4, 583–590, (1993).
Klein, T.M., et al., "Particle Gun Technology: A Novel Method for the Introduction of DNA into Living Cells", *Program and Abstracts for an International Symposium: "Biotechnology in Plant Science: Relevance to Agriculture in the Eighties",* Poster, #28, Ithaca, NY, 25, (Jun. 23–27, 1985).
Klein, T.M., et al., "Stable Genetic Transformation of Intact Nicotiana Cells by the Particle Bombardment Process", *Proc. Natl. Acad. Sci. USA,* 95, 5502–5505, (Nov. 1988).
Klein, T.M., et al., "Transformation of Microbes, Plants and Animals by Particle Bombardment", *Biotechnology,* 10, 286–291, (Mar. 1992).
Knight, M.R., et al., "Transgenic Plant Aequorin Reports the Effects of Touch and Cold–Shock and Elicitors on Cytoplasmic Calcium", *Nature,* 352, 524–526, (Aug. 8, 1991).
Knowles, B.H., et al., "Characterization and Partial Purification of a Plasma Membrane Receptor for *Bacillus thuringiensis* var. *Kurstaki* Lepidopteran–Specific δ–Endotoxin", *J. Cell Sci.,* 83, 89–101, (1986).
Knowles, B.H., et al., "Lectin–Like Binding of *Bacillus thuringiensis* var. *Kurstaki* Lepidopteran–Specific Toxin is an Initial Step in Insecticidal Action", *FEBS Letters,* 168, 197–202, (Mar. 1984).
Kononowicz, H., et al., "Subdomains of the Octopine Synthase Upstream Activating Element Direct Cell–Specific Expression in Transgenic Tobacco Plants", *The Plant Cell,* 4, 17–27, (Jan. 1992).

Lamark, T., et al., "DNA Sequence and Analysis of the bet Genes Encoding the Osmoregulatory Choline–Glycine Betaine Pathway of *Escherichia coli*", *Molecular Microbiology*, 5, 1049–1064, (1991).

Lamppa, G., et al., "Analysis of Two Linked Genes Coding for the Acyl Carrier Protein (ACP) from *Arabidopsis thaliana* (*Columbia*)", *Plant Molecular Biology*, 16, 469–474, (1991).

Langridge, W.H., et al., "Electric Field Mediated DNA Transformation in Plant Protoplasts", *Program and Abstracts for an International Symposium: "Biotechnology in Plant Science: Relevance to Agriculture in the Eighties"*, Ithaca, NY, Poster #30, p. 25, (Jun. 23–27, 1985).

Larkins, B.A., et al., "Modification of Maize–Seed Protein Quality", *Am. J. Clin. Nutr.*, 58, 264S–269S, (1993).

Leason, M., et al., "Inhibition of Pea Leaf Glutamine Synthetase by Methionine Sulphoximine, Phosphinothricin and Other Glutamate Analogues", *Biochemistry*, 21, 855–857, (1982).

Lee, B., "Cereal Transformation", *Plants Today*, 9–11, (Jan.–Feb. 1989).

Lin, F.–F., et al., "Transformation and Analysis of Inducible PAL Genes in Potato", *In Vitro Cellular and Developmental Biology*, 28, Abstract No. P–1129, p. 123A, (Mar. 1992).

Lörz, H., et al., "Gene Transfer to Cereal Cells Mediated by Protoplast Transformation", *Mol. Gen. Genet.*, 199, 178–182, (1985).

Lowe, K., et al., "Plant Regeneration via Organogenesis and Embryogenesis in the Maize Inbred Line B73", *Plant Science*, 41, 125–132, (1985).

Lu, C., et al., "Improved Efficiency of Somatic Embryogenesis and Plant Regeneration on Tissue Cultures of Maize (*Zea mays* L.)", *Theor. Appl. Genet.*, 66, 285–289, (1983).

Lu, C., et al., "Somatic Embryogenesis in *Zea mays* L.", *Theor. Appl. Genet*, 62, 109–112, (1982).

Luckow, V.A., et al., "Trends in the Development of Baculovirus Expression Vectors", *Bio/Technology*, 6, 47–55, (Jan. 1988).

Lüthy, P., "Insecticidal Toxins of *Bacillus thuringiensis*", *FEMS Microbiology Letters*, 8, 1–7, (1980).

Mackey, C.J., et al., "Transgenic Maize", In: *Transgenic Plants*, vol. 2, Kung, S.–D., et al., (eds.), Academic Press, Inc., 21–33, (Oct. 1992).

Malan, C., et al., "Correlation Between CuZn Superoxide Dismutase and Glutathione Reductase, and Environmental and Xenobiotic Stress Tolerance in Maize Inbreds", *Plant Science*, 69, 157–166, (1990).

Mangano, M.L., et al., "Long–Term Cold Storage of Regenerable Maize Callus", *In Vitro Cellular and Developmental Biology*, 25, Abstract No. 224, p. 66A, (Mar. 1989).

Mariani, T., et al., "The Production and Analysis of Genetically–Engineered Male–Sterile Plants of Maize", *Abstracts, 35th Annual Maize Genetics Conference*, St. Charles, IL, Poster No. 46, p. 45 (Mar. 18–21, 1993).

Marks, M.D., et al., "Nucleotide Sequence Analysis of Zein mRNAs from Maize Endosperm", *The Journal of Biological Chemistry*, 260, 16451–16459, (Dec. 25, 1985).

Martens, J.W.M., et al., "Insecticidal Activity of a Bacterial Crystal Protein Expressed by a Recombinant Baculovirus in Insect Cells", *Applied and Environmental Microbiology*, 56, 2764–2770, (Sep. 1990).

Matthews, B.F., et al., "Nutritional Improvement of the Aspartate Family of Amino Acids in Edible Crop Plants", *Amino Acids*, 4, 21–34, (1993).

McElroy, D., et al., "Isolation of an Efficient Actin Promoter for Use in Rice Transformation", *The Plant Cell*, 2, 163–171, (Feb. 1990).

Merryweather, A.T., et al., "Construction of Genetically Engineered Baculovirus Insecticides Containing the *Bacillus thuringiensis* subsp. *Kurstaki* HD–73 Delta Endotoxin", *Journal of General Virology*, 71, 1535–1544, (1990).

Mikula, B.C., "Programming Heritable Epigenetic Change in Gene Expression with Temperature and Light", *Abstracts, 35th Annual Maize Genetics Conference*, St. Charles, IL, p. 5 (Mar. 18–21, 1993).

Mink, G.I., "Pollen– and Seed–Transmitted Viruses and Viroids", *Annu. Rev. Phytopathol.*, 31, 375–402, (1993).

Molnar, S.J., et al., "Initiation of Totipotent Tissue Cultures from Undeveloped Axillary and Secondary Ears", *Maize Genetics Cooperation Newsletter*, 54, 52–53, (Mar. 31, 1980).

Montoliu, L., et al., "A Tandem of α–Tubulin Genes Preferentially Expressed in Radicular Tissues from *Zea mays*", *Plant Molecular Biology*, 14, 1–15, (1989).

Morris, G.D., "Ciba–Geigy Enters the $1.5–Billion/Year Corn Biotech Race", *Chemical Week*, (Sep. 12, 1990).

Mundy, J., et al., "Abscisic Acid and Water–Stress Induce the Expression of a Novel Rice Gene", *The EMBO Journal*, 7, 2279–2286, (1988).

Mundy, J., et al., "Selective Expression of a Probable Amylase/Protease Inhibitor in Barley Aleurone Cells: Comparison to the Barley Amylase/Subtilisin Inhibitor", *Plants*, 169, 51–63, (1986).

Murphy, D.W., et al., "*Bacillus thuringiensis* Enzyme–Digested Delta Endotoxin: Effect on Cultured Insect Cells", *Science*, 194, 954–956, (Nov. 26, 1976).

Murray, E.E., et al., "Analysis of Unstable RNA Transcripts of Insecticidal Crystal Protein Genes of *Bacillus thuringiensis* in Transgenic Plants and Electroporated Protoplasts", *Plant Molecular Biology*, 16, 1035–1050, (1991).

Nishida, I., et al., "The Gene and the RNA for the Precursor to the Plastid–Located Glycerol–3–phosphate Acyltransferase of *Arabidopsis thaliana*", *Plant Molecular Biology*, 21, 267–277, (1993).

Nishiitsutsuji–Uwo, J., et al., "Mode of Action of *Bacillus thuringiensis* δ–Endotoxin: Effect on TN–368 Cells", *Journal of Invertebrate Pathology*, 34, 267–275, (1979).

O'Reilly, D.R., et al., "A Baculovirus Blocks Insect Molting by Producing Ecdysteroid UDP–Glucosyl Transferase", *Science*, 245, 1110–1112, (Sep. 8, 1989).

Ochatt, S.J., et al., "Selection for Salt/Drought Tolerance using Isolated Protoplasts and Protoplast–Derived Calli of Colt Cherry (*Prunus avium x pseudocerasus*)", In: *Progress in Plant Protoplast Research*, Puite, K.J., et al., (eds.), Kluwer Academic Publishers, Dordrecht, The Netherlands, p. 391–392 (1988).

Oeda, K., et al., "Formation of Crystals of the Insecticidal Proteins of *Bacillus thuringiensis* subsp. *aizawai* IPL7 in *Escherichia coli*", *Journal of Bacteriology*, 171, 3568–3571, (Jun. 1989).

Pang, Y., et al., "Synthesis and Toxicity of Full–Length and Truncated Bacterial CryIVD Mosquitocidal Proteins Expressed in Lepidopteran Cells Using a Baculovirus Vector", *Journal of General Virology*, 73, 89–101, (1992).

Park, W.D., et al., "High–Level, Sucrose–Inducible Expression of a Chimeric Patatin–GUS Gene In Leaf Explants of Transgenic Tobacco Plants", *Journal of Cellular Biochemistry,* 13D, Abstract No. M 343, p. 310, (Mar. 27–Apr. 7, 1989).

Perlak, F.J., et al., "Expression of *Bacillus thuringiensis* Proteins in Transgenic Plants", In: *Biotechnology, Biological Pesticides and Novel Plant–Pest Resistance for Insect Pest Management,* Roberts, D.W., et al., (eds.), Insect Pathology Resource Center, Boyce Thompson Institute for Plant Research, Cornel University, Ithaca, NY, 77–81, (1988).

Perlak, F.J., et al., "Genetically Improved Potatoes: Protection from Damage by Colorado Potato Beetles", *Plant Molecular Biology,* 22, 313–321, (1993).

Perlak, F.J., et al., "Insect Resistant Cotton Plants", *Bio/technology,* 8, 939–943, (Oct. 1990).

Poehlman, J.M., In: *Breeding Field Crops,* 3rd Edition, AVI Publishing Company, Inc., Westport, CT, p. 149–152, (1988).

Poehlman, J.M., In: *Breeding Field Crops,* 3rd Edition, AVI Publishing Company, Inc., Westport, CT, p. 452, (1988).

Poethig, R.S., "Maize—The Plant and Its Parts", In: *Maize for Biological Research,* Sheridan, W.F., (ed.), Plant Molecular Biology Association., Charlottesville, VA, 9–18, (1982).

Porobo–Dessai, A., et al., "Expression of gusA Gene with an Intron in Sweet Potato and Garden Egg Plant", *In Vitro Cellular and Developmental Biology,* 13D, Abstract No. P–1130, p. 123A, (Mar. 1992).

Potrykus, I., et al., "Direct Gene Transfer: State of the Art and Future Potential", *Plant Molecular Biology Reporter,* 3, 117–128, (Summer 1985).

Randolph, L.F., et al., "Developmental Morphology of the Caryopsis in Maize", *Journal of Agricultural Research,* 53, 881–916, (Dec. 15, 1936).

Rathinasabapathi, B., et al., "Metabolic Engineering of Glycine Betaine Synthesis: Plant Betaine Aldehyde Dehydrogenases Lacking Typical Transit Peptides are Targeted to Tobacco Chloroplasts Where They Confer Betaine Aldehyde Resistance", *Planta,* 193, 155–162 (1994).

Rhodes, C.A., et al., "Cytogenetic Stability of Aneuploid Maize Tissue Cultures", *Can. J. Genet. Cytol.,* 28, 374–384, (1986).

Rhodes, C.A., et al., "Factors Affecting Tissue Culture Initiation from Maize Tassels", *Plant Science,* 46, 225–232, (1986).

Rice, T.B., "Tissue Culture Induced Genetic Variation in Regenerated Maize Inbreds", *Proceedings of the 37th Annual Corn & Sorghum Industry Research Conference,* 148–162, (1982).

Rosahl, S., et al., "Expression of a Tuber–Specific Storage Protein In Transgenic Tobacco Plants: Demonstration Of An Esterase Activity", *EMBO. J,* 6, Press Limited, Oxford, England, 1155, (1987).

Roth, B.A., et al., "C1– and R–Dependent Expression of the Maize Bz1 Gene Requires Sequences with Homology to Mammalian myb and myc Binding Sites", *The Plant Cell,* 3, 317–325, (Mar. 1991).

Roth, B.A., et al., "Genetic Regulation of Transient Expression of Maize Anthocyanin Pathway Genes Introduced into Intact Maize Tissues by Microprojectile Bombardment", *Journal of Cellular Biochemistry,* 13D, Abstract No. M 344, p. 310, (Mar. 27–Apr. 7, 1989).

Roush, R.T., et al., "Ecological Genetics of Insecticidal and Acaricide Resistance", *Ann. Rev. Entomol.,* 32, 361–380, (1987).

Russell, J.A., et al., "Physical Trauma and Tungsten Toxicity Reduce the Efficiency of Biolistic Transformation", *Plant Physiol.,* 98, 1050–1056, (1992).

Ryan, A.J., et al., "The Expression of the Napin Gene Under the Control of Its Own Promoter in Transgenic Tobacco Plants", *Journal of Cellular Biochemistry,* 13D, Abstract No. M 345, p. 310, (Mar. 27–Apr. 7, 1989).

Sanford, J.C., "The Biolistic Process", *Plant Physiology,* 89, Abstract No. 9, p. 2, (Apr. 1989).

Sanford, J.C., et al., "Delivery of DNA into Regenerable Tissues of Monocots, Using High–Velocity Microprojectiles", Grant Application No. 86–0183, United States Department of Agriculture, Science and Education, 48 p., (Feb. 27, 1986).

Sass, J.E., "Comparative Leaf Number in the Embryos of Some Types of Maize", *Iowa State Coll. J. Sci.,* 25, 509–512, (1951).

Schäfer, W., et al., "T–DNA Integration and Expression in a Monocot Crop Plant after Induction of Agrobacterium", *Nature,* 327, 529–532, (Jun. 11, 1987).

Schardl, C.L., et al., "Design and Construction of a Versatile System for the Expression of Foreign Genes in Plants", *Gene,* 61, 1–11, (1987).

Schnepf, H.E., et al., "Delineation of a Toxin–Encoding Segment of a *Bacillus thuringiensis* Crystal Protein Gene", *The Journal of Biological Chemistry,* 260, 6273–6280, (1985).

Schnepf, H.E., et al., "Specificity–Determining Regions of a Lepidopteran–Specific Insecticidal Protein Produced by *Bacillus thuringiensis*", *The Journal of Biological Chemistry,* 265, 20923–20930, (Dec. 5, 1990).

Sewell, G.H., et al., "Irish Potato, Control of Potato–Infesting Aphids, 1991", *Insecticidal and Acaricide Tests: 1992,* 17, 138, (1992).

Sewell, G.H., et al., "Transgenic Potato Plants, Control of Colorado Potato Beetle, 1991", *Insecticidal and Acaricide Tests: 1992,* 17, 138–139, (1992).

Shaner, D.L., et al., "Mechanism of Action of the Imidazolinones and Cell Culture Selection of Tolerant Maize", In: *Biotechnology in Plant Sciences,* Zaitlin, M., et al., (eds.), Academic Press, Orlando, FL, 287–299, (1985).

Sharman, B.C., "Developmental Anatomy of the Shoot of *Zea mays* L.", *Annals of Botany,* VI, 246–281, (Apr. 1942).

Shields, R., "Towards Insect–Resistant Plants", *Nature,* 328, 12–13, (Jul. 2, 1987).

Shivakumar, A.G., et al., "Vegetative Expression of the δ–Endotoxin Genes of *Bacillus thuringiensis* subsp. *kurstaki* in *Bacillus subtilis*", *Journal of Bacteriology,* 166, 194–204, (Apr. 1986).

Shotwell, M.A., et al., "Analysis of Seed Storage Protein Genes of Oats", *The Journal of Biological Chemistry,* 265, 9652–9658, (Jun. 15, 1990).

Shotwell, M.A., et al., "The Biochemistry and Molecular Biology of Seed Storage Proteins", In: *The Biochemistry of Plants,* vol. 15, Marcus, A., (ed.), Academic Press, Inc., San Diego, CA, pp. 297–345, (1989).

Smith, G.E., et al., "Molecular Engineering of the *Autographa californica* Nuclear Polyhedrosis Virus Genome: Deletion Mutations Within the Polyhedrin Gene", *Journal of Virology,* 46, 584–593, (May 1983).

Smith, I.K., et al., "Properties and Functions of Glutathione Reductase in Plants", *Physiol. Plant.,* 77, 449–456, (1989).

Sorenson, K.A., et al., "Colorado Potato Beetle Control with Bioinsecticides, 1991", *Insecticide and Acaricide Tests: 1992,* 17, 139, (1992).

St. Julian, G., et al., "Bacteria, Spirochetes, and Rickettsia as Insecticides", *Annals of the New York Academy of Sciences,* 217, 65–75, (1973).

Stalker, D.M., et al., "Herbicide Resistance in Transgenic Plants Expressing a Bacterial Detoxification Gene", *Science,* 242, 419–422, (Oct. 21, 1988).

Stark, D.M., et al., "Regulation of the Amount of Starch in Plant Tissues by ADP Glucose Pyrophosphorylase", *Science,* 258, 287–291, (Oct. 9, 1992).

Stiefel, V., et al., "Expression of a Maize Cell Wall Hydroxyproline–Rich Glycoprotein Gene in Early Leaf and Root Vascular Differentiation", *The Plant Cell,* 2, 785–793, (Aug. 1990).

Stolle, C.A., et al., "Cellular Factor Affecting the Stability of β–globulin mRNA", *Gene,* 62, 65–74, (1988).

Stougaard, J., "Substrate–Dependent Negative Selection in Plants Using a Bacterial Cytosine Deaminase Gene", *The Plant Journal,* 3, 755–761, (1993).

Strauch, E., et al., "Cloning of a Phosphinothricin N–Acetyltransferase Gene from *Streptomyces Viridochromogenes* Tu494 and its Expression in *Streptomyces lividans* and *Escherichia coli*", *Gene,* 63, 65–74, (1988).

Stroo, H.F., et al., "Heterotrophic Nitrification in an Acid Forest Soil and by an Acid–Tolerant Fungus", *Applied and Environmental Microbiology,* 52, 1107–1111, (Nov. 1986).

Sukhapinda, K., et al., "Maize Haploid Protoplast Transformation and Regeneration of Transgenic Plants", *In Vitro Cellular and Developmental Biology,* 28, Abstract No. P–1132, p. 123A, (Mar. 1992).

Suprasanna, P., et al., "Plantlet Regeneration from Glume Calli of Maize (*Zea mays* L.)", *Theor. Appl. Genet.,* 72, 120–122, (1986).

Thomas, W.E., et al., "Mechanism of Action of *Bacillus thuringiensis* var *israelensis* Insecticidal δ–Endotoxin", *FEBS Letters,* 154, 362–368, (Apr. 1983).

Tojo, A., et al., "Dissolution and Degradation of *Bacillus thuringiensis* δ–Endotoxin by Gut Juice Protease of the Silkworm *Bombyx mori*", *Applied and Environmental Microbiology,* 45, 576–580, (Feb. 1983).

Tomes, D.T., "Cell Culture, Somatic Embryogenesis and Plant Regeneration in Maize, Rice, Sorghum and Millets", In: *Cereal Tissue and Cell Culture,* Bright, S.W.J., et al., (eds.), Martinus Nijnoff/Dr. W. Junk, Amsterdam, The Netherlands, 175–203, (1985).

Tomes, D.T., "Initiation of Embryogenic Callus Cultures from Immature Embryos of Elite Corn (*Zea mays* L.) Germplasm", *In Vitro,* 20, Abstract No. 146, p. 276, (Mar. 1984).

Tomes, D.T., et al., "The Effect of Parental Genotype on Initiation of Embryogenic Callus from Elite Maize (*Zea mays* L.) Germplasm", *Theor. Appl. Genet.,* 70, 505–509, (1985).

Torne, J.M., et al., "Regeneration of Plants from Mesocotyl Tissue Cultures of Immature Embryos of *Zea mays* L.", *Plant Science Letters,* 17, 339–344, (1980).

Vaeck, M., et al., "*Bacillus thuringiensis* Endotoxin Gene Expression and Insect Resistance in Higher Plants", *Pesticide Science,* 20, 319–320, (1987).

Vaeck, M., et al., "Engineering Improved Crops for Agriculture: Protection from Insects and Resistance to Herbicides", In: *Plant Gene Systems and Their Biology,* Key, J.L., et al., (eds.), Alan R. Liss, Inc., New York, 171–181, (1987).

Vaeck, M., et al., "Engineering of Insect Resistant Plants Using a *B. thuringiensis* Gene", In: *Molecular Strategies for Crop Protection,* New York, Alan R. Liss, Inc., 355–366, (1987).

Vaeck, M., et al., "Insect Resistance in Transgenic Plants Expressing *Bacillus thuringiensis* Toxin Genes", *An. Soc. Entomol. Brasil,* 16, 427–435, (1987).

Vaeck, M., et al., "Protein Engineering in Plants: Expression of *Bacillus thuringiensis* Insecticidal Protein Genes", *Cell Culture and Somatic Cell Genetics of Plants,* 6, 425–439, (1989).

Vaeck, M., et al., "Transgenic Plants Protected from Insect Attack", *Nature,* 328, 33–37, (Jul. 2, 1987).

van den Elzen, P.J., et al., "A Chimaeric Hygromycin Resistance Gene as a Selectable Marker in Plant Cells", *Plant Molecular Biology,* 5, 299–302, (1985).

van den Elzen, P.J., et al., "Simple Binary Vectors for DNA Transfer to Plant Cells", *Plant Molecular Biology,* 5, 149–154, (1985).

Van Lammeren, A.A., "Developmental Morphology and Cytology of the Young Maize Embryo (*Zea mays* L.)", *Acta Bot. Neerl.,* 35, 169–188, (Aug. 1986).

Vasil, I.K., "Isolation and Culture of Protoplasts of Grasses", *International Review of Cytology,* Supplement 16, Bourne, G.H., et al., (eds.), Academic Press, New York, 79–88, (1983).

Vasil, V., et al., "Histology of Somatic Embryogenesis in Cultured Immature Embryos of Maize (*Zea mays* L.)", *Protoplasma,* 127, 1–8, (1985).

Vernon, D.M., et al., "A Novel Methyl Transferase Induced by Osmotic Stress in the Facultative Halophyte *Mesembryanthemum crystallinum*", *The EMBO Journal,* 11, 2077–2085, (1992).

Viotti, A., et al., "Each Zein Gene Class Can Produce Polypeptides of Different Sizes", *The EMBO J.,* 4, 1103–1110, (1985).

Visser, B., et al., "Transgenic Tobacco Plants Expressing a Modified *Bacillus thuringiensis* cryIC Gene", *Journal of Cellular Biochemistry,* Supplement 16F, Abstract No. Y 136, p. 213, (Apr. 3–16, 1992).

Warren, G.W., et al., "Field Evaluation of Transgenic Tobacco Containing a *Bacillus thuringiensis* Insecticidal Protein Gene", *Journal of Economic Entomology,* 85, 1651–1659, (1992).

Watson, S.A., "Corn Marketing, Processing and Utilization", In: *Corn and Corn Improvement,* 3rd Edition, Sprague, G.F., et al., (eds.), American Society of Agronomy, Inc., et al., Madison, WI, 881–939, (1988).

Webb, R.P., et al., "Superoxide Dismutase Gene Expression in Transgenic Plants", *Journal of Cellular Biochemistry,* Supplement 16F, Abstract No. Y 137, 213, (Apr. 3–16, 1992).

Weck, E., "Are Colorized DNA Sequences an Application of Fuzzy Logic?", *Abstracts, 35th Annual Maize Genetics Conference,* St. Charles, IL, Poster No. 45, p. 45 (Mar. 18–21, 1993).

Weeks, J.T., et al., "Rapid Production of Multiple Independent Lines of Fertile Transgenic Wheat (*Triticum aestivum*)", *Plant Physiol.,* 102, 1077–1084, (1993).

Weigel, Jr., R.C., et al., "Somatic Embryogenesis in Barley", *In Vitro*, 20, Abstract No. 147, p. 277, (Mar. 1984).

Weissinger, A., et al., "Maize Transformation via Microprojectile Bombardment", In: *Genetic Improvements of Agriculturally Important Crops,* Fraley, R.T., et al., (eds.), Cold Spring Harbor Laboratory, Cold Spring Harbor, NY, 21–25, (1988).

Weissinger, A., et al., "Microprojectile Bombardment for Maize Transformation", *In Vitro Cellular and Developmental Biology,* 23, Program Issue, 38th Annual Meeting of the Tissue Culture Association, Washington, D.C., Abstract No. 254, (Mar. 1987).

Wernicke, W., et al., "Adventitious Embryoid and Root Formation from Rice Leaves", *Z. Pflanzenphysiol. Bd.,* 103, 361–365, (1981).

Werr, W., et al., "Structure of the Sucrose Synthase Gene on Chromosome 9 of *Zea mays* L.", *The EMBO Journal,* 4, 1373–1380, (1985).

White, D.W., et al., "Auxin–Inducible Response Promoter Elements", *Journal of Cellular Biochemistry,* Supplement 16F, Abstract No. Y 138, p. 213, (Apr. 3–16, 1992).

Williams, R., et al., "Expression of the Maize Homeobox Gene Knotted–1 in Transgenic Maize", *Abstracts, 35th Annual Maize Genetics Conference,* St. Charles, IL, Poster No. 47, p. 46 (Mar. 18–21, 1993).

Williams, S., et al., "Chemical Regulation of *Bacillus thuringiensis* δ–Endotoxin Expression in Transgenic Plants", *Bio/technology,* 10, 540–543, (May 1992).

Wilson, F.D., et al., "Resistance of Cotton Lines Containing a *Bacillus thuringiensis* Toxin to Pink Bollworm (Lepidoptera: Gelechiidae) and Other Insects", *J. Econ. Entomol.,* 85, 1516–1521, (1992).

Withers, L., et al., "Proline: A Novel Cryoprotectant for the Freeze Preservation of Cultured Cells of *Zea mays* L.", *Plant Physiology,* 64, 675–678, (1979).

Witt, D.P., et al., "Cytotoxicity of *Bacillus thuringiensis* δ–Endotoxins to Cultured Cf–1 Cells Does Not Correlate with In Vivo Activity Toward Spruce Budworm Larvae", In: *Fundamental and Applied Aspects of Invertebrate Pathology,* Samson, R.A., et al., (eds.), Fourth International Colloquium of Invertebrate Pathology, Wangingen, The Netherlands, 3–6, (Aug. 18–22, 1986).

Wohlleben, W., et al., "Nucleotide Sequence of the Phosphinothricin N–Acetyltransferase Gene from *Streptomyces vividochromogenes* Tü494 and Its Expression in *Nicotania tabacum"*, *Gene,* 70, 25–37, (1988).

Wolter, F.P., et al., "Chilling Sensitivity of *Arabidopsis thaliana* with Genetically Engineered Membrane Lipids", *The EMBO Journal,* 11, 4685–4692, (1992).

Wong, J.R., et al., "Anthocyanin Regulatory Genes from Maize (B–Peru and C1) Activate the Anthocyanin Pathway in Wheat, Barley and Oat Cells", *Journal of Cellular Biochemistry,* Supplement 15A, p. 159, (1991).

Wood, M., "Blast Those Genes!", *Agricultural Research,* 2 p., (Jun. 1989).

Wu, S., et al., "Characterization of Chitinase cDNA Clones for Acidic and Basic Isoforms of Maize", *Abstracts, 35th Annual Maize Genetics Conference,* St. Charles, IL, Poster No. 48, p. 46 (Mar. 18–21, 1993).

Xiang, C., et al., "The Anti–nptII Gene—A Potential Negative Selectable Marker for Plants", *Plant Physiol.,* 102, 287–293, (1993).

Xu, D., et al., "Expression of a Late Embryogenesis Abundant Protein Gene, HVA1, from Barley Confers Tolerance to Water Deficit and Salt Stress in Transfenic Rice", *Plant Physiol,* 110, 249–257, (1996).

Yang, N.S., et al., "Maize Sucrose Synthase–1 Promoter Directs Phloem Cell–Specific Expression of Gus Gene in Transgenic Tobacco Plants", *Proc. Natl. Acad. Sci. USA,* 87, 4144–4148, (Jun. 1990).

Yenofsky, R.L., et al., "Isolation and Characterization of a Soybean (*Glycine max*) Lipoxygenase–3 Gene", *Mol. Gen. Genet.,* 211, 215–222, (1988).

Zhang, W., et al., "Analysis of Rice Act1 5' Region Activity in Transgenic Rice Plants and the Study of Regulatory Elements in This Region", *Journal of Cellular Biochemistry,* Supplement 16F, Abstract No. Y 139, p. 213, (Apr. 3–16, 1992).

U.S. application No. 07/205,155, Tomes et al., filed Jun. 10, 1988.

U.S. application No. 07/392,176, Adams et al., filed Aug. 9, 1989.

U.S. application No. 07/513,298, Adams et al., filed Apr. 17, 1990.

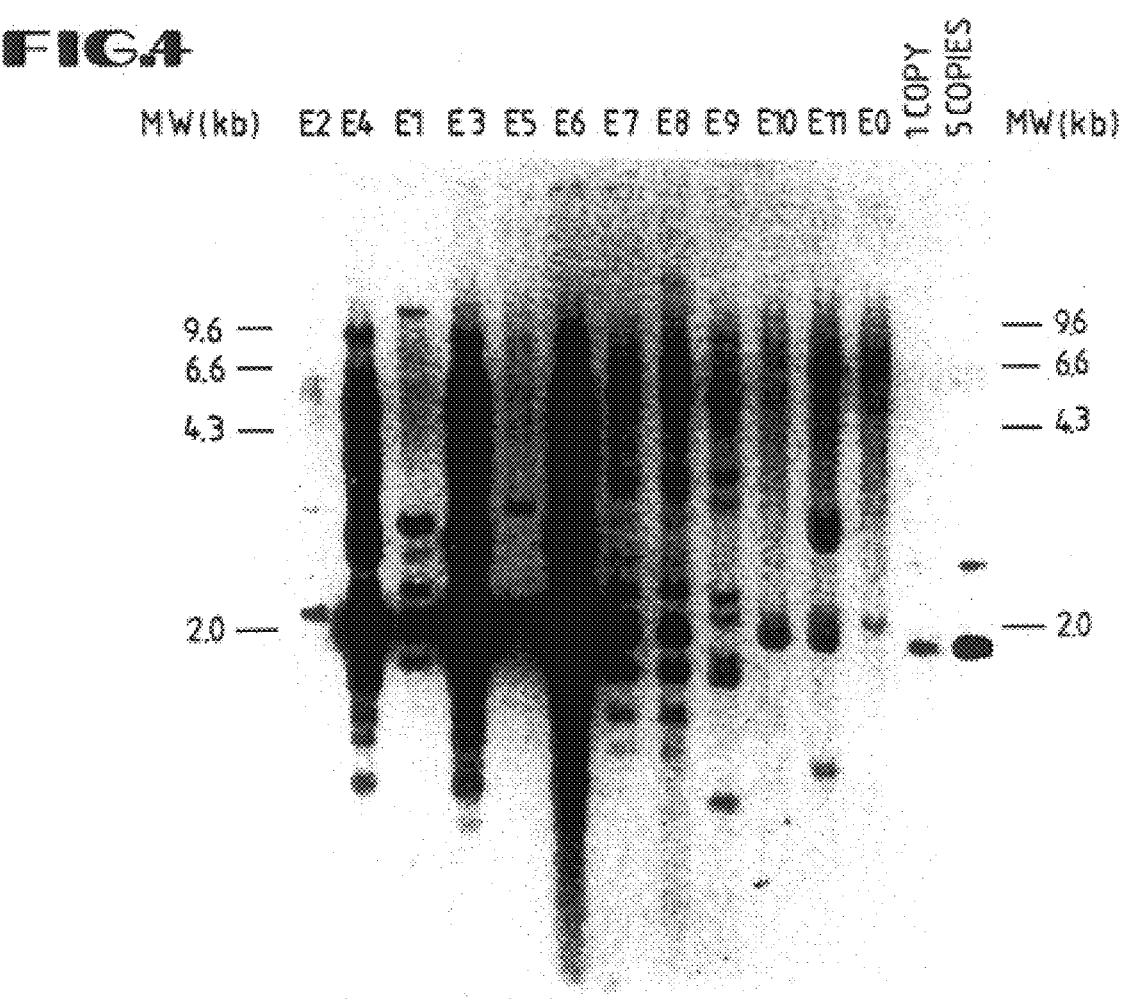

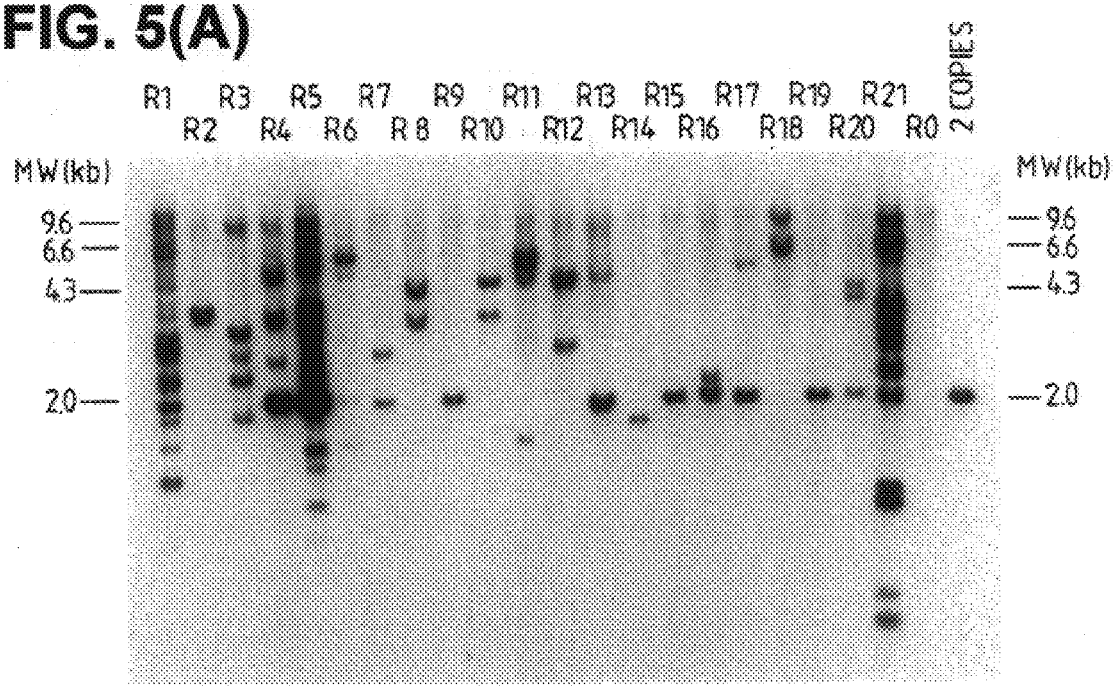

```
              10            20            30            40            50            60
123 456 789 012 345 678 901 234 567 890 123 456 789 012 345 678 901 234 567 890
ATG GAT AAC AAT CCG AAC ATC AAT GAA TGC ATT CCT TAC AAT TGC CTC AGC AAC CCT GAA    60
Met Asp Asn Asn Pro Asn Ile Asn Glu Cys Ile Pro Tyr Asn Cys Leu Ser Asn Pro Glu

GTG GAA GTG CTG GGT GGC GAA CGC ATC GAA ACC GGT TAC ACC CCA ATC GAT ATT TCC CTG   120
Val Glu Val Leu Gly Gly Glu Arg Ile Glu Thr Gly Tyr Thr Pro Ile Asp Ile Ser Leu

TCC CTG ACC CAA TTT CTG CTG AGC GAA TTT GTG CCC GGT GCT GGC TTT GTG CTG GGC CTG   180
Ser Leu Thr Gln Phe Leu Leu Ser Glu Phe Val Pro Gly Ala Gly Phe Val Leu Gly Leu

GTG GAT ATC ATC TGG GGC ATT TTT GGT CCC TCC CAA TGG GAC GCC TTT CTG GTG CAA ATT   240
Val Asp Ile Ile Trp Gly Ile Phe Gly Pro Ser Gln Trp Asp Ala Phe Leu Val Gln Ile

GAA CAG CTG ATT AAC CAA CGC ATC GAA GAA TTC GCT AGG AAC CAA GCC ATT TCC CGC CTG   300
Glu Gln Leu Ile Asn Gln Arg Ile Glu Glu Phe Ala Arg Asn Gln Ala Ile Ser Arg Leu

GAA GGC CTG AGC AAT CTG TAC CAA ATT TAC GCC GAA TCC TTT CGC GAG TGG GAA GCC GAT   360
Glu Gly Leu Ser Asn Leu Tyr Gln Ile Tyr Ala Glu Ser Phe Arg Glu Trp Glu Ala Asp

CCT ACC AAT CCA GCC CTG CGC GAA GAG ATG CGC ATT CAA TTC AAT GAC ATG AAC AGC GCC   420
Pro Thr Asn Pro Ala Leu Arg Glu Glu Met Arg Ile Gln Phe Asn Asp Met Asn Ser Ala

CTG ACC ACC GCT ATT CCT CTG TTT GCC GTG CAA AAT TAC CAA GTG CCT CTG CTG TCC GTG   480
Leu Thr Thr Ala Ile Pro Leu Phe Ala Val Gln Asn Tyr Gln Val Pro Leu Leu Ser Val

TAC GTG CAA GCT GCC AAT CTG CAT CTG TCC GTG CTG CGC GAT GTG TCC GTG TTT GGC CAA   540
Tyr Val Gln Ala Ala Asn Leu His Leu Ser Val Leu Arg Asp Val Ser Val Phe Gly Gln

AGG TGG GGC TTT GAT GCC GCC ACC ATC AAT AGC CGC TAC AAT GAT CTG ACC AGG CTG ATT   600
Arg Trp Gly Phe Asp Ala Ala Thr Ile Asn Ser Arg Tyr Asn Asp Leu Thr Arg Leu Ile

GGC AAC TAC ACC GAT TAC GCT GTG CGC TGG TAC AAT ACC GGC CTG GAA CGC GTG TGG GGC   660
Gly Asn Tyr Thr Asp Tyr Ala Val Arg Trp Tyr Asn Thr Gly Leu Glu Arg Val Trp Gly

CCA GAT TCC CGC GAT TGG GTG AGG TAC AAT CAA TTT CGC CGC GAA CTG ACC CTG ACC GTG   720
Pro Asp Ser Arg Asp Trp Val Arg Tyr Asn Gln Phe Arg Arg Glu Leu Thr Leu Thr Val

CTC GAT ATC GTG GCT CTG TTC CCA AAT TAC GAT AGC CGC CGC TAC CCA ATT CGA ACC GTG   780
Leu Asp Ile Val Ala Leu Phe Pro Asn Tyr Asp Ser Arg Arg Tyr Pro Ile Arg Thr Val

TCC CAA CTG ACC CGC GAA ATT TAC ACC AAC CCA GTG CTG GAA AAT TTT GAT GGT AGC TTT   840
Ser Gln Leu Thr Arg Glu Ile Tyr Thr Asn Pro Val Leu Glu Asn Phe Asp Gly Ser Phe

CGC GGC TCC GCT CAG GGC ATC GAA CGC AGC ATT AGG AGC CCA CAT CTG ATG GAT ATC CTG   900
Arg Gly Ser Ala Gln Gly Ile Glu Arg Ser Ile Arg Ser Pro His Leu Met Asp Ile Leu

AAC AGC ATC ACC ATC TAC ACC GAT GCT CAT AGG GGT TAC TAC TAC TGG TCC GGC CAT CAA   960
Asn Ser Ile Thr Ile Tyr Thr Asp Ala His Arg Gly Tyr Tyr Tyr Trp Ser Gly His Gln
```

FIG. 12A

```
            10          20          30          40          50          60
123 456 789 012 345 678 901 234 567 890 123 456 789 012 345 678 901 234 567 890
ATC ATG GCT TCC CCT GTG GGC TTT TCC GGG CCA GAA TTC ACC TTT CCA CTG TAC GGC ACG   1020
Ile Met Ala Ser Pro Val Gly Phe Ser Gly Pro Glu Phe Thr Phe Pro Leu Tyr Gly Thr

ATG GGC AAT GCC GCT CCA CAA CAA CGC ATT GTG GCT CAA CTG GGT CAG GGC GTG TAC CGC   1080
Met Gly Asn Ala Ala Pro Gln Gln Arg Ile Val Ala Gln Leu Gly Gln Gly Val Tyr Arg

ACC CTG TCC TCC ACC CTG TAC CGC CGC CCT TTT AAT ATC GGC ATC AAC AAC CAG CAA CTG   1140
Thr Leu Ser Ser Thr Leu Tyr Arg Arg Pro Phe Asn Ile Gly Ile Asn Asn Gln Gln Leu

TCC GTG CTG GAC GGC ACC GAA TTT GCT TAC GGC ACC TCC TCC AAT CTG CCA TCC GCT GTA   1200
Ser Val Leu Asp Gly Thr Glu Phe Ala Tyr Gly Thr Ser Ser Asn Leu Pro Ser Ala Val

TAC CGC AAG AGC GGC ACC GTG GAT TCC CTG GAT GAA ATC CCA CCA CAG AAT AAC AAC GTG   1260
Tyr Arg Lys Ser Gly Thr Val Asp Ser Leu Asp Glu Ile Pro Pro Gln Asn Asn Asn Val

CCA CCT AGG CAA GGC TTT AGC CAT CGC CTG AGC CAT GTG TCC ATG TTT CGC TCC GGC TTT   1320
Pro Pro Arg Gln Gly Phe Ser His Arg Leu Ser His Val Ser Met Phe Arg Ser Gly Phe

AGC AAT AGC AGC GTG AGC ATC ATC CGC GCT CCT ATG TTC TCC TGG ATC CAT CGC AGC GCT   1380
Ser Asn Ser Ser Val Ser Ile Ile Arg Ala Pro Met Phe Ser Trp Ile His Arg Ser Ala

GAA TTT AAC AAC ATC ATT GCC TCC GAT AGC ATT ACC CAA ATC CCT GCC GTG AAG GGC AAC   1440
Glu Phe Asn Asn Ile Ile Ala Ser Asp Ser Ile Thr Gln Ile Pro Ala Val Lys Gly Asn

TTT CTG TTT AAT GGT TCC GTG ATT TCC GGC CCA GGC TTT ACC GGT GGC GAC CTG GTG CGC   1500
Phe Leu Phe Asn Gly Ser Val Ile Ser Gly Pro Gly Phe Thr Gly Gly Asp Leu Val Arg

CTG AAT AGC AGC GGC AAT AAC ATT CAG AAT CGC GGC TAC ATT GAA GTG CCA ATT CAC TTC   1560
Leu Asn Ser Ser Gly Asn Asn Ile Gln Asn Arg Gly Tyr Ile Glu Val Pro Ile His Phe

CCA TCC ACC TCC ACC CGC TAC CGC GTG CGC GTG CGC TAC GCT TCC GTG ACC CCA ATT CAC   1620
Pro Ser Thr Ser Thr Arg Tyr Arg Val Arg Val Arg Tyr Ala Ser Val Thr Pro Ile His

CTC AAC GTT AAC TGG GGC AAT TCC TCC ATT TTT TCC AAT ACC GTG CCA GCT ACC GCT ACC   1680
Leu Asn Val Asn Trp Gly Asn Ser Ser Ile Phe Ser Asn Thr Val Pro Ala Thr Ala Thr

TCC CTG GAT AAT CTG CAA TCC AGC GAT TTT GGT TAC TTT GAA AGC GCC AAT GCT TTT ACC   1740
Ser Leu Asp Asn Leu Gln Ser Ser Asp Phe Gly Tyr Phe Glu Ser Ala Asn Ala Phe Thr

TCC TCC CTG GGT AAT ATC GTG GGT GTG CGC AAT TTT AGC GGC ACC GCC GGC GTG ATC ATC   1800
Ser Ser Leu Gly Asn Ile Val Gly Val Arg Asn Phe Ser Gly Thr Ala Gly Val Ile Ile

GAC CGC TTT GAA TTT ATT CCA GTG ACC GCC ACC CTC GAG TAG GTA                       1845
Asp Arg Phe Glu Phe Ile Pro Val Thr Ala Thr Leu Glu AMB Val
```

FIG. 12B

```
                10                  20                  30                  40                  50                  60
       123 456 789 012 345 678 901 234 567 890 123 456 789 012 345 678 901 234 567 890
       ATG GAT AAC AAT CCG AAC ATC AAT GAA TGC ATT CCT TAC AAT TGC CTC AGC AAC CCT GAA       60
       Met Asp Asn Asn Pro Asn Ile Asn Glu Cys Ile Pro Tyr Asn Cys Leu Ser Asn Pro Glu

GTG GAA GTG CTG GGT GGC GAA CGC ATC GAA ACC GGT TAC ACC CCA ATC GAT ATT TCC CTG      120
       Val Glu Val Leu Gly Gly Glu Arg Ile Glu Thr Gly Tyr Thr Pro Ile Asp Ile Ser Leu

TCC CTG ACC CAA TTT CTG CTG AGC GAA TTT GTG CCC GGT GCT GGC TTT GTG CTG GGC CTG      180
       Ser Leu Thr Gln Phe Leu Leu Ser Glu Phe Val Pro Gly Ala Gly Phe Val Leu Gly Leu

GTG GAT ATC ATC TGG GGC ATT TTT GGT CCC TCC CAA TGG GAC GCC TTT CTG GTG CAA ATT      240
       Val Asp Ile Ile Trp Gly Ile Phe Gly Pro Ser Gln Trp Asp Ala Phe Leu Val Gln Ile

GAA CAG CTG ATT AAC CAA CGC ATC GAA GAA TTC GCT AGG AAC CAA GCC ATT TCC CGC CTG      300
       Glu Gln Leu Ile Asn Gln Arg Ile Glu Glu Phe Ala Arg Asn Gln Ala Ile Ser Arg Leu

GAA GGC CTG AGC AAT CTG TAC CAA ATT TAC GCC GAA TCC TTT CGC GAG TGG GAA GCC GAT      360
       Glu Gly Leu Ser Asn Leu Tyr Gln Ile Tyr Ala Glu Ser Phe Arg Glu Trp Glu Ala Asp

CCT ACC AAT CCA GCC CTG CGC GAA GAG ATG CGC ATT CAA TTC AAT GAC ATG AAC AGC GCC      420
       Pro Thr Asn Pro Ala Leu Arg Glu Glu Met Arg Ile Gln Phe Asn Asp Met Asn Ser Ala

CTG ACC ACC GCT ATT CCT CTG TTT GCC GTG CAA AAT TAC CAA GTG CCT CTG CTG TCC GTG      480
       Leu Thr Thr Ala Ile Pro Leu Phe Ala Val Gln Asn Tyr Gln Val Pro Leu Leu Ser Val

TAC GTG CAA GCT GCC AAT CTG CAT CTG TCC GTG CTG CGC GAT GTG TCC GTG TTT GGC CAA      540
       Tyr Val Gln Ala Ala Asn Leu His Leu Ser Val Leu Arg Asp Val Ser Val Phe Gly Gln

AGG TGG GGC TTT GAT GCC GCC ACC ATC AAT AGC CGC TAC AAT GAT CTG ACC AGG CTG ATT      600
       Arg Trp Gly Phe Asp Ala Ala Thr Ile Asn Ser Arg Tyr Asn Asp Leu Thr Arg Leu Ile

GGC AAC TAC ACC GAT TAC GCT GTG CGC TGG TAC AAT ACC GGC CTG GAA CGC GTG TGG GGC      660
       Gly Asn Tyr Thr Asp Tyr Ala Val Arg Trp Tyr Asn Thr Gly Leu Glu Arg Val Trp Gly

CCA GAT TCC CGC GAT TGG GTG AGG TAC AAT CAA TTT CGC CGC GAA CTG ACC CTG ACC GTG      720
       Pro Asp Ser Arg Asp Trp Val Arg Tyr Asn Gln Phe Arg Arg Glu Leu Thr Leu Thr Val

CTC GAT ATC GTG GCT CTG TTC CCA AAT TAC GAT AGC CGC CGC TAC CCA ATT CGA ACC GTG      780
       Leu Asp Ile Val Ala Leu Phe Pro Asn Tyr Asp Ser Arg Arg Tyr Pro Ile Arg Thr Val

TCC CAA CTG ACC CGC GAA ATT TAC ACC AAC CCA GTG CTG GAA AAT TTT GAT GGT AGC TTT      840
       Ser Gln Leu Thr Arg Glu Ile Tyr Thr Asn Pro Val Leu Glu Asn Phe Asp Gly Ser Phe

CGC GGC TCC GCT CAG GGC ATC GAA CGC AGC ATT AGG AGC CCA CAT CTG ATG GAT ATC CTG      900
       Arg Gly Ser Ala Gln Gly Ile Glu Arg Ser Ile Arg Ser Pro His Leu Met Asp Ile Leu

AAC AGC ATC ACC ATC TAC ACC GAT GCT CAT AGG GGT TAC TAC TAC TGG TCC GGC CAT CAA      960
       Asn Ser Ile Thr Ile Tyr Thr Asp Ala His Arg Gly Tyr Tyr Tyr Trp Ser Gly His Gln
```

FIG. 13A

```
                10              20              30              40              50              60
       123 456 789 012 345 678 90_ 234 567 890 123 456 789 012 345 678 901 234 567 890
       ATC ATG GCT TCC CCT GTG GGC TTT TCC GGG CCA GAA TTC ACC TTT CCA CTG TAC GGC ACG     1020
       Ile Met Ala Ser Pro Val Gly Phe Ser Gly Pro Glu Phe Thr Phe Pro Leu Tyr Gly Thr

ATG GGC AAT GCC GCT CCA CAA CAA CGC ATT GTG GCT CAA CTG GGT CAG GGC GTG TAC CGC     1080
       Met Gly Asn Ala Ala Pro Gln Gln Arg Ile Val Ala Gln Leu Gly Gln Gly Val Tyr Arg

ACC CTG TCC TCC ACC CTG TAC CGC CGC CCT TTT AAT ATC GGC ATC AAC AAC CAG CAA CTG     1140
       Thr Leu Ser Ser Thr Leu Tyr Arg Arg Pro Phe Asn Ile Gly Ile Asn Asn Gln Gln Leu

TCC GTG CTG GAC GGC ACC GAA TTT GCT TAC GGC ACC TCC TCC AAT CTG CCA TCC GCT GTA     1200
       Ser Val Leu Asp Gly Thr Glu Phe Ala Tyr Gly Thr Ser Ser Asn Leu Pro Ser Ala Val

TAC CGC AAG AGC GGC ACC GTG GAT TCC CTG GAT GAA ATC CCA CCA CAG AAT AAC AAC GTG     1260
       Tyr Arg Lys Ser Gly Thr Val Asp Ser Leu Asp Glu Ile Pro Pro Gln Asn Asn Asn Val

CCA CCT AGG CAA GGC TTT AGC CAT CGC CTG AGC CAT GTG TCC ATG TTT CGC TCC GGC TTT     1320
       Pro Pro Arg Gln Gly Phe Ser His Arg Leu Ser His Val Ser Met Phe Arg Ser Gly Phe

AGC AAT AGC AGC GTG AGC ATC ATC CGC GCT CCT ATG TTC TCC TGG ATC CAC CGC TCC GCT     1380
       Ser Asn Ser Ser Val Ser Ile Ile Arg Ala Pro Met Phe Ser Trp Ile His Arg Ser Ala

GAG TTC AAC AAC ATC ATC CCG TCC TCC CAA ATC ACC CAA ATC CCG CTC ACC AAG TCC ACG     1440
       Glu Phe Asn Asn Ile Ile Pro Ser Ser Gln Ile Thr Gln Ile Pro Leu Thr Lys Ser Thr

AAC CTC GGC TCC GGC ACG TCC GTC GTC AAG GGC CCG GGC TTC ACC GGC GGC GAC ATC CTC     1500
       Asn Leu Gly Ser Gly Thr Ser Val Val Lys Gly Pro Gly Phe Thr Gly Gly Asp Ile Leu

CGC CGC ACG TCC CCG GGC CAG ATC TCC ACC CTC CGC GTC AAC ATC ACG GCT CCG CTG AGC     1560
       Arg Arg Thr Ser Pro Gly Gln Ile Ser Thr Leu Arg Val Asn Ile Thr Ala Pro Leu Ser

CAG CGC TAC AGG GTG CGC ATC AGA TAC GCT AGC ACG ACC AAC CTG CAA TTC CAC ACG TCC     1620
       Gln Arg Tyr Arg Val Arg Ile Arg Tyr Ala Ser Thr Thr Asn Leu Gln Phe His Thr Ser

ATC GAC GGC AGA CCG ATC AAC CAG GGC AAC TTC AGC GCG ACG ATG AGC TCC GGG TCC AAC     1680
       Ile Asp Gly Arg Pro Ile Asn Gln Gly Asn Phe Ser Ala Thr Met Ser Ser Gly Ser Asn

CTC CAG TCC GGC TCC TTC CGC ACG GTC GGT TTC ACC ACG CCG TTC AAC TTC TCC AAC GGC     1740
       Leu Gln Ser Gly Ser Phe Arg Thr Val Gly Phe Thr Thr Pro Phe Asn Phe Ser Asn Gly

TCC TCC GTC TTC ACG CTC TCC GCT CAC GTC TTC AAC TCC GGC AAC GAG GTG TAC ATC GAC     1800
       Ser Ser Val Phe Thr Leu Ser Ala His Val Phe Asn Ser Gly Asn Glu Val Tyr Ile Asp

CGC ATC GAG TTC GTC CCG GCC GAG GTC ACC TTC GAG CTC GAG TAG GTA                     1848
       Arg Ile Glu Phe Val Pro Ala Glu Val Thr Phe Glu Leu Glu AMB Val
```

FIG. 13B

HIGH LYSINE FERTILE TRANSGENIC CORN PLANTS

This is a division of U.S. Ser. No. 08/440,646, filed May 15, 1995, pending; which is a division of U.S. Ser. No. 08/112,245, filed on Aug. 25, 1993, pending, which is a continuation-in-part of U.S. Ser. No. 07/636,089, filed Dec. 28, 1990, abandoned, which is a continuation-in-part of U.S. Ser. No. 07/508,045, filed Apr. 11, 1990, now U.S. Pat. No. 5,484,956, which is a continuation-in-part of U.S. Ser. No. 07/467,983, filed on Jan. 22, 1990, abandoned. These applications are expressly incorporated by reference herein.

BACKGROUND OF THE INVENTION

1. Field of the Invention

The present invention relates to reproducible systems for genetically transforming monocotyledonous plants such as maize, to methods of selecting stable genetic transformants from suspensions of transformed cells, and to methods of producing fertile plants from the transformed cells. Exemplary transformation methods include the use of microprojectile bombardment to introduce nucleic acids into cells, and selectable and/or screenable marker systems, for example, genes which confer resistance (e.g., antibiotic, herbicide, etc.), or which contain an otherwise phenotypically observable or other detectable trait. In other aspects, the invention relates to the production of stably transformed and fertile monocot plants, gametes and offspring from the transgenic plants.

2. Description of the Related Art

Ever since the human species emerged from the hunting-gathering phase of its existence, and entered an agricultural phase, a major goal of human ingenuity and invention has been to improve crop yield and to alter and improve the characteristics of plants. In particular, man has sought to alter the characteristics of plants to make them more tasty and/or nutritious, to produce increased crop yield or render plants more adaptable to specific environments.

Up until recent times, crop and plant improvements depended on selective breeding of plants with desirable characteristics. Initial breeding success was probably accidental, resulting from observation of a plant with desirable characteristics, and use of that plant to propagate the next generation. However, because such plants had within them heterogenous genetic complements, it was unlikely that progeny identical to the parent(s) with the desirable traits would emerge. Nonetheless, advances in controlled breeding have resulted from both increasing knowledge of the mechanisms operative in hereditary transmission, and by empirical observations of results of making various parental plant crosses.

Recent advances in molecular biology have dramatically expanded man's ability to manipulate the germplasm of animals and plants. Genes controlling specific phenotypes, for example specific polypeptides that lend antibiotic or herbicide resistance, have been located within certain germplasm and isolated from it. Even more important has been the ability to take the genes which have been isolated from one organism and to introduce them into another organism. This transformation may be accomplished even where the recipient organism is from a different phylum, genus or species from that which donated the gene (heterologous transformation).

Attempts have been made to genetically engineer desired traits into plant genomes by introduction of exogenous genes using genetic engineering techniques. These techniques have been successfully applied in some plant systems, principally in dicotyledonous species. The uptake of new DNA by recipient plant cells has been accomplished by various means, including Agrobacterium infection (Nester et al., 1984), polyethylene glycol (PEG)-mediated DNA uptake (Lorz et al., 1985), electroporation of protoplasts (Fromm et al., 1986) and microprojectile bombardment (Klein et al., 1987). Unfortunately, the introduction of exogenous DNA into monocotyledonous species and subsequent regeneration of transformed plants has proven much more difficult than transformation and regeneration in dicotyledonous plants. Moreover, reports of methods for the transformation of monocotyledons such as maize, and subsequent production of fertile maize plants, have not been forthcoming. Consequently, success has not been achieved in this area and commercial implementation of transformation by production of fertile transgenic plants has not been achieved. This failure has been particularly unfortunate in the case of maize, where there is a particularly great need for methods for improving genetic characteristics.

Problems in the development of genetically transformed monocotyledonous species have arisen in a variety of general areas. For example, there is generally a lack of methods which allow one to introduce nucleic acids into cells and yet permit efficient cell culture and eventual regeneration of fertile plants. Only limited successes have been noted. In rice, for example, DNA transfer has only recently been reported using protoplast electroporation and subsequent regeneration of transgenic plants (Shimamoto et al., 1989). Furthermore, in maize, transformation using protoplast electroporation has also been reported (see, e.g., Fromm et al., 1986).

However, recovery of stably transformed plants has not been reproducible. A particularly serious failure is that the few transgenic plants produced in the case of maize have not been fertile (Rhodes et al., 1988). While regeneration of fertile corn plants from protoplasts has been reported (Prioli & Sondahl, 1989; Shillito et al., 1989), these reported methods have been limited to the use of non-transformed protoplasts. Moreover, regeneration of plants from protoplasts is a technique which carries its own set of significant drawbacks. Even with vigorous attempts to achieve fertile, transformed maize plants, reports of success in this regard have not been forthcoming.

A transformation technique that circumvents the need to use protoplasts is microprojectile bombardment. Although transient expression of a reporter gene was detected in bombardment tobacco pollen (Twell et al., 1989), stable transformation by microprojectile bombardment of pollen has not been reported for any plant species. Bombardment of soybean apical meristems with DNA-coated gold particles resulted in chimeric plants containing transgenic sectors. Progeny containing the introduced gene were obtained at a low frequency (McCabe et al., 1988). Bombardment of shoot meristems of immature maize embryos resulted in sectors of tissue expressing a visible marker, anthocyanin, the synthesis of which was triggered by the introduction of a regulatory gene (Tomes, 1990). An analysis of cell lineage patterns in maize (McDaniel & Poethig, 1988) suggests that germline transformation of maize by such an approach may be difficult.

A second major problem is achieving successful monocot transformation has results from the lack of efficient marker gene systems which have been employed to identify stably transformed cells. Marker gene systems are those which allow the selection of, and/or screening for, expression products of DNA. For use as assays for transformed cells, the selectable of screenable products should be those from genetic constructs introduced into the recipient cells. Hence, such marker genes can be used to identify stable transformants.

Of the more commonly used marker gene systems are gene systems which confer resistance to aminoglycosides such as kanamycin. While kanamycin resistance has been used successfully in both rice (Yang et al., 1988) and corn protoplast systems (Rhodes et al., 1988), it remains a very difficult selective agent to use in monocots due to high endogenous resistance (Hauptmann, et al., 1988). Many monocot species, maize, in particular, possess high endogenous levels of resistance to aminoglycosides. Consequently, this class of compounds cannot be used reproducibly to distinguish transformed from non-transformed tissue. New methods for reproducible selection of or screening for transformed plant cells are therefore needed.

Accordingly, it is clear that improved methods and/or approaches to the genetic transformation of monocotyledonous species would represent a great advance in the art. Furthermore, it would be of particular significance to provide novel approaches to monocot transformation, such as transformation of maize cells, which would allow for the production of stably transformed, fertile corn plants and progeny into which desired exogenous genes have been introduced. Furthermore, the identification of marker gene systems applicable to monocot systems such as maize would provide a useful means for applying such techniques generally. Thus, the development of these and other techniques for the preparation of stable genetically transformed monocots such as maize could potentially revolutionize approaches to monocot breeding.

SUMMARY OF THE INVENTION

The present invention addresses one or more of the foregoing or other shortcomings in the prior art by providing compositions and methods for the preparation of stably transformed, monocotyledonous cells and the subsequent regeneration of fertile, transgenic plants and progeny, particularly maize (*Zea mays*). The invention particularly provides techniques for the preparation of transgenic, fertile monocots, such as maize, which have been stably transformed through the introduction of discrete DNA sequences into the plant genome.

Thus, a preferred embodiment of the present invention is a fertile transgenic *Zea mays* plant of the R0 generation, the genome of which has been stably augmented by chromosomally integrated DNA, which encodes only one or more preselected proteins, RNA-transcripts or mixtures thereof, wherein said DNA is expressed so that the transgenic plant exhibits one or more phenotypic characteristics that render it identifiable over the corresponding untransformed *Zea mays* plant which does not comprise said DNA, and wherein the DNA is transmitted through a normal sexual cycle of the transgenic *Zea mays* plant to the R1 generation of plants.

For example, the DNA can be expressed so that the transgenic plant is resistant to an amount of an agent such as a herbicide, which would be toxic to a *Zea mays* plant which does not comprise said gene. The transgenic *Zea mays* plants of the present invention are also distinct from genetically altered or "improved" *Zea mays* plants which have been produced by prior art methods. For example, conventional maize breeding techniques randomly introduce large amounts of genetic material from both parents into the progeny plants. In contrast, the genome of the regenerant or R0 maize plant of the present invention has been augmented by "foreign" or "exogenous" plant or non-plant DNA which encodes one or more proteins, DNA transcripts or mixtures thereof that can be preselected by the art worker. Thus, the number sizes and/or the functional characteristics, if not the precise and preferably, the structures of both the introduced DNA and the products encoded thereby can be controlled, delimited and/or defined.

The *Zea mays* plants of the present invention are also necessarily distinct from *Zea mays* plants which comprise one or more "native" genes which have been altered or deleted by random in vivo mutation, as by chemical mutagens or by radiation.

The invention thus relates generally to methods for the production of transgenic plants. As used herein, the term "transgenic plants" is intended to refer to plants, the genome of which has been augmented by at least one incorporated DNA sequence. Such DNA sequences include but are not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to alter the expression thereof. It is contemplated that is some instances the genome of transgenic plants of the present invention will have been augmented through the stable introduction of the transgene. However, in other instances, the introduced gene will replace an endogenous sequence.

Exemplary genes which may be introduced include, for example, DNA sequences or genes from another species, or even genes or sequences which originate with or are present in the same species, but are incorporated into recipient cells by genetic engineering methods rather than classical reproduction or breeding techniques. However, the term "exogenous", is also intended to refer to DNA sequences or genes which are not normally present in the cell being transformed, or perhaps are simply not present in the form, structure, etc., as found in the transforming DNA segment or gene, or genes which are normally present yet which one desires to alter functionally, e.g., to have overexpressed. Thus, the term "exogenous" gene or DNA refers to any gene or DNA segment that is introduced into a recipient cell, regardless of whether a similar gene may already be present in such a cell. "Introduced", or "augmented" in this context, is known in the art to mean introduced or augmented by the hand of man.

The most preferred monocots for use in the present invention will be cereals such as maize (*Zea mays*). The present invention is exemplified through the use of A188× B73 cell lines, cell lines developed from other genotypes and immature embryos. However, it is to be understood that the invention is in no way limited to a particular genotype or cell line. To date, a variety of different *Zea mays* lines and germplasms have been tested for their ability to be successfully employed in the preparation of fertile, transgenic corn. The status of these studies is set forth in some detail hereinbelow. Generally speaking, these studies have demonstrated that 24 out of 36 maize cultures were transformable. Of those cell lines tested, 11 out of 20 have produced fertile plants.

One exemplary embodiment for generating a stably transformed monocot includes culturing recipient corn cells in suspension cultures using embryogenic cells in Type II callus, selecting for small (10–30μ) isodiametric, cytoplasmically dense cells, introducing a desired DNA segment into these cells, growing the transformed cells in or on culture medium containing hormones, subculturing into a progression of media to facilitate development of shoots and roots, and finally, hardening the transgenic plant and readying it metabolically for growth in soil.

The present invention is suitable for use in transforming any maize variety. While not all cell lines developed out of a particular variety or cross will necessarily show the same degree of stable transformability, it has been the inventors' finding that a reasonable percentage of cell lines developed from essentially every genotype tested to date can be developed into fertile, transgenic plants. Thus, where one desires to prepare transformants in a particular cross or variety, it will generally be desirable to develop several cell lines from the particular cross or variety (e.g., 8 to 10), and subject all of the lines so developed to the transformation protocols hereof.

Another exemplary embodiment for generating a stably transformed monocot includes introducing a desired DNA segment into cells of organized tissues such as immature embryos, growing the embryos on a culture medium, subculturing into a progression of media to facilitate development of shoots and roots, and finally, hardening the transgenic plant and readying it metabolically for growth in soil. In this embodiment, the invention is capable of transforming any variety of maize. Through the use of the present invention it is possible to simultaneously deliver DNA segments to a large number of embryos. It has been the inventor's finding that a percentage of the embryos that are contacted by exogenous DNA will develop into fertile transgenic plants, similar to delivering DNA to a large population of cultured cells. The present invention is exemplified through the use of immature embryos from the genotypes H99 and Hi-II, but is in no way limited to these genotypes. To date only experiments with these genotypes have progressed to the point where one would reasonably expect to recover transformants. Generally speaking one would expect to be able to recover fertile transgenic plants from variety of maize.

Moreover, the ability to provide even a single fertile, transgenic corn line would be generally sufficient to allow the introduction of the transgenic component (e.g., recombinant DNA) of that line into a second corn line of choice. This is because by providing fertile, transgenic offspring, the practice of the invention allows one to subsequently, through a series of breeding manipulations, move a selected gene from one corn line into an entirely different corn line. For example, studies have been conducted wherein the gene for resistance to the herbicide Basta®, bar, has been moved from two transformants derived from cell line SC716 and one transformant derived from cell line SC82 into 18 elite inbred line by backcrossing. It is possible with these inbreds to produce a large number of hybrids. Eleven such hybrids have been made and are in field tests.

I. Recipient Cells

Practicing the present invention includes the generation and use of recipient cells. As used herein, the term "recipient cells" refers to monocot cells that are receptive to transformation and subsequent regeneration into stably transformed, fertile monocot plants.

A. Sources of Cells

Recipient cell targets include, but are not limited to, meristem cells, Type I, Type II, and Type III callus, immature embryos and gametic cells such as microspores pollen, sperm and egg cells. Type I, Type II, and Type III callus may be initiated from tissue sources including, but not limited to, immature embryos, seedling apical meristems, microspores and the such. Those cells which are capable of proliferating as callus are also recipient cells for genetic transformation. The present invention provides techniques for transforming immature embryos followed by initiation of callus and subsequent regeneration of fertile transgenic plants. Direct transformation of immature embryos obviates the need for long term development of recipient cell cultures. Pollen, as well as its precursor cells, microspores, may be capable of functioning as recipient cells for genetic transformation, or as vectors to carry foreign DNA for incorporation during fertilization. Direct pollen transformation would obviate the need for cell culture. Meristematic cells (i.e., plant cells capable of continual cell division and characterized by an undifferentiated cytological appearance, normally found at growing points or tissues in plants such as root tips, stem apices, lateral buds, etc.) may represent another type of recipient plant cell. Because of their undifferentiated growth and capacity for organ differentiation and totipotency, a single transformed meristematic cell could be recovered as a whole transformed plant. In fact, it is proposed that embryogenic suspension cultures may be an in vitro meristematic cell system, retaining an ability for continued cell division in an undifferentiated state, controlled by the media environment.

In certain embodiments, cultures plant cells that can serve as recipient cells for transforming with desired DNA segments include corn cells, and more specifically, cells from *Zea mays* L. Somatic cells are of various types. Embryogenic cells are one example of somatic cells which may be induced to regenerate a plant through embryo formation. Non-embryogenic cells are those which will typically not respond in such a fashion. An example of non-embryogenic cells are certain Black Mexican Sweet (BMS) corn cells. These cells have been transformed by microprojectile bombardment using the neo gene followed by selection with the aminoglycoside, kanamycin (Klein et al., 1989). However, this BMS culture was not found to be regenerable.

The development of embryogenic maize calli and suspension cultures useful in the context of the present invention, e.g., as recipient cells for transformation, has been described in U.S. Ser. No. 06/877,033, filed Jun. 7, 1986, incorporated herein by reference.

The present invention also provides certain techniques that may enrich recipient cells within a cell population. For example, Type II callus development, followed by manual selection and culture of friable, embryogenic tissue, generally results in an enrichment of recipient cells for use in, e.g., micro-projectile transformation. Suspension culturing, particularly using the media disclosed herein, may also improve the ratio of recipient to non-recipient cells in any given population. Manual selection techniques which employed to select recipient cells may include, e.g., assessing cell morphology and differentiation, or may use various physical or biological means. Cryopreservation is also contemplated as a possible method of selecting for recipient cells.

Manual selection of recipient cells, e.g., by selecting embryogenic cells from the surface of a Type II callus, is one means employed by the inventors in an attempt to enrich for recipient cells prior to culturing (whether cultured on solid media or in suspension). The preferred cells may be those located at the surface of a cell cluster, and may further be identifiable by their lack of differentiation, their size and dense cytoplasm. The preferred cells will generally be those cells which are less differentiated, or not yet committed to differentiation. Thus, one may wish to identify and select those cells which are cytoplasmically dense, relatively unvacuolated with a high nucleus to cytoplasm ratio (e.g., determined by cytological observations), small in size (e.g., 10–20 μm), and capable of sustained divisions and somatic proembryo formation.

It is proposed that other means for identifying such cells may also be employed. For example, through the use of dyes, such as Evan's blue, which are excluded by cells with relatively non-permeable membranes, such as embryogenic cells, and taken up by relatively differentiated cells such as root-like cells and snake cells (so-called due to their snake-like appearance).

Other possible means of identifying recipient cells include the use of isozyme markers of embryogenic cells, such as glutamate dehydrogenase, which can be detected by cytochemical stains (Fransz et al., 1989). However, it is cautioned that the use of isozyme markers such as glutamate dehydrogenase may lead to some degree of false positives from non-embryogenic cells such as rooty cells which nonetheless have a relatively high metabolic activity.

B. Media

In certain embodiments, recipient cells are selected following growth in culture. Where employed, cultured cells will preferably be grown either on solid supports or in the form of liquid suspensions. In either instance, nutrients may be provided to the cells in the form of media, and environmental conditions controlled. There are many types of tissue culture media comprised of amino acids, salts, sugars, growth regulators and vitamins. Most of the media employed in the practice of the invention will have some similar components (see, e.g., Table 1 herein below), the media differ in the composition and proportions of their ingredients depending on the particular application envisioned. For example, various cell types usually grow in more than one type of media, but will exhibit different growth rates and different morphologies, depending on the growth media. In some media, cells survive but do not divide.

Various types of media suitable for culture of plant cells have been previously described. Examples of these media include, but are not limited to, the N6 medium described by Chu et al., (1975) and MS media (Murashige & Skoog, 1962). The inventors have discovered that media such as MS which have a high ammonia/nitrate ratio are counterproductive to the generation of recipient cells in that they promote loss of morphogenic capacity. N6 media, on the other hand, has a somewhat lower ammonia/nitrate ratio, and is contemplated to promote the generation of recipient cells by maintaining cells in a proembryonic state capable of sustained divisions.

C. Cell Cultures

1. Initiation

In the practice of the invention it is sometimes, but not always, necessary to develop cultures which contain recipient cells. Suitable cultures can be initiated from a number of whole plant tissue explants including, but not limited to, immature embryos, leaf bases, immature tassels, anthers, microspores, and other tissues containing cells capable of in vitro proliferation and regeneration of fertile plants. In one exemplary embodiment, recipient cell cultures are initiated from immature embryos of *Zea mays* L. by growing excised immature embryos on a solid culture medium containing growth regulators including, but not limited to, dicamba., 2,4-D, NAA, and IAA. In some instances it will be preferred to add silver nitrate to culture medium for callus initiation as this compound has been reported to enhance culture initiation (Vain et al., 1989). Embryos will produce callus that varies greatly in morphology including from highly unorganized cultures containing very early embryogenic structures (such as, but not limited to, type II cultures in maize), to highly organized cultures containing large late embryogenic structures (such as, but not limited to, type I cultures in maize). This variation in culture morphology may be related to genotype, culture medium composition, size of the initial embryos and other factors. Each of these types of culture morphologies is a source of recipient cells.

The development of suspension cultures capable of plant regeneration may be used in the context of the present invention. Suspension cultures may be initiated by transferring callus tissue to liquid culture medium containing growth regulators. Addition of coconut water or other substances to suspension culture medium may enhance growth and culture morphology, but the utility of suspension cultures is not limited to those containing these compounds. In some embodiments of this invention, the use of suspension cultures will be preferred as these cultures grow more rapidly and are more easily manipulated than callus cells growing on solid culture medium.

When immature embryos or other tissues directly removed from a whole plant are used as the target tissue for DNA delivery, it will only be necessary to initiate cultures of cells insofar as is necessary for identification and isolation of transformants. In an illustrative embodiment, DNA is introduced by particle bombardment into immature embryos following their excision from the plant. Embryos are transferred to a culture medium that will support proliferation of tissues and allow for selection of transformed sectors, 0–14 days following DNA delivery. In this embodiment of the invention it is not necessary to establish stable callus cultures capable of long term maintenance and plant regeneration.

2. Maintenance

The method of maintenance of cell cultures may contribute to their utility as sources of recipient cells for transformation. Manual selection of cells for transfer to fresh culture medium, frequency of transfer to fresh culture medium, composition of culture medium, and environment factors including, but not limited to, light quality and quantity and temperature are all important factors in maintaining callus and/or suspension cultures that are useful as sources of recipient cells. It is contemplated that alternating callus between different culture conditions may be beneficial in enriching for recipient cells within a culture. For example, it is proposed that cells may be cultured in suspension culture, but transferred to solid medium at regular intervals. After a period of growth on solid medium cells can be manually selected for return to liquid culture medium. It is proposed that by repeating this sequence of transfers to fresh culture medium it is possible to enrich for recipient cells. It is also contemplated that passing cell cultures through a 1.9 mm sieve is useful in maintaining the friability of a callus or suspension culture and may be beneficial is enriching for transformable cells.

3. Cryopreservation

Additionally, the inventors propose that cryopreservation may effect the development of, or perhaps select for, recipient cells. Cryopreservation selection may operate due to a selection against highly vacuolated, non-embryogenic cells, which may be selectively killed during cryopreservation. The inventors propose that there is a temporal window in which cultured cells retain their regenerative ability, thus, it is believed that they must be preserved at or before that temporal period if they are to be used for future transformation and regeneration.

For use in transformation, suspension or callus culture cells may be cryopreserved and stored for periods of time, thawed, then used as recipient cells for transformation. An illustrative embodiment of cryopreservation methods comprises the steps of slowly adding cryoprotectants to suspension cultures to give a final concentration of 10% dimethyl sulfoxide, 10% polyethylene glycol (6000 MW), 0.23M proline and 0.23M glucose. The mixture is then cooled to −35° C. at 0.5° C. per minute. After an isothermal period of 45 minutes, samples are placed in liquid $N_2$ (modification of methods of Withers and King (1979); and Finkle et al. (1985)). To reinitiate suspension cultures from cryopreserved material, cells may be thawed rapidly and pipetted onto feeder plates similar to those described by Rhodes et al. (Vaeck et al., 1987).

II. DNA Sequences

Virtually any DNA composition may be used for delivery to recipient monocotyledonous cells to ultimately produce fertile transgenic plants in accordance with the present invention. For example, DNA segments in the form of vectors and plasmids, or linear DNA fragments, in some instances containing only the DNA element to be expressed in the plant, and the like, may be employed.

In certain embodiments, it is contemplated that one may wish to employ replication-competent viral vectors in monocot transformation. Such vectors include, for example, wheat dwarf virus (WDV) "shuttle" vectors, such as pW1-11 and PW1-GUS (Ugaki et al., 1991). These vectors are capable of autonomous replication in maize cells as well as E. coli, and as such may provide increased sensitivity for detecting DNA delivered to transgenic cells. A replicating vector may also be useful for delivery of genes flanked by DNA sequences from transposable elements such as Ac, Ds, or Mu. It has been proposed (Laufs et al., 1990) that transposition of these elements within the maize genome requires DNA replication. It is also contemplated that transposable elements would be useful for introducing DNA fragments lacking elements necessary for selection and maintenance of the plasmid vector in bacteria, e.g., antibiotic resistance genes and origins of DNA replication.

It is also proposed that use of a transposable element such as Ac, Ds, or Mu would actively promote integration of the desired DNA and hence increase the frequency of stably transformed cells.

Vectors, plasmids, cosmids, YACs (yeast artificial chromosomes) and DNA segments for use in transforming such cells will, of course, generally comprise the cDNA, gene or genes which one desires to introduce into the cells. These DNA constructs can further include structures such as promoters, enhancers, polylinkers, or even regulatory genes as desired. The DNA segment or gene chosen for cellular introduction will often encode a protein which will be expressed in the resultant recombinant cells, such as will result in a screenable or selectable trait and/or which will impart an improved phenotype to the regenerated plant. However, this may not always be the case, and the present invention also encompasses transgenic plants incorporating non-expressed transgenes.

DNA useful for introduction into Zea mays cells includes that which has been derived or isolated from any source, that may be subsequently characterized as to structure, size and/or function, chemically altered, and later introduced into Zea mays. An example of DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology by genetic engineering. Such DNA is commonly referred to as "recombinant DNA."

Therefore useful DNA includes completely synthetic DNA, semi-synthetic DNA, DNA isolated from biological sources, and DNA derived from introduced RNA. Generally, the introduced DNA is not originally resident in the Zea mays genotype which is the recipient of the DNA, but it is within the scope of the invention to isolate a gene from a given Zea mays genotype, and to subsequently introduce multiple copies of the gene into the same genotype, e.g., to enhance production of a given gene product such as a storage protein.

The introduced DNA includes but is not limited to, DNA from plant genes, and non-plant genes such as those from bacteria, yeasts, animals or viruses; modified genes, portions of genes, chimeric genes, including genes from the same or different Zea mays genotype.

The introduced DNA used for transformation herein may be circular or linear, double-stranded or single-stranded. Generally, the DNA is in the form of chimeric DNA, such as plasmid DNA, that can also contain coding regions flanked by regulatory sequences which promote the expression of the recombinant DNA present in the resultant corn plant. For example, the DNA may itself comprise or consist of a promoter that is active in Zea mays, or may utilize a promoter already present in the Zea mays genotype that is the transformation target. Generally, the introduced DNA will be relatively small, i.e., less than about 30 kb to minimize any susceptibility to physical, chemical, or enzymatic degradation which is known to increase as the size of the DNA increases. As note above, the number of proteins, RNA transcripts or mixtures thereof which is introduced into the Zea mays genome is preferably preselected and defined, e.g., from one to about 5–10 such products of the introduced DNA may be formed.

A. Regulatory Elements

The construction of vectors which may be employed in conjunction with the present invention will be known to those of skill of the art in light of the present disclosure (see e.g., Sambrook et al., 1989; Gelvin et al., 1990). Preferred constructs will generally include a plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang & Russell, 1990), α-tubulin, actin (Wang et al., 1992), cab (Sullivan et al., 1989), PEPCase (Hudspeth & Grula, 1989) or those associated with the R gene complex (Chandler et al., 1989). Tissue specific promoters such as root cell promoters (Conkling et al., 1990) and tissue specific enhancers (Fromm et al., 1989) are also contemplaetd to be particularly useful, as are inducible promoters such as ABA- and turgor-inducible promoters.

Constructs will also include the gene of interest along with a 3' end DNA sequence that acts as a signal to terminate transcription and allow for the poly-adenylation of the resultant mRNA. The most preferred 3' elements are contemplated to be those from the nopaline synthase gene of Agrobacterium tumefasciens (Bevan et al., 1983), the terminator for the T7 transcript from the octopine synthase gene of Agrobacterium tumefasciens, and the 3' end of the protease inhibitor I or II genes from potato or tomato. Regulatory elements such as Adh intron 1 (Callis et al., 1987), sucrose synthase intron (Vasil et al., 1989) or TMV omega elements (Gallie, et al., 1989), may further be included where desired.

As the DNA sequence between the transcription initiation site and the start of the coding sequence, i.e., the untranslated leader sequence, can influence gene expression, one may also wish to employ a particular leader sequence. Preferred leader sequences are contemplated to include those which include sequences predicted to direct optimum expression of the attached gene, i.e. to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants, and in maize in particular, will be most preferred.

It is contemplated that vectors for use in accordance with the present invention may be constructed to include the ocs enhancer element. This element was first identified as a 16 bp palindromic enhancer from the octopine synthase (ocs) gene of agrobacterium (Ellis et al., 1987), and is present in at least 10 other promoters (Bouchez et al., 1989). It is proposed that the use of an enhancer element, such as the ocs element and particularly multiple copies of the element, will act to increase the level of transcription from adjacent promoters when applied in the context of monocot transformation.

Ultimately, the most desirable DNA segments for introduction into a monocot genome may be homologous genes or gene families which encode a desired trait (e.g., increased yield per acre) and which are introduced under the control of novel promoters or enhancers, etc., or perhaps even homologous or tissue specific (e.g., root-, collar/sheath-, whorl-, stalk-, earshank-, kernel- or leaf-specific) promoters or control elements. Indeed, it is envisioned that a particular use of the present invention will be the targeting of a gene in a tissue-specific manner. For example, insect resistant genes may be expressed specifically in the whorl and collar/sheath tissue which are targets for the first and second broods, respectively, of ECB. Likewise, genes encoding proteins with particular activity against rootworm may be targeted directly to root tissues.

Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, an α-tubulin gene that directs expression in roots and promoters derived from zein storage protein genes which direct expression in endosperm. It is particularly contemplated that one may advantageously use the 16 bp ocs enhancer element from the octopine synthase (ocs) gene (Ellis et al., 1987; Bonchez et al., 1989), especially when present in multiple copies, to achieve enhanced expression in roots.

It is also contemplated that tissue specific expression may be functionally accomplished by introducing a constitutively expressed gene (all tissues) in combination with an antisense gene that is expressed only in those tissues where the gene product is not desired. For example, a gene coding for the crystal toxic protein from *B. thuringiensis* (Bt) may be introduced such that it is expressed in all tissues using the 35S promoter from Cauliflower Mosaic Virus. Expression of an antisense transcript of the Bt gene in a maize kernel, using for example a zein promoter, would prevent accumulation of the Bt protein in seed. Hence the protein encoded by the introduced gene would be present in all tissues except the kernel.

Alternatively, one may wish to obtain novel tissue-specific promoter sequences for use in accordance with the present invention. To achieve this, one may first isolate cDNA clones from the tissue concerned and identify those clones which are expressed specifically in that tissue, for example, using Northern blotting. Ideally, one would like to identify a gene that is not present in a high copy number, but which gene product is relatively abundant in specific tissues. The promoter and control elements of corresponding genomic clones may then be localized using the techniques of molecular biology known to those of skill in the art.

It is contemplated that expression of some genes in transgenic plants will be desired only under specified conditions. For example, it is proposed that expression of certain genes that confer resistance to environmental stress factors such as drought will be desired only under actual stress conditions. It is contemplated that expression of such genes throughout a plants development may have detrimental effects. It is known that a large number of genes exist that respond to the environment. For example, expression of some genes such as rbcS, encoding the small subunit of ribulose bisphosphate carboxylase, is regulated by light as mediated through phytochrome. Other genes are induced by secondary stimuli. For example, synthesis of abscisic acid (ABA) is induced by certain environmental factors, including but not limited to water stress. A number of genes have been shown to be induced by ABA (Skriver and Mundy, 1990). It is also anticipated that expression of genes conferring resistance to insect predation would be desired only under conditions of actual insect infestation. Therefore, for some desired traits inducible expression of genes in transgenic plants will be desired.

It is proposed that in some embodiments of the present invention expression of a gene in a transgenic plant will be desired only in a certain time period during the development of the plant. Development timing is frequently correlated with tissue specific gene expression. For example, expression of zein storage proteins is initiated in the encosperm about 15 days after pollination.

Additionally, vectors may be constructed and employed in the intracellular targeting of a specific gene product within the cells of a transgenic plant or in directing a protein to the extracellular environment. This will generally be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane.

A particular example of such a use concerns the direction of a herbicide resistance gene, such as the EPSPS gene, to a particular organelle such as the chloroplast rather than to the cytoplasm. This is exemplified by the use of the rbcS transit peptide which confers plastid-specific targeting of proteins. In addition, it is proposed that it may be desirable to target certain genes responsible for male sterility to the mitochondria, or to target certain genes for resistance to phytopathogenic organisms to the extracellular spaces, or to target proteins to the vacuole.

It is also contemplated that it may be useful to target DNA itself within a cell. For example, it may be useful to target introduced DNA to the nucleus as this may increase the frequency of transformation. Within the nucleus itself it would be useful to target a gene in order to achieve site specific integration. For example, it would be useful to have a gene introduced through transformation replace an existing gene in the cell.

B. Marker Genes

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an apitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). The use of the maize HPRG (Steifel et al., 1990) which is preferred as this molecule is well characterized in terms of molecular biology, expression and protein structure. However, any one of a variety of extensins and/or glycine-rich wall proteins (Keller et al., 1989) could be modified by the addition of an antigenic site to create a screenable marker.

One exemplary embodiment of a secretable screenable marker concerns the use of the maize genomic clone encoding the wall protein HPRG, modified to include the unique 15 residue epitope M A T V P E L N C E M P P S D (seq id no:1) from the pro-region of murine interleukin-1-β (IL-1-β). However, virtually any detectable epitope may be employed in such embodiments, as selected from the extremely wide variety of antigen:antibody combinations known to those of skill in the art. The unique extracellular epitope, whether derived from IL-1-β or any other protein or epitopic substance, can then be straightforwardly detected using antibody labeling in conjunction with chromogenic or fluorescent adjuncts.

Elements of the present disclosure are exemplified in detail through the use of the *bar* and/or GUS genes, and also through the use of various other markers. Of course, in light of this disclosure, numerous other possible selectable and/or screenable marker genes will be apparent to those of skill in the art in addition to the one set forth hereinbelow. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed monocot.

1. Selectable Markers

Possible selectable markers for use in connection with the present invention include, but are not limited to, a neo gene (Potrykus et al., 1985) which codes for kanamycin resistance and can be selected for using kanamycin, G418, etc.; a *bar* gene which codes for bialaphos resistance; a mutant aroA gene which encodes an altered EPSP synthase protein (Hinchee et al., 1988) thus conferring glyphosate resistance; a nitrilase gene such as bxn from *Klebsiella ozaenae* which confers resistance to bromoxynil (Stalker et al., 1988); a mutant acetolactate synthase gene (ALS) which confers resistance to imidaazodinone, sulfonylurea or other ALS inhibiting chemicals (European Patent Application 154,204, 1985); a methotrexate resistant DHFR gene (Thillet et al., 1988), or a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0,218,571, 1987).

An illustrative embodiment of a selectable marker gene capable of being used in systems to select transformants is the genes that encode the enzyme phosphinothricin acetyltransferase, such as the *bar* gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death. The success of the inventors in using this selective system in conjunction with monocots was particularly surprising because of the major difficulties which have been reported in transformation of cereals (Potrykus, 1989).

Where one desires to employ a bialaphos resistance gene in the practice of the invention, the inventors have discovered that a particularly useful gene for this purpose is the *bar* or pat genes obtainable from species of Streptomyces (e.g., ATCC No. 21,705). The cloning of the *bar* gene has been described (Murakami et al., 1986; Thompson et al., 1987) as has the use of the *bar* gene in the context of plants other than monocots (De Block et al., 1987; De Block et al., 1989).

2. Screenable Markers

Screenable markers that may be employed include a β-glucuronidase or uidA gene (GUS) which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; or even an aequorin gene (Prasher et al., 1985) which may be employed in calcium-sensitive bioluminescence detection.

Genes from the maize R gene complex are contemplated to be particularly useful as screenable markers. The R gene complex in maize encodes a protein that acts to regulate the production of anthocyanin pigments in most seed and plant tissue. Maize strains can have one, or as many as four, R alleles which combine to regulate pigmentation in a developmental and tissue specific manner. The present inventors have applied a gene from the R gene complex to maize transformation, because the expression of this gene in transformed cells does not harm the cells. Thus, an R gene introduced into such cells will cause the expression of a red pigment and, if stably incorporated, can be visually scored as a red sector. If a maize line is carries dominant allelles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together.

The inventors further propose that R gene regulatory regions may be employed in chimeric constricts in order to provide mechanisms for controlling the expression of chimeric genes. More diversity of phenotypic expression is known at the R locus than at any other locus (Coe et al., 1988). It is contemplated that regulatory regions obtained from regions 5' to the structural R gene would be valuable in directing the expression of genes for, e.g., insect resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bo13). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening.

C. Transgenes for Corn Modification

A particularly important advance of the present invention is that it provides methods and compositions for the transformation of plant cells with genes in addition to, or other than, marker genes. Such transgenes will often be genes that direct the expression of a particular protein or polypeptide product, but they may also be non-expressible DNA segments, e.g., transposons such as Ds that do no direct their own transposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The invention also contemplates that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

The choice of the particular DNA segments to be delivered to the recipient cells will often depend on the purpose of the transformation. One of the major purposes of transformation of crop plants is to add some commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; drydown; standability; prolificacy; starch properties; oil quantity and quality; and the like. One may desire to incorporate one or more genes conferring any such desirable trait or traits, such as, for example, a gene or genes encoding herbicide resistance.

In certain embodiments, the present invention contemplates the transformation of a recipient cell with more than one advantageous transgene. Two or more transgenes can be supplied in a single transformation event using either distinct transgene-encoding vectors, or using a single vector incorporating two or more gene coding sequences. For example, plasmids bearing the bar and aroA expression units in either convergent, divergent, or colinear orientation, are considered to be particularly useful. Further preferred combinations are those of an insect resistance gene, such as a Bt gene, along with a protease inhibitor gene such as pinII, or the use of bar in combination with either of the above genes. Of course, any two or more transgenes of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired.

1. Herbicide Resistance

The genes encoding phosphinothricin acetyltransferase (bar and pat), glyphosate tolerant EPSP synthase genes, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicides resistant genes for use in transformation. The bar and pat genes code for an enzyme, phosphinothricin acetyltransferase (PAT), which inactivates the herbicide phosphinothricin and prevents this compound from inhibiting glutamine synthetase enzymes. The enzyme 5-enolpyruvylshikimate 3-phosphate synthase (EPSP Synthase), is normally inhibited by the herbicide N-(phosphonomethyl)glycine (glyphosate). However, genes are known that encode glyphosate-resistant EPSP Synthase enzymes. These genes are particularly contemplated for use in monocot transformation. The deh gene encodes the enzyme dalapon dehalogenase and confers resistance to the herbicide dalapon. The bxn gene codes for a specific nitrilase enzyme that converts bromoxynil to a non-herbicidal degradation product.

2. Insect Resistance

An important aspect of the present invention concerns the introduction of insect resistance-conferring genes into monocotyledonous plants such as maize. Potential insect resistance genes which can be introduced include *Bacillus thuringiensis* crystal toxin genes or Bt genes (Watrud et al., 1985). Bt genes may provide resistance to lepidopteran or coleopteran pests such as European Corn Borer (ECB). Preferred Bt toxin genes for use in such embodiments include the CryIA(b) and CryIA(c) genes. Endotoxin genes from other species of *B. thuringiensis* which affect insect growth or development may also be employed in this regard.

The poor expression of procaryotic Bt toxin genes in plants is a well-documented phenomenon, and the use of different promoters, fusion proteins, and leader sequences has not led to significant increases in Bt protein expression (Vaeck et al., 1989; Barton et al., 1987). It is therefore contemplated that the most advantageous Bt genes for use in the transformation protocols disclosed herein will be those in which the coding sequence has been modified to effect increased expression in plants, and more particularly, those in which maize preferred codons have been used. Examples of such modified Bt toxin genes include the variant Bt CryIA(b) gene termed IAb6 (Perlak et al., 1991) and the synthetic CryIA(c) genes termed 1800*a* and 1800*b*.

Protease inhibitors may also provide insect resistance (Johnson et al., 1989), and will thus have utility in maize transformation. The use of a protease inhibitor II gene, pinII, from tomato or potato is envisioned to be particularly useful. Even more advantageous is the use of a pinII gene in combination with a Bt toxin gene, the combined effect of which has been discovered by the present inventors to produce synergistic insecticidal activity. Other genes which encode inhibitors of the insects' digestive system, or those that encode enzymes or co-factors that facilitate the production of inhibitors, may also be useful. This group may be exemplified by oryzacystatin and amylase inhibitors such as those from wheat and barley.

Also, genes encoding lectins may confer additional or alternative insecticide properties. Lectins (originally termed phytohemagglutinins) are multivalent carbohydrate-binding proteins which have the ability to agglutinate red blood cells from a range of species. Lectins have been identified recently as insecticidal agents with activity against weevils, ECB and rootworm (Murdock et al., 1990; Czapla & Lang, 1990). Lectin genes contemplated to be useful include, for example, barley and wheat germ agglutinin (WGA) and rice lectins (Gatehouse et al., 1984), with WGA being preferred.

Genes controling the production of large or small polypeptides active against insects when introduced into the insect pests, such as, e.g., lytic peptides, peptide hormones and toxins and venoms, form another aspect of the invention. For example, it is contemplated that the expression of juvenile hormone esterase, directed towards specific insect pests, may also result in insecticidal activity, or perhaps cause cessation of metamorphosis (Hammock et al., 1990).

Transgenic maize expressing genes which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant maize plants. Genes that code for activities that affect insect molting, such those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests are also encompassed by the present invention. It may be possible, for instance, to confer insecticidal activity on a plant by altering its sterol composition. Sterols are obtained by insects from their diet and are used for hormone syntheses and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occuring plant enzymes that have been shown to exhibit anti-nutritional effects on insects and to reduce the nutritional quality of their diet. Therefore, further embodiments of the invention concern transgeneic plants with enhanced lipoxygenase activity which may be resistant to insect feeding.

The present invention also provides methods and compositions by which to achieve qualitative or quantitative changes in plant secondary metabolites. One example concerns transforming maize to produce DIMBOA which, it is contemplated, will confer resistance to European corn borer, rootworm and several other maize insect pests. Candidate genes that are particularly considered for use in this regard include those genes at the bx locus known to be involved in the synthetic DIMBOA pathway (Dunn et al., 1981). The introduction of genes that can regulate the production of maysin, and genes involved in the production of dhurrin in sorghum, is also contemplated to be of use in facilitating resistance to earworm and rootworm, respectively.

*Tripsacum dactyloides* is a species of grass that is resistant to certain insects, including corn root worm. It is anticipated that genes encoding proteins that are toxic to insects or are involved in the biosynthesis of compounds toxic to insects will be isolated from Tripsacum and that these novel genes will be useful in conferring resistance to insects. It is known that the basis of insect resistance in Tripsacum is genetic, because said resistance has been transferred to *Zea mays* via sexual crosses (Branson and Guss, 1972).

Further genes encoding proteins characterized as having potential insecticidal activity may also be used as transgenes in accordance herewith. Such genes include, for example, the cowpea trypsin inhibitor (CpTI; Hilder et al., 1987) which may be used as a rootworm deterrent; genes encoding avermectin (Avermectin and Abamectin., Campbell, W. C., Ed., 1989; Ikeda et al., 1987) which may prove particularly useful as a corn rootworm deterrent; ribosome inactivating protein genes; and even genes that regulate plant structures. Transgenic maize including anti-insect antibody genes and genes that code for enzymes that can covert a non-toxic insecticide (pro-insecticide) applied to the outside of the plant into an insecticide inside the plant are also contemplated.

3. Environment or Stress Resistance

Improvement of corn's ability to tolerate various environmental stresses such as, but not limited to, drought, excess moisture, chilling, freezing, high temperature, salt, and oxidative stress, can also be effected through expression of novel genes. It is proposed that benefits may be realized in terms of increased resistance to freezing temperatures through the introduction of an "antifreeze" protein such as that of the Winter Flounder (Cutler et al., 1989) or synthetic gene derivatives thereof. Improved chilling tolerance may also be conferred through increased expression of glycerol-3-phosphate acetyltransferase in chloroplasts (Murata et al., 1992; Wolter et al., 1992). Resistance to oxidative stress (often exacerbated by conditions such as chilling temperatures in combination with high light intensities) can be conferred by expression of superoxide dismutase (Gupta et al., 1993), and may be improved by glutathione reductase (Bowler et al., 1992). Such strategies may allow for tolerance to freezing in newly emerged fields as well as extending later maturity higher yielding varieties to earlier relative maturity zones.

It is contemplated that the expression of novel genes that favorably effect plant water content, total water potential, osmotic potential, and turgor will enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments. In this aspect of the invention it is proposed, for example, that the expression of genes encoding for the biosynthesis of osmotically-active solutes may impart protection against drought. Within this class are genes encoding for mannitol dehydrogenase (Lee and Saier, 1982) and trehalose-6-phosphate synthase (Kaasen et al., 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski et al., 1992, 1993).

Similarly, the efficacy of other metabolites in protecting either enzyme function (e.g. alanopine or propionic acid) or membrane integrity (e.g., alanopine) has been documented (Loomis et al., 1989), and therefore expression of genes encoding for the biosynthesis of these compounds might confer drought resistance in a manner similar to or complimentary to mannitol. Other examples of naturally occurring metabolites that are osmotically active and/or provide some direct protective effect during drought and/or desiccation include fructose, erythritol (Coxson et al., 1992), sorbitol, dulcitol (Karsten et al., 1992), glucosylglycerol (Reed et al., 1984; Erdmann et al., 1992), sucrose, stachyose (Koster and Leopold, 1988; Blackman et al., 1992), raffinose (Bernal-Lugo and Leopold, 1992), proline (Rensburg et al., 1993) and glycinebetaine (Wyn-Jones and Storey, 1982), ononitol and pinitol (Vernon and Bohnert, 1992). Continued canopy growth and increased reproductive fitness during times of stress will be augmented by introduction and expression of genes such as those controlling the osmotically active compounds discussed above and other such compounds, as represented in one exemplary embodiment by the enzyme myoinositol 0-methyltransferase.

It is contemplated that the expression of specific proteins may also increase drought tolerance. Three classes of Late Embryogenic Proteins have been assigned based on structural similarities (see Dure et al., 1989). All three classes of LEAs have been demonstrated in maturing (i.e. desiccating) seeds. Within these 3 types of LEA proteins, the Type-II (dehydrin-type) have generally been implicated in drought and/or desiccation tolerance in vegetative plant parts (i.e. Mundy and Chua, 1988; Piatkowski et al., 1990; Yamaguchi-Shinozaki et al., 1992). Recently, expression of a Type-III LEA (HVA-1) in tobacco was found to influence plant height, maturity and drought tolerance (Fitzpatrick, 1993). Expression of structural genes from all three LEA groups may therefore confer drought tolerance. Other types of proteins induced during water stress include thiol proteases, aldolases and transmembrane transporters (Guerrero et al., 1990), which may confer various protective and/or repair-type functions during drought stress. It is also contemplated that genes that effect lipid biosynthesis and hence membrane composition might also be useful in conferring drought resistance on the plant.

Many of these genes for improving drought resistance have complementary modes of action. Thus, it is envisaged that combinations of these genes might have additive and/or synergistic effects in improving drought resistance in corn. Many of these genes also improve freezing tolerance (or resistance); the physical stresses incurred during freezing and drought are similar in nature and may be mitigated in similar fashion. Benefit may be conferred via constitutive expression of these genes, but the preferred means of expressing these novel genes may be through the use of a turgor-induced promoter (such as the promoters for the turgor-induced genes described in Guerrero et al., 1987 and Shagen et al., 1993 which are incorporated herein by reference). Spatial and temporal expression patterns of these genes may enable corn to better withstand stress.

It is proposed that expression of genes that are involved with specific morphological traits that allow for increased water extractions from drying soil would be of benefit. For example, introduction and expression of genes that alter root characteristics may enhance water uptake. It is also contemplated that expression of genes that enhance reproductive fitness during times of stress would be of significant value. For example, expression of genes that improve the synchrony of pollen shed and receptiveness of the femal flower parts, i.e., silks, would be of benefit. In addition it is proposed that expression of genes that minimize kernel abortion during times of stress would increase the amount of grain to be harvested and hence be of value.

Given the overall role of water in determining yield, it is contemplated that enabling corn to utilize water more efficiently, through the introduction and expression of novel genes, will improve overall performance even when soil water availability is not limiting. By introducing genes that improve the ability of corn to maximize water usage across a full range of stresses relating to water availability, yield stability or consistency of yield performance may be realized.

4. Disease Resistance

It is proposed that increased resistance to diseases may be realized through introduction of genes into monocotyledonous plants such as maize. It is possible to produce resistance to diseases caused by viruses, bacteria, fungi and nematodes. It is also contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo et al., 1988, Hemenway et al., 1988, Abel et al., 1986). It is contemplated that expression of antisense genes targeted at essential viral functions may impart resistance to said virus.

For example, an antisense gene targeted at the gene responsible for replication of viral nucleic acid may inhibit said replication and lead to resistance to the virus. It is believed that interference with other viral functions through the use of antisense genes may also increase resistance to viruses. Further it is proposed that it may be possible to achieve resistance to viruses through other approaches, including, but not limited to the use of satellite viruses.

It is proposed that increased resistance to diseases caused by bacteria and fungi may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotics are polypeptide sequences which are inhibitory to growth of bacteria and other microorganisms. For example, the classes of peptides referred to as cecropins and magainins inhibit growth of may species of bacteria and fungi. It is proposed that expression of PR proteins in monocotyledonous plants such as maize may be useful in conferring resistance to bacterial disease. These genes are induced following pathogen attack on a host plant and have been divided into at least five classes of proteins (Bol, Linthorst, and Cornelissen, 1990). Included amongst the PR proteins are β-1, 3-glucanases, chitinases, and osmotin and other proteins that are believed to function in plant resistance to disease organisms. Other genes have been identified that have antifungal properties, e.g., UDA (stinging nettle lectin) and hevein (Broakaert et al., 1989; Barkai-Golan et al., 1978). It is known that certain plant diseases are caused by the production of phytotoxins. It is proposed that resistance to these diseases would be achieved through expression of a novel gene that encodes an enzyme capable of degrading or otherwise inactivating the phytotoxin. It is also contemplated that expression novel genes that alter the interactions between the host plant and pathogen may be useful in reducing the ability the disease organism to invade the tissues of the host plant, e.g., an increase in the waxiness of the leaf cuticle or other morphological characteristics.

Plant parasitic nematodes are a cause of disease in many plants, including maize. It is proposed that it would be possible to make the corn plant resistant to these organisms through the expression of novel genes. It is anticipated that control of nematode infestations would be accomplished by altering the ability of the nematode to recognize or attach to a host plant and/or enabling the plant to produce nematicidal compounds, including but not limited to proteins.

5. Mycotoxin Reduction/Elimination

Production of mycotoxins, including aflatoxin and fumonisin, by fungi associated with monocotyledonous plants such as maize is a significant factor in rendering the grain not useful. These fungal organisms do not cause disease symptoms and/or interfere with the growth of the plant, but they produce chemicals (mycotoxins) that are toxic to animals. It is contemplated that inhibition of the growth of these fungi would be reduce the synthesis of these toxic substances and therefore reduce grain losses due to mycotoxin contamination. It is also proposed that it may be possible to introduce novel genes into monocotyledonous plants such as maize that would inhibit synthesis of the mycotoxin without interfering with fungal growth. Further, it is contemplated that expression of a novel gene which encodes an enzyme capable of rendering the mycotoxin nontoxic would be useful in order to achieve reduced mycotoxin contamination of grain. The result of any of the above mechanisms would be a reduced presence of mycotoxins on grain.

6. Grain Composition or Quality

Genes may be introduced into monocotyledonous plants, particularly commercially important cereals such as maize, to improve the grain for which the cereal is primarily grown. A wide range of novel transgenic plants produced in this manner may be envisioned depending on the particular end use of the grain.

The largest use of maize grain is for feed or food. Introduction of genes that alter the composition of the grain may greatly enhance the feed or food value. The primary components of maize grain are starch, protein, and oil. Each of these primary components of maize grain may be improved by altering its level or composition. Several examples may be mentioned for illustrative purposes but in no way provide an exhaustive list of possibilities.

The protein of cereal grains including maize is suboptimal for feed and food purposes especially when fed to pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. Some amino acids become limiting only after corn is supplemented with other inputs for feed formulations. For example, when corn is supplemented with soybean meal to meet lysine requirements methionine becomes limiting. The levels of these essential amino acids in seeds and grain may be elevated by mechanisms which include, but are not limited to, the introduction of genes to increase the biosynthesis of the amino acids, decrease the degradation of the amino acids, increase the storage of the amino acids in proteins, or increase transport of the amino acids to the seeds or grain.

One mechanism for increasing the biosynthesis of the amino acids is to introduce genes that deregulate the amino acid biosynthetic pathways such that the plant can no longer adequately control the levels that are produced. This may be done by deregulating or bypassing steps in the amino acid biosynthetic pathway which are normally regulated by levels of the amino acid end product of the pathway. Examples include the introduction of genes that encode deregulated versions of the enzymes aspartokinase or dihydrodipicolinic acid (DHDP)-synthase for increasing lysine and threonine production, and anthranilate synthase for increasing tryptophan production. Reduction of the catabolism of the amino acids may be accomplished by introduction of DNA sequences that reduce or eliminate the expression of genes encoding enzymes that catalyse steps in the catabolic pathways such as the enzyme lysine-ketoglutarate reductase.

The protein composition of the grain may be altered to improve the balance of amino acids in a variety of ways including elevating expression of native proteins, decreasing expression of those with poor composition, changing the composition of native proteins, or introducing genes encoding entirely new proteins possessing superior composition. Examples may include the introduction of DNA that decreases the expression of members of the zein family of storage proteins. This DNA may encode ribozymes or antisense sequences directed to impairing expression of zein proteins or expression of regulators of zein expression such as the opaque-2 gene product. It is also proposed that the protein composition of the grain may be modified through the phenomenon of cosupression, i.e., inhibition of expression of an endogenous gene through the expression of an identical structural gene or gene fragment introduced through transformation (Goring et al., 1991). Additionally, the introduced DNA may encode enzymes which degrade zeins. The decreases in zein expression that are achieved may be accompanied by increases in proteins with more desirable amino acid composition or increases in other major seed constituents such as starch. Alternatively, a chimeric gene may be introduced that comprises a coding sequence for a native protein of adequate amino acid composition such as for one of the globulin proteins or 10 kD zein of maize and a promoter or other regulatory sequence designed to elevate expression of said protein. The coding sequence of said gene may include additional or replacement codons for essential amino acids. Further, a coding sequence obtained from another species, or, a partially or completely synthetic sequence encoding a completely unique peptide sequence designed to enhance the amino acid composition of the seed may be employed.

The introduction of genes that alter the oil content of the grain may be of value. Increases in oil content may result in increases in metabolizable-energy-content and—density of the seeds for uses in feed and food. The introduced genes may encode enzymes that remove or reduce rate-limitations or regulated steps in fatty acid or lipid biosynthesis. Such genes may include, but are not limited to, those that encode acetyl-CoA carboxylase, ACP-acyltransferase, β-ketoacyl-ACP synthase, plus other well known fatty acid biosynthetic activities. Other possibilities are genes that encode proteins that do not possess enzymatic activity such as acyl carrier protein. Genes may be introduced that alter the balance of fatty acids present in the oil providing a more healthful or nutritive feedstuff. The introduced DNA may also encode sequences that block expression of enzymes involved in fatty acid biosynthesis, altering the proportions of fatty acids present in the grain such as described below.

Genes may be introduced that enhance the nutritive value of the starch component of the grain, for example by increasing the degree of branching, resulting in improved utilization of the starch in cows by delaying its metabolism.

Besides affecting the major constituents of the grain, genes may be introduced that affect a variety of other nutritive, processing, or other quality aspects of the grain as used for feed or food. For example, pigmentation of the grain may be increased or decreased. Enhancement and stability of yellow pigmentation is desirable in some animal feeds and may be achieved by introduction of genes that result in enhanced production of xanthophylls and carotenes by eliminating rate-limiting steps in their production. Such genes may encode altered forms of the enzymes phytoene synthase, phytoene desaturase, or lycopene synthase. Alternatively, unpigmented white corn is desirable for production of many food products and may be produced by the introduction of DNA which blocks or eliminates steps in pigment production pathways.

Feed or food comprising primarily maize or other cereal grains possesses insufficient quantitities of vitamins and must be supplemented to provide adequate nutritive value. Introduction of genes that enhance vitamin biosynthesis in seeds may be envisioned including, for example, vitamins A, E, $B_{12}$, choline, and the like. Maize grain also does not possess sufficient mineral content for optimal nutritive value. Genes that affect the accumulation or availability of compounds containing phosphorus, sulfur, calcium, manganese, zinc, and iron among others would be valuable. An example may be the introduction of a gene that reduced phytic acid production or encoded the enzyme phytase which enhances phytic acid breakdown. These genes would increase levels of available phosphate in the diet, reducing the need for supplementation with mineral phosphate.

Numerous other examples of improvement of maize or other cereals for feed and food purposes might be described.

The improvements may not even necessarily involve the grain, but may, for example, improve the value of the corn for silage. Introduction of DNA to accomplish this might include sequences that alter lignin production such as those that result in the "brown midrib" phenotype associated with superior feed value for cattle.

In addition to direct improvements in feed or food value, genes may also be introduced which improve the processing of corn and improve the value of the products resulting from the processing. The primary method of processing corn is via wetmilling. Maize may be improved though the expression of novel genes that increase the efficiency and reduce the cost of processing such as by decreasing stepping time.

Improving the value of wetmilling products may include altering the quantity or quality of starch, oil, corn gluten meal, or the components of corn gluten feed. Elevation of starch may be achieved through the identification and elimination of rate limiting steps in starch biosynthesis or by decreasing levels of the other components of the grain resulting in proportional increases in starch. An example of the former may be the introduction of genes encoding ADP-glucose pyrophosphorylase enzymes with altered regulatory activity or which are expressed at higher level. Examples of the latter may include selective inhibitors of, for example, protein or oil biosynthesis expressed during later stages of kernel development.

The properties of starch may be beneficially altered by changing the ratio of amylose to amylopectin, the size of the starch molecules, or their branching pattern. Through these changes a broad range of properties may be modified which include, but are not limited to, changes in gelatinization temperature, heat of gelatinization, clarity of films and pastes, rheological properties, and the like. To accomplish these changes in properties, genes that encode granule-bound or soluble starch synthase activity or branching enzyme activity may be introduced alone or combination. DNA such as antisense constructs may also be used to decrease levels of endogenous activity of these enzymes. The introduced genes or constructs may possess regulatory sequences that time their expression to specific intervals in starch biosynthesis and starch granule development. Furthermore, it may be worthwhile to introduce and express genes that result in the in vivo derivatization, or other modification, of the glucose moieties of the starch molecule. The covalent attachment of any molecule may be envisioned, limited only by the existence of enzymes that catalyze the derivatizations and the accessibility of appropriate substrates in the starch granule. Examples of important derivations may include the addition of functional groups such as amines, carboxyls, or phosphate groups which provide sites for subsequent in vitro derivatizations or affect starch properties through the introduction of ionic charges. Examples of other modifications may include direct changes of the glucose units such as loss of hydoxyl groups or their oxidation to aldehyde or carboxyl groups.

Oil is another product of wetmilling of corn, the value of which may be improved by introduction and expression of genes. The quantity of oil that can be extracted by wetmilling may be elevated by approaches as described for feed and food above. Oil properties may also be altered to improve its performance in the production and use of cooking oil, shortenings, lubricants or other oil-derived products or improvement of its health attributes when used in the food-related applications. Novel fatty acids may also be synthesized which upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids and the lipids possessing them or by increasing levels of native fatty acids while possibly reducing levels of precursors. Alternatively DNA sequences may be introduced which slow or block steps in fatty acid biosynthesis resulting in the increase in precursor fatty acid intermediates. Genes that might be added include desaturases, epoxidases, hydratases, dehydratases, and other enzymes that catalyze reactions involving fatty acid intermediates. Representative examples of catalytic steps that might be blocked include the desaturations from stearic to oleic acid and oleic to linolenic acid resulting in the respective accumulations of stearic and oleic acids. Another example is the blockage of elongation steps resulting in the accumulation of $c_8$ to $c_{12}$ saturated fatty acids.

Improvements in the other major corn wetmilling products, corn gluten meal and corn gluten feed, may also be achieved by the introduction of genes to obtain novel corn plants. Representative possibilities include but are not limited to those described above for improvement of food and feed value.

In addition it may further be considered that the corn plant be used for the production or manufacturing of useful biological compounds that were either not produced at all, or not produced at the same level, in the corn plant previously. The novel corn plants producing these compounds are made possible by the introduction and expression of genes by corn transformation methods. The vast array of possibilities include but are not limited to any biological compound which is presently produced by any organism such as proteins, nucleic acids, primary and intermediary metabolites, carbohydrate polymers, etc. The compounds may be produced by the plant, extracted upon harvest and/or processing, and used for any presently recognized useful purpose such as pharmaceuticals, fragrances, industrial enzymes to name a few.

Further possibilities to exemplify the range of grain traits or properties potentially encoded by introduced genes in transgenic plants include grain with less breakage susceptibility for export purposes or larger grit size when processed by dry milling through introduction of genes that enhance γ-zein synthesis, popcorn with improved popping quality and expansion volume through genes that increase pericarp thickness, corn with whiter grain for food uses though introduction of genes that effectively block expression of enzymes involved in pigment production pathways, and improved quality of alcoholic beverages or sweet corn through introduction of genes which affect flavor such as the shrunken gene (encoding sucrose synthase) for sweet corn.

7. Plant Agronomic Characteristics

Two of the factors determining where corn can be grown are the average daily temperature during the growing season and the length of time between frosts. Within the areas where it is possible to grow corn, there are varying limitations on the maximal time it is allowed to grow to maturity and be harvested. The corn to be grown in a particular area is selected for its ability to mature and dry down to harvestable moisture content within the required period of time with maximum possible yield. Therefore, corn of varying maturities is developed for different growing locations. Apart from the need to dry down sufficiently to permit harvest is the desirability of having maximal drying take place in the field to minimize the amount of energy required for additional drying post-harvest. Also the more readily the grain can dry down, the more time there is available for growth and kernel fill. It is considered that genes that influence maturity and/or dry down can be identified and introduced into corn lines using transformation techniques to create new corn varieties adapted to different growing locations or the same growing location but having improved yield to moisture ratio at harvest. Expression of genes that are involved in regulation of plant development may be especially useful, e.g., the liguleless and rough sheath genes that have been identified in corn.

It is contemplated that genes may be introduced into corn that would improve standability and other plant growth characteristics. Expression of novel genes which confer stronger stalks, improved root systems, or prevent or reduce ear droppage would be of great value to the farmer. It is proposed that introduction and expression of genes that increase the total amount of photoassimilate available by, for example, increasing light distribution and/or interception would be advantageous. In addition the expression of genes that increase the efficiency of photosynthesis and/or the leaf canopy would further increase gains in productivity. Such approaches would allow for increased plant populations in the field.

Delay of late season vegetative senescence would increase the flow of assimilate into the grain and thus increase yield. It is proposed that overexpression of genes within corn that are associated with "stay green" or the expression of any gene that delays senescence would achieve be advantageous. For example, a nonyellowing mutant has been identified in *Festuca pratensis* (Davies et al., 1990). Expression of this gene as well as others may prevent premature breakdown of chlorophyll and thus maintain canopy function.

8. Nutrient Utilization

The ability to utilize available nutrients may be a limiting factor in growth of monocotyledonous plants such as maize. It is proposed that it would be possible to alter nutrient uptake, tolerate pH extremes, mobilization through the plant, storage pools, and availability for metabolic activities by the introduction of novel genes. These modifications would allow a plant such as maize to more efficiently utilize available nutrients. It is contemplated that an increase in the activity of, for example, an enzyme that is normally present in the plant and involved in nutrient utilization would increase the availability of a nutrient. An example of such an enzyme would be phytase. It is also contemplated that expression of a novel gene may make a nutrient source available that was previously not accessible, e.g., an enzyme that releases a component of nutrient value from a more complex molecule, perhaps a macromolecule.

9. Male Sterility

Male sterility is useful in the production of hybrid seed. It is proposed that male sterility may be produced through expression of novel genes. For example, it has been shown that expression of genes that encode proteins that interfere with development of the male inflorescence and/or gametophyte result in male sterility. Chimeric ribonuclease genes that express in the anthers of transgenic tobacco and oilseed rape have been demonstrated to lead to male sterility (Mariani et al, 1990).

A number of mutations were discovered in maize that confer cytoplasmic male sterility. One mutation in particular, referred to as T cytoplasm, also correlates with sensitivity to Southern corn leaf blight. A DNA sequence, designated TURF-13 (Levings, 1990), was identified that correlates with T cytoplasm. It is proposed that it would be possible through the introduction of TURF-13 via transformation to separate male sterility from disease sensitivity. As it is necessary to be able to restore male fertility for breeding purposes and for grain production it is proposed that genes encoding restoration of male fertility may also be introduced.

10. Negative Selectable Markers

Introduction of genes encoding traits that can be selected against may be useful for eliminating undesirable linked genes. It is contemplated that when two or more genes are introduced together by cotransformation that the genes will be linked together on the host chromosome. For example, a gene encoding a Bt gene that confers insect resistance on the plant may be introduced into a plant together with a bar gene that is useful as a selectable marker and confers resistance to the herbicide Ignite® on the plant. However, it may not be desirable to have an insect resistant plant that is also resistant to the herbicide Ignite®. It is proposed that one could also introduce an antisense bar gene that is expressed in those tissues where one does not want expression of the bar gene, e.g., in whole plant parts. Hence, although the bar gene is expressed and is useful as a selectable marker, it is not useful to confer herbicide resistance on the whole plant. The bar antisense gene is a negative selectable marker.

It is also contemplated that a negative selection is necessary in order to screen a population of transformants for rare homologous recombinants generated through gene targeting. For example, a homologous recombinant may be identified through the inactivation of a gene that was previously expressed in that cell. The antisense gene to neomycin phosphotransferase II (nptII) has been investigated as a negative selectable marker in tobacco (*Nicotiana tabacum*) and *Arabidopsis thaliana* (Xiang, C. and Guerra, D. J. 1993). In this example both sense and antisense npt II genes are introduced into a plant through transformation and the resultant plants are sensitive to the antibiotic kanamycin. An introduced gene that integrates into the host cell chromosome at the site of the antisense nptII gene, and inactivates the antisense gene, will make the plant resistant to kanamycin and other aminoglycoside antibiotics. Therefore, rare site specific recombinants may be identified by screening for antibiotic resistance. Similarly, any gene, native to the plant or introduced through transformation, that when inactivated confers resistance to a compound, may be useful as a negative selectable marker.

It is contemplated that negative selectable markers may also be useful in other ways. One application is to contruct transgenic lines in which one could select for transposition to unlinked sites. In the process of tagging it is most common for the transposable element to move to a genetically linked site on the same chromosome. A selectable marker for recovery of rare plants in which transposition has occurred to an unlinked locus would be useful. For example, the enzyme cytosine deaminase may be useful for this purpose (Stouggard, J., 1993). In the presence of this enzyme the compound 5-fluorocytosine is converted to 5-fluoruracil which is toxic to plant and animal cells. If a transposable element is linked to the gene for the enzyme cytosine deaminase, one may select for transposition to unlinked sites by selecting for transposition events in which the resultant plant is now resistant to 5-fluorocytosine. The parental plants and plants containing transpositions to linked sites will remain sensitive to 5-fluorocytosine. Resistance to 5-fluorocytosine is due to loss of the the cytosine deaminase gene through genetic segregation of the transposable element and the cytosine deaminase gene. Other genes that encode proteins that render the plant sensitive to a certain compound will also be useful in this context. For example, T-DNA gene 2 from *Agrobacterium tumefaciens* encodes a protein that catalyzes the conversion of α-naphthalene acetamide (NAM) to α-napthalene acetic acid (NAA) renders plant cells sensitive to high concentrations of NAM (Depicker et al., 1988).

It is also contemplated that negative selectable markers may be useful in the contruction of transposon tagging lines. For example, by marking an autonomous transposable element such as Ac, Master Mu, or En/Spn with a negative selectable marker, one could select for transformants in which the autonomous element is not stabily integrated into the genome. It is proposed that this would be desirable, for example, when transient expression of the autonomous element is desired to activate in trans the transposition of a defective transposable element, such as Ds, but stable integration of the autonomous element is not desired. The presence of the autonomous element may not desired in order to stabilize the defective element, i.e., prevent it from further transposing. However, it is proposed that if stable integration of an autonomous transposable element is desired in a plant the presence of a negative selectable marker may make it possible to eliminate the autonomous element during the breeding process.

D. Non-Protein-Expressing Sequences

1. RNA-Expressing

DNA may be introduced into corn and other monocots for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes.

Genes may be constructed or isolated, which when transcribed, produce antisense RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes. An antisense gene may thus be introduced into a plant by transformation methods to produce a novel transgenic plant with reduced expression of a selected protein of interest. For example, the protein may be an enzyme that catalyzes a reaction in the plant. Reduction of the enzyme activity may reduce or eliminate products of the reaction which include any enzymatically synthesized compound in the plant such as fatty acids, amino acids, carbohydrates, nucleic acids and the like. Alternatively, the protein may be a storage protein, such as a zein, or a structural protein, the decreased expression of which may lead to changes in seed amino acid composition of plant morphological changes respectively. The possibilities cited above are provided only by way of example and do not represent the full range of applications.

Genes may also be constructed or isolated, which when transcribed produce RNA enzymes, or ribozymes, which can act as endoribonucleases and catalyze the cleavage of RNA molecules with selected sequences. The cleavage of selected messenger RNA's can result in the reduced production of their encoded polypeptide products. These genes may be used to prepare novel transgenic plants which possess them. The transgenic plants may possess reduced levels of polypeptides including but not limited to the polypeptides cited above that may be affected by antisense RNA.

It is also possible that genes may be introduced to produce novel transgenic plants which have reduced expression of a native gene product by a mechanism of cosuppression. It has been demonstrated in tobacco, tomato, and petunia (Goring et al, 1991; Smith et al., 1990; Napoli, C. et al., 1990; van der Krol et al., 1990) that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

2. Non-RNA-Expressing

For example, DNA elements including those of transposable elements such as Ds, Ac, or Mu, may be inserted into a gene and cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer together with PCR gene cloning techniques (Shapiro, 1983; Dellaporta et al., 1988). Once identified, the entire gene(s) for the particular trait, including control or regulatory regions where desired may be isolated, cloned and manipulated as desired. The utility of DNA elements introduced into an organism for purposed of gene tagging is independent of the DNA sequence and does not depend on any biological activity of the DNA sequence, i.e., transcription into RNA or translation into protein. The sole function of the DNA element is to disrupt the DNA sequence of a gene.

It is contemplated that unexpressed DNA sequences, including novel synthetic sequences could be introduced into cells as propietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labelled source. It is proposed that inclusion of label DNAs would enable one to distinguish proprietary germplasm or germplasm derived from such, from unlabelled germplasm.

Another possible element which may be introduced is a matrix attachment region element (MAR), such as the chicken lysozyme A element (Stief, 1989), which can be positioned around an expressible gene of interest to effect an increase in overall expression of the gene and diminish position dependant effects upon incorporation into the plant genome (Stief et al., 1989; Phi-Van et al., 1990).

III. DNA Delivery

Following the generation of recipient cells, the present invention generally next includes steps directed to introducing an exogenous DNA segment, such as a cDNA or gene, into a recipient cell to create a transformed cell. The frequency of occurrence of cells receiving DNA is believed to be low. Moreover, it is most likely that not all recipient cells receiving DNA segments will result in a transformed cell wherein the DNA is stably integrated into the plant genome and/or expressed. Some may show only initial and transient gene expression. However, certain cells from virtually any monocot species may be stably transformed, and these cells developed into transgenic plants, through the application of the techniques disclosed herein.

There are many methods for introducing transforming DNA segments into cells, but not all are suitable for delivering DNA to plant cells. Suitable methods are believed to include virtually any method by which DNA can be introduced into a cell, such as by Agrobacterium infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

A. Electroporation

Where one wishes to introduce DNA by means of electroporation, it is contemplated that the method of Krzyzek et al. (U.S. Ser. No. 07/635,279 filed Dec. 28, 1990, incorporated herein by reference) will be particularly advantageous. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding.

To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

B. Microprojectile Bombardment

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic BMS cells were bombarded with intact cells of the bacteria *E. coli* or *Agrobacterium tumefaciens* containing plasmids with either the β-glucoronidase or bar gene engineered for expression in maize. Bacteria were inactivated by ethanol dehydration prior to bombardment. A low level of transient expression of the β-glucoronidase gene was observed 24–48 hours following DNA delivery. In addition, stable transformants containing the bar gene were recovered following bombardment with either *E. coli* or *Agrobacterium tumefaciens* cells. It is contemplated that particles may contain DNA rather than be coated with DNA. Hence it is proposed that DNA-coated particles may increase the level of DNA delivery via particle bombardment but are not, in and of themselves, necessary.

An advantage of microprojectile bombardment, in addition to it being an effective means of reproducibly stably transforming monocots, is that neither the isolation of protoplasts (Cristou et al., 1988) nor the susceptibility to Agrobacterium infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with corn cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Results from such small scale optimization studies are disclosed herein and the execution of other routine adjustments will be known to those of skill in the art in light of the present disclosure.

IV. Production and Characterization of Stable Transgenic Corn

After effecting delivery of exogenous DNA to recipient cells by any of the methods discussed above, the next steps of the invention generally concern identifying the transformed cells for further culturing and plant regeneration. As mentioned above, in order to improve the ability to identify transformants, one may desire to employ a selectable or screenable marker gene as, or in addition to, the expressible gene of interest. In this case, one would then generally assay the potentially transformed cell population by exposing the cells to a selective agent or agents, or one would screen the cells for the desired marker gene trait.

A. Selection

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for 0–28 days on nonselective medium and subsequently transferred to medium containing from 1–3 mg/l bialaphos or 1–3 mM glyphosate as appropriate. While ranges of 1–3 mg/l bialaphos or 1–3 mM glyphosate will typically be preferred, it is proposed that ranges of 0.1–50 mg/l bialaphos or 0.1–50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic type II callus of *Zea mays L.* was selected with sub-lethal levels of bialaphos. Slowly growing tissue was subsequently screened for expression of the luciferase gene and transformants were identified. In this example, neither selection nor screening conditions employed were sufficient in and of themselves to identify transformants. Therefore it is proposed that combinations of selection and screening will enable one to identify transformants in a wider variety of cell and tissue types.

B. Regeneration and Seed Production

Cells that survive the exposure to the selective agent, or cells that have been scored positive in a screening assay, may be cultured in media that supports regeneration of plants. In an exemplary embodiment, the inventors have modified MS and N6 media (see Table 1) by including further substances such as growth regulators. A preferred growth regulator for such purposes is dicamba or 2,4-D. However, other growth regulators may be employed, including NAA, NAA+2,4-D or perhaps even picloram. Media improvement in these and like ways was found to facilitate the growth of cells at specific developmental stages. Tissue is preferably maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are transferred every two weeks on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber at about 85% relative humidity, 600 ppm $CO_2$, and 25–250 microeinsteins $m^{-2}s^{-1}$ of light. Plants are preferably matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con®S. Regenerating plants are preferably grown at about 19 to 28° C. After the regenerating plants have reached the stage of shoot and root development, they may be transferred to a greenhouse for further growth and testing.

In one study, $R_0$ plants were regenerated from transformants of an A188×B73 suspension culture line (SC82), and these plants exhibited a phenotype expected of the genotype of hybrid A188×B73 from which the callus and culture were derived. The plants were similar in height to seed-derived A188 plants (3–5 ft tall) but had B73 traits such as anthocyanin accumulation in stalks and prop roots, and the presence of upright leaves. It would also be expected that some traits in the transformed plants would differ from their source, and indeed some variation will likely occur.

In an exemplary embodiment, the proportion of regenerating plants derived from transformed callus that successfully grew and reached maturity after transfer to the greenhouse was 97% (73 of 76). $R_0$ plants in the greenhouse are tested for fertility by backcrossing the transformed plants with seed-derived plants by pollinating the $R_0$ ears with pollen from seed derived inbred plants and this resulted in kernel development. In addition, pollen was collected from $R_0$ plants and used to pollinate seed derived inbred plants, resulting in kernel development. Although fertility can vary from plant to plant greater than 100 viable progeny can be routinely recovered from each transformed plant through use of both the ear and pollen for doing crosses.

Note, however, that occasionally kernels on transformed plants may require embryo rescue due to cessation of kernel development and premature senescence of plants. To rescue developing embryos, they are excised from surface-disinfected kernels 10–20 days post-pollination and cultured. An embodiment of media used for culture at this stage comprises MS salts, 2% sucrose, and 5.5 g/l agarose. In an illustrative embodiment of embryo rescue, large embryos (defined as greater than 3 mm in length) are germinated directly on an appropriate media. Embryos smaller than that were cultured for one week on media containing the above ingredients along with $10^{-5}M$ abscisic acid and then transferred to growth regulator-free medium for germination.

Progeny may be recovered from the transformed plants and tested for expression of the exogenous expressible gene by localized application of an appropriate substrate to plant parts such as leaves. In the case of bar transformed plants, it was found that transformed parental plants ($R_0$) and their progeny ($R_1$) exhibited no bialaphos-related necrosis after localized application of the herbicide Basta® to leaves, if there was functional PAT activity in the plants as assessed by an in vitro enzymatic assay. In one study, of 28 progeny ($R_1$) plants tested, 50% (N=14) had PAT activity. All PAT positive progeny tested contained bar, confirming that the presence of the enzyme and the resistance to bialaphos were associated with the transmission through the germline of the marker gene.

C. Characterization

To confirm the presence of the exogenous DNA or "transgene (s)" in the regenerating plants, a variety of assays may be performed. Such assays include, for example, "molecular biological" assays, such as Southern and Northern blotting and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

1. DNA Integration, RNA Expression and Inheritance

Genomic DNA may be isolated from callus cell lines or any plant parts to determine the presence of the exogenous gene through the use of techniques well known to those skilled in the art. Note, that intact sequences will not always be present, presumably due to rearrangement or deletion of sequences in the cell.

The presence of DNA elements introduced through the methods of this invention may be determined by polymerase chain reaction (PCR). Using this technique discreet fragments of DNA are amplified and detected by gel electrophoresis. This type of analysis permits one to determine whether a gene is present in a stable transformant, but does not prove integration of the introduced gene into the host cell genome. It is the experience of the inventors, however, that DNA has been integrated into the genome of all transformants that demonstrate the presence of the gene through PCR analysis. In addition, it is not possible using PCR techniques to determine whether transformants have exogenous genes introduced into different sites in the genome, i.e., whether transformants are of independent origin. It is contemplated that using PCR techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a gene.

Both PCR and Southern hybridization techniques can be used to demonstrate transmission of a transgene to progeny. It is the experience of the inventors that in most instances the characteristic Southern hybridization pattern for a given transformant will segregate in progeny as one or more Mendelian genes (Spencer et al., 1992; Spencer et al, in press) indicating stable inheritance of the transgene. For example, in one study, of 28 progeny ($R_1$) plants tested, 50% (N=14) contained bar, confirming transmission through the germline of the marker gene. The nonchimeric nature of the callus and the parental transformants ($R_0$) was suggested by germline transmission and the identical Southern blot hybridization patterns and intensities of the transforming DNA in callus, $R_0$ plants and $R_1$ progeny that segregated for the transformed gene.

Whereas DNA analysis techniques may be conducted using DNA isolated from any part of a plant, RNA will only be expressed in particular cells or tissue types and hence it will be necessary to prepare RNA for analysis from these tissues. PCR techniques may also be used for detection and quantitation of RNA produced from introduced genes. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

2. Gene Expression

While Southern blotting and PCR may be used to detect the gene(s) in question, they do not provide information as to whether the gene is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focussing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their fuctionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabelled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may beanalyzed by near infrared reflectance spectrometry. Morphological changes may include greater stature or thicker stalks. Most often changes in response of plants or plant parts to imposed treatments are evaluated under carefully controlled conditions termed bioassays. An example is to evaluate resistance to insect feeding.

D. Establishment of the Introduced DNA in Other Maize Varieties

Fertile, transgenic plants may then be used in a conventional maize breeding program in order to incorporate the introduced DNA into the desired lines or varieties. Methods and references for convergent improvement of corn are given by Hallauer et al., (1988) incorporated herein by reference. Among the approaches that conventional breeding programs employ is a conversion process (backcrossing). Briefly, conversion is performed by crossing the initial transgenic ferile plant to elite inbred lines. The progeny from this cross will segregate such that some of the plants will carry the recombinant DNA whereas some will not. The plants that do not carry the DNA are then crossed again to the elite inbred lines resulting in progeny which segregate once more. This backcrossing process is repeated until the original elite inbred has been converted to a line containing the recombinant DNA, yet possessing all important attributed originally found in the parent. Generally, this will require about 6–8 generations. A separate backcrossing program will be generally used for every elite line that is to be converted to a genetically engineered elite line.

Generally, the commercial value of the transformed corn produced herein will be greatest if the recombinant DNA can be incorporated into many different hybrid combinations. A farmer typically grows several hybrids based on differences in maturity, standability, and other agronomic traits. Also, the farmer must select a hybrid based upon his or her geographic location since hybrids adapted to one region are generally not adapted to another because of differences in such traits as maturity, disease, and insect resistance. As such, it is necessary to incorporate the introduced DNA into a large number of parental lines so that many hybrid combinations can be produced containing the desirable DNA.

Corn breeding and the techniques and skills required to transfer genes from one line or variety to another are well known to those skilled in the art. Thus, introducing recombinant DNA into any other line or variety can be accomplished by these breeding procedures.

E. Uses of Transgenic Plants

The transgenic plants produced herein are expected to be useful for a variety of commercial and research purposes.

Transgenic plants can be created for use in traditional agriculture to possess traits beneficial to the grower (e.g., agronomic traits such as pest resistance, herbicide resistance or increased yield), beneficial to the consumer of the grain harvested from the plant (e.g., improved nutritive content in human food or animal feed), or beneficial to the food processor (e.g., improved processing traits). In such uses, the plants are generally grown for the use of their grain in human or animal foods. However, other parts of the plants, including stalks, husks, vegetative parts, and the like, may also have utility, including use as part of animal silage or for ornamental purposes. Often, chemical constitutents (e.g., oils or starches) of corn and other crops are extracted for foods or industrial use and transgenic plants may be created which have enhanced or modified levels of such components.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules.

The transgenic plants may also be used in commercial breeding programs, or may be crossed or bred to plants of related crop species. Improvements encoded by the recombinant DNA may be transferred, e.g., from corn cells to cells of other species, e.g., by protoplast fusion.

The transgenic plants may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation. The methods of the invention may also be used to create plants having unique "signature sequences" or other marker sequences which can be used to identify proprietary lines or varieties.

The inventors have been successful in producing fertile transgenic monocot plants (maize) where others have failed. Aspects of the methods of the present invention for producing the fertile, transgenic corn plants comprise, but are not limited to, isolation of recipient cells using media conducive to specific growth patterns, choice of selective systems that permit efficient detection of transformation; modifications of DNA delivery methods to introduce genetic vectors with exogenous DNA into cells; invention of methods to regenerate plants from transformed cells at a high frequency; and the production of fertile transgenic plants capable of surviving and reproducing.

BRIEF DESCRIPTION OF THE DRAWINGS

FIG. 1(AA). Map of plasmid pDPG427 containing a maize EPSPS gene mutated to confer resistance to glyphosate.

FIG. 1(BB). Map of plasmid pDPG451 containing the 35S promoter—adh intron- mtlD- Tr7 expression cassette. Expression of this cassette will lead to accumulation of mannitol in the cells.

FIG. 1(CC). Map of plasmid pDPG354 containing a synthetic Bt gene (see FIG. 12).

FIG. 1(DD). Map of plasmid pDPG344 containing the proteinase inhibitor II gene from tomato.

FIG. 1(EE). Map of plasmid pDPG337 containing a synthetic Bt gene (see FIG. 12).

FIG. 2. Appearance of cell colonies which emerge on selection plates with bialaphos. Such colonies appear 6–7 weeks after bombardment.

FIG. 4. Integration of the bar gene in bialaphos-resistant SC82 callus isolates E1–E11. DNA gel blot of genomic DNA (4 $\mu$g/digest) from E1–E11 and a nonselected control (EO) digested with EcoRI and HindIII. The molecular weights in kb are shown on the left and right. The blot was hybridized with $^{32}$P-labeled bar from pDPG165 (~25×10$^6$ Cerenkov cpm). Lanes designated 1 and 5 copies refer to the diploid genome and contain 1.9 and 9.5 pg respectively of the 1.9 kb bar expression unit released from pDPG165 with EcoRI and HindIII.

FIG. 5. Integration of exogenous genes in bialaphos-resistant SC716 isolates R1–R21.

FIG. 5(A). DNA gel blot of genomic DNA (6 $\mu$g/digest) from transformants isolated from suspension culture of A188×B73 (SC716), designated R1–R21, were digested with EcoRI and HindIII and hybridized to $^{32}$p-labeled bar probe (~10×10$^6$ Cerenkov cpm). Molecular weight markers in kb are shown on the left and right. Two copies of the bar expression unit per diploid genome is 5.7 pg of the 1.9 kb EcoRI/Hind fragment from pDPG165.

FIG. 7. Mature $R_0$ Plant, Developing Kernels and Progeny.

FIG. 11. PAT Activity and DNA Gel Blot Analysis of Segregating Progeny of E2/E5 $R_0$ Plants.

FIG. 12. DNA sequence of a synthetic Bt gene coding for the to

TABLE 1-continued

Figure 1A:
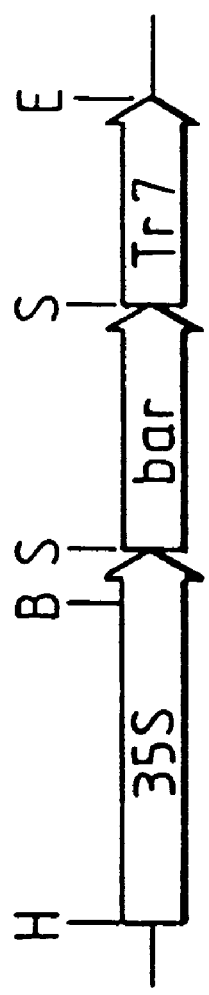
FIG. 1(A). Schematic representation of the expression cassette of pDPG165 containing the bar gene.

Illustrative Embodiments of Tissue Culture Media Which are Used for Type II Callus Development, Development of Suspension Cultures and Regeneration of Plant Cells (Specifically Maize Cells)

| MEDIA NO. | BASAL MEDIUM | SUCROSE | pH | OTHER COMPONENTS** (Amount/L) |
|---|---|---|---|---|
| 163 | MS | 3% | 6.0 | MS vitamins<br>3.3 mg dicamba<br>100 mg myo-inositol<br>Bactoagar |
| 171 | MS | 3% | 6.0 | MS vitamins<br>.25 mg 2,4-D<br>10 mg BAP<br>100 mg myo-inositol<br>Bactoagar |
| 173 | MS | 6% | 6.0 | MS vitainins<br>5 mg BAP<br>.186 mg NAA<br>.175 mg IAA<br>.403 mg 21P<br>$10^{-7}$ M ABA<br>200 mg myo-inositol<br>Bactoagar |
| 177 | MS | 3% | 6.0 | MS vitamins<br>.25 mg 2,4-D<br>10 mg BAP<br>$10^{-7}$ M ABA<br>100 mg myo-inositol<br>Bactoagar |
| 185 | MS | — | 5.8 | 3 mg BAP<br>.04 mg NAA<br>RT vitamins<br>1.65 mg thiamine<br>1.38 g L-proline<br>20 g sorbitol<br>Bactoagar |
| 189 | MS | — | 5.8 | 3 mg BAP<br>.04 mg NAA<br>.5 mg niacin<br>800 mg L-asparagine<br>100 mg casaminio acids<br>20 g sorbitol<br>1.4 g L-proline<br>100 mg myo-inositol<br>Gelgro |
| 201 | N6 | 2% | 5.8 | N6 vitamins<br>2 mg L-glycine<br>1 mg 214-D<br>100 mg casein hydrolysate<br>2.9 g L-proline<br>Gelgro |
| 205 | N6 | 2% | 5.8 | N6 vitamins<br>2 mg L-glycine<br>.5 mg 2,4-D<br>100 mg casein hydrolysate<br>2.9 g L-proline<br>Gelgro |
| 209 | N6 | 6% | 5.8 | N6 vitamins<br>2 mg L-glycine<br>100 mg casein hydrolysate<br>0.69 g L-proline<br>Bactoagar |
| 210 | N6 | 3% | 5.5 | N6 vitamins<br>2 mg 2,4-D<br>250 mg Ca pantothenate<br>100 mg myo-inositol<br>790 mg L-asparagine<br>100 mg casein hydrolpate<br>1.4 g L-proline<br>Hazelton agar****<br>2 mg L-glycine |
| 212 | N6 | 3% | 5.5 | N6 vitamins<br>2 mg L-glycine<br>2 mg 2,4-D<br>250 mg Ca pantothenate<br>100 mg myo-inositol<br>100 mg casein hydrolysate<br>1.4 g L-proline<br>Hazelton agar**** |
| 227 | N6 | 2% | 5.8 | N6 vitamins<br>2 mg L-glycine<br>13.2 mg dicamba<br>100 mg casein hydrolysate<br>2.9 g L-proline<br>Gelgro |
| 273 | N6 | 2% | 5.8 | N6 vitamins<br>2 mg L-glycine<br>1 mg 2,4-D<br>16.9 mg AgNO$_3$<br>100 mg casein hydrolysate<br>2.9 g L-proline |
| 279 | N6 | 2% | 5.8 | 3.3 mg dicamba<br>1 mg thiamine<br>.5 mg niacin<br>800 mg L-asparagine<br>100 mg casein hydrolysate<br>100 mg myoinositol<br>1.4 g L-proline<br>Gelgro**** |
| 288 | N6 | 3% | | 3.3 mg dicamba<br>1 mg thiamine<br>.5 mg niacin<br>.8 g L-asparagine<br>100 mg myo-inosital<br>1.4 g L-proline<br>100 mg casein hydrolysate<br>16.9 mg AgNO$_3$<br>Gelgro |
| 401 | MS | 3% | 6.0 | 3.73 mg Na$_2$EDTA<br>.25 mg thiamine<br>1 mg 2,4-D<br>2 mg NAA<br>200 mg casein hydrolysate<br>500 mg K$_2$SO$_4$<br>400 mg KH$_2$PO$_4$<br>100 mg myo-inositol |
| 402 | MS | 3% | 6.0 | 3.73 mg Na$_2$EDTA<br>.25 mg thiamine<br>1 mg 2,4-D<br>200 mg casein hydrolysate<br>2.9 g L-proline<br>500 mg K$_2$SO$_4$<br>400 mg KH$_2$PO$_4$<br>100 mg myo-inositol |
| 409 | MS | 3% | 6.0 | 3.73 mg Na$_2$EDTA<br>.25 mg thiamine<br>9.9 mg dicamba<br>200 mg casein hydrolysate<br>2.9 g L-proline |

TABLE 1-continued

Illustrative Embodiments of Tissue Culture Media Which are Used for Type II Callus Development, Development of Suspension Cultures and Regeneration of Plant Cells (Specifically Maize Cells)

| MEDIA NO. | BASAL MEDIUM | SUCROSE | pH | OTHER COMPONENTS** (Amount/L) |
|---|---|---|---|---|
| 401 | Clark's Medium*** | 2% | 5.7 | 500 mg $K_2SO_4$<br>400 mg $KH_2PO_4$<br>100 mg myo-inositol |
| 607 | ½ × MS | 3% | 5.8 | 1 mg thiamine<br>1 mg niacin<br>Gelrite |
| 615 | MS | 3% | 6.0 | MS vitamins<br>.6 mg BAP<br>100 mg myo-inositol<br>Bactoagar |
| 617 | ½ × MS | 1.5% | 6.0 | MS vitamins<br>50 mg myo-inositol<br>Bactoagar |
| 708 | N6 | 2% | 5.8 | N6 vitamins<br>2 mg L-glycine<br>1.5 mg 2,4-D<br>200 mg casein hydrolysate<br>0.69 g L-proline<br>Gelrite |
| 721 | N6 | 2% | 5.8 | 3.3 mg dicamba<br>1 mg thiamine<br>.5 mg niacin<br>800 mg L-asparagine<br>100 mg myo-inositol<br>100 mg casein hydrolysate<br>1.4 g L-proline<br>54.65 g mannitol<br>Gelgro |
| 726 | N6 | 3% | 5.8 | 3.3 mg dicamba<br>.5 mg niacin<br>1 mg thiamine<br>800 mg L-asparagine<br>100 mg myo-inositol<br>100 mg casein hydrolysate<br>1.4 g L-proline |
| 727 | N6 | 3% | 5.8 | N6 vitamins<br>2 mg L-glycine<br>9.9 mg dicamba<br>100 mg casein hydrolysate<br>2.9 g L-proline<br>Gelgro |
| 728 | N6 | 3% | 5.8 | N6 vitamins<br>2 mg L-glycine<br>9.9 mg dicamba<br>16.9 mg $AgNO_3$<br>100 mg casein hydrolysate<br>2.9 g L-proline<br>Gelgro |
| 734 | N6 | 2% | 5.8 | N6 vitamins<br>2 mg L-glycine<br>1.5 mg 2,4-D<br>14 g Fe sequestreene (replaces Fe-EDTA)<br>200 mg casein hydrolyste<br>0.69 g L-proline<br>Gelrite |
| 735 | N6 | 2% | 5.8 | 1 mg 2,4-D<br>.5 mg niacin<br>.91 g L-asparagine<br>100 mg myo-inositol<br>1 mg thiamine<br>.5 g MES |
| 2004 | N6 | 3% | 5.8 | .75 g $MgCl_2$<br>100 mg casein hydrolysate<br>0.69 g L-proline<br>Gelgro<br>1 mg thiamine<br>0.5 mg niacin<br>3.3 mg dicamba<br>17 mg $AgNO_3$<br>1.4 g L-proline<br>0.8 g L-asparagine<br>100 mg casein hydrolysate<br>100 mg myo-inositol<br>Gelrite |
| 2008 | N6 | 3% | 5.8 | 1 mg thiamine<br>0.5 mg niacin<br>3.3 mg dicamba<br>1.4 g L-proline<br>0.8 g L-asparagine<br>Gelrite |

*Basic MS medium described in Murashige and Skoog (1962). This medium is typically modified by decreasing the $NH_4NO_3$ from 1.64 g/l to 1.55 g/l, and omitting the pyridoxine HCl, nicotinic acid, myo-inositol and glycine.
**NAA = Napthol Acetic Acid
IAA = Indole Acetic Acid
2-IP = 2, isopentyl adenine
2,4-D = 2, 4-Dichlorophenoxyacetic Acid
BAP = 6-benzyl aminopurine
ABA = abscisic acid
***Basic medium described in Clark (1982)
****These media may be made with or without solidifying agent.

A number of transformable maize cultures have been developed using the protocols outlined in the following examples. A compilation of the cultures initiated and tested for transformability is set forth in Table 2, with the results of the studies given in the two right-hand columns. The Table indicates the general selection protocol that was used for each of these cultures. The numeral designations under "Protocol" represent the following:

1. Tissue (suspension) was plated on filters, bombarded and then filters were transferred to culture medium. After 2–7 days, the filters were transferred to selective medium. Approximately 3 weeks after bombardment, tissue was picked from filters as separate callus clumps onto fresh selective medium.
2. As in 1. above, except after bombardment the suspension was put back into liquid—subjected to liquid selection for 7–14 days and then pipetted at a low density onto fresh selection plates.
3. Callus was bombarded while sitting directly on medium or on filters. Cells were transferred to selective medium 1–14 days after particle bombardment. Tissue was transferred on filters 1–3 times at 2 weeks intervals to fresh selective medium. Callus was then briefly put into liquid to disperse the tissue onto selective plates at a low density.
4. Callus tissue was transferred onto selective plates one to seven days after DNA introduction. Tissue was subcultured as small units of callus on selective plates until transformants were identified.

The totals demonstrate that 27 of 37 maize cultures were transformable. Of those cell lines tested 11 out of 20 have produced fertile plants and 7 are in progress. As this table indicates, transformable cultures have been produced from ten different genotypes of maize, including both hybrid and inbred varieties. These techniques for development of transformable cultures are also important in direct transformation of intact tissues, such as immature embryos as these techniques rely on the ability to select transformants in cultured cell systems.

TABLE 2

| Genotype | Culture | Method | Transformable | Fertile Plants |
|---|---|---|---|---|
| A188 × B73 | G(1 × 6)92 | 1 | + | − |
| | G(1 × 6)716 | 1,2 | + | + |
| | G(1 × 6)82 | 1 | + | + |
| | G(1 × 6)98 | 1 | − | NA |
| | G(1 × 6)99 | 1 | − | NA |
| | D(1 × 6)122#3 | 2 | − | NA |
| | D(1 × 6)114 | 2 | − | NA |
| | D(1 × 6)17#33 | 2 | In progress | In progress |
| | HB13-3 | 3 | + | In progress |
| | HA133-227 | 2 | − | NA |
| | G(6 × 1)17#25 C | 3 | + | In progress |
| | ABT4 | 4 | + | + |
| | ABT3 | 4 | + | + |
| | AB60 | 4 | + | + |
| | AB61 | 4 | + | + |
| | AB63 | 4 | + | + |
| | AB80 | 4 | + | + |
| | AB82 | 4 | + | In progress |
| | ABT6 | 4 | + | ND |
| | AB12 | 4 | + | + |
| | PH2 | 4 | + | + |
| | AB69 | 4 | + | − |
| | AB44 | 4 | + | − |
| | AB62 | 4 | + | ND |
| A188 × B84 | G(1 × M)82 | 1 | + | − |
| A188 × H99 | HJ11-7 | 3 | + | In progress |
| B73 × A188 | G(6 × 1)12#7 | 2 | − | NA |
| | D(6 × 1)11#43 | 2 | − | NA |
| | E1 | 2 | + | |
| Hi-II | G(CW)31#24 | | + | In progress |
| B73 | (6)91#3 | 2 | − | NA |
| | (6)91#2 | 2 | − | NA |
| B73-derived | AT824 | 1,2,3 | + | + |
| N1017A | AZ11137a | 2 | + | In progress |
| Cat 100 | CB | 2 | + | ND |
| | CC | 2 | + | ND |
| A188 | E4 | 2 | + | − |

The symbol "−" indicates that the line was not transformable after 3 attempts or plants were sterile
NA indicates Not Applicable
ND indicates Not Done

EXAMPLE 1

Initiation of the Suspension Culture G(A188XB73) 716 (designated SC716) for Use in Transformation This Example describes the development of a maize suspension culture, designated SC716, which was employed in various of the transformation studies described hereinbelow. The Type II tissue used to initiate the cell suspension was initiated from immature embryos of A188×B73 plated onto N6-based medium with 1 mg/ml 2,4-D (201; see Table 1). A Type II callus was initiated by visual selection of fast growing, friable embryogenic cells. The suspension was initiated within 6 months after callus initiation. Tissue chosen from the callus to initiate the suspension consisted of undifferentiated Type II callus. The characteristics of this undifferentiated tissue include the earliest stages of embryo development and soft, friable, undifferentiated tissue underlying it.

Approximately one gram of tissue was added to 20 mls of liquid medium. In this example, the liquid medium was medium 402 to which different slow-release growth regulator capsule treatments were added (Adams, W. R., Adams, T. R., Wilston, H. M., Krueger, R. W., and Kausch, A. P., Silicone capsules for controlled Auxin Release, in preparation). These capsule treatments included 2,4-D, NAA, 2,4-D plus NAA, and two NAA capsules. One flask was initiated for each of the different 402 media plus growth regulator combinations. Every 7 days each culture was subcultured into fresh medium by transferring a small portion of the cellular suspension to a new flask. This involved swirling the original flask to suspend the cells (which tend to settle to the bottom of the culture vessel), tilting the flask on its side and allowing the denser cells and cell aggregates to settle slightly. One ml of packed cells was then drawn off from this pool of settled cells together with 4 mls of conditioned medium and added to a flask containing 20 ml fresh medium. A sterile ten ml, wide tip, pipet was used for this transfer (Falcon 7304). Any very large aggregates of cells which would not pass easily through the pipet tip were excluded. If a growth regulator capsule was present, it was also transferred to the new flask.

After approximately 7 weeks, the loose embryogenic cell aggregates began to predominate and fragment in each of the cultures, reaching a state referred to as "dispersed". The treatment which yielded the highest proportion of embryogenic clusters was the 402 medium plus one NAA capsule. After the cultures became dispersed and were doubling approximately every two to three days as determined by increase in packed cell volume, a one ml packed cell volume inoculum from each culture was transferred into 20 ml 401 medium using a ten ml narrow tip pipet (Falcon 7551). These transfers were performed about every 3½ days. An inoculum from the 402 plus 2,4-D plus NAA capsules culture was also used to initiate a culture in 409 medium (402 without 2,4-D and including 10 mg/l dicamba) either with or without 1 ml coconut water (Gibco 670-8130AG) per 25 ml culture medium.

The most dispersed cultures were cryopreserved after 2 weeks, 2 months or 5 months.

The culture grown on 409 with coconut water was thawed eight months after cryopreservation, cultured for two weeks on solid 201 culture medium using BMS as a feeder layer (Rhodes et al., 1988) and transferred to media 409 without coconut water. The culture was maintained by subculturing twice weekly in 409 medium by the method described above.

EXAMPLE 2

Initiation of the Suspension Culture (A188×B73)82 (Designated SC82) for Use in Transformation This example describes the development of another cell line employed in various of the transformation studies set forth below, termed SC82. In the development of SC82, inoculum for suspension culture initiation was visually selected from a Type II callus that was initiated from A188×B73 immature embryos plated on a N6-based medium containing 13.2 mg/l dicamba (227, Table 1). The suspension culture was initiated within 3 months of initiation of the Type II callus. Small amounts (50–100 mg) of callus distinguishable by visual inspection because of its highly proembryonic morphology, were isolated from more mature or organized structures and inoculated into a 50 ml flask containing 5 mls of filter-sterilized conditioned medium from the various G(A188×B73) 716 suspension cultures (402 medium with four types of capsule treatments and 409 medium).

After one week, this 5 ml culture was sieved through a 710 micron mesh and used to inoculate 20 mls of corresponding fresh and filter-sterilized conditioned medium from the established G(A188×B73) 716 cultures in 150 ml flasks. After one week or more of growth, two mls of packed cells were subcultured to fresh media by the method described above. The suspension culture maintained on 409 by this method was then cryopreserved within 3 months. The original cell line, which was maintained on 409 (not a reinoculated cryopreserved culture) was used in experiments 1 and 2 months later which resulted in stable transformation and selection (see Table 6 below). The cryopreserved culture was used for experiment 6 (see Table 6 below).

EXAMPLE 3

Initiation and Maintenance of Cell Line AT824

This example describes the initiation and maintenance of cell line AT824 which has been used routinely for transformation experiments. Immature embryos (0.5–1.0 mm) were excised from the B73-derived inbred line AT and cultured on N6 medium with 100 uM silver nitrate, 3.3 mg/L dicamba, 3% sucrose and 12 mM proline (2004). Six months after initiation type I callus was transferred to medium 2008. Two months later type I callus was transferred to a medium with a lower concentration of sucrose (279). A sector of type II callus was identified 17 months later and was transferred to 279 medium. This cell line is uniform in nature, unorganized, rapid growing, and embryogenic. This culture is desirable in the context of this invention as it is easily adaptable to culture in liquid or on solid medium.

The first suspension cultures of AT824 were initiated 31 months after culture initiation. Suspension cultures may be initiated in a variety of culture media including media containing 2,4-D as well as dicamba as the auxin source, e.g., media designated 210, 401, 409, 279. Cultures are maintained by transfer of approximately 2 ml packed cell volume to 20 ml fresh culture medium at 3½ day intervals. AT824 can be routinely transferred between liquid and solid culture media with no effect on growth or morphology.

Suspension cultures of AT824 were initially cryopreserved 33–37 months after culture initiation. The survival rate of this culture was improved when it was cryopreserved following three months in suspension culture. AT824 suspension cultures have been cryopreserved and reinitiated from cryopreservation at regular intervals since the initial date of freezing. Repeated cycles of freezing have not affected the growth or transformability of this culture.

EXAMPLE 4

Initiation and Maintenance of Cell Lines ABT3, ABT4, ABT6, AB80, AB82, AB12, AB44, AB60, AB61, AB62, AB63, AB69

Friable, embryogenic maize callus cultures were initiated from hybrid immature embryos produced by pollination of inbred A188 plants (University of Minnesota, Crop Improvement Association) with pollen of inbred line B73 plants (Iowa State University). Ears were harvested when the embryos had reached a length of 1.5 to 2.0 mm. The whole ear was surface sterilized in 50% v/v commercial bleach (2.63% w/v sodium hypochlorite) for 20 min. at room temperature. The ears were then washed with sterile distilled, dionized water. Immature embryos were aseptically isolated and placed on nutrient agar initiation/maintenace media with the root/shoot axis exposed to the medium. Initiation/maintenance medium (hereinafter referred to as medium 734) consisted of N6 basal medium (Chu 1975) with 2% (w/v) sucrose, 1.5 mg per liter 2,4-dichlorophenoxyacetic acid (2,4-D), 6 mM proline, and 0.25% Gelrite (Kelco, Inc. San Diego). The pH was adjusted to 5.8 prior to autoclaving. Unless otherwise stated, all tissue culture manipulations were carried out under sterile conditions.

The immature embryos were incubated at 26° C. in the dark. Cell proliferation from the scutellum of the immature embryos were evaluated for friable consistency and the presence of well defined somatic embryos. Tissue with this morphology was transferred to fresh media 10 to 14 days after the initial plating of the immature embryos. The tissue was then subcultured on a routine basis every 14 to 21 days. Sixty to eighty milligram quantities of tissue were removed from pieces of tissue that had reached a size of approximately one gram and transferred to fresh medium. Subculturing always involved careful visual monitoring to be sure that only tissue of the correct morphology was maintained. The presence of somatic embryos ensured that the cultures would give rise to plants under the proper conditions. The cell cultures named ABT3, ABT4, ABT6, AB80, AB82, AB12, AB44, AB60, AB61, AB62, AB63, AB69 were initiated in this manner. The cell lines ABT3, ABT4, and ABT6 were initiated from immature embryos of a 5-methyltryptophan resistant derivative of A188×B73.

EXAMPLE 5

Initiation and Maintenance of Type II Callus of the Genotype Hi-II

The Hi-II genotype of corn was developed from an A188×B73 cross. This genotype was developed specifically for a high frequency of initiation of type II cultures (100% response rate, Armstrong et al., 1991). Immature embryos (8–12 days post-pollination, 1 to 1.2 mm) were excised and cultured embryonic axis down on N6 medium containing 1 mg/L 2,4-D, 25 mM L-proline (201) or N6 medium containing 1.5 mg/L 2,4-D, 6 mm L-proline (734). Type II callus can be initiated either with or without the presence of 100 $\mu$M AgNo$_3$. Cultures initiated in the presence of AgNo$_3$ was transferred to medium lacking this compound 14–28 days after culture initiation. Callus cultures were incubated in the dark at 23–28° C. and transferred to fresh culture medium at 14 day intervals.

Hi-II type II callus is maintained by manual selection of callus at each transfer. Alternatively, callus can be resuspended in liquid culture medium, passed through a 1.9 mm sieve and replated on solid culture medium at the time of transfer. It is believed that this sequence of manipulations is one way to enrich for recipient cell types. Regenerable type II callus that is suitable for transformation can be routinely developed from the Hi-II genotype and hence new cultures are developed every 6–9 months. Routine generation of new cultures reduces the period of time over which each culture is maintained and hence insures reproducible, highly regenerable, cultures that routinely produce fertile plants.

EXAMPLE 6

Initiation of Cell Line E1

An ear of the genotype B73 was pollinated by A188. Immature embryos (1.75–2.00 mm) were excised and cultured on 212 medium (see Table 1). About 4 months after embryo excision, approximately 5 ml PCV type II callus was inoculated into 50 ml liquid 210 medium (see Table 1). The suspension was maintained by transfer of 5 ml suspension to 50 ml fresh 210 medium every 3½ days. This suspension culture was cryopreserved about 4 months after initiation.

D. Cryopreservation Methods

Cryopreservation is important because it allows one to maintain and preserve a known transformable cell culture for future use, while eliminating the cummulative detrimental effects associated with extended culture periods.

Cell suspensions and callus were cryopreserved using modifications of methods previously reported (Finkle, 1985; Withers & King, 1979). The cryopreservation protocol comprised adding a pre-cooled (0° C.) concentrated cryoprotectant mixture stepwise over a period of one to two hours to pre-cooled (0° C.) cells. The mixture was maintained at 0° C. throughout this period. The volume of added cryoprotectant was equal to the initial volume of the cell suspension (1:1 addition), and the final concentration of cryoprotectant additives was 10% dimethyl sulfoxide, 10% polyethylene glycol (6000 MW), 0.23M proline and 0.23M glucose. The mixture was allowed to equilibrate at 0° C. for 30 minutes, during which time the cell suspension/cryoprotectant mixture was divided into 1.5 ml aliquot (0.5 ml packed cell volume) in 2 ml polyethylene cryo-vials. The tubes were cooled at 0.5° C./minute to −8° C. and held at this temperature for ice nucleation.

Once extracellular ice formation had been visually confirmed, the tubes were cooled at 0.5° C./minute from −8° C. to −35° C. They were held at this temperature for 45 minutes (to insure uniform freeze-induced dehydration throughout the cell clusters). At this point, the cells had lost the majority of their osmotic volume (i.e. there is little free water left in the cells), and they could be safely plunged into liquid nitrogen for storage. The paucity of free water remaining in the cells in conjunction with the rapid cooling rates from −35 to −196° C. prevented large organized ice crystals from forming in the cells. The cells are stored in liquid nitrogen, which effectively immobilizes the cells and slows metabolic processes to the point where long-term storage should not be detrimental.

Thawing of the extracellular solution was accomplished by removing the cryo-tube from liquid nitrogen and swirling it in sterile 42° C. water for approximately 2 minutes. The tube was removed from the heat immediately after the last ice crystals had melted to prevent heating the tissue. The cell suspension (still in the cryoprotectant mixture) was pipetted onto a filter, resting on a layer of BMS cells (the feeder layer which provided a nurse effect during recovery). Dilution of the cryoprotectant occurred slowly as the solutes diffused away through the filter and nutrients diffused upward to the recovering cells. Once subsequent growth of the thawed cells was noted, the growing tissue was transferred to fresh culture medium. The cell clusters were transferred back into liquid suspension medium as soon as sufficient cell mass had been regained (usually within 1 to 2 weeks). After the culture was reeastablished in liquid (within 1 to 2 additional weeks), it was used for transformation experiments. When desired, previously cryopreserved cultures may be frozen again for storage.

E. DNA Segments Comprising Exogenous Genes

As mentioned previously, there are several methods to construct the DNA segments carrying DNA into a host cell that are well known to those skilled in the art. The general construct of the vectors used herein are plasmids comprising a promoter, other regulatory regions, structural genes, and a 3' end.

Several plasmids encoding a variety of different genes have been constructed by the present inventors, the important features of which are represented below in Table 3. Certain of these plasmids are also shown in FIG. 1: pDPG165, FIG. 1(A, C); pDPG208, FIG. 1(B, D); pDPG141, FIG. 1(E); pDPG237, FIG. 1(F); pDPG313 through pDPG319, FIG. 1(H) through FIG. 1(N); pDPG290, FIG. 1(O); pDPG300 through pDPG304, FIG. 1(P) through FIG. 1(S); pDPG386 through pDPG389, FIG. 1(T) through FIG. 1(W); pDPG140, FIG. 1(X); pDPG172, FIG. 1(Y); pDPG425, FIG. 1(Z); pDPG427, FIG. 1(AA); pDPG451, FIG. 1(BB); pDPG354, FIG. 1(CC); pDPG344, FIG. 1(DD); pDPG337, FIG. 1(EE).

TABLE 3

| RECOMBINANT VECTOR DESIGNATION & SOURCE | PARENT REPLICON | INSERT DNA | DELIBERATE EXPRESSION ATTEMPT |
|---|---|---|---|
| pDPG140 | pUC19 | 1,118,102, 103 | 1 |
| pDPG141 | pUC19 | 1, 100, 101 | 1 |
| pDPG165 | pUC19 | 2, 100, 101 | 2 |
| pDPG172 | pUC19 | 3,118,102, 103 | 3 |
| pDPG182 | pUC19 | 2,118,102, 103 | 2 |
| pDPG205 | pVK101 | 1, 101, 102 | 1 |
| pDPG2 08 | pUC19 | 1, 100 | 1 |
| pDPG215 | pUC18 | 3, 100, 102, 103 | 3 |
| pDPG215 | pUC19 | 3, 100, 101, 102 | 3 |
| pDPG226 | pUC19 | 4, 100, 101 | 4 |
| pDPG230–231, 251, 262–264, 279, 282, 283 | pUC19 | 1, 2, 100, 101 | 1, 2 |
| pDPG238-239 | pUC19 | 2, 4, 100, 101 | 2, 4 |
| pDPG240-241 | pUC19 | 2, 5, 100, 101 | 2, 5 |
| pDPG243-244 | pUC19 | 2, 6, 100, 101 | 2, 6 |
| pDPG246 | pUC19 | 7, 100, 101 | 7 |
| pDPC265 | pBR325 | 9, 100 | 9 |
| pDPG266-267 | pUC19 | 8, 100, 101 | 8 |
| pDPG268-269 | pUC19 | 1, 100, 102 | 1 |
| pDPG270-273 | pUC19 | 9, 100, 101 | 1 |
| pDPG274 | pUC19 | 101 | 9 |
| pDPG275 | pUC18 | 10, 3, 100 | 10, 3 |
| pDPG287 | pUC19 | 2, 103, 105 | 2 |
| pDPG288 | pUC13 | 11, 100, 103 | 11 |
| pDPG290 | pUC19 | 12, 100, 103 | 12 |
| pDPG291 | pUC19 | 1, 103, 104 | 1 |
| pDPG300 | PUC19 | 2, 12, 100, 101, 102, 103 | 2, 12 |

TABLE 3-continued

| RECOMBINANT VECTOR DESIGNATION & SOURCE | PARENT REPLICON | INSERT DNA | DELIBERATE EXPRESSION ATTEMPT |
|---|---|---|---|
| pDPG301 | pUC19 | 2, 12, 100, 101, 102, 103 | 2, 12 |
| pDPG302 | pUC18 | 2, 12, 100, 101, 102, 103 | 2, 12 |
| pDPG303 | pUC18 | 2, 12, 100, 101, 102, 103 | 2, 12 |
| pDPC304 | ColE1 | 13, 100, 103 | 13 |
| pDPG313 | pUC18 | 2, 4, 100, 103, 106, 107 | 2, 4 |
| pDPG314 | pUC19 | 2, 4, 100, 103, 106, 107 | 2, 4 |
| pDPG315 | pUC23 | 2, 4, 100, 103, 106, 108 | 2, 4 |
| pDPG316 | pUC23 | 2, 4, 100, 103, 106, 108 | 2, 4 |
| pDPG317 | pUC23 | 2, 4, 100, 103, 106, 107 | 2, 4 |
| pDPG318 | pUC23 | 2, 4, 100, 103, 106, 109 | 2, 4 |
| pDPG319 | pUC23 | 2, 4, 100, 103, 106, 109 | 2, 4 |
| pDPG320 | pUC18 | 11, 100, 102, 103 | 11 |
| pDPG324 | pUC19 | 1, 2, 100, 101 | 1, 2 |
| pDPG325 | pUC19 | 1, 2, 100, 101 | 1, 2 |
| pDPG326 | pUC19 | 1, 2, 100, 101, 102 | 1, 2 |
| pDPG327 | pUC19 | 1, 2, 100, 101, 102 | 1, 2 |
| pDPG328 | pUC19 | 1, 2, 100, 101, 113 | 1, 2 |
| pDPG329 | pUC19 | 1, 2, 100, 101, 113 | 1, 2 |
| pDPG332 | pUC19 | 14, 100, 110 | 14 |
| pDPG334 | pGEM3 | 15, 111, 121, 103 | 15 |
| pDPG335 | pUC119 | 15, 112, 122, 114 | 15 |
| pDPG336 | PIC20H | 19, 100, 117, 103 | 19 |
| pDPG337 | p1C20H | 19, 100, 117, 103 | 19 |
| pDPG338 | pUC120 | 16, 112, 114, 115 | 16 |
| pDPG339 | pUC119 | 17, 111, 103 | 17 |
| pDPG340 | pUC19 | 18, 111, 103 | 18 |
| pDPG344 | pSK | 11, 100, 102, 110 | 11 |
| pDPG345 | pSK | 2, 14, 100, 102, 110, 103 | 2, 14 |
| pDPG346 | pSK | 2, 14, 100, 102, 110, 103 | 2, 14 |
| pDPG347 | pSK | 2, 14, 100, 102, 110, 103 | 2, 14 |
| pDPG348 | pSK | 2, 14, 100, 102, 110, 103 | 2, 14 |
| pDPG351 | pUC19 | 3, 100, 101 | 3 |
| pDPG354 | pSK– | 19, 100, 101, 110 | 19 |
| pDPG355 | pUC19 | 1, 100, 102, 103 | 1 |
| pDPG356 | pUC19 | 1, 100, 116, 103 | 1 |
| pDPG357 | p1C20H | 1, 100, 117, 103 | 1 |
| pDPG358 | pUC8 | 1, 118, 102, 103 | 1 |
| pDPG359 | pUC119 | 1, 119, 103 | 1 |
| pDPG360 | pUC119 | 1, 120, 103 | 1 |
| pDPG361 | pUC19 | 1, 111, 103 | 1 |
| pDPG362 | pUC120 | 1, 112, 103 | 1 |
| pDPG363 | pSP73 | 2, 100, 102, 103 | 2 |
| pDPG364 | pUC119N | 20, 100 | 20 |
| pDPG365 | PUC19 | 21, 100, 103 | 21 |
| pDPG366 | pSP73 | 22, 100, 102, 103 | 22 |
| pDPG367 | pBS+ | 22, 100, 102, 103 | 22 |
| pDPG368 | pSP73 | 24, 100, 102, 103 | 24 |
| pDPG369 | p1C20H | 24, 100, 117, 103 | 24 |
| pDPG370 | pBS+ | 5, 100, 116, 103 | 5 |
| pDPG371 | pSP73 | 15, 100, 121, 103 | 15 |
| pDPG372 | pUC119 | 15, 100, 122, 103 | 15 |
| pDPG373 | pUC119 | 16, 120, 115 | 16 |
| pDPG374 | pUC120 | 16, 112, 114 | 16 |
| pDPG375 | pUC119 | 16, 111, 115 | 16 |
| pDPG376 | pUC119 | 18, 111, 103 | 18 |
| pDPG377 | pUC119 | 18, 111, 103 | 18 |
| pDPG378 | PUC119 | 17, 111, 103 | 17 |
| pDPG379 | pUC119 | 17, 111, 103 | 17 |
| pDPG380 | pUC119 | 17, 111, 103 | 17 |
| pDPG381 | p1C20H | 19, 100, 117, 103 | 19 |
| pDPG382 | p1C20H | 19, 100, 117, 103 | 19 |
| pDPG384 | pUC8 | 19, 100, 102, 103 | 19 |
| pDPG385 | PSP73 | 23, 100, 121, 103 | 23 |
| pDPG386 | pACYC177 | 6,114 | 6 |
| pDPG387 | pACYC177 | 1,6,100,114 | 1,6 |
| pDPG388 | pACYC177 | 2,6,100,103, 114 | 2,6 |
| pDPG389 | pACYC177 | 2,6,100,103, 114, | 2,6 |
| pDPG391 | pUC8 | 19, 100, 102, 103 | 19 |

TABLE 3-continued

| RECOMBINANT VECTOR DESIGNATION & SOURCE | PARENT REPLICON | INSERT DNA | DELIBERATE EXPRESSION ATTEMPT |
|---|---|---|---|
| pDPG392 | pUC19 | 2, 100, 101 | 2 |
| pDPG393 | pSK– | 4, 109, 102, 106, 103 | 4 |
| pDPG394 | pSK– | 4, 124, 106, 103 | 4 |
| pDPG396 | PBS+ | 19, 100, 102, 7, 103, 121 | 19 |
| pDPG404 | pSK– | 1, 108, 103 | 1 |
| pDPG405 | pSK– | 1, 107, 103 | 1 |
| pDPG406 | pSK– | 1, 109, 103 | 1 |
| pDPG407 | pSK– | 1, 109, 102, 103 | 1 |
| pDPG408 | pSK– | 1, 124, 103 | 1 |
| pDPG411 | pBS+ | 19, 100, 103, 121 | 19 |
| pDPG415 | pUC8 | 19, 118, 103 | 19 |
| pDPG418 | PGEM | 15, 122, 123 | 15 |
| pDPG419 | pUC19 | 3,100,101, 116, | 3 |
| pDPG420 | pUC19 | 3,100,101, 116 | 3 |
| pDPG421 | pSP72 | 2,103,126 | 2 |
| pDPG422 | pBS | 1,103,126 | 1 |
| pDPG424 | pSK– | 4, 124, 102, 103 | 4 |
| pDPG427 | pSK– | 25, 124, 102, 103 | 25 |
| pDPG434 | pSK– | 25,103,126 | 25 |
| pDPG436 | pSK– | 25,100,102 103 | 25 |
| pDPG437 | pUC19 | 2.100,101, 102 | 2 |
| pDPG438 | pUC19 | 2,100,101, 102 | 2 |
| pDPG439 | pUC19 | 2,100,101, 102 | 2 |
| pDPG441 | pSK– | 25,103,108 | 25 |
| pDPG443 | pSK– | 25,100,103 , 108 | 25 |
| pDPG447 | pSK– | 25,102,103 , 109 | 25 |
| pDPG451 | pUC18 | 26,100,102 , 103 | 26 |
| pDPG452 | pGEM | 2,123 | 2 |
| pDPG453 | pUC19 | 2, 103,127 | 2 |
| pDPG456 | pSK– | 19, 100, 101, 110 | 19 |
| pDPG457 | pSK– | 19, 100, 101, 110 | 19 |
| pDPG458 | pSK– | 1,103,127 | 1 |
| pDPG465 | pSK– | 25,100,101 , 102 | 25 |
| pDPG467 | pSK– | 25,102,118 | 25 |
| pDPG469 | pUC19 | 26,118,102 , 103 | 26 |
| pDPG474 | pUC19 | 27,100,102 , 103 | 27 |

KEY

Insert DNA and Deliberate Expression Attempt

1. The uidA gene from *E. coli* encodes β-glucuronidase (GUS). Cells expressing uidA produce a blue color when given the appropriate substrate. Jefferson, R. A. 1987. Plant Mol. Biol. Rep 5: 387–405.

2. The bar gene from *Streptomyces hygroscopicus* encodes phosphinothricin acetyltransferase (PAT). Cells expressing PAT are resistant to the herbicide Basta. White, J., Chang, S.-Y. P., Bibb, M. J., and Bibb, M. J. 1990. Nucl. Ac. Research 18: 1062.

3. The lux gene from firefly encodes luciferase. Cells expressing lux emit light under appropriate assay conditions. deWet, J. R., Wood, K. V., DeLuca, M., Helinski, D. R., Subramani, S. 1987. Mol. Cell. Biol. 7: 725–737.

4. The aroA gene from *Salmonella typhimurium* encodes 5-enolpyruvylshikimate 3-phosphate synthase (EPSPS). Comai, L., Sen, L. C., Stalker, D. M., Science 221: 370–371, 1983.

5 The dhfr gene from mouse encodes dihydrofolate reductase (DHFR). Cells expressing dhfr are resistant to methotrexate. Eichholtz, D. A., Rogers, S. G., Horsch, R. B., Klee, H. J., Hayford, M., Hoffman, N. L., Bradford, S. B., Fink, C., Flick, J., O'Connell, K. M., Frayley, R. T. 1987. Somatic Cell Mol. Genet. 13: 67–76.

6. The neo gene from *E. coli* encodes aminoglycoside phosphotransferase (APH). Cells expressing neo are resistant to the aminoglycoside antibiotics. Beck, E., Ludwig, G., Auerswald, E. A., Reiss, B., Schaller, H. 1982. Gene 19: 327–336.

7. The amp gene from *E. coli* encodes β-lactamase. Cells expressing β-lactamase produce a chromogenic compound when given the appropriate substrate. Sutcliffe, J. G. 1978. Proc. Nat. Acad. Sci. USA 75: 3737–3741.

8. The xylE gene from *Ps. putida* encodes catechol dihydroxygenase. Cells expressing xylE produce a chromogenic compound when given the appropriate substrate. Zukowsky et al. 1983. Proc. Nat. Acad. Sci. USA 80: 1101–1105.

9. The R, C1 and B genes from maize encode proteins that regulate anthocyanin biosynthesis in maize. Goff, S., Klein, T., Ruth, B., Fromm, M., Cone, K., Radicella, J., Chandler, V. 1990. EMBO J.: 2517–2522.

10. The als gene from *Zea mays* encodes acetolactate synthase. The enzyme was mutated to confer resistance to sulfonylurea herbicides. Cells expressing als are resistant to the herbicide Gleen. Yang, L. Y., Gross, P. R., Chen, C. H., Lissis, M. 1992. Plant Molecular Biology 18: 1185–1187.

11. The proteinase inhibitor II gene was cloned from potato and tomato. Plants expressing the proteinase inhibitor II gene show increased resistance to insects. Potato: Graham, J. S., Hall, G., Pearce, G., Ryan, C. A. 1986 Mol. Cell. Biol. 2: 1044–1051. Tomato: Pearce, G., Strydom, D., Johnson, S., Ryan, C. A. 1991. Science 253: 895–898.

12. The Bt gene from *Bacillus thuringensis* berliner 1715 encodes a protein that is toxic to insects. Plants expressing this gene are resistent to insects. This gene is the coding sequence of Bt 884 modified in two regions for improved expression in plants. Vaeck, M., Reynaerts, A., Hofte, H., Jansens, S., DeBeuckeleer, M., Dean, C., Aeabeau, M., Van Montagu, M., and Leemans, J. 1987. Nature 328: 33–37.

13. The bxn gene from *Klebsiella ozaeneae* encodes a nitrilase enzyme specific for the herbicide bromoxynil. Cells expressing this gene are resistant to the herbicide bromoxynil. Stalker, D. m., McBride, K. E., and Malyj, L. Science 242: 419–422, 1988.

14. The WGA-A gene encodes wheat germ agglutinin. Expression of the WGA-A gene confers resistance to insects. The WGA-A gene was cloned from wheat. Smith, J. J., Raikhel, N. V. 1989. Plant Mol. Biology 13: 601–603.

15. The dapA gene was cloned from *E. coli*. The dapA gene codes for dihydrodipicolinate synthase. Expression of this gene in plant cells produces increased levels of free lysine. Richaud, F., Richaud, C., Rafet, P. and Patte, J. C. 1986. J. Bacteriol. 166: 297–300.

16. The Z10 gene codes for a 10 kd zein storage protein from maize. Expression of this gene in cells alters the quantities of 10 kD Zein in the cells. Kirihara, J. A., Hunsperger, J. P., Mahoney, W. C., and Messing, J. 1988. Mol. Gen. Genef. 211: 477–484.

17. The A20 sequence encodes the 19 kd zein storage protein of *Zea mays*. Expression of the construct in maize alters quantities of the native 19 kd zein gene.

18. The Z4 sequence is for the 22 kd zein storage protein of *Zea mays*. Expression of this construct in maize alters quantities of the native 22 kd zein gene.

19. The Bt gene cloned from *Bacillus thuringensis* Kurstaki encodes a protein that is toxic to insects. The gene is the coding sequence of the cry IA(c) gene modified for improved expression in plants. Plants expressing this gene are resistant to insects. Höfte, H. and Whiteley, H. R., 1989. Microbiological Reviews. 53: 242–255.

20. The als gene from *Arabidopis thaliana* encodes a sulfonylurea herbicide resistant acetolactate synthase enzyme. Cells expresing this gene are resistant to the herbicide Gleen. Haughn, G. W., Smith, J., Mazur, B., and Somerville, C. 1988. Mol. Gen. Genet. 211: 266–271.

21. The deh1 gene from *Pseudomonas putida* encodes a dehalogenase enzyme. Cells expressing this gene are resistant to the herbicide Dalapon. Buchanan-Wollaston, V., Snape, A., and Cannon, F. 1992. Plant Cell Reports 11: 627–631.

22. The hygromycin phosphotransferase II gene was isolated from *E. coli*. Expression of this gene in cells produces resistance to the antibiotic hygromycin. Waldron, C., Murphy, E. B., Roberts, J. L., Gustafson, G. D., Armour, S. L., and Malcolm, S. K. Plant Molecular Biology 5: 103–108, 1985.

23. The lysC gene from *E. coli* encodes the enzyme aspartyl kinase III. Expression of this gene leads to increased levels of lysine in cells.

24. The hygromycin phosphotransferase II gene was isolated from *Streptomyces hygroscopicus*. Expression of this gene in cells produces resistance to the antibiotic hygromycin.

25. The EPSPS gene (5-enolpyruvy/shikimate-3-phosphate synthase) gene from *Zea mays* was mutated to confer resistance to the herbicide Roundup®. An isoleucine has been substituted for threonine at amino acid position 102 and a serine has been substituted for proline at amino acid position 106.

26. The mtlD gene was cloned from *E. coli*. This gene encodes the enzyme mannitol-1-phosphate dehydrogenase. Lee and Saier, 1983. J. of Bacteriol. 153:685.

27. The HVA-1 gene encodes a Late Embryogenisis Abundant (LEA) protein. This gene was isolated from barley. Dure, L., Crouch, M., Harada, J., Ho, T.-H. D. Mundy, J., Quatrano, R, Thomas, T, and Sung, R., Plant Molecular Biology 12: 475–486.

Regulatory Sequences

100. Promoter sequences from the Cauliflower Mosaic Virus genome. Odell, J. T., Nagy, F., and Chua, N.-H. 1985. Nature 313: 810–812.

101. Promoter and terminator sequences from the Ti plasmid of *Agrobacterium tumefaciens*. (a) Bevan, M., 1984. Nucleic Acid Research 12: 8711–8721; (b) Ingelbrecht, I. L. W., Herman, L. M. F., DeKeyser, R. A., Van Montagu, M. C., Depicker, A. G. 1989. The Plant Cell 1: 671–680; (c) Bevan, M., Barnes, W. M., Chilton, M. D., 1983. Nucleic Acid Research. 11: 369–385; (d) Ellis, J. G., Llewellyn, D. J., Walker, J. C., Dennis, E. S., Peacocu, W. J. 1987. EMBO J. 6: 3203–3208.

102. Enhancer sequences from the maize alcohol dehydrogenase gene. Callis, J., Fromm, M. E., Walbot, V., 1987. Genes Dev. 1: 1183–1200.

103. Terminator sequences from Ti plasmid of *Agrobacterium tumefaciens*. (a) Bevan, M., 1984. Nucleic Acid Research 12: 8711–8721; (b) Ingelbrecht, I. L. W., Herman, L. M. F., DeKeyser, R. A., Van Montagu, M. C., Depicker, A. G. 1989. The Plant Cell 1: 671–680; (c) Bevan, M., Barnes, W. M., Chilton, M. D., 1983. Nucleic Acid Research. 11: 369–385.

104. Pollen specific promoter sequence ZM13 from maize.

105. Transit peptide sequence from rbcS gene from pea. Fluhr, R., Moses, P., Morelli, G., Coruzzi, C., Chua, N.-H. 1986. EMBO J. 5: 2063–2071.

106. Optimized transit peptide sequence consisting of sequences from sunflower and maize. Constructed by Rhône Poulenc Agrochimie.

107. Fused promoter sequences from Cauliflower Mosaic Virus genome and *Arabidopsis thaliana* H4 histone gene. Constructed by Rhône Poulenc Agrochimie.

108. Promoter sequences from *Arabidopsis thaliana* histone H4 gene. Chaboute, H. E., Chambet, N., Philipps, G., Ehling, M. and Grigot, C. 1987. Plant Mol. Biol. 8: 179–191.

109. Promoter sequence from maize α-tubulin gene.

110. Terminator sequences from the potato proteinase inhibitor II gene. An, G., Mitra, A., Choi, H. K., Costa, M. A., An, K., Thornburg, R. W., Ryan, C. A. 1989. Plant Cell 1: 115–122.

111. Promoter from the maize 10 kd zein gene.

112. Promoter from the maize 27 kd zein gene. Ueda, T. and Messing, J. 1991. Theor. Appl. Genet. 82: 93–100.

113. The matrix attachment region (MAR) was isolated from chicken. Use of this DNA sequence reduces variations in gene expression due to integration position effects. Stief, A., Winter, D., Stratling, W. H., Sippel, A. E. 1989. Nature 341: 343.

114. Terminator sequences from the Cauliflower Mosaic Virus genome. Timmermans, M. C. P., Maliga, P., Maliga, P., Vieniera, J. and Messing, J. 1990. J. Biotechnol. 14: 333–344.

115. Terminator from maize 10 kd zein gene. Kirihara, J. A., Hunsperger, J. P., Mahoney, W. C., Messing, J. 1988. Mol. Gen. Genet. 211: 477–484.

116. Enhancer sequence from the shrunken-1 gene of *Zea mays*. Vasil, V., Clancy, M., Ferl, R. J., Vasil, I. K., Hannah, L. C. 1989. Plant Physiol. 91: 1575–1579.

117. RNA leader sequence from the ribulose-bisphosphate carboxylase gene from *Glycine max*. Joshi, C. P. 1987. Nucleic Acids Res. 15: 6643–9640.

118. Promoter sequence from the alcohol dehydrogenase gene of *Zea mays*. Walker, J. C., Howard, E. A., Dennis, E. S., Peacock, W. J. 1987. P.N.A.S. 84: 6624–6628.

119. Promoter sequence from the glutamine synthetase gene of *Zea mays*.

120. Promoter sequence from the 22 kD (Z4) zein gene of *Zea mays*. Schmidt, R. J., Ketudat, M., Ankerman, M. J. and Hoschek, G. 1992. Plant Cell 4: 689–700.

121. Transit peptide sequence of the ribulose bisphosphate carboxylase small subunit gene from *Zea mays*. GenBank Accession Y00322.

122. Transit peptide sequence of the dihydropicolinic acid synthase gene of *Zea mays*.

123. Globulin-1, glb1, promoter and terminator sequences from *Zea mays*. Belanger and Kriz. 1991

124. Promoter sequence from maize histone H3C4. Chaubet, N., Clement, B., Philipps, G. and Gigot, C. 1991. Plant Molecular Biology 17: 935–940.

125. DNA sequence encoding first 8 amino acids of the mature ribulose bisphosphate carboxylase gene of *Zea mays*.

126. Actin-1 5' region including promoter from *Zea mays*. Wang, Y., Zhang, W., Cao, J., McEhoy, D. and Ray Wu. 1992. Molecular and Cellular Biology 12: 3399–3406.

127. The DS element isolated from *Zea mays*.

DNA segments encoding the bar gene were constructed into a plasmid, termed pDPG165, which was used to introduce the bialophos resistance gene into recipient cells (see FIGS. 1A and C). The bar gene was cloned from *Streptomyces hygroscopicus* (White et al., 1990) and exists as a 559-bp Sma I fragment in plasmid pIJ4101. The sequence of the coding region of this gene is identical to that published (Thompson et al., 1987). To create plasmid pDPG165, the Sma I fragment from pIJ4104 was ligated into a pUC19-based vector containing the Cauliflower Mosaic Virus (CaMV) 35S promoter (derived from pBI221.1, provided by R. Jefferson, Plant Breeding Institute, Cambridge, England), a polylinker, and the transcript 7 (Tr7) 3' end from *Agrobacterium tumefaciens* (3' end provided by D. Stalker, Calgene, Inc., Davis, Calif.).

Figure 1B:
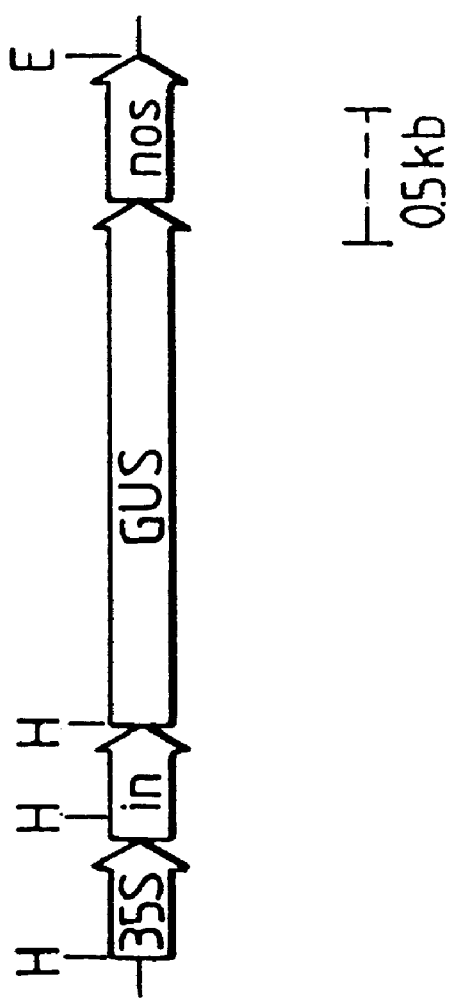
FIG. 1(B). Schematic representation of the expression cassette of pDPG208 containing the uidA gene encoding β-glucoronidase (GUS).
Figure 1C:
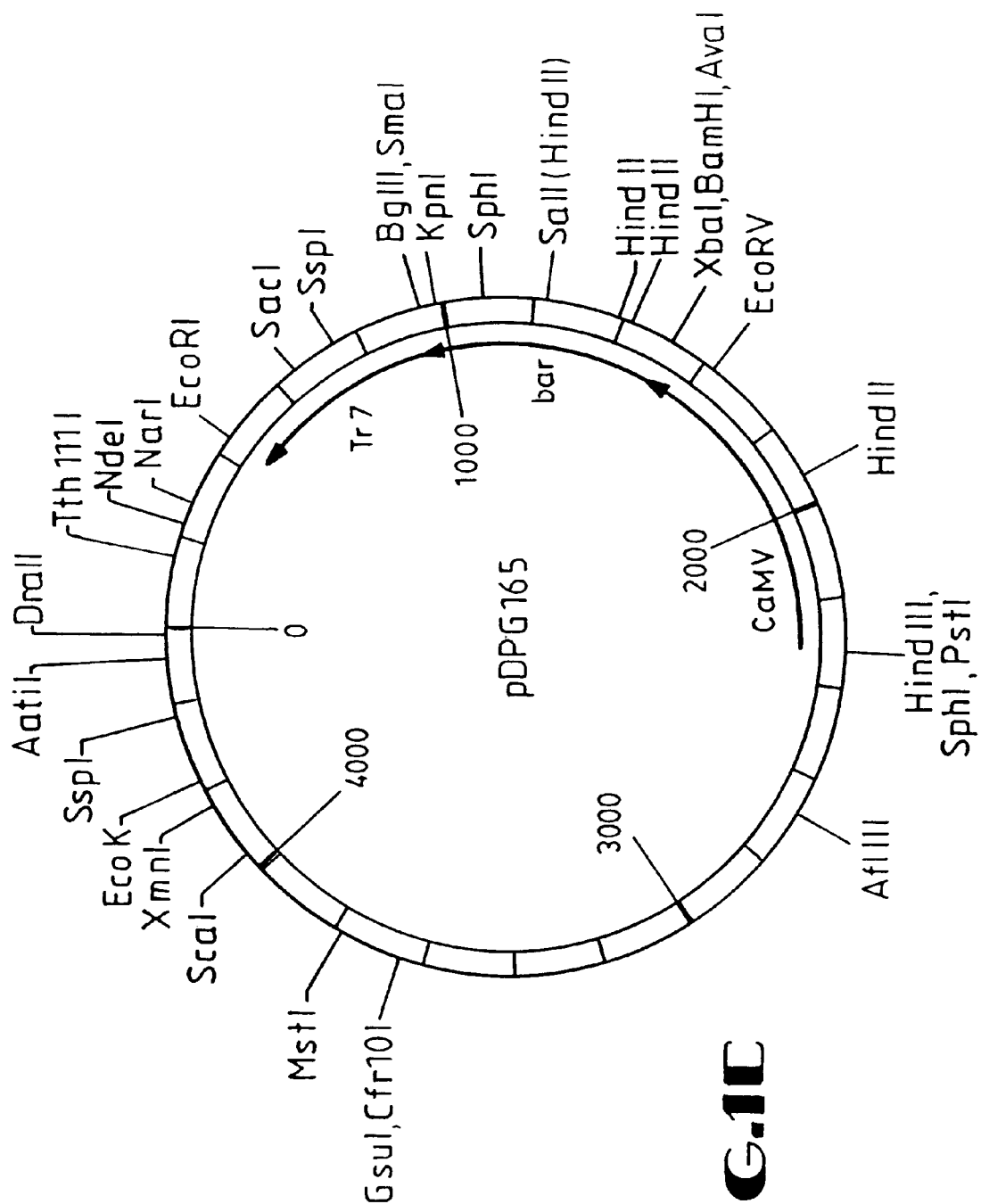
FIG. 1(C). Map of plasmid pDPG165 containing the bar gene.
Figure 1D:
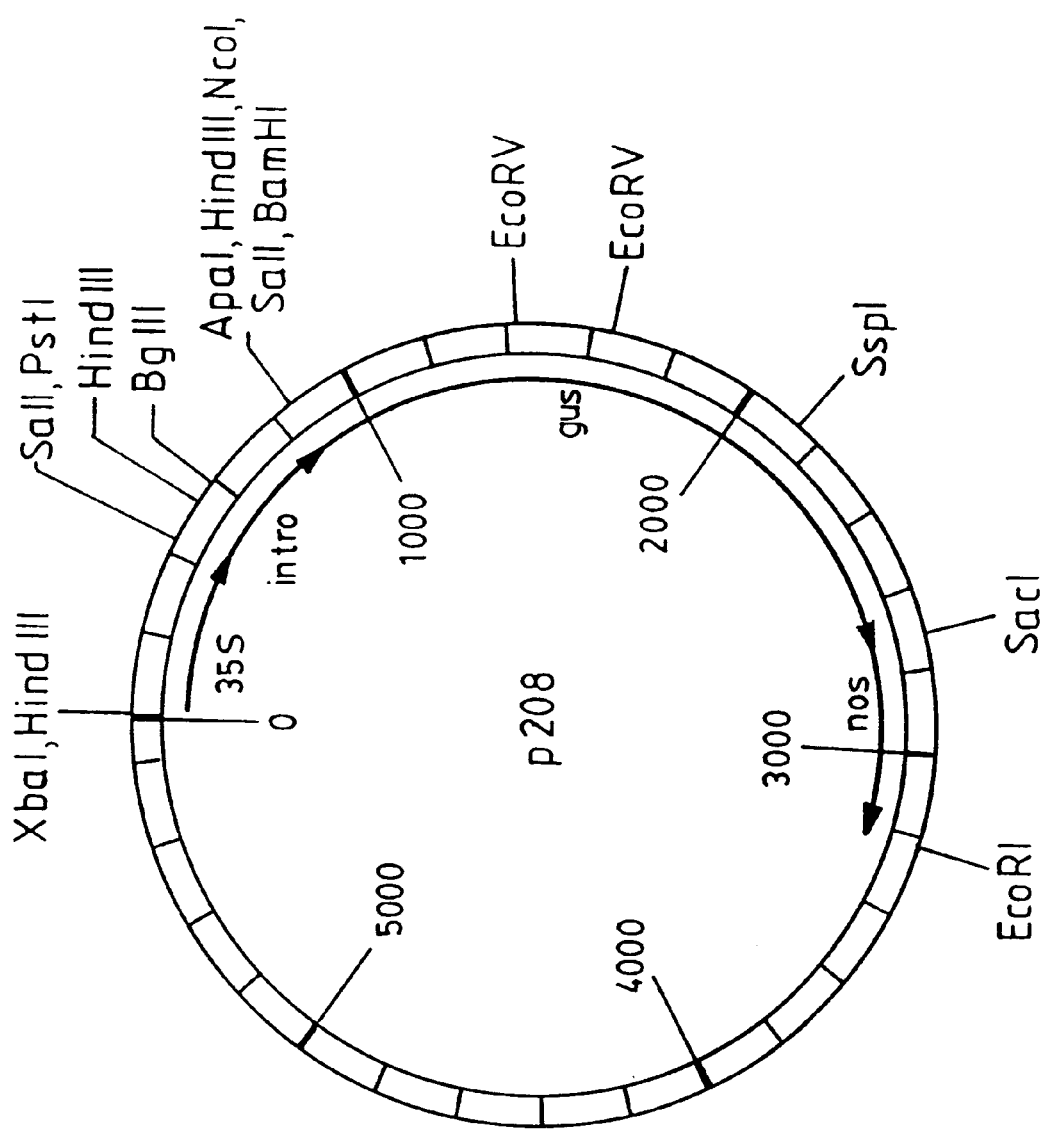
FIG. 1(D). Map of plasmid pDPG208 containing the uidA gene.
Figure 1E:
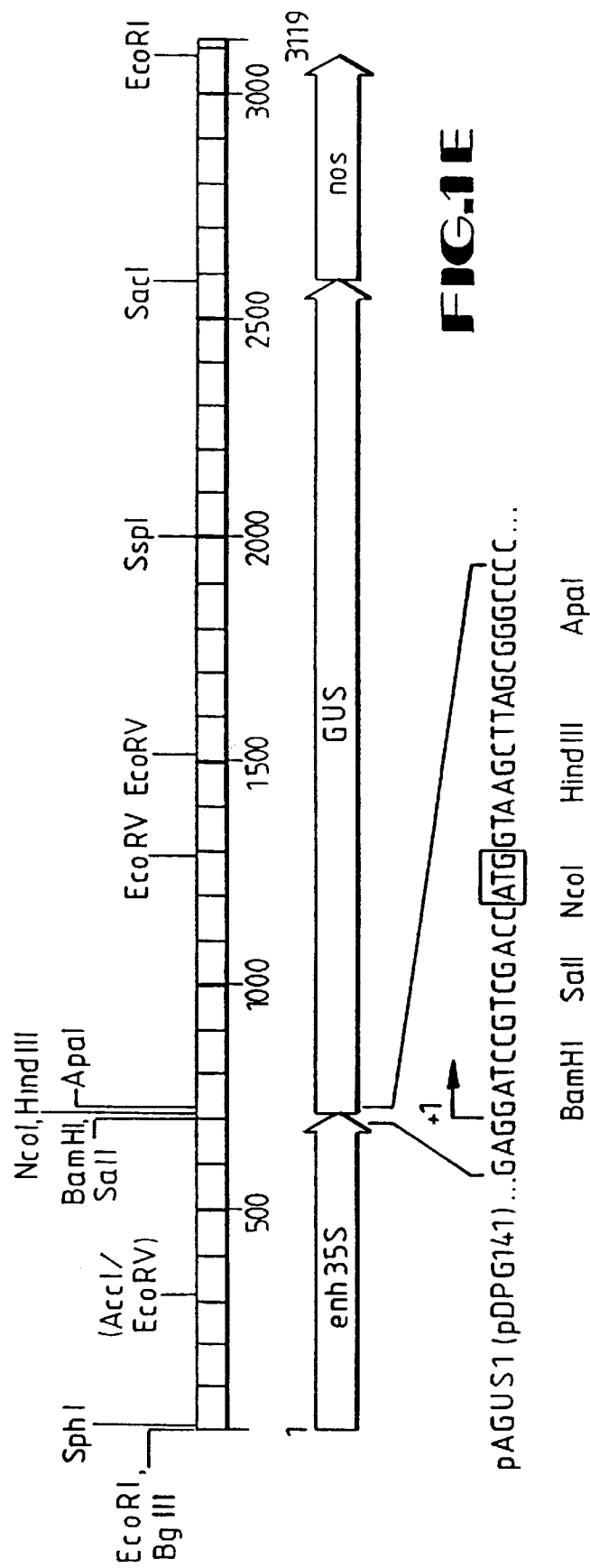
FIG. 1(E). Map of plasmid pAGUS1, also known as pDPG141, in which the 5'-noncoding and 5'-coding sequences were modified to incorporate the Kozak consensus sequence and HindIII restriction site. The nucleotide sequence is seq id no:2.

An additional vector encoding GUS, pDPG208, (FIGS. 1B and 1D) was used in these experiments. It was constructed using a 2.1 kb BamHI/EcoRI fragment from pAGUS1 (provided by J. Skuzeski, University of Utah, Salk Lake City, Utah) containing the coding sequence for GUS and the nos 3'-end from *Agrobacterium tumefaciens*. In pAGUS1 the 5'-noncoding and 5'-coding sequences for GUS were modified to incorporate the Kozak consensus sequence (Kozak, 1984) and to introduce a new HindIII restriction site 6 bp into the coding region of the gene (see FIG. 1E). The 2.1 kb BamHI/EcoRI fragment from pAGUS1 was ligated into a 3.6 kb BamHI/EcoRI fragment of a pUC19-based vector pCEV1 (provided by Calgene, Inc., Davis, Calif.). The 3.6 kb fragment from pCEV1 contains pUC19 and a 430 bp 35S promoter from cauliflower mosaic virus adjacent to the first intron from maize Adh1.

In terms of a member of the R gene complex for use in connection with the present invention, the most preferred vectors contain the 35S promoter from Cauliflower Mosaic Virus, the first intron from maize Adh1 gene, the Kozak consensus sequence, Sn:bol3 cDNA, and the transcript 7 3' end from *Agrobacterium tumefaciens*. One such vector prepared by the inventors is termed pDPG237. To prepare pDPG237 (see FIG. 1F), the cDNA clone of Sn:bol3 was obtained from S. dellaporta (Yale University, USA). A genomic clone of Sn was isolated from genomic DNA of Sn:bol3 which had been digested to completion with HindIII, ligated to lambda arms and packaged in vitro. Plaques hybridizing to two regions of cloned R alleles, R-nj and R-sc (Dellaporta et al., 1988) were analyzed by restriction digest. A 2 kb Sst-HincII fragment from the pSn7.0 was used to screen a cDNA library established in lambda from RNA of light-irradiated scutellar nodes of Sn:bol3. The sequence and a restriction map of the cDNA clone was established.

The cDNA clone was inserted into the same plant expression vector described for pDPG165, the bar expression vector (see above), and contains the 35S Cauliflower mosaic virus promoter, a polylinker and the transcript 3 3' end from *Agrobacterium tumefaciens*. This plasmid, pDPG232, was made by inserting the cDNA clone into the polylinker region; a restriction map of pDPG232 is shown in FIG. 1G. The preferred vector, pDPG237, was made by removing the cDNA clone and Tr7 3' end from pDPG232, with AvaI and EcoRI and ligating it with a BamHI/EcoRI fragment from pDPG208. The ligation was done in the presence of a BamHI linker as follows (upper strand, seq id no:3; lower strand, seq id no:4):

```
GATCCGTCGACCATGGCGCTTCAAGCTTC

GCAGCTGGTACCGCGAAGTTCGAAGGGCT
```

Figure 1F:
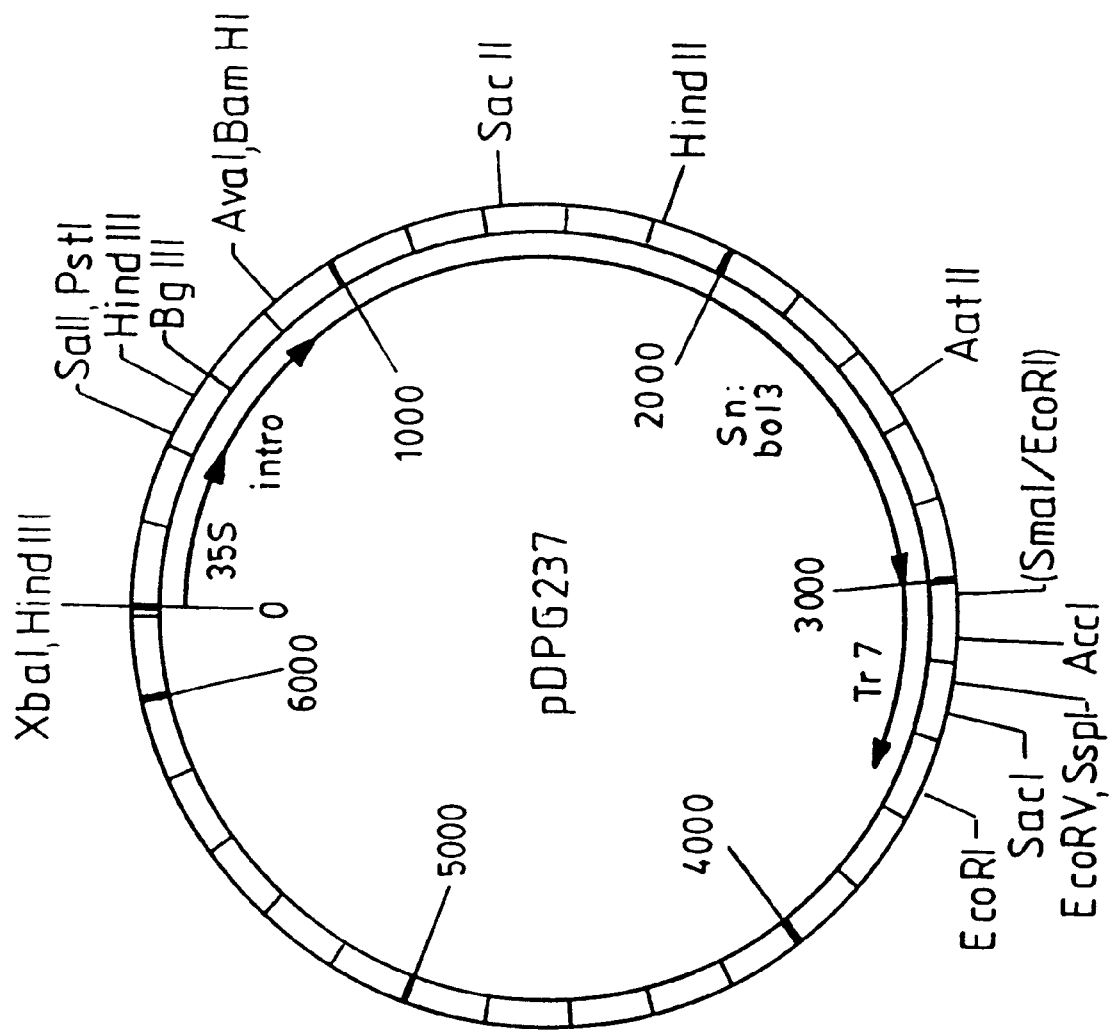
FIG. 1(F). Restriction map of the plasmid pDPG237 containing the Sn:bo13 cDNA.
Figure 1G:
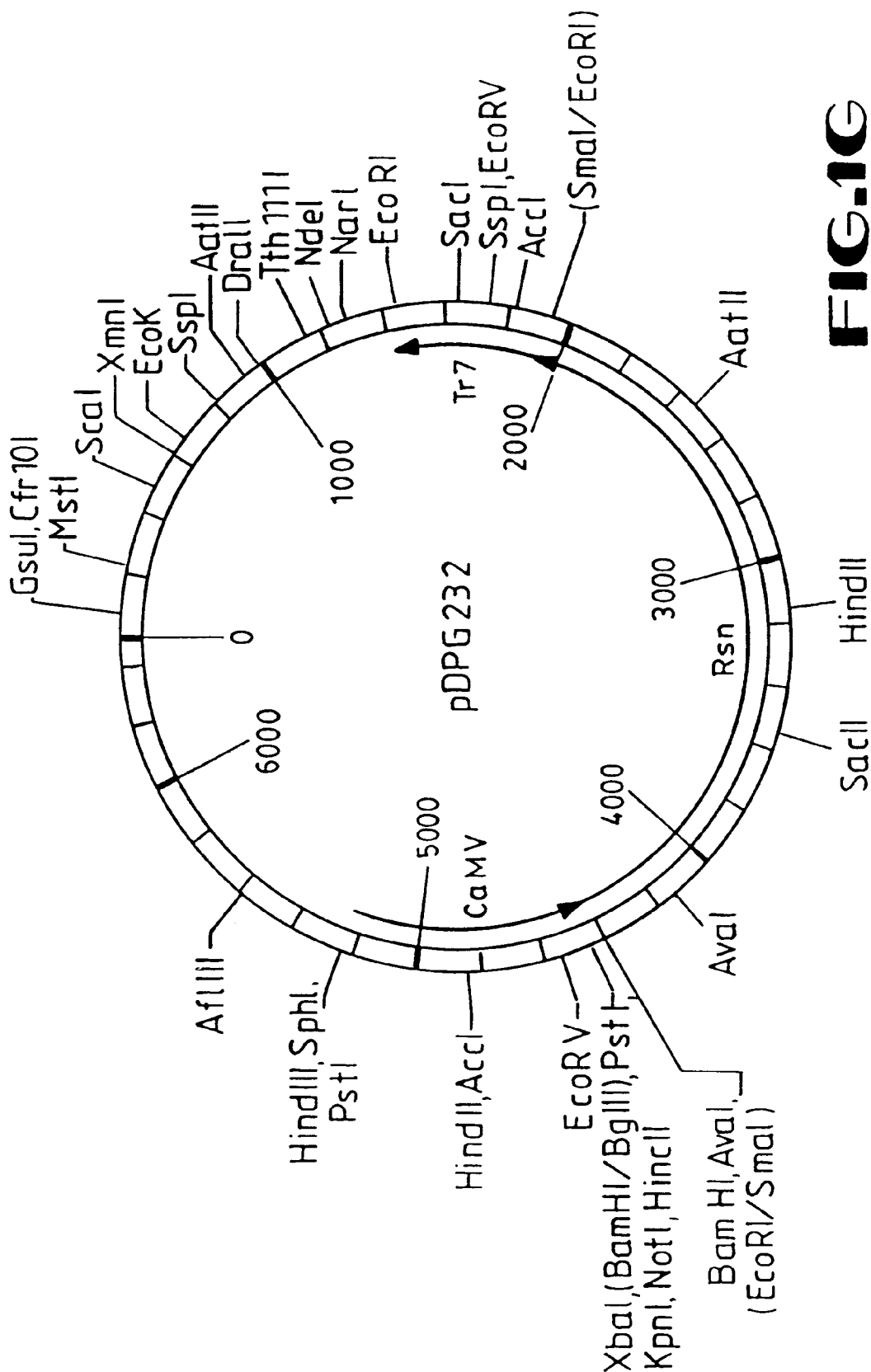
FIG. 1(G). Map of plasmid pDPG232 incorporating the Rsn cDNA with a 35S promoter and Tr 7 3' end.
Figure 1H:
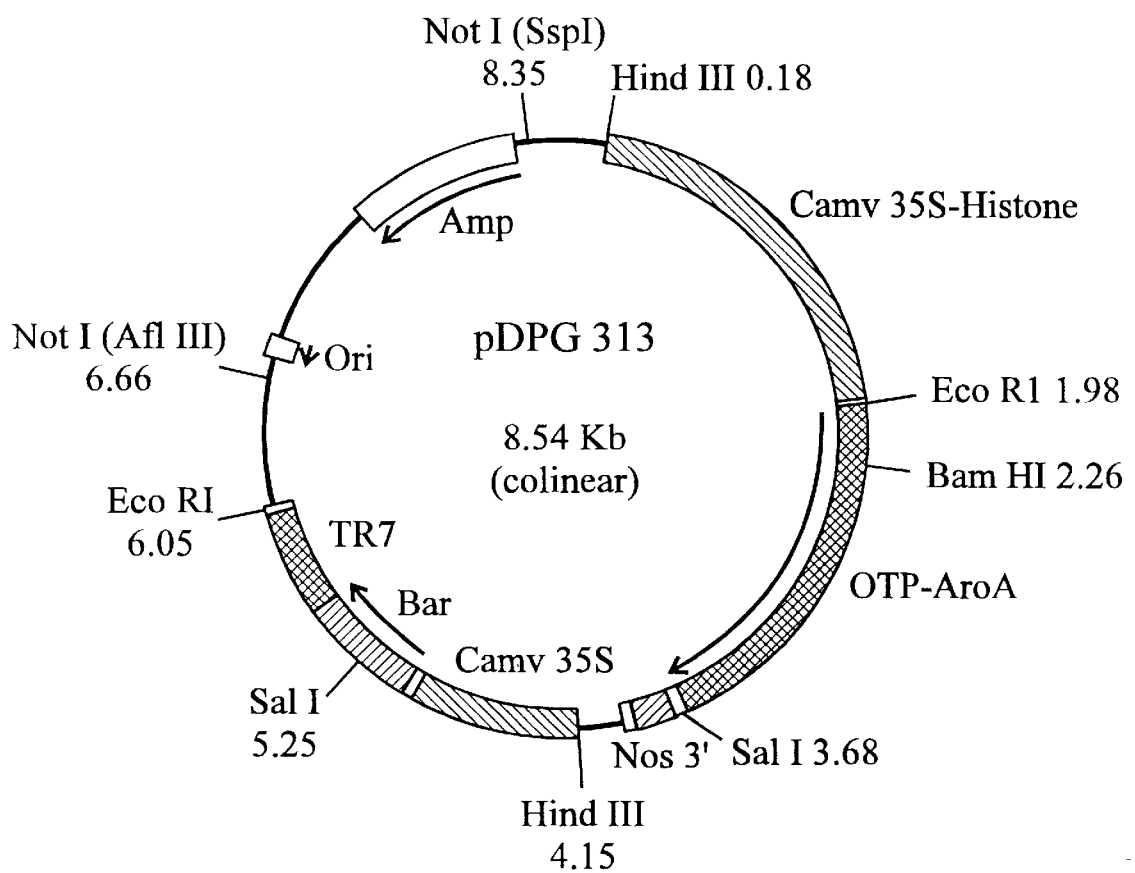
FIG. 1(H). Map of plasmid pDPG313 containing the aroA gene and the 35S-histone fusion promoter in addition to the bar expression cassette.
Figure 1I:
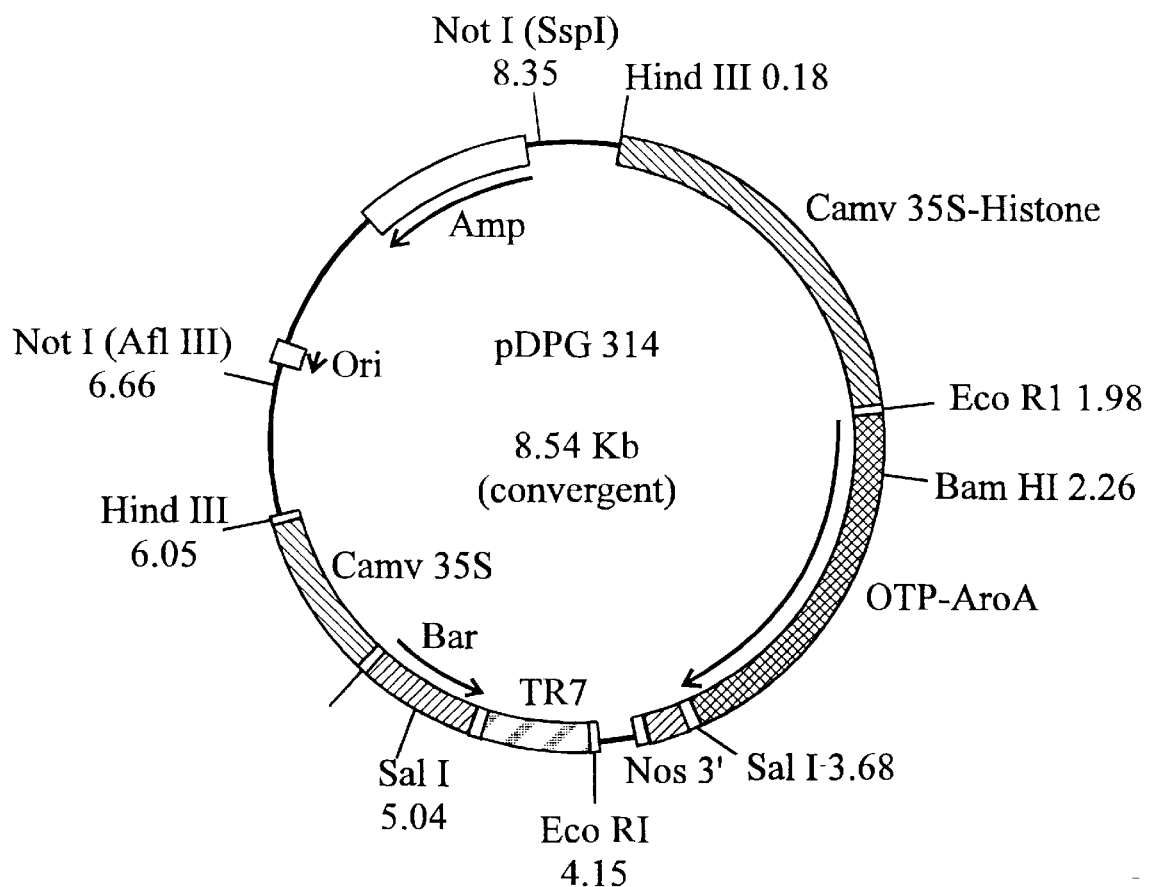
FIG. 1(I). Map of plasmid pDPG314 containing the aroA gene and the 35S-histone fusion promoter in addition to the bar expression cassette.
Figure 1J:
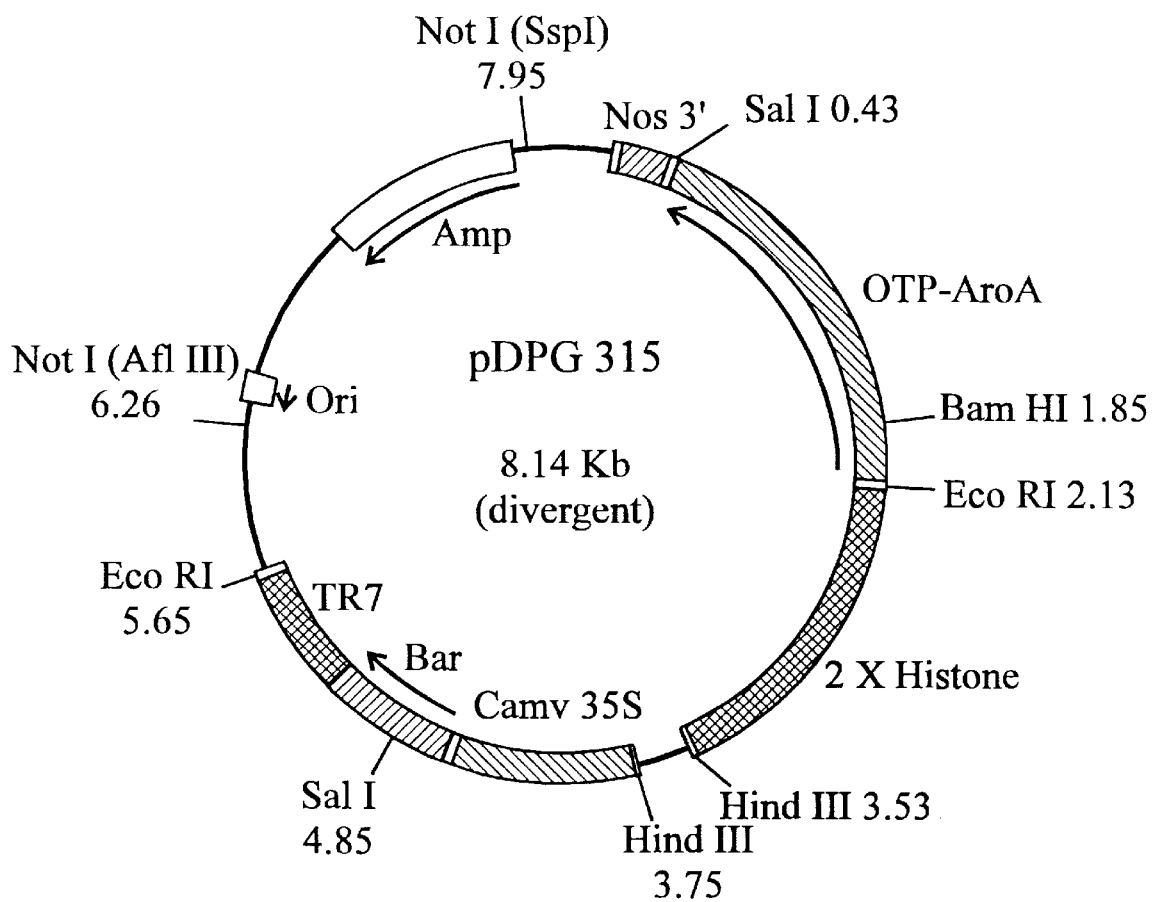
FIG. 1(J). Map of plasmid pDPG315 containing the aroA gene and the histone fusion promoter in addition to the bar expression cassette.
Figure 1K:
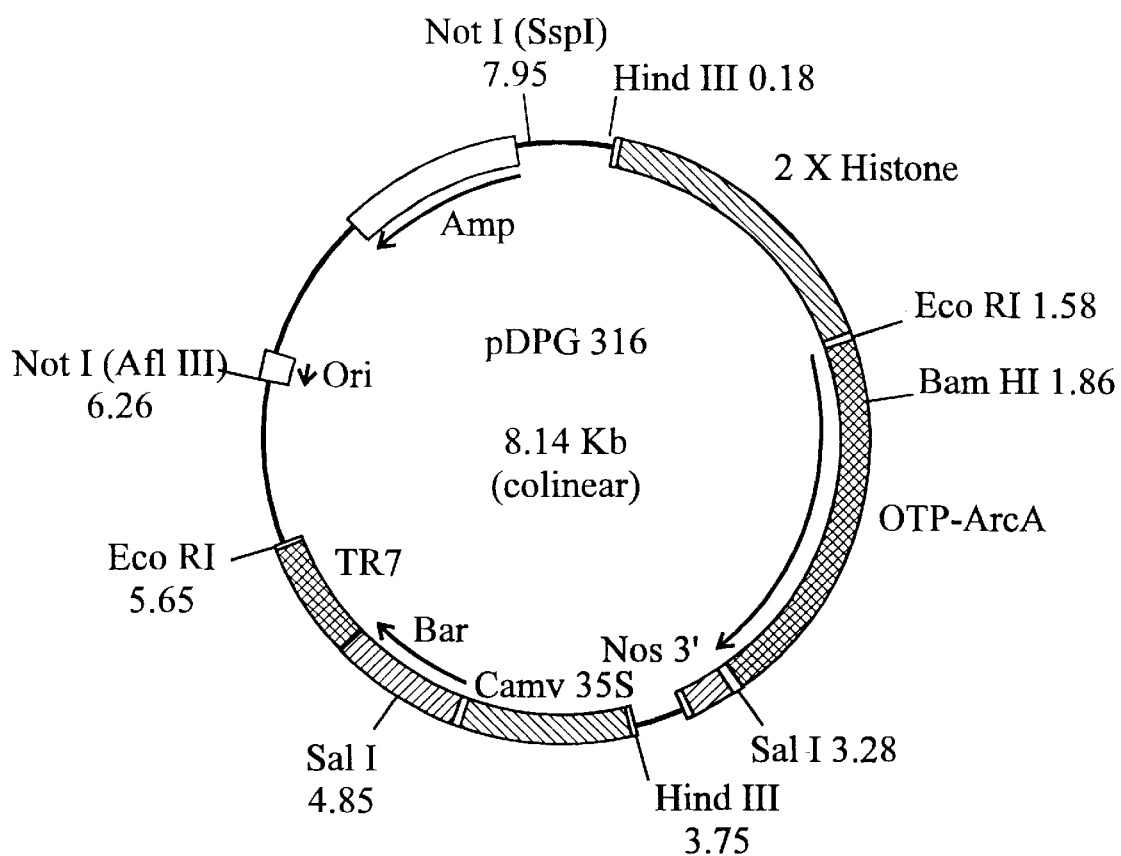
FIG. 1(K). Map of plasmid pDPG316 containing the aroA gene and the histone fusion promoter in addition to the bar expression cassette.
Figure 1L:
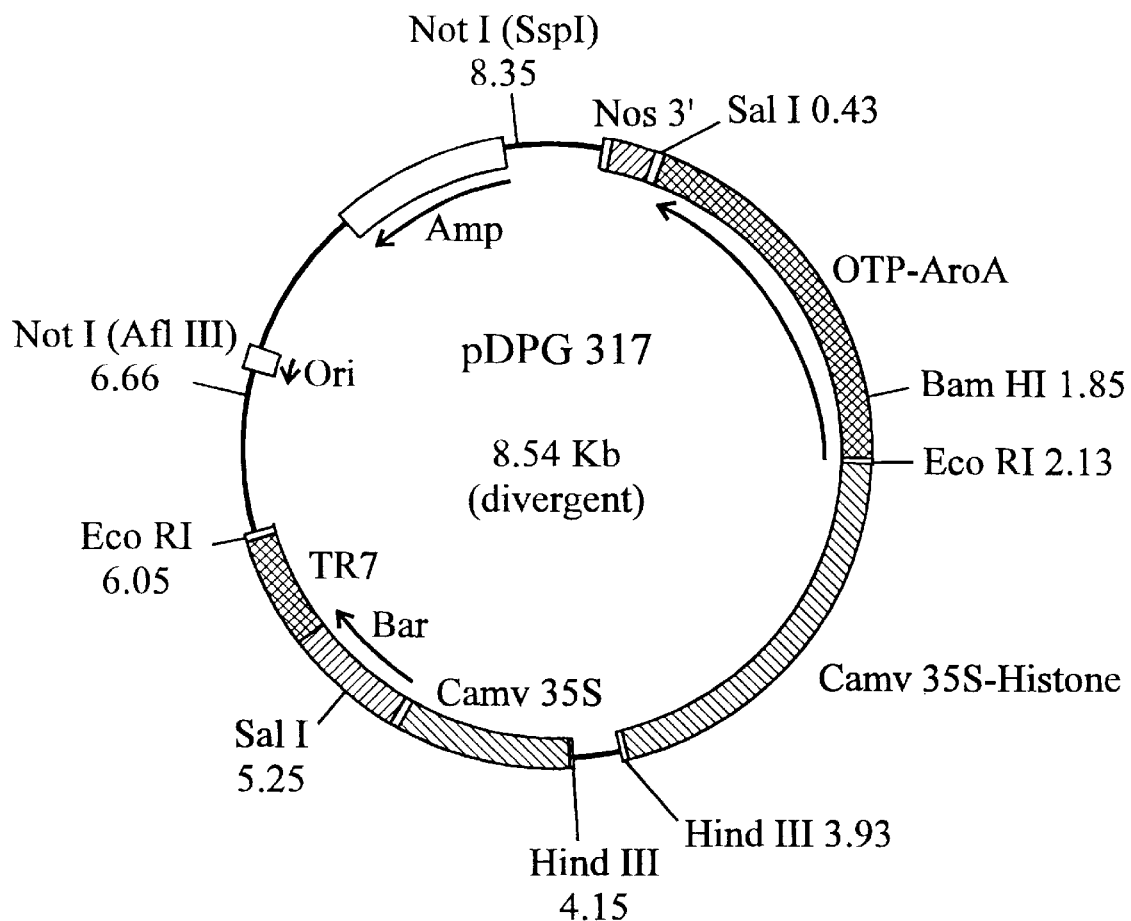
FIG. 1(L). Map of plasmid pDPG317 containing the aroA gene and the 35S-histone fusion promoter in addition to the bar expression cassette.
Figure 1M:
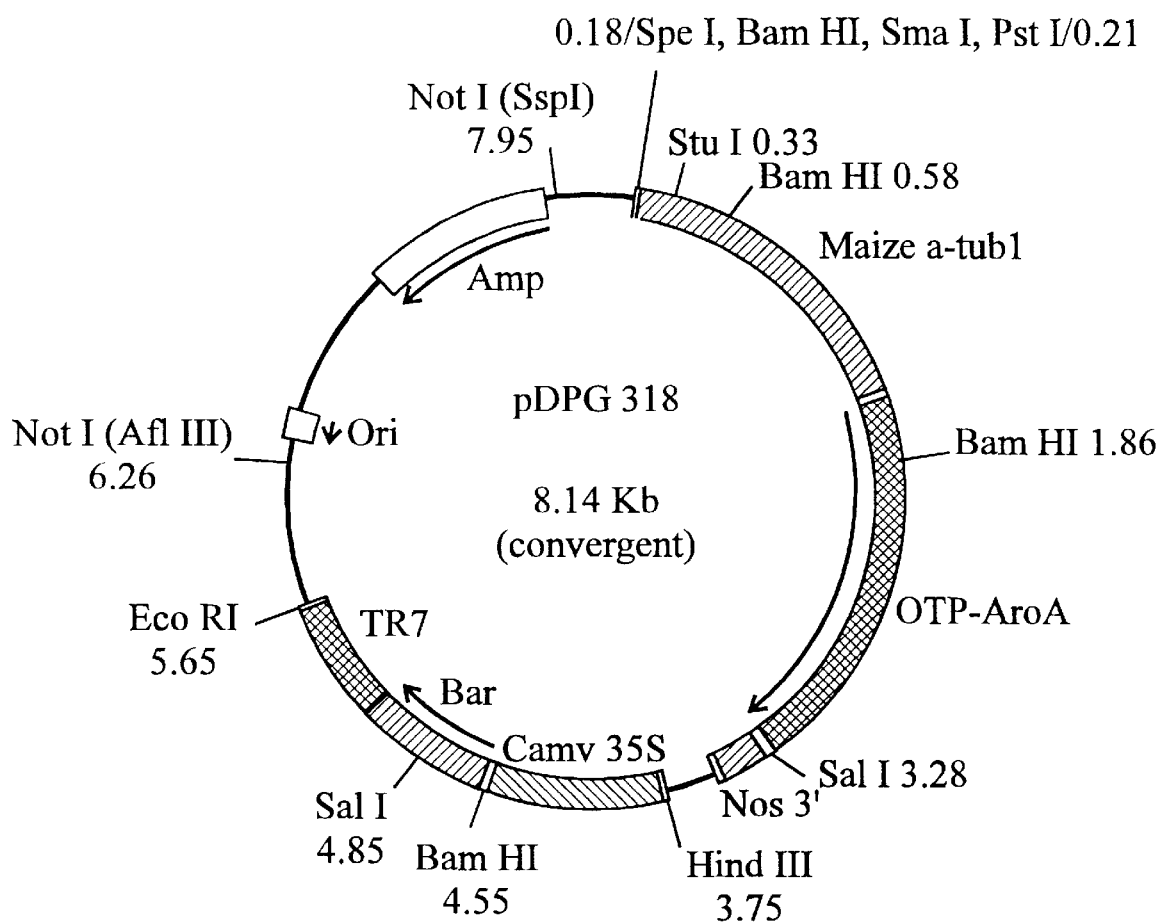
FIG. 1(M). Map of plasmid pDPG318 containing the aroA gene and the α-tubulin promoter in addition to the bar expression cassette.
Figure 1N:
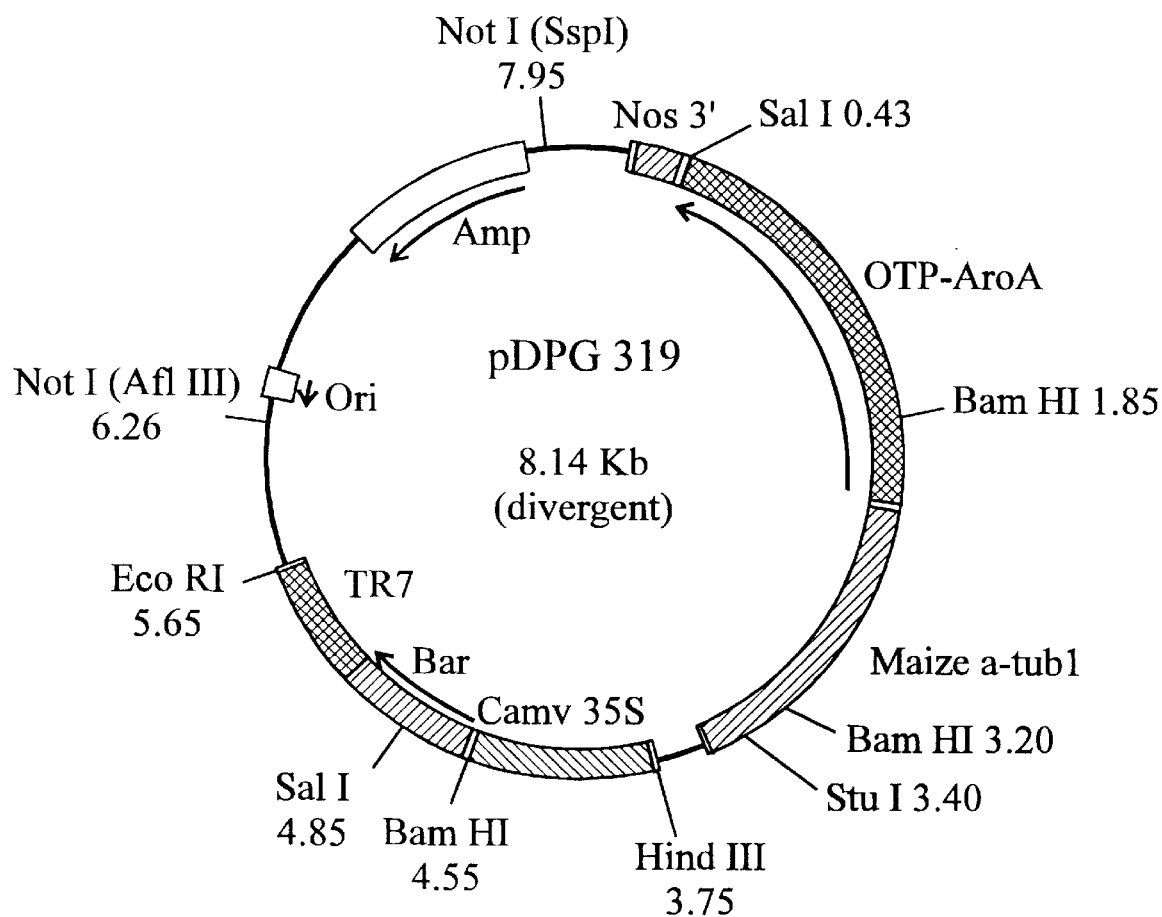
FIG. 1(N). Map of plasmid pDPG319 containing the aroA gene and the α-tubulin promoter in addition to the bar expression cassette.
Figure 1O:
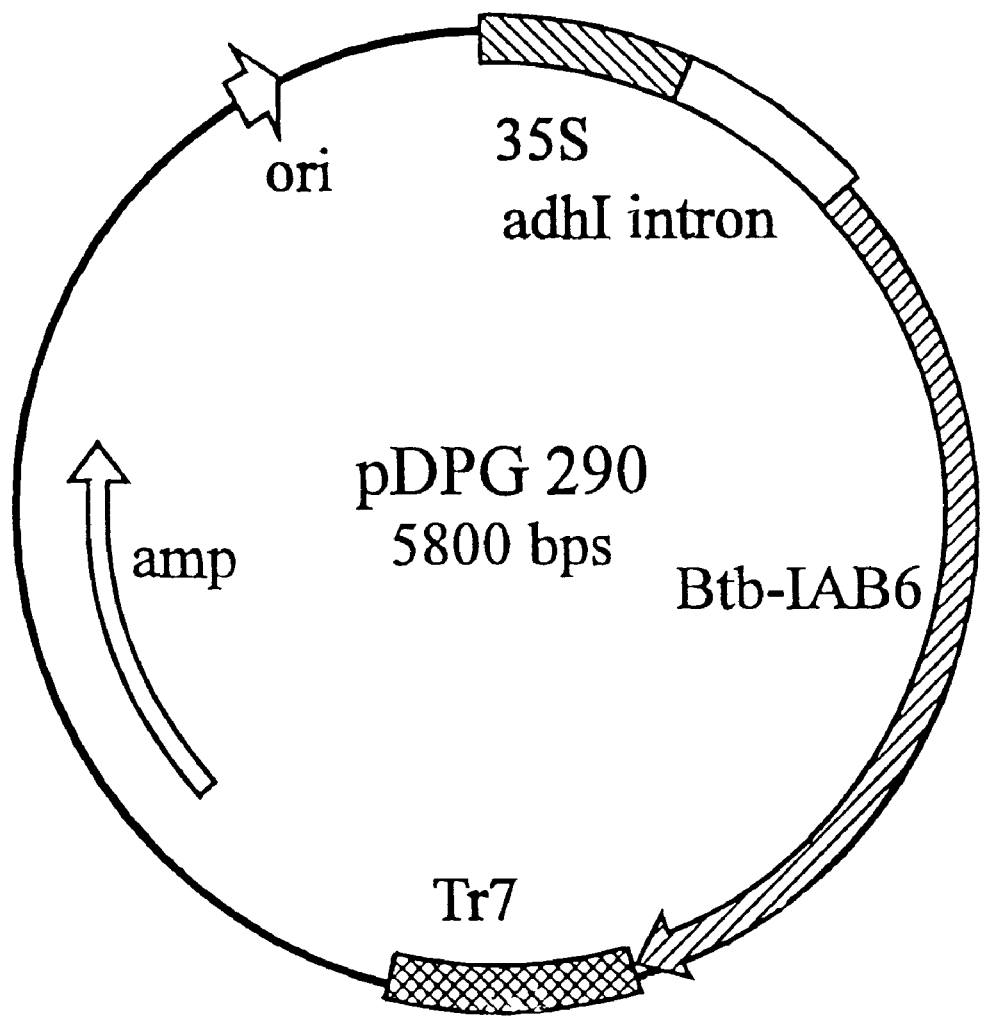
FIG. 1(O). Map of plasmid pDPG290 containing the B. thuringiensis crystal toxin protein gene Iab6 with a 35S promoter.
Figure 1P:
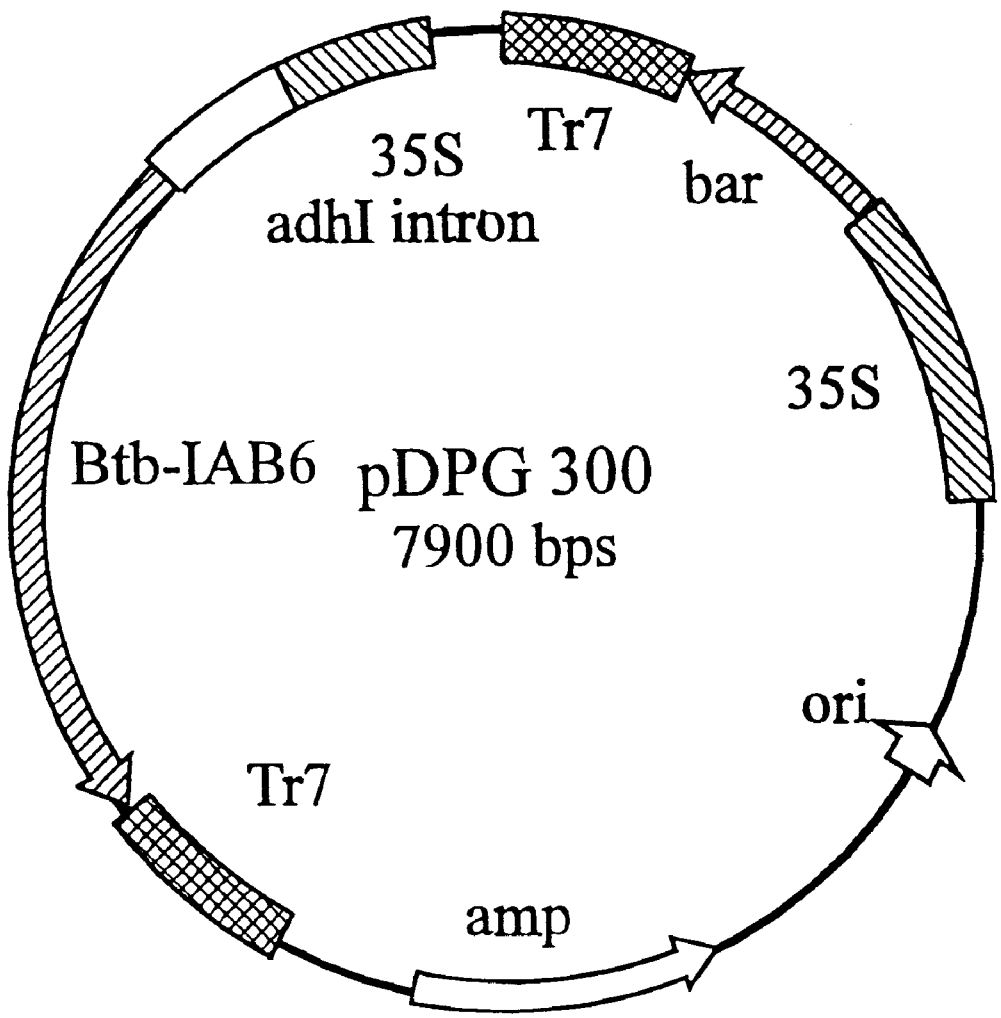
FIG. 1(P). Map of plasmid pDPG300 containing containing the B. thuringiensis crystal toxin protein gene Iab6 with a 35S promoter in addition to the bar expression cassette from pDPG165.
Figure 1Q:
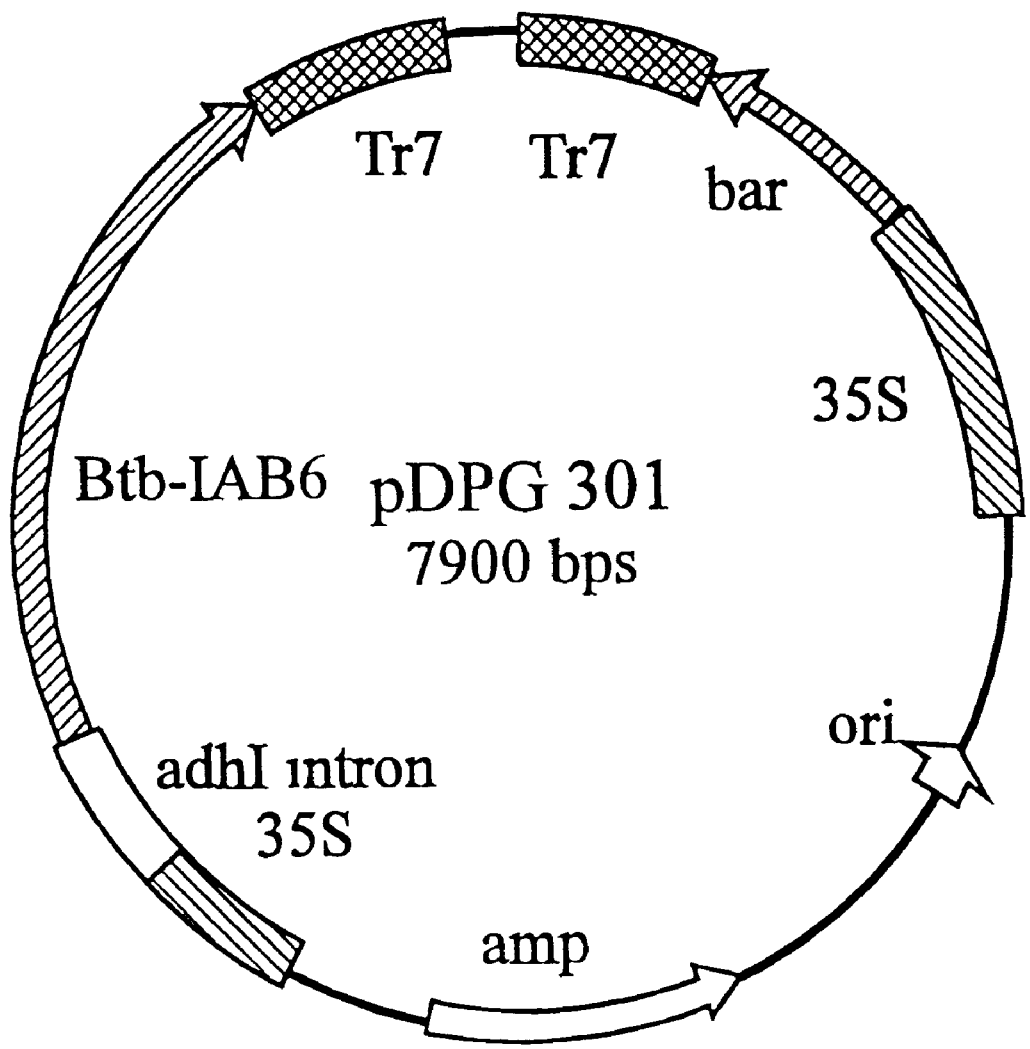
FIG. 1(Q). Map of plasmid pDPG301 containing contain
Figure 1R:
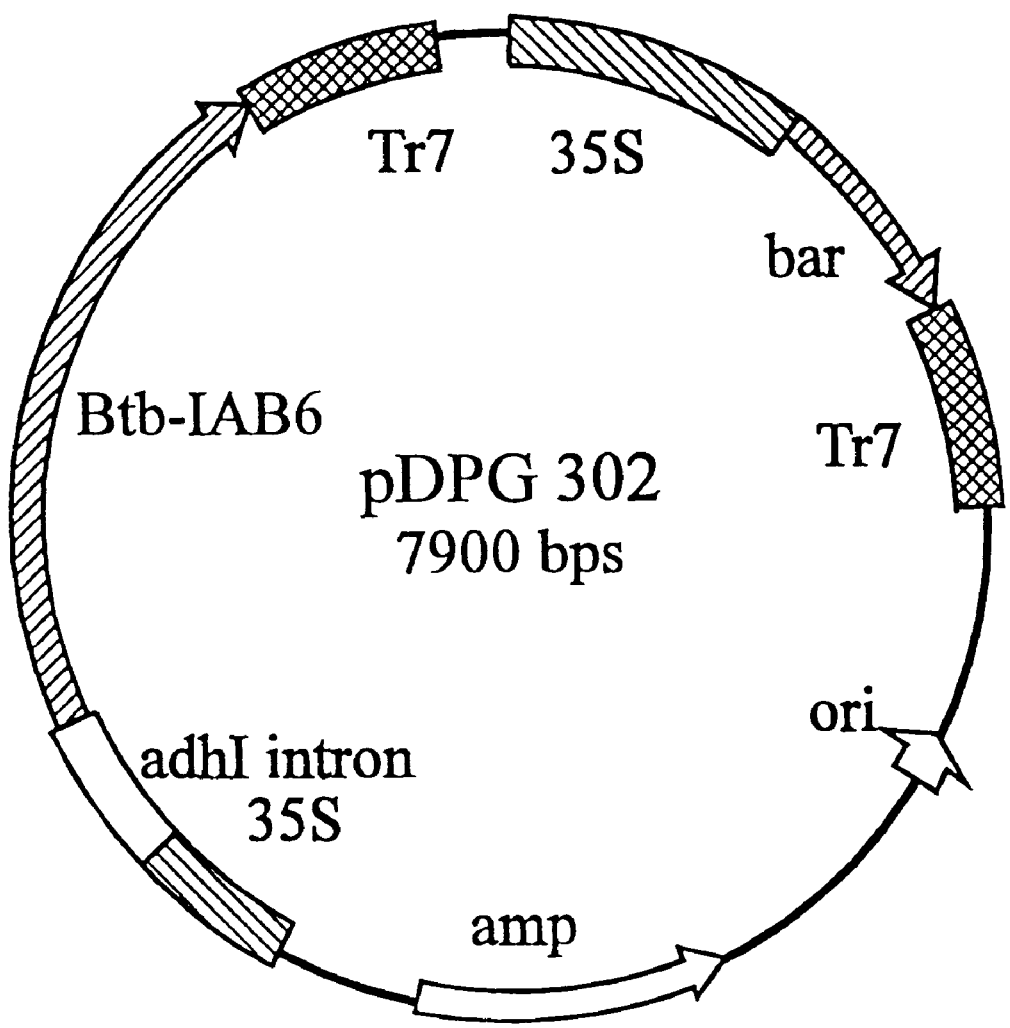
FIG. 1. Schematic representation of plasmids (vectors) used in bombardment experiments.
FIG. 1(Y). Map of plasmid pDPG172 containing the luciferase gene and the maize alcohol dehydrogenase I promoter and intron one.
FIG. 1(Z). Map of plasmid pDPG425 containing a maize EPSPS gene mutated to confer resistance to glyphosate.
Figure 1S:
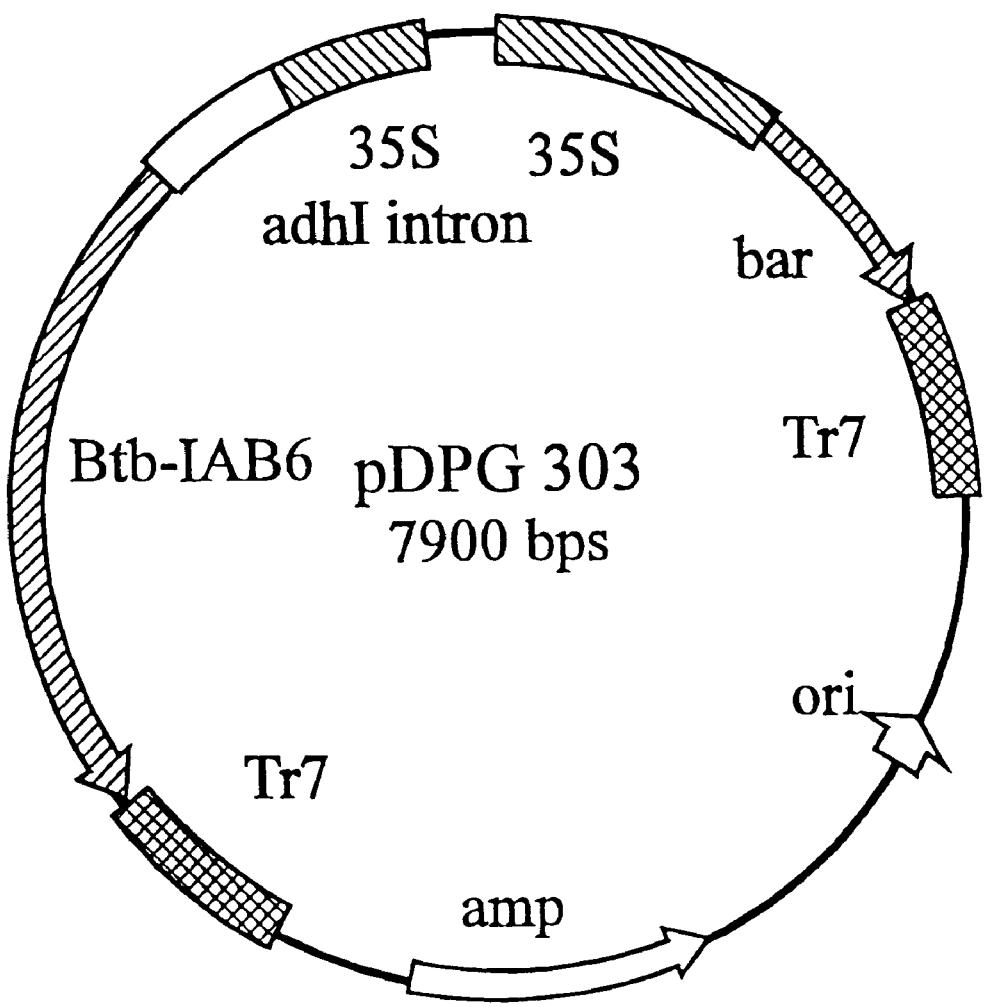
Figure 1T:
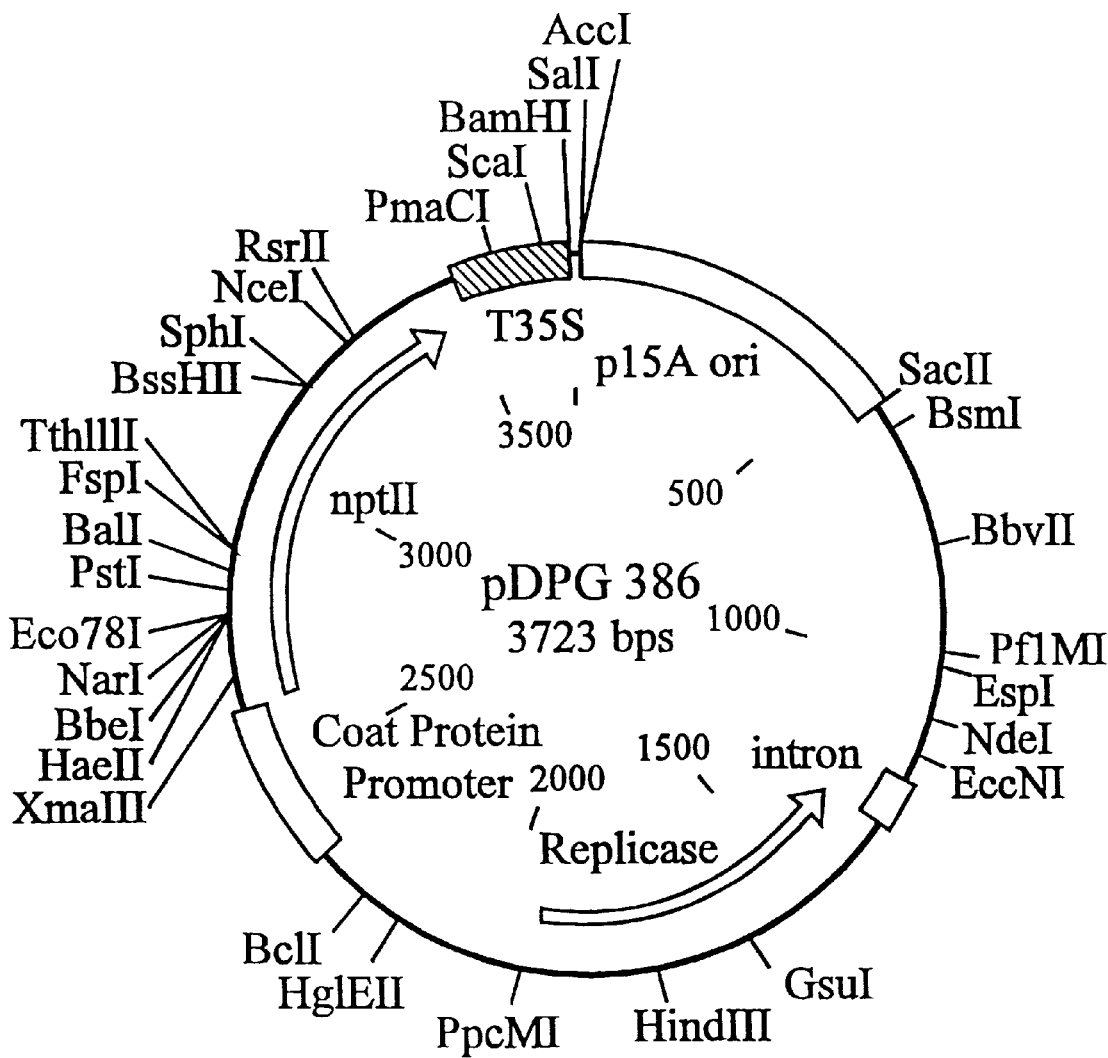
Figure 1U:
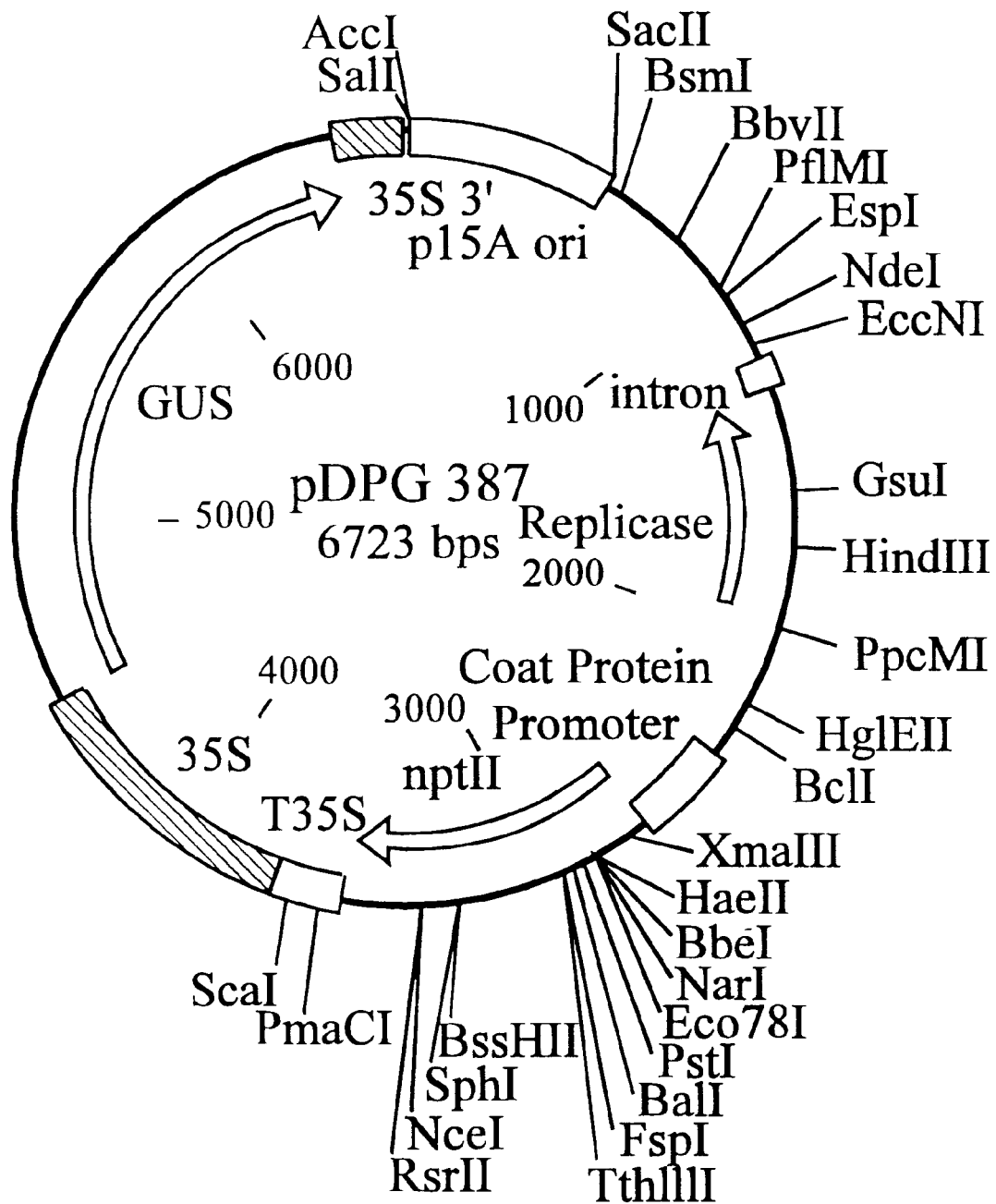

The final construct of pDPG237 contained a Cauliflower mosaic virus 35S promoter, the first intron of Adh1, Kozak consensus sequence, the BamHI linker, cDNA of Sn:Bol3, and the Tr7 3' end and is shown in FIG. 1F.

Additional vectors have been prepared using standard genetic engineering techniques. For example, a vector, designated pDPG128, has been constructed to include the neo coding sequence (neomycin phosphotransferase (APH(3')-II)). Plasmid pDPG128 contains the 35S promoter from CaMV, the neomycin phosphotransferase gene from Tn5 (Berg et al., 1980) and the Tr7 terminator from *Agrobacterium tumefaciens*. Another vector, pDPG154, incorporates the crystal toxin gene and was also prepared by standard techniques. Plasmid pDPG154 contains the 35S promoter, the entire coding region of the crystal toxin protein of *Bacillus thuringiensis* var. *kurstaki* HD 263, and the Tr7 promoter.

Various tandem vectors have also been prepared. For example, a bar/aroA tandem vector (pDPG238) was constructed by ligating a blunt-ended 3.2 kb DNA fragment containing a mutant EPSP synthase aroA expression unit (Barkai-Golan et al., 1978) to NdeI-cut pDPG165 that had been blunted and dephosphorylated (NdeI introduces a unique restriction cut approximately 200 bp downstream of the Tr7 3'-end of the bar expression unit). Transformants having aroA in both orientations relative to bar were identified.

Additional bar gene vectors employed are pDPG284 and pDPG313–pDPG319 (FIGS. 1H–N), the latter series being obtained from Rhône-Poulenc Agrochimie (RPA). The orientation of the bar gene in DPG165 was inverted with respect to the pUC vector, to obtain pDPG284. An additional 32 bp of DNA has been inserted into the NdeI site of pDPG165 and DPG284, to obtain pDPG295 and pDPG297 and pDPG298, respectively. This extra 32 bp of sequence preserves the unique NdeI site in each vector and adds four additional restriction sites with the following orientation, relative to the unique NarI site:

NarI-52 bp-HpaI-NotI-NruI-EcoRI-NdeI.

Tandem bar-aroA vectors with a 35S-histone promoter (constitutive and meristem enhanced expression) in convergent (pDPG314), divergent (pDPG313), and colinear orientations (pDPG317) have also been employed, as have aroA vectors with a histone promoter (meristem-specific promoter, (pDPG315/pDPG316) and an α-tubulin promoter (root-specific, pDPG318/pDPG319) in colinear and divergent orientations to bar respectively.

Plasmid pDPG290 incorporates the modified Bt CryIA(B) gene, IAb6, obtained from Plant Genetic Systems, PGS. A 1.8 kb NcoI-NheI fragment containing IAb6 was ligated together with the Tr7 3+ region on a 0.5 Kb NheI-EcoRI fragment from pDPG145 and 3.6 Kb NcoI-EcoRI fragment from pDPG208 containing the 35S promoter, Adh1 intron I, and the required plasmid functions to create pDPG290 (FIG. 1, O).

In the construction of IAb6-bar tandem vectors, modifications were made to the separate bar and IAb6 expression units so that IAb6 could be inserted as a NotI-flanked cassette into the bar-containing plasmid. A NotI recognition site was introduced through a series of ligations into plasmids which contained the bar expression unit in two orientations with respect to the new NotI recognition site. The bar expression unit was removed from pDPG165 as a HindIII-EcoRI fragment and ligated to HindIII-EcoRI cut pUC18 to give the plasmid pDPG284. This reversed the orientation of the bar expression unit with respect to the pUC plasmid. An oligonucleotide containing HpaI, PmlI, NruI, EcoRI, and NdeI restriction sites was ligated to NdeI cut pDPG165 and pDPG284 to produce pDPG285/pDPG286 and pDPG292/pDPG293, respectively. These pairs of plasmids were the two orientations of the oligonucleotide. These four plasmids were then cut with PmlI in order to introduce a NotI linker which destroyed the PmlI recognition site. Plamids pDPG292 and pDPG293 containing the NotI linker were designated pDPG298 and pDPG297, respectively. A NotI site was introduced adjacent to the 3' end of the Tr7 3' region by removing a 200 bp EcoRI fragment from pDPG294. This vector was designated pDPG296.

An IAb6 vector with flanking NotI sites was constructed via a 4-way ligation consisting of the Tr7 3' region (as a 500 bp HpaI-BglII fragment from pDPG296), the IAb6 gene (as a 1.8 Kb BamHI-NcoI fragment from pDPG290), the 35S promoter-Adh1 intron 1 cassette (as a 800 bp XbaI-NcoI fragment from pDPG208), and the pBluescript II SK(-) plasmid (as a 2.95 Kb XbaI-HindII fragment). The pBluescript plasmid has a polylinker that positioned a second NotI recognition site next to the 5' end of the IAb6 expression unit. The plasmid which contained the NotI-flanked IAb6 expression unit was designated pDPG299. The IAb6 expression unit was excised from pDPG299 as a 3.1 kb NotI fragment and ligated to NotI cut pDPG295 pDPG298 to yield pDPG300/pDPG301 and pDPG302/pDPG303, respectively (FIGS. 1P–S). The pairs are the two orientations possible for each ligation.

A plasmid DNA, pDPG310, was constructed that contains a bar expression unit and a single copy of the matrix attachment region from the chicken lysozyme gene. The nuclear matrix attachment region (MAR, or "A-element") from the chicken genomic DNA region 5' to the lysozyme gene is contained on a 2.95 kb KpnI-PstI fragment in plasmid pUC19 B1-X1 (received from A. E. Sippel, Freiburg). It has been reported that genes flanked by MAR elements result in tissue independent gene expression and enhanced transcriptional activity. Plasmid DNA pDPG310 was constructed by performing a 3-way litigation among the following DNAs:

1) 2.9 kb NotI-KpnI fragment from pBluescript II SK(-),
2) 2.95 kb KpnI-PstI MAR fragment from pUC19 B1-X1, and
3) 2.1 kp PstI-NotI bar-containing fragment from pDPG294.

Plasmid pDPG310 contains three SacI sites, one in each of the above DNA fragments. A second MAR element was inserted into the SacI site at the end of the pBluescript II SK(-) multiple cloning region. The resulting plasmid has a unique NotI site, into which future traits of interest could be cloned.

In regard to vectors encoding protease inhibitors, plasmid DNA, pRJ15, containing the genomic DNA sequence for the potato pinII gene, was obtained from Clarence Ryan (Washington State University) and renamed pDPG288. Another plasmid DNA, pT2-47, containing the cDNA sequence for the tomato pinII gene, was obtained from Clarence Ryan and renamed pDPG289. The potato pinII gene in pDPG288 is flanked by a 35S promoter and a Tr7 3' end.

Tandem vectors were constructed containing a bar expression unit and a potato or tomato pinII expression unit in either convergent or colinear orientation. In each construct, the bar and pinII expression units were contained on a HindIII fragment that also contains a 1.9 kb fragment of Adh1 but lacks the $Amp^R$ gene and the plasmid origin of replication. The 1.9 kb Adh1 region provides a locus for recombination into the plant genome without disruption of either the bar or pinII expression units. These HindIII fragments are available for bombardment experiments as either linear, circular, or supercoiled DNAs.

To construct a plant expression vector containing the potato pinII terminator, the potato pinII terminator was cloned into pBluescript II SK(-) via a three-part ligation. To obtain the pinII terminator, a 3.7 kb PstI fragment was first removed from pDPG288 and subsequently digested with RsaI/PstI to yield the 930 bp pinII terminator. The pBluescript II vector was digested with ScaI/PstI and ScaI/SmaI in two separate reactions; the appropriate two plasmid fragments were gel-purified. These fragments and the pinII terminator were ligated to give plasmid pDPG331.

In order to construct pDPG320, a pinII expression vector containing the 35S promoter-AdhI intronI-pinII (with intron and terminator)-Tr7 terminator vector, the following protocol was used. pDPG309 was cut with BglII/EcoRI and the vector fragment was isolated. pDPG157 was cut with PstI/EcoRI and the 500 bp Tr7 fragment was isolated. To isolate the AdhI intron 3'-end, pDPG309 was cut with BglII/XbaI. Finally, pDPG288 was restricted with XbaI/PstI and the potato pinII gene (with intron and terminator) was isolated. After purification, the four fragments were ligated together and transformed into competent DH5α cells. Miniprep analysis identified the correct clone.

A further plant expression vector that contains the potato pinII terminator is pDPG343. This plasmid contains the 420-bp 35S promoter, maize Adh1 intron I, a multiple cloning region, and the potato pinII terminator. pDPG343 was constructed by way of a three-part ligation of the following DNAs:

1) 3330 bp EcoRI-PstI fragment of pDPG309, containing the pBluescript SK(-) and the 420 bp 35S promoter,
2) 580 bp PstI-XbaI fragment of pDPG309, containing the maize Adh1 intron 1, and
3) 960 bp XbaI-EcoRI fragment of pDPG331, containing the potato pinII terminator.

Plasmid pDPG343 contains the following restriction sites between the Adh1 intron I and the potato pinII terminator:
BamHI-SalI-XbaI-SpeI-BamHI Of the above sites, SpeI in the only unique one in pDPG343. While BamHI can readily be used for one-step cloning of trait genes, use of SalI or XbaI will require either three-part (or greater) ligations, or multiple cloning steps.

The DNA fragment encoding the firefly luciferase protein was inserted into a pUC18-based vector containing the 35S promoter from Cauliflower Mosaic Virus, the first intron from the maize Adh1 gene, and the transcript 7 3' end from *Agrobacterium tumefaciens* (provided in the plasmid pCEV1 from Calgene, Inc., Davis, Calif.). This luciferase expression vector is referred to as pDPG215, and contains the same regulatory elements as the bar-expression vector pDPG165.

Two additional luciferase vectors were created, both utilizing intron VI from Adh1 (derived from vector pDPG273) fused to firefly luciferase (obtained from vector pDPG215). These elements were inserted into either the pDPG282 (4 OCS inverted-35S) to create pDPG350, or into the pDPG283 (4 OCS-35S) backbone to create pDPG351 (bar was excised as a BamHI/NheI fragment and the intron plus luciferase gene inserted). The 4 OCS-35S promoter has been shown with the uidA gene to give very high levels of transient expression.

Replication-competent viral vectors are also contemplated for use in maize transformation. Two wheat dwarf virus (WDV) "shuttle" vectors were obtained from J. Messing (Rutgers). These vectors, pWI-11 (pDPG386) and pWI-GUS (pDPG387) (FIGS. 1T,U), are capable of autonomous replication in cells derived from electroporated maize endosperm protoplasts (Ugaki et al., 1991). Both of these vectors encode a viral replicase and contain viral and E. coli origins of replication. In both of these vectors, the viral coat protein coding sequence has been replaced by the neo gene. pDPG387 (pWI-GUS) was created by insertion of a GUS expression cassette (35S-GUS-35S 3') into the BamHI site of pDPG386 (pWI-11).

The expression and integration of marker genes introduced into maize cells on a replicating vector was examined using pDPG387 (pWI-GUS) and BMS cells. Six filters of BMS cells were bombarded with pDPG387/pDPG165 (35S-bar-Tr7) and as a control, six filters were bombarded with pDPG128 (35S-neo-Tr7)/pDPG165. Tissue from three filters of each cotransformation was selected on bialaphos (1 mg/l) and tissue from the remaining three filters of each cotransformation was selected on kanamycin (100 mg/l). Selection of kanamycin-resistant colonies from tissue bombarded with pDPG387 was very inefficient (4 colonies) as compared to the control treatment in which cells were bombarded with pDPG128/pDPG165 (364 colonies). It also appears that bialaphos selection was less efficient for cells bombarded with pDPG387/pDPG165 (59 colonies) than it was for the control in which cells were bombarded with pDPG128/pDPG165 (274 colonies).

There are several potential reasons for the low selection efficiencies in bombardments using pDPG387. The neo gene carried by pDPG387 is driven by the native WDV coat protein promoter; this promoter may not be strong enough to confer kanamycin resistance. Alternatively, the relatively low number of bialaphos-resistant colonies recovered from cells bombarded with pDPG387/pDPG165, infers some sort of negative impact of pDPG387 on the ultimate selection for expression of a marker gene on a separate, non-replicating vector. The nature of this negative impact, and its relationship to the low yield of kanamycin-resistant colonies, is currently been investigated.

Figure 1V:
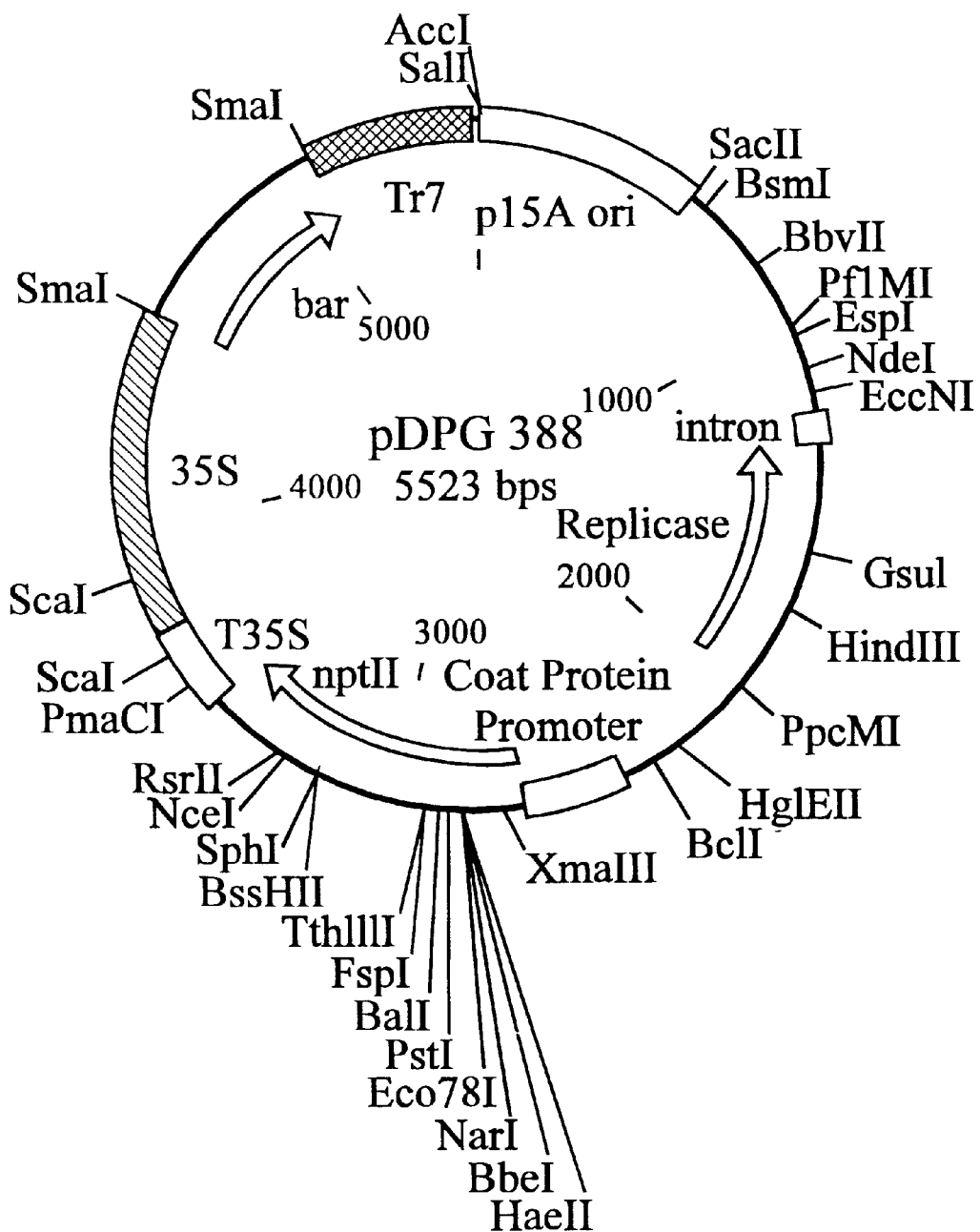
Figure 1W:
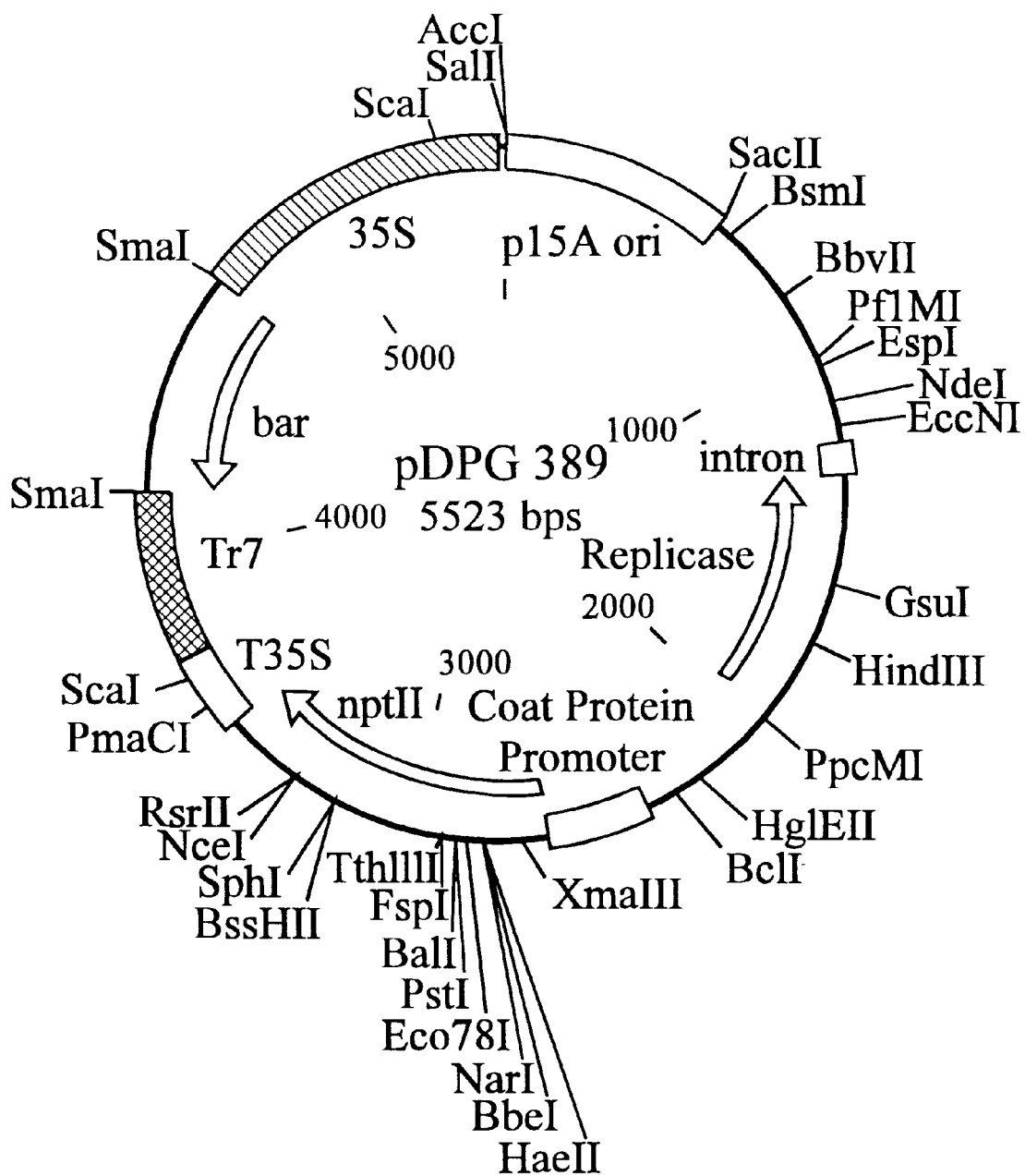
Figure 1X:
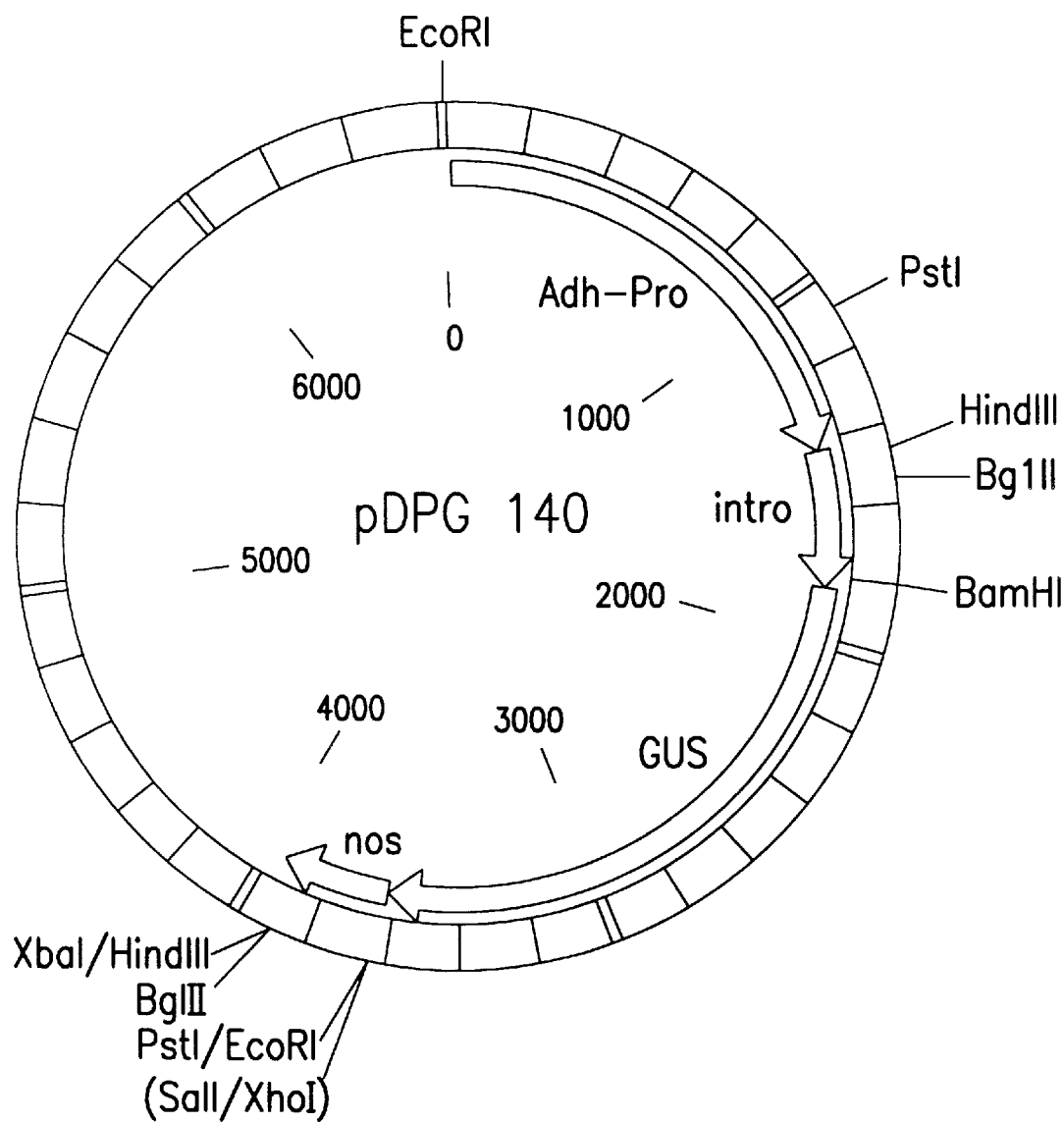
Figure 1Y:
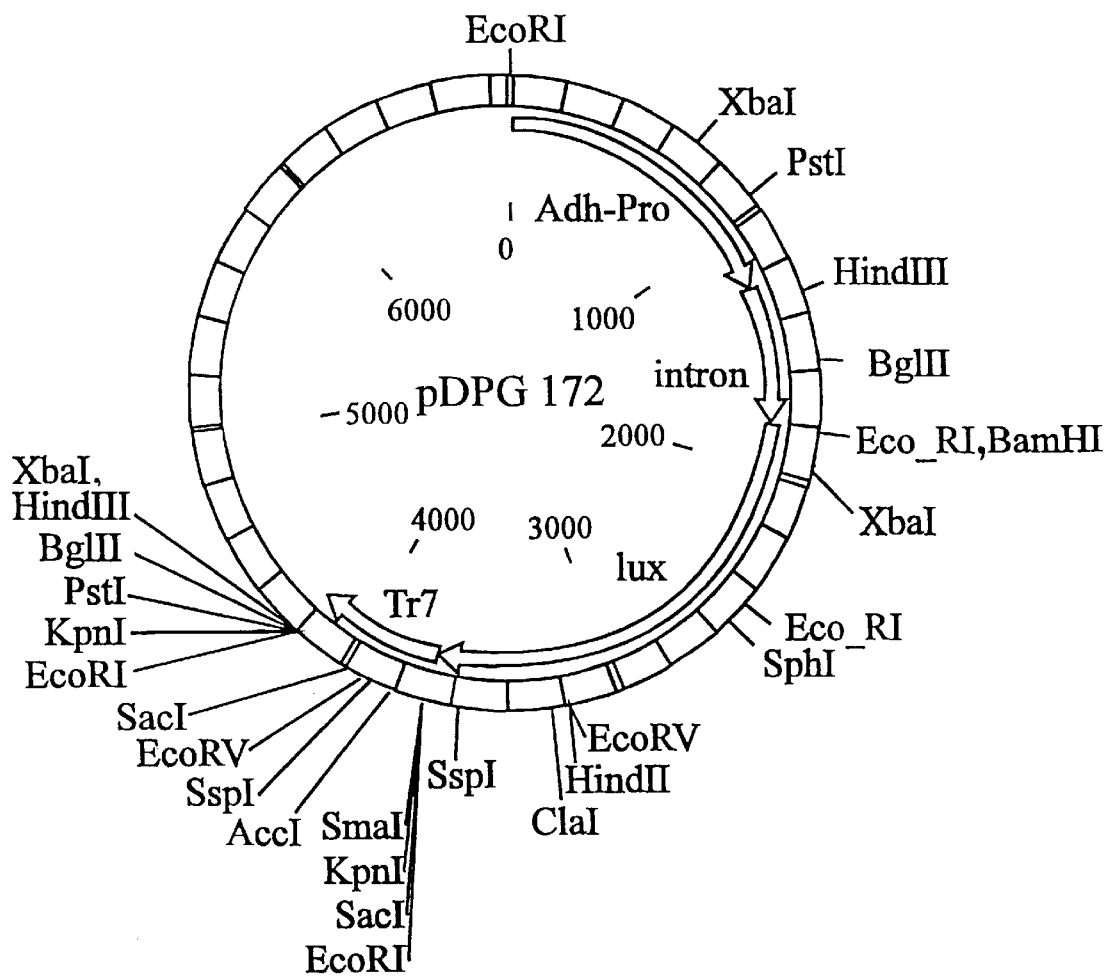
Figure 1Z:
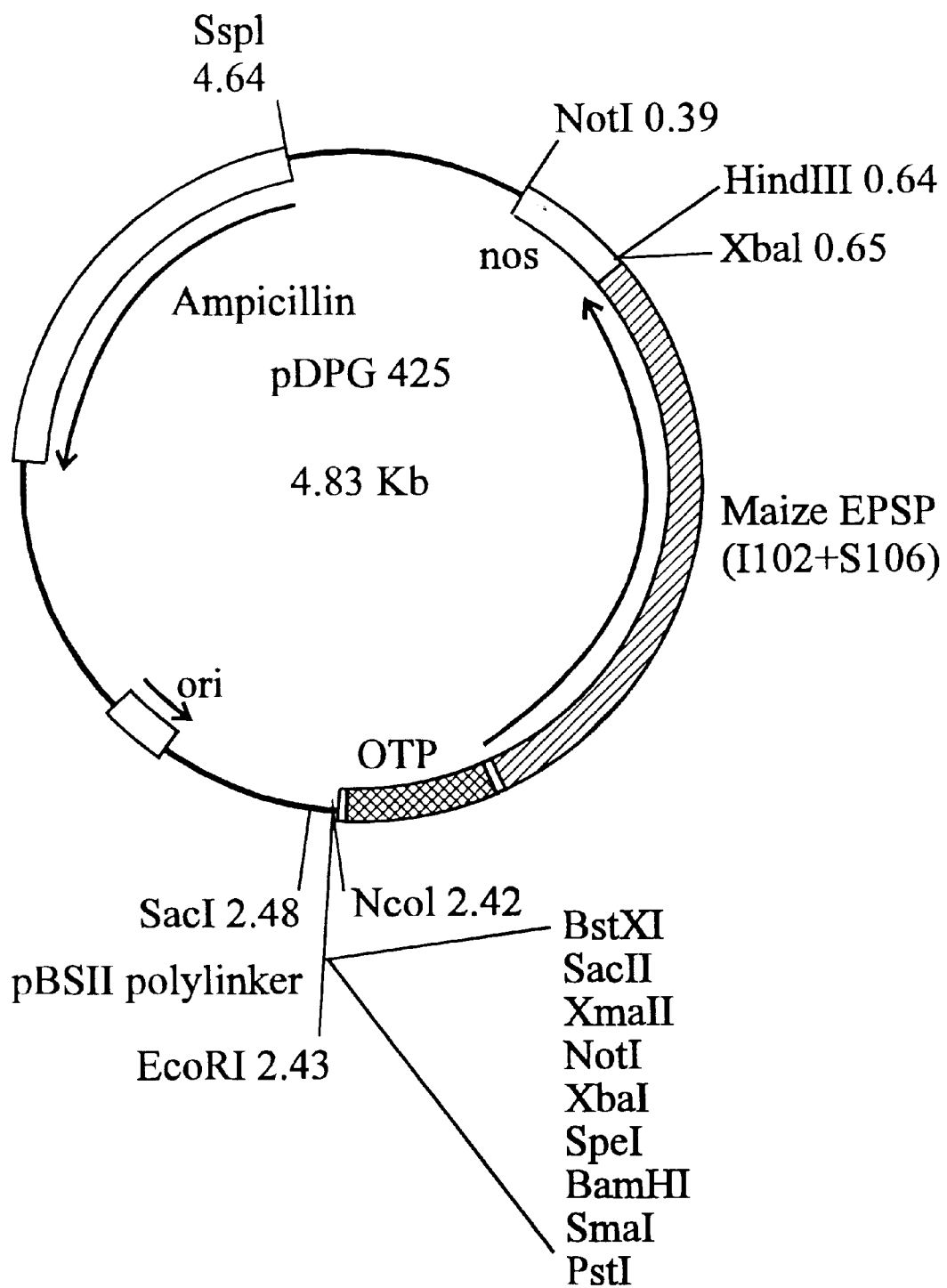
Figure 1:
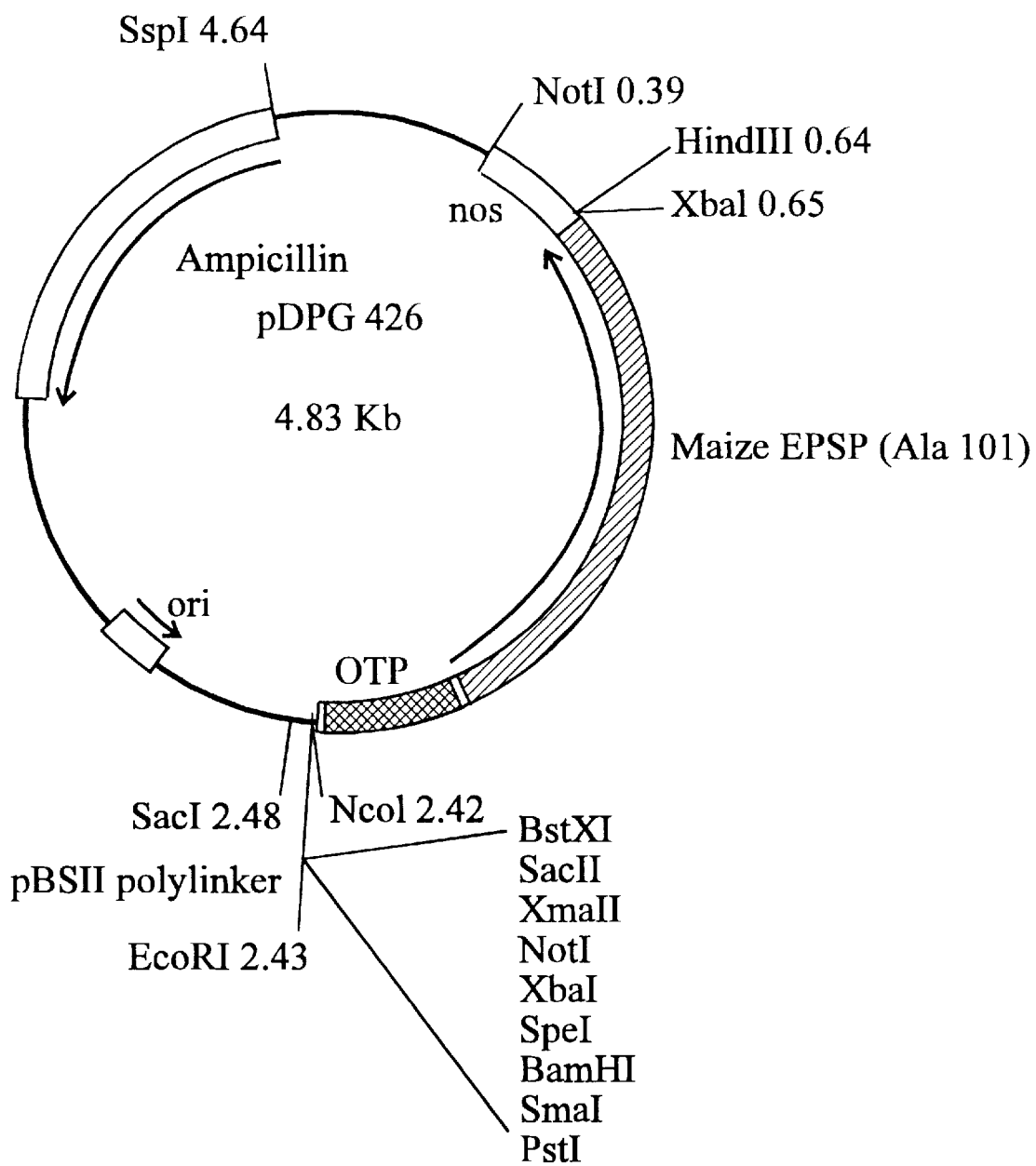
Figure 1:
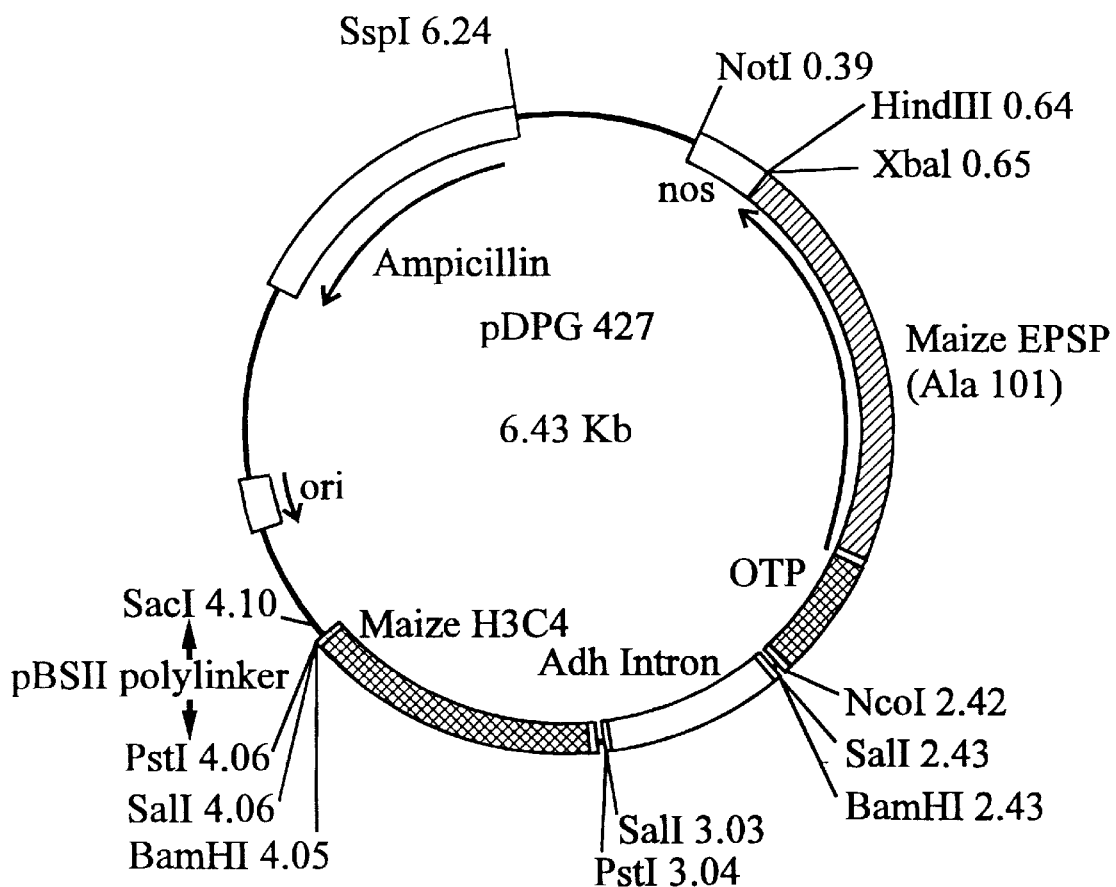
Figure 1:
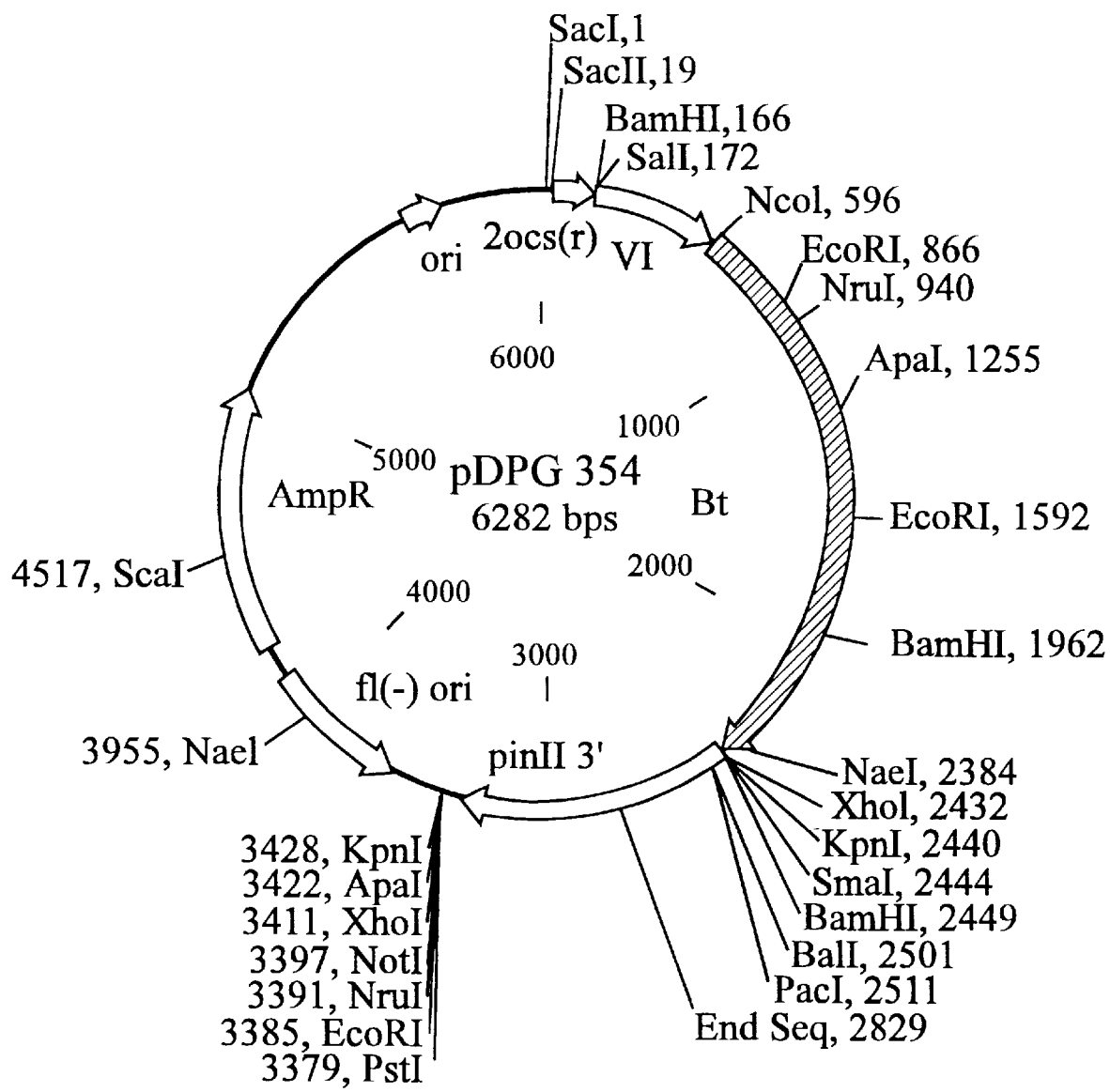
Figure 1:
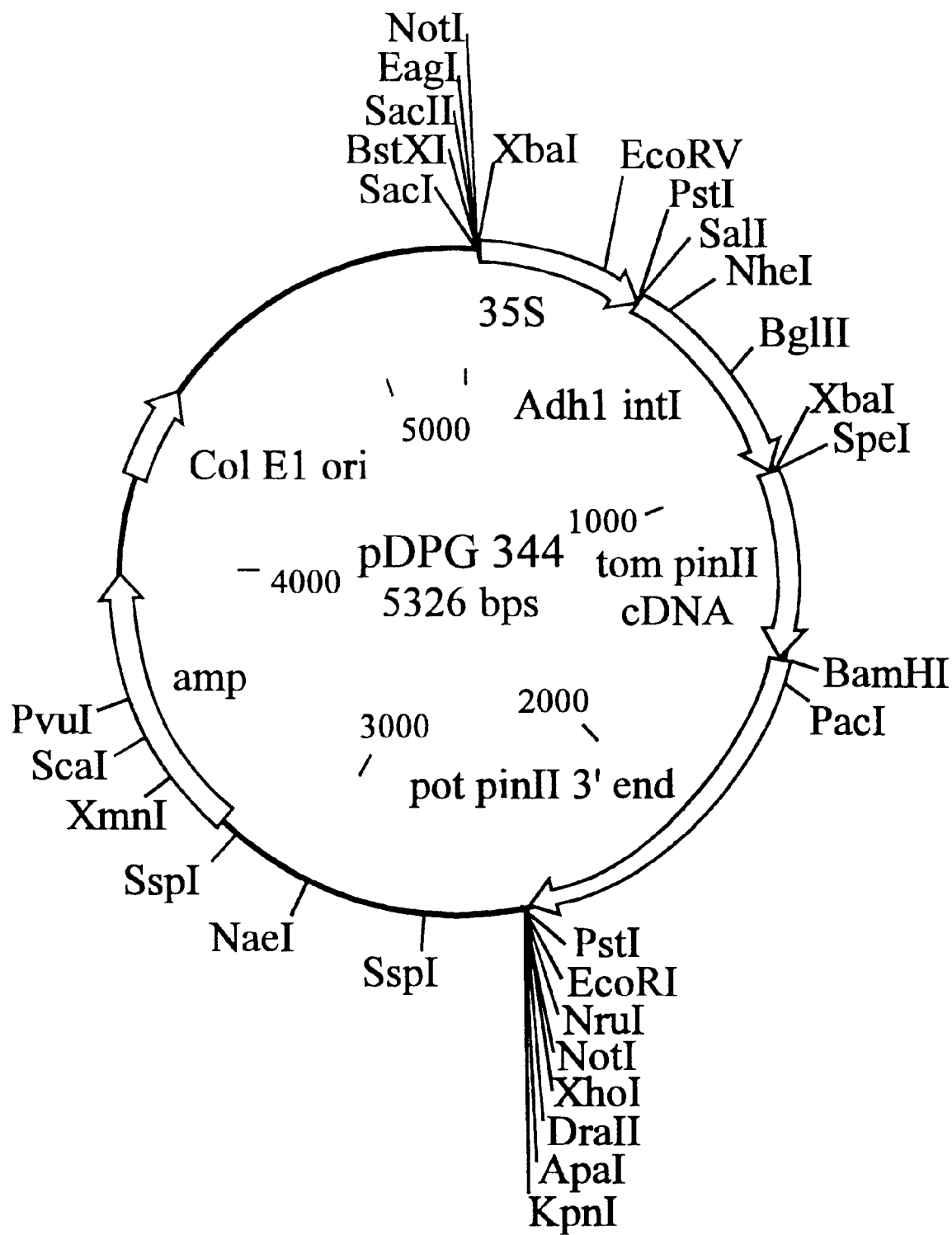
Figure 1:
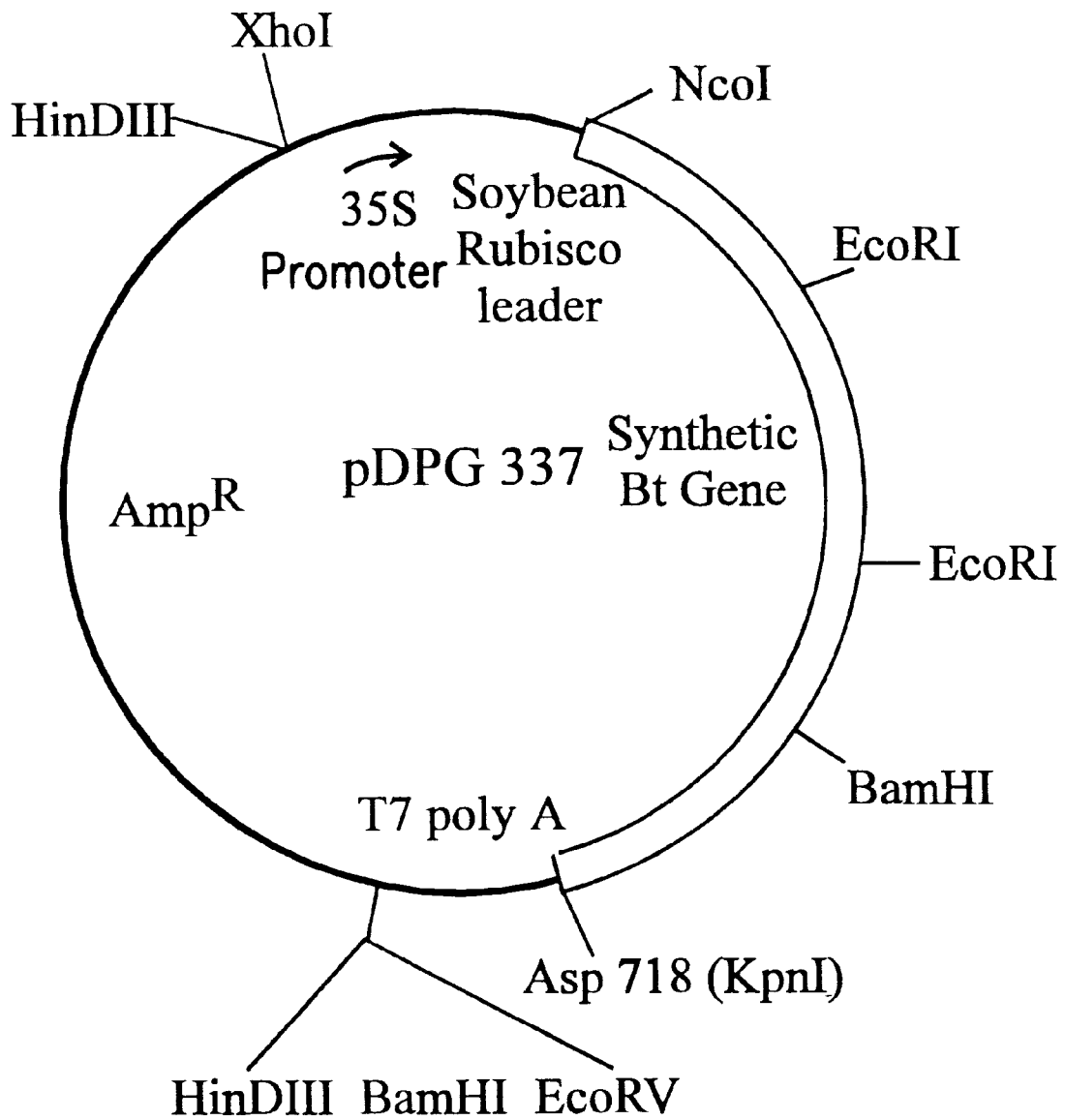

WDV-bar vectors were constructed to help address the question of the effect of promoter strength on selection as well as to provide replicating vectors for eventual use with embryogenic cultures. The 35S-bar-Tr7 expression cassette was isolated from pDPG165 as an EcoRI/HindIII fragment and protruding ends were filled in with T4 DNA polymerase. This fragment was ligated into pDPG386 (pWI-11) that had been linearized with BamHI, filled in with T4 DNA polymerase, and alkaline phosphatase treated. Vectors containing both orientations of the insert were generated and disignated pDPG388 and pDPG389 (FIGS. 1V,W).

A gene encoding the enzyme EPSPS was cloned from Zea mays. Two mutations were introduced into the amino acid sequence of EPSPS to confer glyphosate resistance, i.e., a substitution of isoleucine for threonine at amino acid position 102 and a substitution of serine for proline at amino acid position 106. Seven plant expression vectors were constructed using the promoterless mutant maize EPSPS expression vector received from Rhone Poulenc (pDPG425). The mutant EPSPS gene in this vector encodes an enzyme with amino acid changes at positions 102 (threonine to isoleucine) and 106 (proline to serine). Seven promoters (±introns) were used in vector constructions using the mutant maize EPSPS gene. A description of the construction of these vectors is presented below.

Four vectors (pDPG434, 436, 441, and 443) were constructed by cloning four promoters into SmaI-linearized pDPG425. Linearized vectors were treated with calf alkaline phosphatase to prevent recircularization prior to ligation. The rice actin promoter and intron were isolated as a 1.5 kb HindIII fragment from pDPG421 (pDM302; Cao et al., Plant Cell Rep (1992) 11:586–591). The 35S/adh1 intron I promoter was isolated from pDPG208 as a 0.9 kb HindIII fragment. The 2X Arabiodopsis histone promoter was isolated as a 1.4 kb EcoRI/HindIII fragment from pDPG404. The 2X 35S/Arabidopsis histone promoter was isolated as a 1.8 kb EcoRI/HindIII fragment from pDPG405. The above mentioned promoter fragments were T4 DNA polymerase-treated to create blunt ends prior to ligation into SmaI linearized pDPG425 (FIG. 1(Z)). To create pDPG447, a 2.1 EcoRI/NcoI α-tubulin/adh1 intron I fragment was isolated from pDPG407 and ligated into EcoRI/NcoI digested pDPG425 (FIG. 1(Z)). The adh1 promoter and intron I were isolated from pDPG172 (FIG. 1(Y), a derivative of pDPG140 (FIG. 1(X), as a 1.8 kb EcoRI fragment and ligated into EcoRI digested, calf alkaline phosphatase-treated pDPG425 (FIG. 1(Z)). The resulting plasmid was designated pDPG465. The 2X OCS promoter and adh1 intron VI were isolated from pDPG354 as a 0.6 kb SacI/NcoI fragment and ligated into SacI/NcoI digested pDPG425 (FIG. 1(Z)). This plasmids was designated pDPG467. A list of all of the mutant maize EPSPS vectors that were constructed is shown in Table 4.

TABLE 4

List of mutant maize EPSPS plant expression vectors constructed using pDPG425, and various promoters.

| DEKALB Plasmid Designation | Plant Expression Cassette |
| --- | --- |
| pDPG434 | actin - EPSPS - nos |
| pDPG436 | 35S/adh1 intron I - EPSPS - nos |
| PDPG441 | 2X Arabidopsis histone - EPSPS - nos |
| pDPG443 | 2X 35S/Arabidopsis histone - EPSPS - nos |
| pDPG447 | α-tubulin/adh1 intron I - EPSPS - nos |
| pDPG465 | 2X OCS/adh1 intron VI - EPSPS - nos |
| pDPG467 | adh1 promoter/adh1 intron I - EPSPS - nos |

Several vectors were constructed containing genes which may increase stress resistance in transgenic plants, including the mtlD gene from E. coli and the HVA-1 gene from barley. The mannitol operon was originally cloned and characterized by Lee and Saier, 1983. The mtlD gene has been shown to confer stress resistance on transgenic tobacco plants (Tarczynski, M. C. et al., 1993). A plasmid designated pCD7.5, containing the mtlD gene from this operon (encoding mannitol-1-phosphate dehydrogenase) was obtained from M. Müller, University of Freiburg. The structural gene was isolated as a 1500 bp fragment after digestion of pCD7.5 with NsiI and PstI, and was ligated into a pUC18-based vector containing the 35S promoter from Cauliflower Mosaic Virus, the first intron from the maize Adh1 gene, and the transcript 7 3' end from *Agrobacterium tumefaciens*. The backbone and regulatory elements were prepared for this construction by removing the luciferase structural gene from pDPG215 (35s-AdhI$_1$-luc-Tr7 3'; further described in this document), and then religating with an oligonucleotide that created a unique NsiI site between the intron and Tr7 element (this intermediate vector was designated pDPG431). pDPG431 was then linearized using NsiI and the mtlD gene was inserted. The final vector was designated pDPG451 (FIG. 1(BB)).

A second expression vector for the mtlD gene was created by removing the bar gene from pDPG182 using SmaI. After blunting the ends of the mtlD gene, it was ligated into the pUC-based vector; between the maize AdhIpromoter/AdhI$_1$ intron and the transcript 7 3' end from *Agrobacterium tumefaciens* (provided in pCEV5 from Calgene, Inc., Davis, Calif.). This plasmid vector was designated pDPG469.

A gene isolated from barley that encodes a Late Embryogenic Abundant protein (Dure, L., et al., 1989). (HVa-1) was obtained from Dr. H. D. Ho (Washington University), isolated as an NciI/SphI fragment and cloned into the polylinker of pCDNA II (Invitrogen, Inc). It was then reisolated as a BamHI/NsiI fragment and cloned into the polylinker site of pDPG431 (see above). The result was the pUC-based vector with the following expression unit, 35s-AdhI$_1$-HVa1-Tr7 3' (designated pDPG474).

Plasmid constructs designed for increasing the level of lysine in the plant were designed to place a dapA polypeptide-coding sequence, modified to contain a sequence corresponding to one of two maize plastid transit peptide sequences, under the control of various plant promoter elements. These constructs include the widely-used CaMV 35S promoter, maize endosperm-specific promoters from genes encoding either a 27 kD (Z27) or a 10 kD (Z10) zein storage protein, and an embryo-specific promoter from the maize Globulin1 gene (Glb1), which encodes an abundant embryo storage protein. The transit peptide sequences used here correspond to those present in genes encoding either a maize rubisco small subunit polypeptide (MZTP) or the native maize DHDPS polypeptide (DSTP). Features of these constructs, along with their lab designations, are as follows:

| expression construct | promoter/transit peptide/coding seq./3' regulatory sequence |
|---|---|
| pDPG 334 | Z10/MZTP/dapA/nos |
| 335 | Z27/DSTP/dapA/35S |
| 371 | 35S/MZTP/dapA/nos |
| 372 | 35S/DSTP/dapA/nos |
| 418 | Glb1/DSTP/dapA/Glb1 |

Construction of these plasmids was performed as follows:

pDPG371: In this construct, the synthetic pea chloroplast transit peptide encoding sequence described in U.S. patent application Ser. No. 07/204,388 was replaced with a synthetic sequence corresponding to that encoding a maize chloroplast transit peptide (from a rubisco small subunit sequence; GenBank Accession Y00322). Eight oligonucleotides were synthesized in order to reconstruct the maize ssu transit peptide sequence by the same strategy described for synthesis of the pea chloroplast transit peptide sequence (in U.S. patent application Ser. No. 07/204,388). Sequences of these oligonucleotides, in the the final context of the synthetic gene fragment, are as follows (The upper nucleic acid sequence is represented by seq id no:9, the lower nucleic acid sequence by seq id no:10):

```
HindIII                                    MZTP46
MZTP49
AGCTTGCAGCGAGTACATACATACTAGGCAGCCAGGCAGCCATGGCGCCCACC ACGTCGCTCATGTATGTATGATCCGTCGGTCCGTCGGTACCGCGGGTGG
             MZTP25                              MZTP45

MZTP51
GTGATGATGGCCTCGTCGGCCACCGCCGTCGCTCCGTTCCAGGGGCTCAAGTCC

CACTACTACCGGAGCAGCCGGTGGCGGCAGCGAGGCAAGGTCCCCGAGTTCAGG
                          MZTP53

MZTP39
ACCGCCAGCCTCCCCGTCGCCCGCCGGTCCTCCAGAAGCCTCGGCAACGTCAGC

TGGCGGTCGGAGGGGCAGCGGGCGGCCAGGAGGTCTTCGGAGCCGTTGCAGTCG
                                                  MZTP54

SphI
AACGGCGGAAGGATCCGGTGCATG

TTGCCGCCTTCCTAGGCCAC
```

The sequence is identical to that of the rubisco ssu gene described in GenBank Y00322, except for the introduction of a HindIII-compatible sequence generated by the addition of AGCTT to the 5' end of MZTP46 and an A residue to the 3' end of MZTP25. The ATG initiation codon is indicated in bold type, as is the TGC cysteine codon corresponding to the carboxyterminal residue of the native maize ssu transit peptide. This corresponds to a 47 amino acid transit peptide sequence, from the initiating methionione to the carboxyterminal cysteine.

Using the same strategy as described for synthesis and reconstruction of the pea transit peptide sequence, equimolar amounts of oligonucleotides MZTP49, 51, 39, 25, 45, and 53 were phosphorylated at their 5' ends in a polynucleotide kinase reaction; these were then combined with equimolar amounts of MZTP46 and MZTP54. This mixture was then added to a ligation reaction mixture containing the pGem3 vector (Promega Biotec, Madison, Wis.) which had previously been cleaved with the restriction enzymes HindIII and SphI to yield plasmid 9106. To fuse the ssu transit peptide sequence (MZTP) to the dapA polypeptide coding sequence, a 1170 bp SphI/EcoRI fragment, corresponding to the dapA/nos 3' cassette present in plasmid pDAP4201 (in U.S. patent application Ser. No. 07/204,388), was ligated into plasmid 9106 that had been cleaved with SphI and EcoRI to yield pDAP9284. To place this novel construct under control of the plant 35S promoter, a 1300 bp HindIII fragment from pDAP9284, containing the MZTP/dapA/nos3' cassette, was ligated into the HindIII site of plasmid 35-227 (U.S. patent application Ser. No. 07/204,388), which contains the 35S promoter, to yield plasmid 9305. To facilitate use of the 35S/MZTP/dapA/nos3' cassette in future manipulations, the entire cassette was isolated as a 1790 bp ClaI/SmaI fragment from plasmid 9305 and inserted into the commercial cloning vector pSP73 (Promega) which had been cleaved with ClaI and SmaI. This final construct is designated pDPG371.

pDPG335: In this construct the synthetic MZTP ssu transit peptide sequence was replaced with DNA encoding the transit peptide sequence from the native maize DHDPS enzyme. The plasmid pMDS-1, containing a cDNA clone corresponding to maize DHDPS (Frisch et al. Mol. Gen. Genet. 228:287–293, 1991), was a gift from B. Gengenbach, University of Minnesota, Minneapolis. The EcoRI fragment containing the full-length maize DHDPS cDNA was inserted into EcoRI-cleaved pSP73 to yield pMDS73A; this step was performed to facilitate subsequent cloning steps. A 215 bp ClaI/XbaI fragment from pMDS73A containing the transmit peptide cloning region was inserted into the ClaI and XbaI sites of plasmid p35-227, thereby fusing the transit peptide sequence to the 35S promoter sequence contained in p35-227 and yielding the plasmid pPol35SDTP. The 35S/DSTP cassette was subsequently fused to the dapA coding sequence. This was performed by cloning the cassette into the plasmid pHDAP73, which was constructed as follows: The 2728 bp hygromycin phosphotransferase cassette from plasmid pHygI1 (U.S. patent application Ser. No. 07/204, 388) was cloned as an EcoRI/HindIII fragment into the EcoRI and HindIII sites of pSP73, to yield pHyg73. This plasmid was then cleaved with BglII and ClaI, and the 35S/MZTP/dapA/nos cassette obtained as an 1800 bp BglII/ClaI fragment from pDPG371 was inserted to yield pHDAP73. This latter plasmid was then cleaved at the SpHI site, at which point the MZTP sequence joins the dap A sequence. The SphI 3' overhang was filled in by using Klenow fragment to produce a blunt end, and the resultant linear plasmid was subsequently cleaved with BglII, removing the 35S/MZTP portion from pHDAP73. The 35S/DSTP cassette was isolated from pPol35SDTP by cleavage with XbaI, followed by digestion with mung bean nuclease to remove the resultant 5' overhang. This treatment was followed by BamHI cleavage, which yielded a 674 bp fragment that was inserted into the cleaved pHDAP73 plasmid in place of the 35S/MZTP sequence. This novel plasmid, containing the cassette 35S/DSTP/dapA/nos, is designated pHDTP. A 1095 bp EcoRI/BamHI fragment, containing the DSTP/dapA region, was cloned into the EcoRI and BamHI sites of the commercial vector pUC119 (BRL) to yield pDSTP199. Nucleotide sequence analysis of this latter clone revealed a 2 bp deletion, apparently caused by the cloning process, at the junction of the DSTP and dapA sequences. This mutation was corrected in such a way as to restore the original reading frame and to introduce an additional MaeII restriction enzyme site as follows:

|  | DSTP | dapA |
|---|---|---|
| target sequence: | ATC A<u>CT</u> \| | TTC ACG GGA |
| <u>CT</u> deleted in pDSTP119 | ile thr | phe thr gly |
| modify to: | ATC ACG \| | TTC ACG GCA |

This manipulation leaves the desired reading frame intact and introduces the ACGT MaeII site at the junction between the DSTP and dapA sequences. Mutagenesis was accomplished with the reagents supplied in the BioRad Mutagene kit by using the oligonucleotide (seq id no:14):

5'CCTTGGCAGCCATCA<u>CG</u>TTCACGGGAAGTATTGTC 3'

The resultant plasmid, designated pMae2-1, was cleaved with EcoRI, treated with Klenow polymerase to generate blunt ends, then cleaved with BamHI to yield an 1100 bp fragment consisting of the DSTP/dapA cassette. This fragment was cloned into the Sma and BamHI sites of pZ27Z10 (in U.S. patent application Ser. No. 07/636,089), replacing the Z10 coding region and placing the DSTP/dapA sequence under control of the Z27 promoter and the 35S 3' regulatory region. This final construct is designated pDPG3353.

pDPG372: To place the DSTP/dapA cassette under control of the 35S promoter, a 1221 bp ScaI/EcoRI fragment from pHDTP, containing pSP73 vector sequences and the 35S promoter, was inserted into the ScaI and EcoRI sites of pMae2-1 to yield p35MDAP. To join the nos 3' regulatory region to the 35S/DSTP/dapA cassette, an 800 bp fragment of p35MDAP from the NdeI site just upstream of the 35S promoter to an NheI site internal to the dapA sequence was inserted into the NdeI and NheI sites of pDPG371, effectively replacing the 35S/MZTP cassette with the 35S/DSTP sequence. The resultant plasmid, containing the 35S/DSTP/dapA/nos 3' cassette, is designated p35DSD. Subsequent nucleotide sequence analysis of 35DSD revealed the presence of a cloning artifactor that introduced an ATG translation initiation codon 13 codons upstream of the authentic DSTP initiation codon. This problem was corrected by substituting this region of p35SDS with the corresponding region from pDPG335, as follows: a 525 bp fragment from pDPG335, extending from a KpnI site at the 3' end of the 35S promoter to a BstEII site internal to the dapA sequence, was inserted into KpnI/BstEII-cleaved p35DSD to yield pDPG372, which contains a functional 35S/DSTP/dap/nos cassette.

pDPG334: In this construct, the MZTP/dapA/nos cassette was placed under control of the Z10 promoter region as follows: a 1137 bp HindIII/NcoI fragment from pG10B-H3 (Kirihara et al, Gene 71:359–370, 1988), consisting of the Z10 promoter, was inserted into HindIII/NcoI cleaved pDAP9284, yielding pDPG334 which consists of the Z10/MZTP/dapA/nos cassette.

pDPG418: In this construct, the DSTP/dapA cassette was placed under control of the 5' and 3' regulatory regions of the maize Globulin1 (Glb1) gene (Belanger and Kriz Genetics 129:863–872, 1991) as follows: a 1050 bp KpnI/PstI fragment from pDPG335, consisting of the DSTP/dapA cassette, was inserted into the KpnI/PstI sites of the Glb1 expression vector pGEMSV3 (GenBank Accession No. L22295) to yield pDPG418.

Features of introduced genes used for selection of transformed cells are described above. Specific plasmid constructs used in these experiments are as follows:

| selection construct | Selectable/screenable marker |
|---|---|
| pDPG 165 | bar |
| 231 | bar , gus |
| 283 | bar |
| 355 | gus |
| 363 | bar |
| 366 | hpt |
| 367 | hpt |

Constructs pDPG 165, 231, 283, and 363 are as described above. Constructs pDPG355 and 367 are described in Walters et al., 1992 as pBII221 and pHygI1, respectively. Construct pDPG366 was made by transferring the hygromycin expression cassette (35S/AdhI1/hpt/nos) from pDPG367 as an EcoRI/HindIII fragment into EcoRI/HindIII cleaved pSP73.

Three plasmids containing the gene encoding the 10 kD zein protein were constructed. The plasmid pDPG375 is a 7 kb pUC119 plasmid containing a 3.9 kd HindIII fragment of a genomic clone encoding the 10 kD zein (Kirihara et al., 1988). This gene is under control of the native promoter and contains the native 3' sequence. The plasmid pDPG373 is a pUC199-based plasmid containing a HindIII-RsI Z4 (22 kD zein) promoter fragment and an NcoI-EcoRI fragment with the 10 kD zein coding and 3' sequences, and pDPG338 is a pUC119-based plasmid containing the 1.1 kg 27 kD zein promoter, 2.3 kb of the 10 kD zein coding and 3' sequences, and a cauliflower mosaic virus (CaMV) 35S poly(A) sequence. These plasmids are hereafter designated as the methionine constructs. Selectable marker genes used were hygromycin phosphotransferase (HPT, pHYGI1 also known as pDPG367; 35S promoter::Adh1 intron::HPT coding sequence::nos poly(A)sequence; Walters eta l., 1992) and bar, the gene conferring resistance to the herbicide Basta (35S::bar::Tr7, pDPG165, described earlier in this CIP), or pDPG363 (35S::Adh1::bar::nos). The plasmid pDPG363 was constructed by inserting a 0.5 kb SmaI fragment with BamHI linkers containing the bar gene into pHYG73, replacing the HPT gene. The plasmid pHYG73 was constructed by insertion of a 2.1 kb EcoRI-HindIII fragment containing the HPT coding sequence from pDPG367 (cited above) into pSP73 (Promega). The screenable marker gene of pBII221, which encodes β-glucuronidase (GUS) was also used (35S::Adh1::GUS::nos). The plasmid pBII221 was constructed by adding a 0.75 kb fragment containing the Adh1 intron between the 35S CaMV promoter and the GUS coding sequence of pBI221 (Clontech; pBI221 is pBI121 in pUC19 rather than pBIN19; Jefferson et al., 1987).

The plasmid pDPG380 contains the entire BalI-EcoRI 711 kp coding sequence of the gene encoding the 19 kD A20 zein and the 0.5 kb 5' sequence encoding the A20 preprotein (reconstructed independently from the coding sequence by PCR) in antisense orientation, with 1137 bp of the 10 kD zein promoter and 250 bp of nos 3' sequence. The plasmid pDPG340 is a pUC119-based plasmid containing 1137 bp of Z10 promoter sequence, a 980 bp XbaI-ScaI fragment with the entire Z4 coding sequence in antisense orientation, and 250 bp of nos 3' sequence. These genes are hereafter referred to an antisense constructs. For transformation experiments, pDPG165 (35S::bar::Tr7, described elsewhere in this CIP), pDPG363 (35S::Adh1::bar::nos, also described elsewhere in this CIP) or pDPG367 (35S::Adh1::HPT::nos, described elsewhere) were used as selectable marker genes, and were cobombarded with the antisense constructs.

The vector pDPG354 contains an expression cassette for producing Bt endotoxin in maize (see FIG. 1 (CC) for map). It was constructed to contain the following DNA:
(i) A promoter, consisting of two ocs enhancers (J. G. Ellis et al., 1987) placed in the reverse orientation and located upstream of the TATA box derived from the cauliflower mosaic virus (CaMV) 35S promoter (Eco RV site to the transcription start site; H. Guilley et al., 1982; R. Kay et al. 1987), located upstream from:

(ii) an intron (intron VI) derived from the maize Adh1 gene (Callis, J. Fromm, M., Walbot, V., 1987), a 432 bp AccI-MspI fragment from a genomic clone of the Adh1 gene) that was located upstream from:

(iii) a synthetic Bt gene on a Nco I to Kpn I fragment of DNA coding for the toxin portion of the endotoxin protein produced by *Bacillus thuringiensis* subsp. kurstaki strain HD73 (M. J. Adang et al., 1985). This gene was synthesized and assembled using standard techniques to contain codons that are more preferred for translation in maize cells. A translation stop codon was introduced after the 613th codon to terminate the translation and allow synthesis of a Bt endotoxin protein consisting of the first 613 amino acids (including the f-met) of the Bt protein (see FIG. 12 for sequence of gene).

(iv) The DNA coding for the Bt protein was followed by a 930 bp RsaI-PstI segment of DNA derived from the potato proteinase II inhibitor gene (G. An et al., 1989).

This expression cassette was inserted into the *E. coli* plasmid pBluescript SK- (Stratagene, Inc.) and can be made available from the ATCC.

The vector pDPG344 was designed to mediate the expression of the tomato protease inhibitor II (pin) gene in maize and was constructed to contain the following DNA (see FIG. 1 (DD):

(i) 420 bp of DNA derived from the 35S promoter from CaMV located upstream of:

(ii) 550 bp derived form the intronI of the maize AdhI gene (Callis, J., Fromm, M. E., Walbot, V., 1987.) located immediately upstream from:

(iii) 470 bp of DNA coding for the cDNA of the tomato protease inhibitor II gene (Graham et al., 1985), followed by:

(iii) 930 bp of DNA derived from the 3' region of the potato protease inhibitor II gene (derived from pRJ13; Johnson et al., 1989);

This cassette was assembled on the *E. coli* plasmid pBluescript SK(-) (Stratagene Inc.) and can be made available from the ATCC.

The plasmid vector pDPG337 (also known as pLK487) consists of an *E. coli* replicon (pBS+; Stratagene Inc.) containing the following DNA (see FIG. 1 (EE):

1. a segment of DNA containing the promoter for the 35S transcript derived from CaMV, fused at the location of initiation of transcription of the 35S transcript to:
2. a segment of DNA (5' ATC TGG CAG CAG AAA AAC AAG TAG TTG AGA ACT AAG AAG AAG AAA 3') (seq id no:15) derived from the untranslated 5' leader sequence to the small subunit of the ribulose biscarboxylase gene of soybean (S. L. Berry-Lowe et al., 1982) which is joined at its 3' terminus to:
3. a synthetic Bt gene coding for the endotoxin from *Bacillus thuringiensis* subsp. kurstaki strain HD73 (see construction of pDPG 354 above).
4. The Bt gene was followed by a segment of DNA derived from the 3' of "transcript 7" gene from *Agrobacterium tumefasciens* (P. Dhaese et al., 1983).

Samples of E. coli containing pDPG337 can be made available through the ATCC.

EXAMPLE 7

Intracellular Targeting of the bar Gene

As mentioned above, the bar gene codes for an enzyme, PAT, that inactivates the herbicide phosphinothricin. Phosphinothricin is an inhibitor of both cytoplasmic and chloroplast glutamine synthetases. Current expression vectors target PAT to the cell cytoplasm. To determine if there is an advantage to also targeting PAT to the chloroplast, a transit:bar chimeric gene was constructed. A sequence encoding the rbcS transit peptide and part of the rbcS mature polypeptide, present on a 300 bp XbaI-BamHI fragment from pDPG226, was cloned adjacent to the bar sequence in pDPG165, to produce pDPG287. This resulted in an in-frame fusion of the two protein coding regions, with the intervening sequence coding for the following amino acids (seq id no:22):

rbcS-Pro-Arg-Gly-Ser-Thr-bar

Protoplasts were electroporated with pDPG287 and assayed for PAT activity. Using proteinase treatment and protection studies, it was then determined that the PAT enzyme is sequestered within an organelle, particularly the plastid.

F. Preferred Methods of Delivering DNA to Cells

Preferred DNA delivery systems do not require protoplast isolation or use of Agrobacterium DNA. There are several potential cellular targets for DNA delivery to produce fertile transgenic plants: pollen, microspores, meristems, immature embryos and cultured embryogenic cells are but a few examples. Germline transformation in maize has not been previously reported.

One of the newly emerging techniques for the introduction of exogenous DNA constructs into plant cells involves the use of microprojectile bombardment. The details of this technique and its use to introduce exogenous DNA into various plant cells are discussed in Klein, 1989, Wang, et al., 1988 and Christou, et al., 1988. One method of determining the efficiency of DNA delivery into the cells via microprojectile bombardment employs detection of transient expression of the enzyme β-glucuronidase (GUS) in bombarded cells. For this method, plant cells are bombarded with a DNA construct which directs the synthesis of the GUS enzyme.

Apparati are available which perform microprojectile bombardment. A commercially available source is an apparatus made by Biolistics, Inc. (now DuPont), but other microprojectile or acceleration methods are within the scope of this invention. Of course, other "gene guns" may be used to introduce DNA into cells.

Several modifications of the microprojectile bombardment method were made by the inventors. For example, stainless steel mesh screens were introduced below the stop plate of the bombardment apparatus, i.e., between the gun and the cells. Furthermore, modifications to existing techniques were developed by the inventors for precipitating DNA onto the microprojectiles.

Another newly emerging technique for the production of DNA into plant cells is electroporation of intact cells. The details of this technique are described in Krzyzek and Laursen (PCT publication WO 92/12250). Similar to particle bombardment, the efficiency of DNA delivery into cells by electroporation can be determined by using the β-glucuronidase gene. The method of electroporation of intact cells and by extension intact tissues, e.g., immature embryos, were developed by Krzyzek and Laursen and represent improvements over published procedures. Generation of fertile plants using these techniques were described by Spencer et al. (Spencer, T. M., Laursen, C. M., Krzyzek, R. A., Anderson, P. C., and Flick, C. E., 1993, Transgenic maize by electroporation of pectolyase-treated suspension culture cells. Proceedings of the NATO Advanced Study Institute on Plant Molecular Biology, Molecular-Genetic Analysis of Plant Metabolism and Development, In Press.) and Laursen et al. (Laursen, C. M., Krzyzek, R. A., Flick, C. E., Anderson, P. C. and Spencer, T. M. Transformation of maize by electroporation of suspension culture cells. Submitted to Plant Molecular Biology.)

Other methods may also be used for introduction of DNA into plant cells, e.g., agitation of cells with DNA and silicon carbide fibers.

EXAMPLE 8

Microprojectile Bombardment—SC82, SC94 and SC716

For bombardment, friable, embryogenic Type-II callus (Armstrong & Green, 1985) was initiated from immature embryos essentially as set forth above in Examples 1 and 2. The callus was initiated and maintained on N6 medium (Chu et al., 1975) containing 2 mg/l glycine, 2.9 g/l L-proline, 100 mg/l casein hydrolysate, 13.2 mg/l dicamba or 1 mg/l 2,4-D, 20 g/l sucrose, pH 5.8, solidified with 2 g/l Gelgro (ICN Biochemicals). Suspension cultures initiated from these callus cultures were used for bombardment.

in the case of SC82, suspension culture SC82 was initiated from Type-II callus maintained in culture for 3 months. SC82 cells (see Example 2) were grown in liquid medium for approximately 4 months prior to bombardment (see Table 5, experiments #1 and #2). SC82 cells were also cryopreserved 5 months after suspension culture initiation, stored frozen for 5 months, thawed and used for bombardment (experiment #6).

In the case of suspension culture SC716 (see Example 1), it was initiated from Type-II callus maintained 5 months in culture. SC716 cells were cultured in liquid medium for 5 months, cryopreserved for 8 months, thawed, and used two months later in bombardment experiments #4 and #5. SC94 was initiated from 10 month old Type-II callus; and cultured in liquid medium for 5 months prior to bombardment (experiment #3).

Prior to bombardment, recently subcultured suspension culture cells were sieved through 1000 µm stainless steel mesh. From the fraction of cell clusters passing through the sieve, approximately 0.5 ml packed cell volume (PCV) was pipetted onto 5 cm filters (Whatman #40 and vacuum-filtered in a Buchner funnel. The filters were transferred to petri dishes containing three 7 cm filters (Whatman #4) moistened with 2.5 ml suspension culture medium.

The dish containing the filters with the suspension cells was positioned 6 cm below the lexan plate used to stop the nylon macroprojectile. With respect to the DNA, when more than a single plasmid was used, plasmid DNA was precipitated in an equimolar ratio onto tungsten particles (average diameter approximately 1.2 µm, GTE Sylvania) using a modification of the protocol described by Klein, et al. (1987). In the modified procedure, tungsten was incubated in ethanol at 65° C. for 12 hours prior to being used for precipitation. The precipitation mixture included 1.25 mg tungsten particles, 25 µg plasmid DNA, 1.1M $CaCl_2$ and 8.7 mM spermidine in a total volume of 575 µl. After adding the components in the above order, the mixture was vortexed at 4° C. for 10 min, centrifuged (500×G) for 5 min and 550 µl of supernatant was decanted. From the remaining 25 µl of suspension, 1 µl aliquots were pipetted onto the macroprojectile for bombardment.

Each plate of suspension cells was bombarded twice at a vacuum of 28 inches Hg. In bombarding the embryogenic suspensions of A188×B73 and A188×B84, 100 µm or 1000 µm stainless steel screens were placed about 2.5 cm below the stop plate in order to increase the number of foci while decreasing their size and also to ameliorate injury to the bombarded tissue. After bombardment, the suspension cells and the supporting filter were transferred onto solid medium or the cells were scraped from the filter and resuspended in liquid culture medium.

Cells from embryogenic suspension cultures of maize were bombarded with the bar-containing plasmid pDPG165 alone or in combination with a plasmid encoding GUS, pDPG208 (FIG. 1). In experiments in which a GUS plasmid was included, two of the filters containing bombarded cells were histochemically stained 48 h post-bombardment. The total number of foci (clusters of cells) per filter transiently expressing GUS was at least 1000. In two separate studies designed to quantitate transiently expressing cells (using an SC82 (A188×B73) suspension culture), the mean number of GUS-staining foci per filter was 1472 and 2930. The number of cells in individual foci that expressed GUS averaged 2–3 (range 1–10). Although histochemical staining can be used to detect cells transformed with the gene encoding GUS, those cells will no longer grow and divide after staining. For detecting stable transformants and growing them further, e.g., into plants, selective systems compatible with viability are required.

EXAMPLE 9

Microprojectile bombardment: AB12

Cell line AB12 was initiated as described in example 4. The microprojectile bombardment instrument, microprojectiles and stopping plates were obtained from Biolistics (Ithaca, N.Y.). Five clumps of 7- to 12-day-old callus, each approximately 50 mg in wet weight, were arranged in a cross pattern in the center of an empty 60 mm×15 mm Petri plate. Plates were stored in a closed container with moist paper towels throughout the bombardment process.

Plasmids were coated onto M-10 tungsten particles (Biolistics) as described by Klein et al. (1988, 1989) except that 5 µg of DNA was used, the DNA precipitation onto the particles was performed at 0° C. and the tube containing the DNA-coated tungsten particles were stored on ice throughout the bombardment process. When both plasmids were used, each was present in an amount of 2.5 µg. Control bombardments contained TE buffer (10 mM Tris, 1 mM EDTA, pH 8.0) with no DNA.

The sample plate tray was placed 5 cm below the bottom of the stopping plate tray of the microprojectile instrument, with the stopping plate platform in the slot nearest to the barrel. A 3 mm×3 mm mesh galvanized steel screen was placed over the open dish. The instrument was operated as described by the manufacturer (Biolistics, Inc.) using a gunpowder charge as the motive force. Each plate of tissue was bombarded once.

EXAMPLE 10

Microprojectile Bombardment—AT824

Suspension culture AT824 (described in example 3) was subcultured to fresh medium 409 2 days prior to particle bombardment. Cells were plated on solid 409 medium 16–24 hours before bombardment (about 0.5 ml packed cell volume per filter). Tissue was treated with 409 medium containing 200 mOsm sorbitol (medium 431) for 1 hour prior to bombardment.

DNA was introduced into cells using the DuPont Biolistics PDS1000He particle bombardment device.

DNA was precipitated onto gold particles as follows. A stock solution of gold particles was prepared by adding 60 mg of 1 um gold particles to 1000 us absolute ethanol and incubating for at least 3 hours at room temperature followed by storage at −20° C. Twenty to thirty five ul sterile gold particles are centrifuged in a microcentrifuge for 1 min. The supernatant is removed and one ml sterile water is added to the tube, followed by centrifugation at 2000 rpm for 5 minutes. Microprojectile particles are resuspended in 30 ul of DNA solution (30 ug total DNA) containing 10 ug each of the following vectors: pDPG165 (bar), pDPG344 (tomato proteinase inhibitor II gene), and pDPG354 (*B. thuringiensis* crystal toxin protein gene). Two hundred twenty microliters sterile water, 250 ug 2.5M $CaCl_2$ and 50 ul spermidine are added. The mixture is thoroughly mixed and placed on ice, followed by vortexing at 4C for 10 minutes and centrifugation at 500 rpm for 5 minutes. The supernatant is removed and the pellet resuspended in 600 ul absolute ethanol. Following centrifugation at 500 rpm for 5 minutes the pellet is resuspended in 36 ul of absolute ethanol.

Ten ul of the particle preparation were dispensed on the surface of the flyer disk and the thanol was allowed to dry completely. Particles were accelerated by a helium blast of approximately 1100 psi. One day following bombardment cells were transferred to liquid medium 409 (10 ml). Tissue was subcultured twice per week. During the first week there was no selection pressure applied.

EXAMPLE 11

Further Optimization of Ballistic Transformation

This example describes the optimization of the ballistic transformation protocol. Both physical and biological parameters for bombardment have been addressed. Physical factors are those that involve manipulating the DNA/microprojectile precipitate or those that affect the flight and velocity of either the macro- or microprojectiles. Biological factors include all steps involved in manipulation of cells immediately after bombardment. The prebombardment culturing conditions, such as osmotic environment, the bombardment parameters, and the plasmid configuration have been adjusted to yield the maximum numbers of stable transformants.

Physical Parameters

Gap Distance The variable nest (macro holder) can be adjusted to vary the distance between the rupture disk and the macroprojectile, i.e., the gap distance. This distance can be varied from 0 to 2 cm. The predicted effects of a shorter gap are an increase of velocity of both the macro- and microprojectiles, an increased shock wave (which leads to tissue splattering and increased tissue trauma), and deeper penetration of microprojectiles. Longer gap distances would have the opposite effects but may increase viability and therefore the total number of recovered stable transformants.

The effect of gap distance was investigated by bombarding the E1 suspension with pDPG208. Plates were shot in triplicate at gaps of 3, 6, 9, and 12 mm. Tissue was assayed for GUS activity and foci were counted. Using a 3 mm gap, GUS foci were the most numerous and well distributed across the filter. The gas shock wave appeared to be the greatest at this distance as shown by the degree of tissue splattering. Previous experiments performed at this gap size have also shown poor tissue recovery. Gaps of 6 mm and 9 mm showed little to no tissue splattering. GUS foci were well distributed across the filter but were fewer in number than those in the 3 mm samples. Samples bombarded with a gap distance of 12 mm showed nearly equivalent numbers of GUS foci as with sample bombarded at 6 mm and 9 mm but they were located almost exclusively at the center of the filter. No tissue splattering was observed. Based on these observations, it is suggested that bombardments be conducted with a gap distance of 6 to 9 mm.

Flight Distance The fixed nest (contained within the variable nest) can be varied between 2 and 2 cm in predetermined increments by the placement of spacer rings to adjust the flight path traversed by the macroprojectile. Short flight paths allow for greater stability of the macroprojectile in flight but reduce the overall velocity of the microprojectiles. Increased stability in flight increases the number of centered GUS foci. Greater flight distances (up to some point) increase velocity but also increases instability in flight.

The effect of the macroprojectile flight path length was investigated using E1 suspension cells. The flight distances tested were 0, 1.0, 1.5, and 2.0 cm. Samples were bombarded with pDPG208 GUS vector and were assayed 48 hours after bombardment for GUS activity. The number of GUS foci was the greatest at a flight path length of 1.0 cm and least at 0 cm. No tissue splattering was observed at 0 cm, very little at 1.0 cm, and greater amount at 1.5 and 2.0 cm. Based on these observations, it is recommended that bombardments be done with a flight path length of 1.0 cm.

Tissue distance Placement of tissue within the gun chamber should have significant effects on microprojectile penetration. Increasing the flight path of the microprojectiles will decrease velocity and trauma associated with the shock wave. A decrease in velocity will also result in shallower penetration of the microprojectiles.

Helium pressure By manipulation of the type and number of rupture disks, pressure can be varied between 400 and 2000 psi within the gas acceleration tube. Optimum pressure for stable transformation has been determined to be between 1000 and 1200 psi.

Biological Parameters

Culturing conditions and other factors can influence the physiological state of the target cells and may have profound effects on transformation and integration efficiencies. First, the act of bombardment could stimulate the production of ethylene which could lead to senescence of the tissue. The addition of antiethylene compounds could increase transformation efficiencies. Second, it is proposed that certain points in the cell cycle may be more appropriate for integration of introduced DNA. Hence synchronization of cell cultures may enhance the frequency of production of transformants. Third, the degree of tissue hydration may also contribute to the amount of trauma associated with bombardment as well as the ability of the microprojectiles to penetrate cell walls.

It has also been reported that slightly plasmolyzed yeast cells allow increased transformation efficiencies (Armaleo et al., 1990). It was hypothesized that the altered osmotic state of the cells helped to reduce trauma associated with the penetration of the microprojectiles. Lastly, the growth an cell cycle stage may be important with respect to transformation.

Osmotic adjustment It has been suggested that osmotic pre-treatment could potentially reduce bombardment associated injury as a result of the decreased turgor pressure of the plasmolyzed cell. Two studies were done in which E1 suspension cells were osmotically adjusted with media supplemented with sorbitol. Cells were plated onto osmotic media 24 hours prior to bombardment. The osmotic values of the media were 200, 400, and 600 mOSM/kg. Samples were bombarded with either pDPG208 (GUS) or a coprecipitate of pDPG165 (bar) and pDPG290 (Bt). GUS samples were assayed and foci were counted and plotted. Cells osmotically adjusted at 400 mOSM/kg showed an approximately 25% increase in the number of transient GUS foci. Samples bombarded with bar/Bt were selected in liquid (2 mg/l bialaphos) and thin plated on medium containing 3 mg/l bialaphos. Cells treated with 600 mOSM/kg medium grew more slowly than cells treated with media of other osmotic strengths in this study.

A second study investigated the effects of short duration osmotic adjustment at 500 mOSM/kg on both transient GUS expression and stable transformation. The rationale for the short duration of osmotic adjustment was that cells should be plasmolyzed just before bombardment, using longer time periods of pretreatment may allow the cells to adjust to the osmoticum (i.e. re-establishing turgor). The first control was bombarded (0 min., no new medium) followed by cells pretreated for 45 minutes and 90 minutes with 500 mOSM/kg medium with either pDPG208 or pDPG165 with pDPG290. Since the pretreatment required media changes (i.e. fresh 500 mOSM/kg media), a set of controls were also washed using fresh medium without the osmoticum. After bombardment the cells were put on to solid medium to recover overnight followed by resuspension in liquid medium. After one week, liquid selection was started using 2 $\mu$g/ml bialaphos. Cells were plated on 3 $\mu$g/ml bialaphos at 0.1 ml PCV eleven days after bombardment. Transient GUS activity was assayed 48 hours after bombardment.

The number of cells transiently expressing GUS increased following subculture into both fresh medium and osmotically adjusted medium. Pretreatment times of 90 minutes showed higher numbers of GUS expressing foci than shorter times. Cells incubated in 500 mOSM/kg medium for 90 minutes showed an approximately 3.5 fold increase in transient GUS foci than the control.

Plasmid configuration In some instances it will be desirable to deliver DNA to maize cells that does not contain DNA sequences necessary for maintenance of the plasmid vector in the bacterial host, e.g., E. coli, such as antibiotic resistance genes, including but not limited to ampicillin, kanamycin, and tetracycline resistance, and prokaryotic origins of DNA replication. In one such experiment the 4.4 kb HindIII fragment of pDPG325 containing the bar expression cassette and 2 kb of the uidA expression cassette (structural gene and 3' end) were purified by gel electrophoresis on a 1.2% low melting temperature agarose gel. The 4.4 kb DNA fragment was recovered from the agarose gel by melting gel slices in a 6–10 fold excess of Tris-EDTA buffer (10 mM Tris-HCl pH8.0, 1 mM EDTA, 70–72C); frozen and thawed (37C); and the agarose pelleted by centrifugation. A Qiagen Q-100 column was used for purification of DNA. For efficient recovery of DNA it was necessary to reduce the flow rate of the column to 40 ml/hr. Isolated DNA fragments can be recovered from agarose gels using a variety of electroelution techniques, enzyme digestion of the agarose, or binding of DNA to glass beads (e.g. Gene Clean). In addition HPLC and/or use of magnetic particles may be used to isolated DNA fragments. This DNA was delivered to AT824 cells using microprojectile bombardment. Twenty four transformants were recovered following selection on bialaphos containing culture medium. No transformants contained the ampicillin resistance gene or origin of DNA replication present in the plasmid vector. $R_0$ plants have been produced from 11 of these transformed cell lines. Fertility has been demonstrated in plants from ten transformants and $R_1$ seed has been planted in field tests.

As an alternative to isolation of DNA fragments a plasmid vector can be digested with a restriction enzyme and this DNA delivered to maize cells without prior purification of the expression cassette fragment. In one experiment pDPG165 was digested with EcoRI and HindIII. This digestion produces an approximately 1900 base pair fragment containing the 35S-bar-Tr7 expression cassette and an approximately 2600 base pair DNA fragment containing the ampicillin resistance gene and bacterial origin of DNA replication. This DNA was delivered to AT824 cells using microprojectile bombardment and 2/9 transformants (22%) isolated and did not contain the ampicillin resistance gene. In a second experiment pDPG165 digested with restriction enzyme as described above was delivered to AT824 cells via electroporation. Eight of twenty four transformants (33%) recovered lacked the ampicillin resistance gene. Plant regeneration is in progress from transformants lacking the ampicillin resistance gene that were produced in these two experiments.

EXAMPLE 12

Bombardment of Immature Embryos

Immature embryos (1.2–2.0 mm in length) were excised from surface-sterilized, greenhouse-grown ears of Hi-II 11–12 days post-pollination. The Hi-II genotype was developed from an A188×B73 cross for high frequency development of type II callus from immature embryos (Armstrong et al., 1991). Approximately 30 embryos per petri dish were plated axis side down on a modified N6 medium containing 1 mg/l 2,4-D, 100 mg/l casein hydrolysate, 6 mM L-proline, 0.5 g/l 2-(N-morpholino)ethanesulfonic acid (MES), 0.75 g/l $MgCl_2$, and 2% sucrose solidified within 2 g/l Gelgro, pH 5.8 (#735 medium) Embryos were cultured in the dark for two days at 24° C.

Approximately four hours prior to bombardment, embryos were transferred to the above culture medium with the sucrose concentration increased from 3% to 12%. When embryos were transferred to the high osmoticum medium they were arranged in concentric circles on the plate, starting 2 cm from the center of the dish, positioned such that their coleorhizal end was orientated toward the center of the dish. Usually two concentric circles were formed with 25–35 embryos per plate.

Preparation of gold particles carrying plasmid DNA was described in example 10. Particles were prepared containing 10 ug pDPG215 (luciferase), pDPG415 (Bt), and pDPG417 (bar) or 30 ug pDPG265 containing the maize R and C1B genes for anthocyanin biosynthesis.

The plates containing embryos were placed on the third shelf from the bottom, 5 cm below the stopping screen. The 1100 psi rupture discs were used. Each plate of embryos was bombarded once. A total of 420 embryos were bombarded on 14 plates with the luciferase, bar, and Bt genes. Embryos were allowed to recover overnight on high osmotic strength medium prior to initiation of selection. A set of plates was also bombarded with the C1B vector pDPG265. Red spots representing transient expression of anthocyanin pigments are observed 24 hours after DNA introduction.

EXAMPLE 13

Electroporation Experiment EP413: Stable Transformation of SC716 and AT824 cells using pDPG165 and pDPG208

Maize suspension culture cells were enzyme treated and electroporated using conditions described in Krzyzek and Laursen (PCT Publication WO 92/12250). SC716 or AT824 suspension culture cells, three days post subculture, were sieved through 1000 $\mu$m stainless steel mesh and washed, 1.5 ml packed cells per 10 ml, in incubation buffer (0.2 M mannitol, 0.1% bovine serum albumin, 80 mM calcium chloride, and 20 mM 2-(N-morpholino)-ethane sulfonic acid, pH 5.6). Cells were then treated for 90 minutes in incubation buffer containing 0.5% pectolyase Y-23 (Seishin Pharmaceutical, Tokyo, Japan) at a density of 1.5 ml packed cells per 5 ml on enzyme solution. During the enzyme treatment, cells were incubated in the ark at approximately 25° C. on a rotary shaker at 60 rpm. Following pectolyase treatment, cells were washed once with 10 ml of incubation buffer followed by three washes with electroporation buffer (10 mM HEPES, 0.4 mM mannitol). Cells were resuspended in electroporation buffer at a density of 1.5 ml packed cells in a total volume of 3 ml.

Linearized plasmid DNA, 100 ug of EcoRI digested pDPG165 and 100 ug of EcoRI digested pDPG208, was added to 1 ml aliquots of electroporation buffer. The DNA/electroporation buffer was incubated at room temperature for approximately 10 minutes. To these aliquots, 1 ml of suspension culture cells/electroporation buffer (containing approximately 0.5 ml packed cells) were added. Cells and DNA in electroporation buffer were incubated at room temperature for approximately 10 minutes. One half ml aliquots of this mixture were transferred to the electroporation chamber (Puite, 1985) which was placed in a sterile 60×15 mm petri dish. Cells were electroporated with a 70, 100, or 140 volt (V) pulse discharged from a 140 microfarad ($\mu$f) capacitor.

Approximately 10 minutes post-electroporation, cells were diluted with 2.5 ml 409 medium containing 0.3 M mannitol. Cells were then separated from most of the liquid medium by drawing the suspension up in a pipet, and expelling the medium with the tip of the pipet placed against the petri dish to retain the cells. The cells, and a small amount of medium (approximately 0.2 ml) were dispensed onto a filter (Whatman #1, 4.25 ml) overlaying solid 227 medium (Table 1) containing 0.3 M mannitol. After five days, the tissue and the supporting filters were transferred to 227 medium containing 0.2 M mannitol. After seven days, tissue and supporting filters were transferred to 227 medium without mannitol.

EXAMPLE 14

Electroporation of Immature Embryos

Immature embryos (0.4–1.8 mm in length) were excised from a surface-sterilized, greenhouse-grown ear of the genotype H99 11 days post-pollination. Embryos were plated axis side down on a modified N6 medium containing 3.3 mg/l dicamba, 100 mg/l casein hydrolysate, 12 mM L-proline, and 3% sucrose solidified with 2 g/l Gelgro®, pH 5.8 (#726 medium), with about 30 embryos per dish. Embryos were cultured in the dark for two days at 24° C.

Immediately prior to electroporation, embryos were enzymatically treated with 0.5% Pectolyase Y-23 (Seishin Pharmaceutical Co.) in a buffer containing 0.2 M mannitol, 0.2% bovine serum albumin, 80 mM calcium chloride and 20 mM 2-(N-morpholino)-ethane sulfonic acid (MES) at pH 5.6. Enzymatic digestion was carried out for 5 minutes at room temperature. Approximately 140 embryos were treated in batch in 2 ml of enzyme and buffer. The embryos were washed two times with 1 ml of 0.2 M mannitol, 0.2% bovine serum albumin, 80 mM calcium chloride and 20 mM MES at pH5.6 followed by three rinses with electroporation buffer consisting of 10 mM 4-(2-Hydroxyethyl)-1-piperazineethanesulfonic acid (HEPES) and 0.4 M mannitol at pH 7.5. For the electroporations, the final rinse of electroporation buffer was removed and the embryos were incubated with 0.33 mg/ml linearized pDPG165, 0.33 mg/ml supercoiled pDPG215 and 0.33 mg/ml linearized pDPG344 in electroporation buffer. One half ml aliquots of DNA in electroporation buffer and twenty embryos were transferred to the electroporation chamber that was placed in a sterile 60×15 mm Petri dish. An electrical pulse was passed through the cells from a 500 µf capacitor that was charged to 100 volts (400 V/cm field strength, 160 ms pulse decay time; exponential pulse).

Immediately following electroporation, embryos were diluted 1:10 with 726 medium containing 0.3 M mannitol. Embryos were then transferred to Gelgro® solidified 726 medium containing 0.3 M mannitol. Embryos were incubated in the dark at 24° C. After five days embryos were transferred to Gelgro solidified 726 medium containing 0.2 M mannitol. Two days later embryos were transferred to selection medium.

EXAMPLE 15

DNA delivery using silicon carbide fibers

Kaeppler et al. 1990 reported transformation of tobacco and BMS suspensions using fibers having a size of 0.6×10 to 80 µm. Transformations were accomplished by vortexing the silar fibers together with cells in a DNA solution. DNA passively enters as the cell are punctured. It is contemplated that fibers and/or particles of other types would also be useful. The suspension culture SC82 was tested for transformability using the silicon carbide (silar) transformation method described by Kaeppler et al. The initiation of cell line SC82 is described in example 2.

A 2% mixture of silar in absolute ethanol was prepared. Microfuge tubes were prepared (one per sample) by pipetting 80 µl of silar into each tube. The fibers were pelleted and the ethanol removed. Samples were then washed with sterile water, pelleted, and the water removed. Plasmid DNA (25 µl of 1 µmg/ml) was added to each tube. Tissue samples were prepared by adding 0.25 ml PCV of cells to a second set of microfuge tubes. Cells were pelleted and the medium removed. A 100 µl aliquot of fresh medium was next added to each tissue sample. The silar/DNA mixture was resuspended and added to the cells. The transformation was carried out by inverting the microfuge tubes and vortexing for 10 seconds followed by placing the tube upright and vortexing for an additional one minute. Samples were then removed and cultured in small petri dishes with 3 ml of medium. Transient GUS activity was observed two days after DNA delivery.

In a second experiment with SC82 a bead beater or a vortex was utilized to agitate samples. Samples were prepared as described above. Two samples were vortexed and the remaining samples were agitated with the bead beater for 5, 15, and 30 seconds at either the low or the high setting. The bead beater method showed a substantial increase in transient GUS activity as compared to vortexed samples. In all cases samples agitated on the "slow" setting of the bead beater showed higher transient GUS activity and less tissue damage than those on the "high" setting.

Three samples were vortexed in the presence of pDPG165 for selection of stably transformed cell lines. Each sample (0.25 ml PCV) was returned to a 25 ml flask and grown to 2 ml PCV at which time it was used as inoculum for a 125 ml flask. These were passaged once before plating onto 1 mg/l bialaphos containing medium. Cultures were plated onto filters at differing densities. Flask #1 was plated at 0.5 ml PCV, flask #2 at 0.25 ml PCV and flask #3 at 0.1 ml PCV. Filters containing cells were transferred three times onto bialaphos containing medium. Tissue arising from flask #1 was quite dense at the end of this phase of selection, tissue was scraped from a filter, divided into fourths and spread onto solidified selective medium. No transformants were recovered from this method. Tissue arising from flasks #2 and #3 were selected as described in example 8 and 18 bialaphos resistant transformants were recovered. No plant regeneration was attempted.

G. Identification of Transformed Cells Using Selectable Markers

It is believed that DNA is introduced into only a small percentage of cells in any one experiment. In order to provide a more efficient system for identification of those cells receiving DNA and integrating it into their genomes, therefore, one may desire to employ a means for selecting those cells that are stably transformed. One exemplary embodiment of such a method is to introduce into the host cell, a marker gene which confers resistance to some normally inhibitory agent, e.g. an antibiotic or herbicide. The potentially transformed cells are then exposed to the agent. In the population of surviving cells are those cells wherein generally the resistance-conferring gene has been integrated and expressed at sufficient levels to permit cell survival. Cells may be tested further to confirm stable integration of the exogenous DNA. Using embryogenic suspension cultures, stable transformant are recovered at a frequency of approximately 1 per 1000 transiently expressing foci. A specific embodiment of this procedure is shown in Example 17.

One of the difficulties in cereal transformation, e.g., corn, has been the lack of an effective selective agent for transformed cells, from totipotent cultures (Potrykus, 1989). Stable transformants were recovered from bombarded non-embryogenic Black Mexican Sweet (BMS) maize suspension culture cells, using the neo gene and selection with the aminoglycoside, kanamycin (Klein, 1989). This approach, while applicable to the present invention, is not preferred because many monocots are insensitive to high concentrations of aminoglycosides (Dekeyser et al., 1989; Hauptmann et al., 1988). The stage of cell growth, duration of exposure and concentration of the antibiotic, may be critical to the successful use of aminoglycosides as selective agents to identify transformants (Lyznik et al., 1989; Yang et al., 1988; Zhang et al., 1988). For example, D'Halluin et al. (1992) demonstrated that using the neo gene and selecting with kanamycin transformants could be isolated following electroporation of immature embryos of the genotype H99 or type I callus of the genotype PA91. In addition, use of the aminoglycosides, kanamycin or G418, to select suitable transformants from embryogenic maize cultures, in the inventors' experience, often results in the isolation of resistant calli that do not contain the neo gene.

One herbicide which has been suggested as a desirable selection agent is the broad spectrum herbicide bialaphos. Bialaphos is a tripeptide antibiotic produced by *Streptomyces hydroscopicus* and is composed of phosphinothricin (PPT), and analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicides Basta® or Ignite® is also effective as a selection agent. Inhibition of GS in plants by PPT causes the rapid accumulation of ammonia and death of the plant cells.

The organism producing bialaphos and other species of the genus Streptomyces also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A wherein the gene is isolated from *Streptomyces viridochromogenes*. In the bacterial source organism this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato and potato plants (De Block, 1987) and Brassica (De Block, 1989). In previous reports, some transgenic plants which expressed the resistance gene were completely resistant to commercial formulations of PPT and bialaphos in greenhouses.

PCT Application No. WO 87/00141 refers to the use of a process for protecting plant cells and plants against the action of glutamine synthetase inhibitors. This application also refers to the use of such a process to develop herbicide resistance in determined plants. The gene encoding resistance to the herbicide BASTA (Hoechst, phosphinothricin) or Heriace (Meiji Seika, Bialaphos) was said to be introduced by Agrobacterium infection into tobacco (*Nicotiana tabacum* cv Petit Havan SR1), potato (*Solanum tuberosum* cv Benolima) and tomato (*Lycopersicum esculentum*) and conferred on plants resistance to application of herbicides.

Another herbicide which is useful for selection of transformed cell lines in the practice of this invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which infer glyphosate resistance on the *Salmonella typhimurium* gene for EPSPS, aroA. The EPSPS gene was cloned from *Zea mays* and mutations similar to those found in a glyphosate resistant aroA gene were introduced in vitro. The mutant gene encodes a protein with amino acid changes at residues 102 and 106. Although these mutations confer resistance to glyphosate on the enzyme EPSPS it is anticipated that other mutations will also be useful.

An exemplary embodiment of vectors capable of delivering DNA to plant host cells is the plasmid, pDPG165 and the vectors pDPG433, pDPG434, pDPG435, and pDPG436. The plasmid pDPG165 is illustrated in FIGS. 1A and 1C. A very important component of this plasmid for purposes of genetic transformation is the bar gene which encodes a marker for selection of transformed cells exposed to bialaphos or PPT. Plasmids pDPG434 and pDPG436 contain a maize EPSPS gene with mutations at amino acid residues 102 and 106 driven by the actin promoter and 35S promoter-Adh1 intron I respectively. A very important component of these plasmids for purposes of genetic transformation is the mutated EPSPS gene which encodes a marker for selection of transformed cells.

EXAMPLE 16

Selection of bar Transformants Using Bialaphos in the Cell Line SC82 Following Particle Bombardment The suspension culture (designated SC82) used in the initial experiments (see Example 8) was derived from embryogenic Type-II callus of A188×B73. Following bombardment (see Example 8), cells on filters were resuspended in nonselective liquid medium, cultured for 1 to 2 weeks and transferred to filters overlaying solid medium containing 1 or 3 mg/l bialaphos. The degree of inhibition of tissue growth during selection was dependent upon the density of the cells on the filter and on the concentration of bialaphos used. At the density plated (0.5 PCV/filter), growth of cells cultured on 1 ml/l bialaphos was only partially inhibited (~30–50% of nonselected growth) and after 3 to 4 weeks much of this tissue was transferred as discrete clumps (~5 mm in diameter) to identical medium. On medium containing 3 ml/l bialaphos, the growth of cells on the original selection filter was severely inhibited (~10% of nonselected growth) and selection was carried out without removing the tissue from the original filter.

Figure 2A:
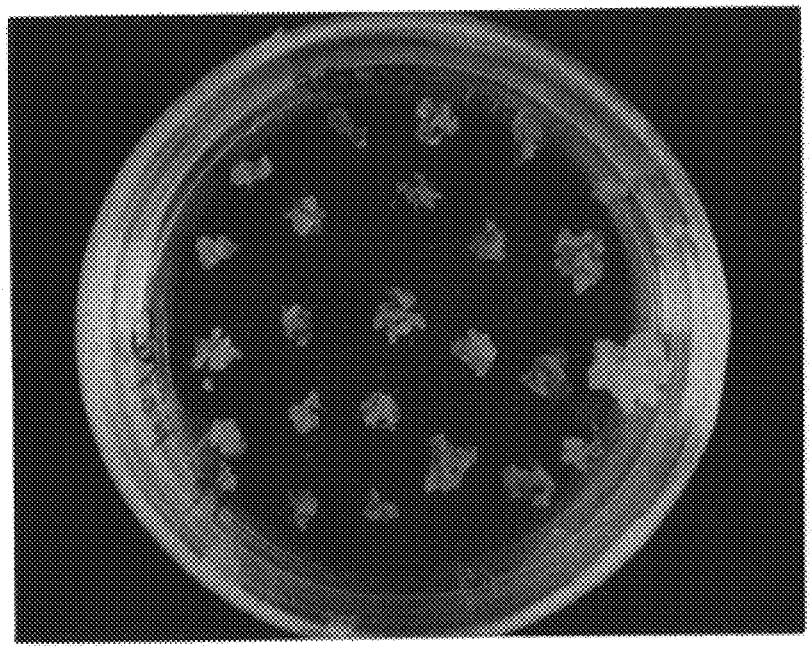
FIG. 2(A). SC82 bialaphos-resistant colony selected on 1 mg/l bialaphos.
Figure 2B:
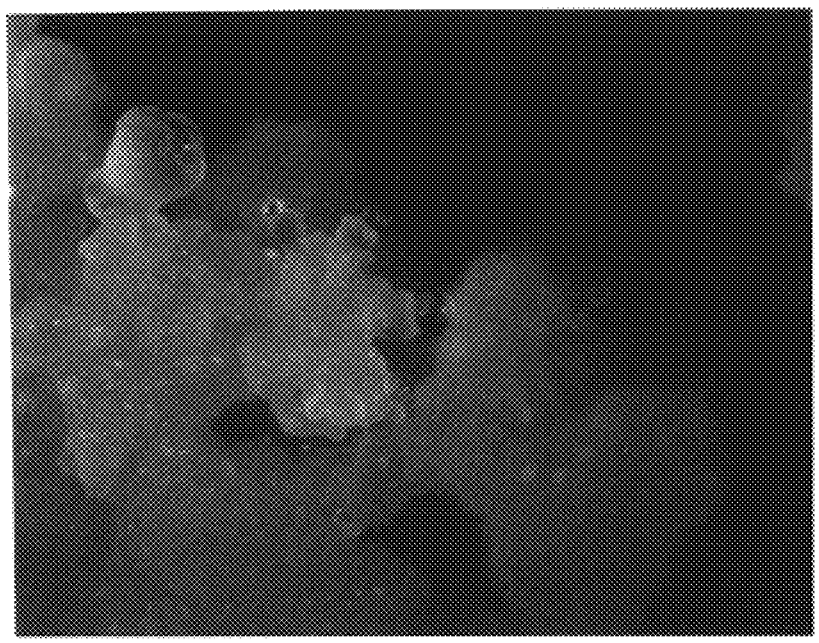
FIG. 2(B). Embryogenic SC82 bialaphos-resistant callus selected and maintained on 1 mg/l bialaphos.

Using either selection protocol (1 or 3 mg/l bialaphos), resistant cell colonies emerged on the selection plates of SC82 bombarded with pDPG165 approximately 6 to 7 weeks after bombardment (FIG. 2A). Bialaphos-resistant calli were maintained and expanded on selection medium. Much of this tissue was embryogenic (FIG. 2B). No colony growth occurred on plates to which cells were added from untransformed suspension cultures. These were controls which confirm the prediction that cells without the bar gene are not resistant to bialaphos.

Colonies on solid supports are visible groups of cells formed by growth and division of cells plated on such support. Colonies can be seen in FIG. 2A on a petri dish. In this figure, the cells capable of growth are those that are resistant to the presence of the herbicide bialaphos, said resistance resulting from integration and expression of the bar gene. Exposure of cells was to 1 mg/l bialaphos. FIG. 2B is a magnification showing the morphology of one bialaphos-resistant culture maintained on selection media indicating that growth is embryogenic.

Figure 3:
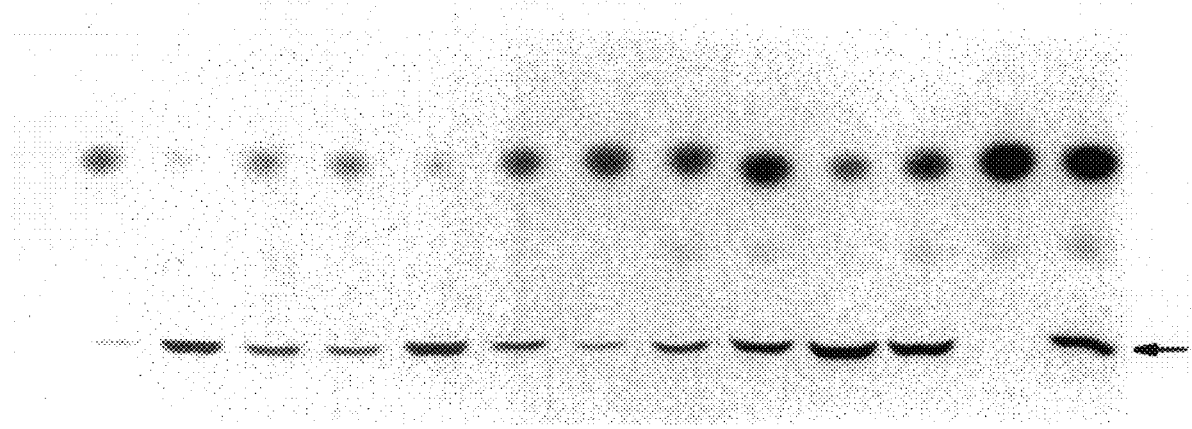
FIG. 3. Phosphinothricin acetyl transferase (PAT) activity in embryogenic SC82 callus transformants designated E1–E11 and a nonselected control (EO). 25 $\mu$g of protein extract were loaded per lane. B13 is a BMS-bar transformant. BMS is Black Mexican Sweet corn. Activities of the different transformants varied approximately 10 fold based on the intensities of the bands.

As a confirmation that the cells forming the colonies shown in FIG. 2 had indeed incorporated the bar gene and were expressing it, bialaphos-resistant callus lines were analyzed for activity of the bar gene product, phosphinothricin acetyl transferase (PAT), by thin-layer chromatography. Protein extracts from eleven callus lines (E1–11) isolated from SC82 bombardment experiments contained PAT activity as shown in FIG. 3 and activity levels varied approximately 10-fold among the isolates.

Still further and more direct confirmation of the presence of the bar gene was obtained by analysis of the genomic DNA of potential transformant by DNA gel blots (FIG. 4). The sources of DNA which were electrophoresed through the gel were the bialaphos-resistant callus lines designated E1–E11 and a non-selected control, E0. (FIG. 1 indicates the cleavage sites of those enzymes within the bar gene plasmid). After the DNA was electrophoresed through the gel and transferred to nylon membranes, the resulting blot was hybridized with a $^{32}$P-labeled bar gene sequence from the plasmid pDPG165. The radioactivity used per blot was approximately 25×10$^6$ Cerenkov cpm. The lane in FIG. 4 designated "1" and "5" copies contain 1.9 and 9.5 pg respectively of the 1.9 kb bar expression unit released from the plasmid pDPG165 by application of the EcoRI and HindIII enzymes; these amounts represent about 1 and 5 copies per diploid genome.

Genomic DNA from all eleven bialaphos-resistant isolates contained bar-hybridizing sequences as shown in FIG. 4. The hybridization in all isolates to a fragment migrating slightly larger than 2 kb may be due to contaminating pUC19 sequences contained in this bar probe preparation; no such hybridization occurred in subsequent experiments using the same genomic DNA and a different preparation of the bar probe. Hybridization to a 1.9 kb fragment in eight of the eleven isolates indicated that these isolates contained intact copies of the 1.9 kb bar expression unit. The estimated copy numbers of the intact unit ranged from one or two (E1, E7, E8, E10, E11) to approximately 20 (E3, E4, E6). Hybridization with the bar probe in isolates E2 and E5 occurred only to a single, higher molecular weight fragment (~3 kb).

To establish that the PAT coding sequence was intact in isolates E2 and E5, genomic DNA was digested with SmaI, which releases a 559 bp fragment containing the PAT structural gene (FIG. 1A), and subjected to DNA gel blot analysis using $^{32}$P-labeled bar. This analysis confirmed the presence of a single intact copy of bar. Expression of PAT in these isolates may not be dependent on the 35S promoter or the Tr7 3' end. The hybridization patterns of some of the isolates were identical (E2 and E5; E7 and E8; E3, E4, and E6); therefore, it is probable that some isolates did not arise from independent transformation events but represent transformants that were separated during selection.

Seven hybridization patterns were unique, likely representing seven independent single-cell transformation events. The patterns and intensities of hybridization for the seven transformants were unchanged during four months in culture, providing evidence for the stability of the integrated sequences. The seven independent transformants were derived from two separate bombardment experiments. Four independent transformants representing isolates E2/E5, E5/E4/E6, E1 and E7/E8, were recovered from a total of four original filters from bombardment experiment #1 and the three additional independent transformants, E9, E10, and E11, were selected from tissue originating from six bombarded filters in experiment #2. These data are summarized in Table 5.

Studies with other embryogenic suspension cultures produced similar results. Using either an SC82 culture that was reinitiated from cryopreserved cells (experiment #6) or an A188×B84 (SC94) suspension culture (experiment #3), numerous independent transformants were recovered (19 and 18 respectively; Table 5). All transformants contained the bar gene and expressed PAT. The copy number of bar-hybridizing sequences and levels of PAT expression were comparable to the studies described above.

EXAMPLE 17

Integration of the Bar Game into Cell Lines Derived from the SC716 Suspension Culture Bombardment studies and subsequent analyses were also performed on the A188×B73 suspension culture, termed SC716 (see Example 1). The resultant transformed plant cells were analyzed for integration of bar genes. To carry out this analysis, genomic DNA was obtained from R1–R21 isolates; 6 μg of DNA was digested with the restriction endonucleases EcoRI and HindIII, and DNA gel blot analysis was performed using the bar gene as probe. In FIG. 5, molecular weights in kb are shown to the right and left. The untransformed control is designated "RO," and the last column to the right contains the equivalent of two copies of the bar gene expression unit per diploid genome. For the DNA load used, two copies the bar expression unit per diploid genome is 5.7 pg of the 1.9 kb EcoRI/Hind fragment from the plasmid pDPG165. The DNA separated on the gel blot was hybridized to a $^{32}$P-labeled bar probe. The label activity in the hybridization was approximately $10 \times 10^6$ Cerenkov cpm. In A, the presence of an intact bar expression unit is inferred from the hybridization of the bar probe to a 1.9 band in the gel.

EXAMPLE 18

Assays for Integration and Expression of GUS

Figure 5B:
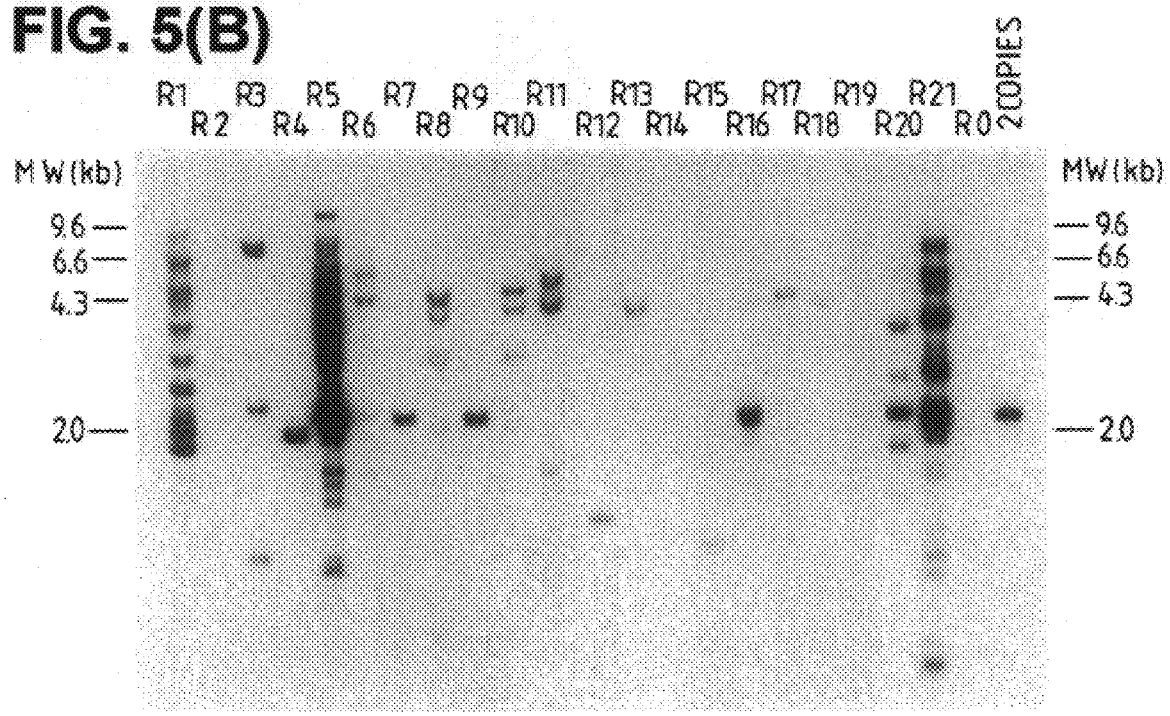
FIG. 5(B). The blot from A was washed and hybridized with $^{32}$p-labelled GUS probe (~35×10$^6$ Cerenkov cpm). Two copies of the 2.1 kb GUS-containing EcoRI/HindIII fragment from pDPG208 is 6.3 pg.

SC716 transformants discussed in Example 17, were further analyzed for integration and expression of the gene encoding GUS. As determined by histochemical assay, four of the SC716 transformants (R5, R7, R16, and R21) has detectable GUS activity 3 months post-bombardment. Expression patterns observed in the four coexpressing callus lines varied. The number of cells with GUS activity within any given transformant sampled ranged from ~5% to ~90% and, in addition, the level of GUS activity within those cells varied. The cointegration frequency was determined by washing the genomic blot hybridized with bar (FIG. 5A) and probing with $^{32}$P-labeled GUS sequence as shown in FIG. 5B. EcoRI and HindIII, which excise the bar expression unit from pDPG165, also release from pDPG208 a 2.1 kb fragment containing the GUS coding sequence and the nos 3' end (FIG. 1B).

Seventeen of the independent bar transformants contained sequences that hybridized to the GUS probe; three, R2, R14 and R19 did not. Transformants in which GUS activity was

TABLE 5

Summary of Maize Transformation Experiments

| Exp. # | Culture Bombarded | # of Filters Bombarded | # of Independent bar Transformants Recovered | # with Intact bar Expression Units | # with GUS Coding Sequence | # with GUS Activity | Cointegration Frequency (%) | Coexpression Frequency (%) |
|---|---|---|---|---|---|---|---|---|
| 1 | SC82 | 4 | 4 | 3 | n.a |  |  |  |
| 2 | SC82 | 6 | 3 | 2 | n.a. |  |  |  |
| 3 | SC94 | 10 | 8 | 6 | n.a. |  |  |  |
| 4 | SC716* | 8 | 13 | 8 | 11 | 3 | 85 | 23 |
| 5 | SC716* | 8 | 7 | 4 | 6 | 1 | 86 | 14 |
| 6 | SC82* | 4 | 19 | 17 | 13 | 3 | 68 | 16 |
| | TOTALS | 40 | 54 | 40 | 30 | 7 | 77(30/39) | 18(7/39) |

*culture reinitiated from cryopreserved cells
n.a. not applicable; only pDPG165 DNA used or co-transformation analysis not done detected (R5, R7, R16 and R21) had intact copies of the 2.1 kb EcoRI/HindIII fragment containing the GUS structural gene (FIG. 5B). Transformants that contained large numbers of fragments that hybridized to bar (R1, R5, R21) also contained comparable number of fragments that hybridized to the gene encoding GUS (FIGS. 5A and B). This observation is consistent with those reported using independent plasmids in PEG-mediated transformation of A188×BMS protoplasts (Lyznik et al., 1989) and in studies conducted by the inventors involving bombardment-mediated transformation of BMS suspension cells.

EXAMPLE 19

Transformation of Cell Line AT824 Using Bialaphos Selection Following Particle Bombardment—Selection in Liquid Medium The suspension culture (designated AT824) used in this experiment was derived from an elite B73-derived inbred (described in example 3). The culture was maintained in medium 409. Four filters were bombarded as described in example 10.

Following one week culture in liquid medium 409 without selection pressure, tissue was transferred to fliquid medium 409 containing 1 mg/L bialaphos. Cells were transferred twice per week into fresh medium containing 1 mg/L bialaphos for two weeks. Tissue was thin planted 3 weeks following bombardment at a concentration of 0.1 ml packed cell volume per petri dish containing medium 425 (with 3 mg/L bialaphos). Transformants were identified as discreet colonies 6 weeks following bombardment. It is the experience of the inventors that all cell lines that grow on 3 mg/L bialaphos contain the bar gene. Fifty transformed cell lines were recovered from this experiment. Twenty four of these cell lines contained the Bt gene.

EXAMPLE 20

Transformation of Cell Line AT824 Using Bialaphos Selection Following Particle Bombardment—Solid Medium Selection Cells in experiment S10 were bombarded as described in example 10 except the gold particle-DNA preparation was made using 25 ul pDPG319 DNA (bar gene and aroA expression cassette containing the α-tubulin promoter). Following particle bombardment cells remained on solid 279 medium in the absence of selection for one week. At this time cells were removed from solid medium, resuspended in liquid 279 medium, replated on Whatman filters at 0.5 ml PCV per filter, and transferred to 279 medium containing 1 mg/L bialaphos. Following one week, filters were transferred to 279 medium containing 3 mg/L bialaphos. One week later, cells were resuspended in liquid 279 medium and plated at 0.1 ml PCV on 279 medium containing 3 mg/L bialaphos. Nine transformants were identified 7 weeks following bombardment.

EXAMPLE 21

Transformation of Cell Line ABT4 Using Bialaphos Following Particle Bombardment

Initiation of cell line ABT4 is described in example 4. ABT4 was maintained as a callus culture. At the time of subculture, tissue was scraped off the solid culture medium and resuspended in 20 mls of 708 medium containing 0.2M mannitol. Tissue was dispersed with a large bore 10 ml pipette by picking up and dispensing several times until one could pickup 0.5 ml packed cell volume (PCV) for subculture to fresh solid 708 medium. Prior to bombardment three week old 708 maintenance cultures of ABT4 were transferred from solid medium to 20 mls 708+0.2M mannitol and 0.5 ml PCV was plated on glass fiber filters over 708+0.2M mannitol medium. Cultures were allowed to plasmolyze for 2–4 hours prior to bombardment. At the time of bombardment tissue on a glass fiber filter was placed on top of 3 filter papers moistened with 2.5 mls of 708+0.2M mannitol. Six ul of DNA/gold particles (described in example 10) was placed on flyers prior to bombardment with the Dupont Biolistics PDS1000He particle delivery device. Particles were accelerated by a 1100 psi blast of helium gas. Following bombardment tissue was returned to 708+0.2M mannitol and allowed to recover for 2–5 days. Selection began at this point by moving the tissue/filter to 708+1 mg/L bialaphos for 12 days. At this time tissue was transferred to 30–40 ml 708+0.5 mg/L bialaphos, dispersed, and thin plated at 0.05 to 0.10 PCV on 708+0.5 mg/L bialaphos solid medium. Transformants were identified 5–12 weeks following thin plating. Following identification transformants were maintained on 708+3 mg/L bialaphos.

EXAMPLE 22

Transformation of Immature Embryos of the Genotype Hi-II Using Bialaphos as a Selective Agent Following Particle Bombardment Immature embryos of the genotype Hi-II were bombarded as described in example 12. Embryos were allowed to recover on high osmoticum medium (735, 12% sucrose) overnight (16–24 hours) and were then transferred to selection medium containing 1 mg/l bialaphos (#739, 735 plus 1 mg/l bialaphos or #750, 735 plus 0.2M mannitol and 1 mg/l bialaphos). Embryos were maintained in the dark at 24° C. After three to four week on the initial selection plates about 90% of the embryos had formed Type II callus and were transferred to selective medium containing 3 mg/l bialaphos (#758). Responding tissue was subcultured about every two weeks onto fresh selection medium (#758). Nineteen transformants were identified six to eight weeks after bombardment. Fifteen of nineteen transformants contained the B. thuringiensis (Bt) crystal toxin gene. Plants have been regenerated from one transformant containing the Bt gene and transferred to soil in the greenhouse. Regeneration of plants from remaining lines containing the Bt gene is in progress.

EXAMPLE 23

Transformation of AT824 and SC716 Using Bialaphos Selection Following Electroporation Cells of AT824 and SC716 were electroporated and allowed to recover from electroporation as described in example 13. Five days later, tissue growing on filters was removed from the filter and transferred as clumps (approximately 0.5 cm in diameter) to the surface of solid selection medium. The selection medium consisted of 227 medium supplemented with 1 mg/L bialaphos. Three weeks later, slowly growing tissue was transferred, as 0.5 cm clumps, to 227 medium containing 3 mg/L bialaphos. Three to four weeks later, callus sectors that continued to grow were transferred to fresh 227 medium containing 3 mg/L bialaphos. Callus lines that continued to grow after this subculture were considered to be transgenic and perpetuated further, by transfer to fresh selection medium every two weeks. One SC716 and seven AT824 callus lines were selected in this example. The SC716 callus line was recovered from an electroporation at 140 μf, 100 V. Three AT824 callus lines were recovered from 140 μf, 70 V electroporations and four AT824 callus lines were recovered from electroporation at 140 μf, 140 V.

Three bialaphos resistant callus lines selected in this example, one derived from SC716 and two derived from AT824, were randomly chosen and assayed for phosphinothricin acetyltransferase (PAT) activity. PAT is the bar gene product, and PAT activity is determined by the ability of total protein extracts from potentially transformed cells to acetylate phosphinothricin (PPT), using $^{14}C$-acetyl coenzyme A as the acetyl donor. This transfer is detected, using thin layer chromatography and autoradiography, by a shift in the mobility of $^{14}C$-labelled compound from that expected for $^{14}C$-acetyl coenzyme A to that expected for $^{14}C$-N-acetyl PPT. The assay used for detection of PAT activity has been described in detail (Adams et al., published PCT application no. WO91/02071; Spencer et al. 1990). All three callus lines tested contained PAT activity.

In this example, suspension culture cells were electroporated with a second plasmid, pDPG208, encoding β-glucuronidase (GUS). Detection of GUS activity can be performed histochemically using 5-bromo-4-chloro-3-indolyl glucuronide (X-gluc) as the substrate for the GUS enzyme, yielding a blue precipitate inside of cells containing GUS activity. This assay has been described in detail (Jefferson 1987). One of the seven AT824 callus lines selected in this example, EP413-13, contained cells that turned blue in the histochemical assay. The callus line derived from SC716 in this example did not contain detectable GUS activity.

Southern blot analysis was performed on three bialaphos resistant callus lines to determine the presence and integration of the bar gene in genomic callus DNA. Southern blot analysis was performed as follows. Genomic DNA was isolated using a procedure modified from Shure et al. (1983). Approximately one gram of callus tissue from each line was lypholyzed overnight in 15 ml polypropylene tubes. Freeze-dried tissue was ground to a powder in the tube using a glass rod. Powdered tissue was mixed thoroughly with 3 ml extraction buffer (7.0 M urea, 0.35M NaCl, 0.05M Tris-HCl pH 8.0, 0.01M EDTA, 1% sarcosine). Tissue/buffer homogenate was extracted with 3 ml phenol/chloroform. The aqueous phase was separated by centrifugation, and precipitated twice using 1/10 volume of 4.4M ammonium acetate pH 5.2, and an equal volume of isopropanol. The precipitate was washed with 75% ethanol and resuspended in 100–500 μl TE (0.01M Tris-HCl, 0.001 M EDTA, pH 8.0). Genomic DNA was digested with a 3-fold excess of restriction enzymes, electrophoresed through 0.8% agarose (FMC), and transferred (Southern, 1975) to Nytran (Schleicher and Schuell) using 10× SCP (20× SCP: 2M NaCl, 0.6M disodium phosphate, 0.02M disodium EDTA). Filters were prehybridized in 6× SCP, 10% dextran sulfate, 2% sarcosine, and 500 μg/ml heparin (Chomet et al., 1987) for approximately 10 minutes. Filters were hybridized overnight at 65° C. in 6× SCP containing 100 μg/ml denatured salmon sperm DNA and $^{32}P$-labelled probe. Probe was generated by random priming (Feinberg and Vogelstein, 1983); Boehringer-Mannheim). Hybridized filters were washed in 2× SCP, 1% SDS at 65° for 30 minutes and visualized by autoradiography using Kodak XAR5 film.

In this example, genomic DNA isolated from bialaphos resistant callus lines was digested with HindIII and EcoRI, which release a 1.9 kb bar fragment from pDPG165 (FIG. 1A). Genomic DNA was probed with $^{32}P$ labelled 0.6 kb SmaI bar fragment from pDPG165 (FIG. 1A). All three EP413 callus lines analyzed contained DNA that hybridized to the bar probe. Copy number in the transformed callus ranged from one to two copies (EP413-3) to greater than 20 copies of bar (EP413-1). Furthermore, the restriction digest used, yielded bar-hybridizing fragments in callus DNA samples that were larger than the bar fragment released from pDPG165 in the same restriction digest. This result is indicative of stable integration of introduced DNA into the maize genome.

Thirty-nine plants were regenerated from seven of the eight bialaphos resistant callus lines selected in this example. Plants were regenerated from six AT824 callus lines and the single SC716 callus line. The plant regenerated from the SC716 callus line (EP413-4) did not survive to maturity. For plant regeneration, callus growing on 227 medium containing 3 mg/L bialaphos, was transferred to 189 medium (Table 1). Somatic embryos matured on 189 medium after one, two, or three two week subculture periods in the dark at 25° C. As somatic embryos developed on 189 medium, clumps of tissue containing these embryos were transferred to growth regulator free 101 medium (Table 1) and placed in the light (25–250 μE $M^{-2}$ $s^{-1}$). Plantlets developed on this medium after one, two, or three subculture periods. Plantlets were subsequently transferred to 501 medium (Table 1) in Plant Con® containers for rooting and further growth. Regenerates ($R_0$ plants) were subsequently transferred to a soilless mix in 0.5 liter pots and acclimated to ambient humidity in a growth chamber (200–450 μE $M^{-2}$ $s^{-1}$; 14 h photoperiod). The soilless mix has been described in detail (Adams et al., published PCT application no. WO91/02071). Plants were then transferred to a soilless mix in 16 liter pots and grown to maturity in a greenhouse.

Plants regenerated from five different EP413 callus lines were assayed for PAT activity as described for callus earlier in this example. All five plants contained PAT activity. Three plants regenerated from the single EP413 callus line that exhibited GUS activity (EP413-13) were analyzed for GUS activity. All three EP413-13 $R_0$ plants were positive for GUS activity. Files of blue cells were observed in leaf tissue of EP413-13 plants upon incubation with X-Gluc.

EP413 $R_0$ plants were also analyzed for the presence and integration of bar by Southern blot. DNA was isolated from leaf tissue as described for callus except that fresh, rather than lypholyzed tissue was used. Prior to the addition of extraction buffer, fresh leaf tissue was frozen in liquid nitrogen and ground to a fine powder in a 15 ml polypropylene tube using liquid nitrogen and a glass rod. DNA was isolated from four EP413 $R_0$ plants, each representing a different callus line. DNA was analyzed, digested with HindIII and BglII, or undigested, for hybridization to bar. $R_0$ DNA was probed with $^{32}P$ labelled 0.6 kb SmaI bar fragment from pDPG165 (FIG. 1A). HindIII/BglII digestion of pDPG165 releases a fragment containing 35S-bar of approximately 1.3 kb (FIG. 1A). Genomic DNA from all four plants contained at least one copy of the 1.3 kb HindIII/BglII 35S-bar fragment. In addition, undigested genomic DNA from all four plants exhibited hybridization to bar only in high molecular weight DNA (>20 kb), indicating integration of pDPG165 into maize chromosomal DNA.

Progeny were recovered from outcrosses made between electroporation-derived, transgenic $R_0$ plants and non-transformed inbred plants. Four EP413-3 $R_0$ plants were the first of the plants to reach maturity and flower. One of the plants was outcrossed as the male to a CD inbred plant. This cross resulted in 22 kernels. Sixteen of these kernels were planted in soilless mix and all germinated. Approximately two weeks post-germination, the progeny ($R_1$) plants were analyzed for PAT activity. Three of sixteen plants contained PAT activity. Four transgenic EP413-3 $R_0$ plants were also outcrossed as the female, using pollen collected from non-transformed inbred plants. Kernels developed on ears of all four EP413-3 $R_0$ plants. Thirty-seven kernels were recovered from an ear on an EP413-3 $R_0$ plant treated with pollen collected from a seed-derived, non-transformed FBLL inbred plant. Sixteen of these kernels were planted in soil and twelve germinated. Eight of these plants were analyzed for PAT activity; three of eight were positive for PAT activity.

These eight plants were also analyzed by Southern blot hybridization for the presence of bar. Genomic DNA isolated from these eight EP413-3 $R_1$ plants was digested with restriction enzymes HindIII and BglII, which release a 1.3 kb fragment containing bar from pDPG165 (FIG. 1A). In addition to DNA from the eight EP413-3 $R_1$ plants, DNA isolated from EP413-3 callus and DNA from the EP413-3 $R_0$ plant yielding these eight $R_1$ plants was included in the analysis. Genomic DNA was probed with $^{32}P$ labelled 0.6 kb SmaI bar fragment from pDPG165 (FIG. 1A). Hybridization to bar was detected in the DNA isolated from callus, $R_0$ and the three $R_1$ plants that contained PAT activity. Each of the bar-positive plants contained the expected 1.3 kb HindIII/BglII fragment from pDPG165 (FIG. 1A) as well as an additional, larger bar-hybridizing fragment of approximately 2.0 kb. This result, as well as the PAT activity found to be present in EP413-3 $R_1$ plants, conclusively demonstrates the sexual transmission to progeny of a functional gene introduced into maize cells by electroporation.

EXAMPLE 24

Transformation of H99 Immature Embryos Using Bialaphos as the Selective Agent Following Electroporation Immature embryos of H99 were electroporated as described in example 14. Five days after electroporation embryos were transferred to Gelgro solidified 726 medium containing 0.2 M mannitol. Two days later embryos were transferred to selection medium, 726 medium containing 1 mg/l bialaphos, 16 embryos per dish.

Embryos were cultured in the dark at 24° C. for about seven weeks. Seventy-eight of the approximately one hundred and twenty embryos plated on selection medium produced Type I callus. All responding callus was transferred to modified MS-based medium containing 1 mg/l NAA, 1 mg/l BAP and 3% sucrose solidified with 8 g/l Bactoagar (20 medium) for maturation. After about two weeks the tissue was transferred to 20 medium containing 1 mg/l bialaphos. Two weeks later the tissue was transferred to a modified MS-based medium containing 0.5 mg/l NAA, 0.5 mg/l BAP and 2% sucrose solidified with 8 g/l Bactoagar (7 medium) with 1 mg/l bialaphos. For rooting the tissue was transferred to a modified MS-based medium containing 0.25 mg/l NAA, 0.25 mg/l BAP and 2% sucrose solidified with 8 g/l Bactoagar and finally ½ strength MS0.

Tissue from twenty-three of initial seventy-eight responding embryos survived the regeneration and selection and produced plants. A total of seventy-five plants were transferred to soil. Four of the plants died and the remaining seventy-one plants were transferred to the greenhouse.

Plants in the greenhouse were tested for the presence of the bar gene by PCR analysis of DNA extracted from leaf tissue or by painting the leaves with 2% Basta. One PCR positive plant from embryo #31 was identified. All of the other plants were either PCR negative or showed severe necrosis in the Basta painting assay. DNA from leaf tissue of plant 3101 was further analyzed by Southern blot hybridization and gave a positive signal when probed with the Sma I fragment of pDPG165. This plant was selfed on June 7 and June 8 and backcrossed on Jun. 9, 1993. Nine seed were harvested from this plant. All seed germinated and seven of nine $R_1$ plants contain the bar gene as determined by PCR analysis.

EXAMPLE 25

Transformation of AB12 Using Hygromycin as a Selective Agent Following Particle Bombardment AB12 callus was bombarded as described in example 9. Callus was transferred (ten 25 mg clumps per plate) onto 734 medium (see Table 1) containing 15 mg/l hygromycin B (Calbiochem) immediately after bombardment. After 14 days all tissue was transferred to round 2 selection plates that contained 60 mg/l hygromycin. After 21 days on the round 2 selection plates, most of the material was transferred to F medium containing 60 mg/l hygromycin (round 3 selection plates). Both round 2 and round 3 plates were then observed periodically for the appearance of viable sectors of callus. Putative transformed callus line PH1 was observed on a round 2 plate, 70 days after bombardment. Putative transformants PH2 and PH3 were observed on round 3 plates, 58 and 79 days after bombardment, respectively. Lines were then maintained on F medium containing 60 mg/l hygromycin. Plant regeneration and analysis of transformants are described in Walters et al. (1992). Fertile transgenic plants were regenerated and transmission of the chimeric gene for hygromycin resistance was demonstrated through two complete generations.

EXAMPLE 26

Transformation of AT824 Using Glyphosate as a Selective Agent Following Particle Bombardment A mutant maize EPSPS gene was introduced into AT824 suspension culture cells via particle bombardment as described in example 10. In this example, the mutant maize EPSPS gene was carried by plasmid pDPG436. Plasmid pDPG436 contains a maize EPSPS gene with two amino acid changes, Thr to Ile at position 102 and Pro to Ser at position 106. In this plasmid, the mutant maize EPSPS expression cassette contains a 35S promoter/adh1 intron I combination and the nos 3' end. Following bombardment with gold particles coated with pDPG436, AT824 cells were cultured on 279 medium (Table 1) for four days. Subsequently, the cells were returned to liquid 401 medium (Table 1), at a density of 2 ml packed cell volume (PCV) per 20 ml, and cultured for four days. The cells were then transferred, at a density of 2 ml PCV/20 ml, to fresh 401 medium containing 1 mM glyphosate and cultured for four days. The subculture into 401 plus 1 mM glyphosate was repeated and after four days the cells were plated at a density of 0.1 ml PCV per 100×15 mm petri dish containing 279 plus 1 mM glyphosate. Six to eight weeks after bombardment, glyphosate resistant colonies were removed from the selection plates and subcultured onto fresh 279 plus 1 mM glyphosate. Seven glyphosate resistant callus lines were recovered in this example, at a frequency of zero to seven callus lines per bombardment. Two randomly chosen callus lines were analyzed for the presence of the introduced DNA by Southern blot hybridization (see example 23). Genomic DNA isolated from the callus lines was analyzed undigested or digested with NotI, which releases the mutant EPSPS expression cassette from pDPG436. The callus DNA was probed with $^{32}$P-labelled nos fragment. The nos fragment was isolated as an approximately 250 bp NotI/XbaI fragment from pDPG425. The nos fragment was chosen as the probe to avoid background hybridization possible using an EPSPS probe due to the presence of an endogenous maize EPSPS gene. Genomic DNA from both callus lines was positive for hybridization to nos in both the undigested and NotI-digested samples. Both callus DNA samples contained nos-hybridizing bands identical in size to the 35S/adh1 intron I-EPSPS-nos fragments released from pDPG436 upon digestion with NotI, as well as additional nos-hybridizing bands.

In a second embodiment, AT824 cells were bombarded with a mutant EPSPS gene under control of the rice actin promoter and intron (Cao et al., Plant Cell Rep (1992) 11:586–591). The plasmid used, pDPG434, contains the rice actin 5' region, the mutant EPSPS gene described in the previous example, and the nos 3' end. Bombarded AT824 cells were cultured and selected as described in the previous example. Thirteen glyphosate resistant callus lines were isolated in this example. Four to seven glyphosate resistant callus lines were recovered per bombardment in this example. As in the previous example, two randomly chosen callus lines were analyzed for the introduced DNA by Southern blot hybridization. Using the same analysis as in the previous example, both callus lines were found to contain DNA sequence that hybridized to the nos probe, confirming introduction of, and selection for expression of, the introduced mutant EPSPS gene.

H. Identification of Transformed Cells Using Screenable Markers

In addition to selectable markers such as the bar and aroA genes, various screenable marker genes have been employed by the present inventors in maize transformation. It is contemplated that screenable markers may be used to ultimately achieve three objectives: (1) the detection of expressing colonies in a population, which may not necessarily employ a visible marker; (2) the visualization, by microscope or unaided eye, of expressing cells within a population or tissue; and (3) the ability to assess tissue- and/or cell-specific expression in gene expression studies. A screenable marker which meets either objective would be useful and one that meets both criteria would be particularly advantageous. Of the potential candidates being considered as screenable markers, luciferase (Example 27) and aequorin satisfy only the first requirement, while modified extensin (Example 28) and tyrosinase could potentially meet both goals.

Tyrosinase

The tyrosinase gene is considered to be a potential screenable marker. Normally, melanin production requires the expression of two genes which encode for tyrosinase and a $Cu^{++}$ transfer protein. Recently, an *E. coli* transformant was isolated by Claudio Denoyo (Pfizer) in which the Cu-transfer protein does not appear to be required. There is still a requirement for copper as a coenzyme for tyrosinase, but this is satisfied by 1 mM $Cu^{++}$ and the tyrosinase acts as a copper scavenger. The gene itself is small with a high GC content which should be expressed in maize.

Aequorin

This gene was cloned by Dr. M. Cormier (University of Georgia) and encodes a protein called apoaequorin that is normally produced in jellyfish. When this protein complexes with a class of lipophilic fuorophores referred to as coelenterazines, the activated complex becomes sensitive to $Ca^{++}$. When the complex comes into contact with $Ca^{++}$, the coelenterazine is reduced to an amide and a photon of light is emitted. Thus, this gene encoded the proteinaceous portion of a calcium-sensitive bioluminescent complex.

This gene has been placed behind the 35S promoter and used to generate aequorin expressing tobacco plants which are being employed to study calcium levels in plant tissue. However, there are certain technical difficulties with developing this system into a screenable marker. Firstly, coelenterazines are difficult to obtain. Secondly, the intensity of the bioluminescence emitted by this complex is probably an order of magnitude lower than luciferase and the detection systems needed to visualize this reaction are very sophisticated and expensive.

However light emission from aequorin expressing cells have never been measured while the cells were being flooded with both coelenterazine and $Ca^{++}$. This is an important point. The apoaequorin protein is not the rate limiting factor in this reaction, it is the regeneration of reduced coelenterazine from the coelenteramide. Thus there is a requirement for a strong reducing agent in the assay. Using 1% DMSO, coelenterazine and calcium could drive the light emission up to detectable levels. Conversely, when these substrates are not present, i.e. in the plant, this normally energy-requiring reaction would not be occurring.

EXAMPLE 27

Luciferase as a Screenable Marker

The lux gene, encoding firefly luciferase, was initially tested as a potential screenable marker using C16 protoplast electroporation to evaluate transient expression, and cotransformation of BMS. Using X-ray film to detect bioluminescence, transient expression in C16 protoplasts was detected, but expression in BMS was not high enough for detection on X-ray film. Published results on luciferase expression in tobacco (Ow et al., 1986), indicate that as few as 350 expressing cells could be viably detected.

Two technical developments prompted the inventors to re-examine the feasibility of using this marker. The first is a Polaroid ASA 20,000 ELISA-type film detection system that is easy to use, with sensitivity comparable to, or slightly more sensitive than, X-ray film. The second is a new Luciferase Assay System (Promega), which through the oxidation of luciferyl-CoA, as opposed to luciferin, is claimed to provide a light reaction with greater total intensity and with a greatly extended half-life.

While the scintillation counter and multiwell luminometer afford one means of testing the utility of luciferase screening, i.e. populational screening for bioluminescence, it would be ideal to be able to visualize transformants on the tissue culture plate. This would be even more valuable if the method was not limited to specific cultures and/or tissue types, and if it could be extended to the whole plant (i.e. for gene expression studies). Computer-enhanced video microscopy has been recognized as a potentially valuable tool for these applications. Recently, the Photon Counting Camera (Hamamatsu) has provided a new level of sensitivity for the video-imaging of bioluminescence.

Bombarded E1 suspension cells were assayed using both the scintillation counter and the Polaroid detection system. Extracting ¼ of the cells on a filter 48 hours after bombardment, luciferase activity was at the lower limit of detection using the scintillation counter. Using much smaller aliquots of cells, due to the microtiter wells in the assay system, no discernable activity was observed using the Polaroid detection system.

Using dilutions of purified luciferin in both the scintillation counter and the Polaroid system, and comparing these results to scintillation counts of transient lux expression after bombardment of E1 cells, it was estimated that there is probably only a 10-fold discrepancy between the transient expression levels and the ability to detect a signal using this film. Further studies were thus conducted to bridge this detection gap. The luciferase system was optimized both with respect to the assay mixture and also with the creation of further luciferase expression vectors.

Luciferase Assay Mixture

The first step in this process was to re-evaluate the composition of the assay mixture, both in terms of relative luminescence and subsequent viability of the tissue. The addition of coenzyme A to the reaction mix has been reported to improve the bioluminescence kinetics of the luciferase assay. This has been one of the features incorporated into the Luciferase Assay System sold by Promega. In comparing the Promega mixture to the luciferase assay mixture usually employed, no significant difference was observed in assaying purified luciferase enzyme. However, when cell extract from a transformed E1 callus line was used, the Promega mixture produced approximately an 18-fold increase in signal (measured over a two minute period using the scintillation counter).

Multiple experiments were performed to assess the influence of the components of these assay mixtures; varying both the species and concentration of reducing agent, salts, coenzymes, protective proteins, and the substrate itself, luciferin. The type and amount of reducing agent was a point of concern for tissue viability, so two alternatives were compared for signal strength and tissue viability. Both glutathione (i.e. 10–50 mM) and DTT (5–33 mM) were found to produce strong bioluminescence signals in intact cell clusters, although the results were more variable with glutathione. 5 mM DDT provided the best compromise for enhanced signal strength and growth of callus after exposure to the mixture for 20 minutes. The most effective combination found to date is a hybrid, taking components from both the Promega recipe and the previously used standard mixture. This combination resulted in a 2–4 fold increase in signal over the Promega mixture. The recipe for this improved mix is:

25 mM Tris, $PO_4$ (pH 7.8), 1% BSA (Fraction 5), 5 mM DTT, 1 mM EDTA, 0.3 mM ATP, 8 mM $MgCl_2$, 0.47 mM firefly luciferin, 0.3 mM coenzyme A.

Detection of Luciferase Expression

Once the assay mixture had been optimized, the scintillation counter and luminometer were evaluated as to their utility for screening of transformants. Using cell clusters ranging between 100 to 200 um in diameter, both instruments were capable of detecting luciferase activity in transformants with high expression levels. The luminometer was more sensitive, being able to detect transformants with lower expression levels and/or smaller groups of cells consistently. Plastic covers for the multiwell dishes were obtained that have a minimal effect on reducing the bioluminescent signal, and allow this assay to be performed under sterile conditions.

Reconstruction studies were initiated, placing 10–15 small transformed tissue pieces (all below 150 μm diameter) into 0.75 ml of non-transformed suspension cells. Initial screening was encouraging as luciferase activity could be detected even within this large non-transformed population. This also illustrated the advantages and disadvantages of the two detection devises; the scintillation counter is convenient for screening large aliquots of cells, while the luminometer is more sensitive but more labor intensive.

To take advantage of the relative merits of both devises, in the second reconstruction experiment the scintillation counter and then the luminometer were used for sequential screening. Again, 10–15 transformed cell clusters were mixed into a non-transformed population (1.25 ml of suspension) and placed on the shaker for 2 hours. The suspension was then pipetted into seven scintillation vials and assayed for luciferase activity. Positive signals were recorded for 5/7 samples, and these five were pipetted onto fresh 227 solid medium and allowed to grow for one week. At this time, two of the samples were aliquoted into multiwell dishes and assayed for activity using the luminometer. Each of these wells contained approximately 25 μl of tissue. Six and 7 positive wells were recorded for these two samples, and the tissue again was transferred back onto fresh 227 medium.

These results exemplify the power of the luminometer, because the same size in each well is small the enrichment is much greater (this single screen eliminated approximately 95% of the population). The drawback to this type of screening is the amount of tissue manipulation and risk of contamination. Despite some contamination it is extremely encouraging that the enrichment technique was successful and that the tissue remained healthy (based on visual assessment and subsequent growth).

Improved Luciferase Expression Vectors

Recent improvements in the luciferase assay mixture increased the sensitivity enough so that detection of stable transformed sectors appeared feasible. To further improve the chances of successfully screening for transformants, expression should also be optimized. Toward this goal, two new luciferase vectors were constructed to boost expression levels in maize cells. Both vectors utilize intron VI from Adh1 (derived from vector pDPG273) fused to firefly luciferase (obtained from vector pDPG215). These elements were inserted into either the pDPG282 (4 OCS inverted-35S) or the pDPG283 (4 OCS-35S) backbone (bar was excised as a BamHI/NheI fragment and the intron plus luciferase gene inserted). The 4 OCS-35S promoter has been shown with the uidA gene to give very high levels of transient expression. When this promoter is fused to luciferase it was anticipated that it would result in high levels of expression.

Transient expression levels from each of these vectors was determined in bombarded E1 suspension culture cells. The two new vectors were also compared to pDPG215 (35S-intron 1-luciferase-Tr7 3') as the standard. At least for transient expression, the 4 OCS-35S promoter was not found to be better than the 35S promoter. Vector pDPG351 gave significantly higher levels of transient expression than pDPG350, but not higher than pDPG215.

For independent stable transformants, a wide range of luciferase expression has been observed in experiments using either pDPG215 or pDPG315. For both plasmids luciferase expression as measured in callus using the scintillation counter ranged between 100 and $2 \times 10^6$ CPM. Luciferase expression has been confirmed in $R_0$ plants.

Microspore-derived cell clusters (genotype G238) were bombarded with the p350 and p351 constructs. This tissue was grown on non-selective 227 medium, and was screened 2–3 weeks post-bombardment using the multiwell luminometer. Out of six plates screened, two wells, two wells produced readings potentially above background. This tissue was transferred to fresh 227. Also, AT824 suspension samples were bombarded with the p350 and p351. After 3 days on the filter, the tissue was put back into liquid and screening for luciferase activity was started 12 days post-bombardment.

EXAMPLE 28

Extensin: A Secreted Screenable Marker

Initially, candidates considered as screenable markers have been genes encoding intracellular proteins that require diffusible substrates or permeation of cells to perform the assay. An alternative is a secretable marker. Three general types have been considered: (i) functional secreted enzymes detectable by assaying catalytic activity, (ii) small diffusible proteins detectable by ELISA, such as IL-2, or (iii) secreted markers that remain sequestered in the cell wall that also contain unique epitopes for antibody detection.

Candidates for functional secreted markers that could be detected through catalytic action would include such enzymes as β-galactosidase and β-glucuronidase. Unfortunately, these enzymes are modified during the secretion process in a manner which renders them inactive. For example, GUS enters the endoplasmic reticulum and is N-glycosylated which blocks enzyme activity (Iturraga et al., 1989). Recently, the N-linked glycosylation site was altered by site-directed mutagenesis (Farrell & Beachy, 1990), but no reports on secretion and/or functional activity have yet followed. In using GUS, it is not clear whether the colorimetric product would remain localized to the point where clear demarcation of expressing and non-expressing cells could be achieved, but this is still a promising marker.

A number of small proteins such as interleukins have been well characterized in terms of molecular genetics and immunodetection. However, even if properly targeted across the plasma membrane, the best candidates are all small enough to diffuse readily through the cell wall into the extracellular solution. Thus, they could be detected by ELISA methods, but could not be localized to specific cells. A variety of mammalian genes are known that would provide a unique epitope for labeling. However, large mammalian proteins secreted across the plasma membrane would not be likely to reach the surface of the wall (and hence be relatively inaccessible), while small proteins would diffuse into the extracellular space.

The requirements of a secreted antigen construct were thus determined to be: encoding a unique epitope sequence that would provide low background in plant tissue; a promoter-leader sequence that would impart efficient expression and targeting across the plasma membrane; and the production of a protein which is bound in the cell wall and yet accessible to antibodies. The expression of a modified, but otherwise normally-secreted, cell wall constituent was considered to be an ideal candidate for a secretable marker. Extensin, HPRG, was the cell wall protein chosen since this molecule is fairly well characterized in terms of molecular biology, expression and protein structure, and the maize genomic HPRG sequence was available (from Dr. Pedro Puigdomenech).

The strategy for visualizing the expression of the introduced extensin gene revolves around introducing a novel epitope into the secreted protein, which could then be localized using immunological techniques. Certain preliminary tests need to be performed before making such a construct. A novel epitope must be identified for which a high-titer antibody is available; maize extracts should be reacted with the antibody to ensure there is no non-specific background labeling; and the feasibility of immunolabeling the cell wall of living cells should be determined.

The epitope chosen was a 15 amino acid sequence from the pro-region of murine interleukin-1-β, MATVPELNCEMPPSD (seq id no:1), which was recognized by polyclonal antibodies. A dot-blot was performed loading either 0, 10, or 50 ng of a 31 kd recombinant protein, and testing with either R1682 serum, normal rabbit serum, Fc-purified R1684, or Fc-purified normal rabbit. With the higher protein load (50 ng), background was observed in the normal rabbit and the Fc-purified normal rabbit at the higher antibody concentrations (i.e. 1:300, and 1:100). No background was observed in the 10 ng dots at antibody dilutions greater (less concentrated) than 1:100. For the R1682 serum, protein was detected for both the 10 and 50 ng dots at all antibody dilutions, even down to 1:3000. The Fc-purified R1684 was approximately 10-fold less sensitive. This result indicates that the R1682 antibody is very high-titer, and should be useful as a marker system.

On analyzing the IL-1-β pro sequence in computer gene and protein data banks, no sequence homology was found in either plants or fungi. Testing extracts from maize suspension cells and from cell walls confirmed that no background labeling exists.

Using colloidal gold conjugated secondary antibody followed by silver enhancement, surface labeling of "living" root tips was verified. The labeling of the surface with both the primary and secondary antibodies was performed under physiological conditions (low concentrations of organic buffers and/or salts). However, in order to visualize the gold label a silver enhancement process was then utilized, and this is toxic. The use of a new fluorophore, phycoerythrin, conjugated to the secondary antibody is also contemplated. This should eliminate problems with endogenous background fluorescence and increase resolution.

The necessary oligonucleotides were made and a cloning strategy was developed for inserting the novel IL-1 sequence into the carboxyl-end of the extensin structural gene and placing this into a plant expression vector (CaMV 35S promoter, *Agrobacterium tumefaciens* transcript 7 3' region).

K. Co-Transformation

Co-transformation may be achieved using a vector containing the marker and another gene or genes of interest. Alternatively, different vectors, e.g., plasmids, may contain the different genes of interest, and the plasmids may be concurrently delivered to the recipient cells. Using this method, the assumption is made that a certain percentage of cells in which the marker has been introduced, have also received the other gene(s) of interest. As can be seen in the following examples, not all cells selected by means of the marker, will express the other genes of interest which had been presented to the cells concurrently. For instance, in Example 29, successful cotransformation occurred in 17/20 independent transformants (see Table 5), coexpression occurred in 4/20. In some transformants, there was variable expression among transformed cells.

EXAMPLE 29

Figure 6:
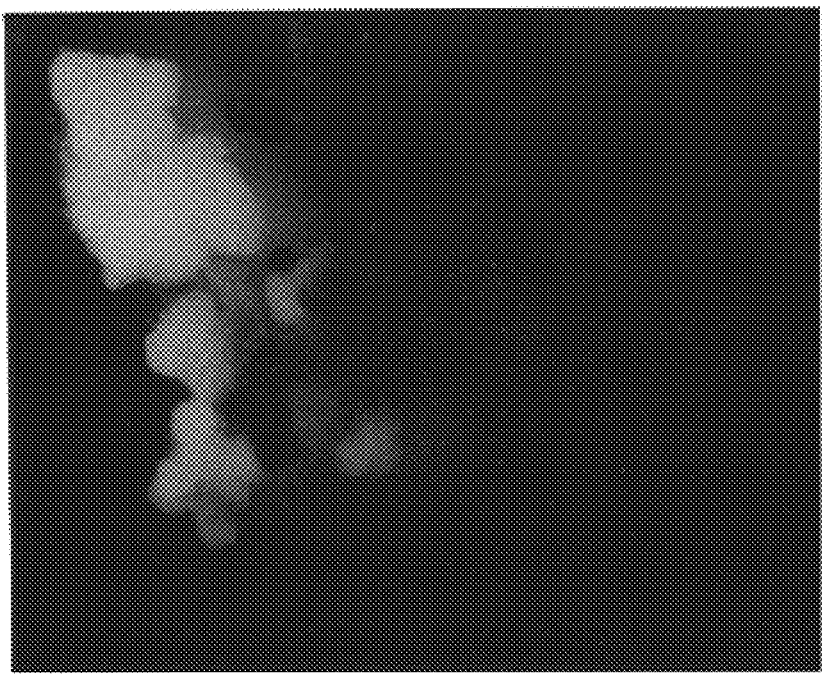
FIG. 6. Histochemical determination of GUS activity in bar-transformed SC82 callus line Y13. This bialaphos-resistant callus line, Y13, which contained intact GUS coding sequences was tested for GUS activity three months post-bombardment. In this figure, differential staining of the callus was observed.

Co-Integration and Co-Expression of the Bar Gene and the GUS Gene to Cell Lines Derived from the SC82 Suspension Culture Of the bialaphos-resistant isolates selected from a reinitiation of cryopreserved SC82 cells transformed with separate plasmids (as described for SC716), nineteen independent transformants were selected in this experiment (experiment #6, Table 5). The frequency of cointegration and coexpression in those isolates was similar to that described for SC716 isolates (Table 5). The pattern of GUS staining in these transformants varied in a manner similar to that described for coexpressing SC716 transformants. A transformant, Y13, which contained intact GUS coding sequence, exhibited varying levels of GUS activity as shown in FIG. 6. This type of expression pattern has been described previously in cotransformed BMS cells (Klein et al., 1989). Variable activity detected in the cells from a single transformant may be attributed to unequal penetration of the GUS substrate, or differential expression, methylation, or the absence of the gene in some cells.

These results show that both the bar gene and the GUS gene are present in some of the cells bombarded with the two plasmids containing these genes. Co-transformation has occurred. In the cotransformation examples described herein and summarized in Table 5, cotransformation frequency of the non-selected gene was 77%; coexpression frequency was 18%.

L. Regeneration of Plants From Transformed Cells

For use in agriculture, transformation of cells in vitro is only one step toward commercial utilization of these new methods. Plants must be regenerated from the transformed cells, and the regenerated plants must be developed into full plants capable of growing crops in open fields. For this purpose, fertile corn plants are required. The invention disclosed herein is the first successful production of fertile maize plants (e.g., see FIG. 7A) from transformed cells.

During suspension culture development, small cell aggregates (10–100 cells) are formed, apparently from larger cell clusters, giving the culture a dispersed appearance. Upon plating these cells to solid media, somatic embryo development can be induced, and these embryos can be matured, germinated and grown into fertile seed-bearing plants. The characteristics of embryogenicity, regenerability, and plant fertility are gradually lost as a function of time in suspension culture. Cryopreservation of suspension cells arrests development of the culture and prevents loss of these characteristics during the cryopreservation period.

EXAMPLE 30

Regeneration of Plants from SC82 and SC716

One efficient regeneration system involves transfer of embryogenic callus to MS (Murashige & Skoog, 1962) medium containing 0.25 mg/l 2,4-dichlorophenoxyacetic acid and 10.0 mg/l 6-benzyl-aminopurine. Tissue was maintained on this medium for approximately 2 weeks and subsequently transferred to MS medium without growth regulators (Shillito et al., 1989). Shoots that developed after 2–4 weeks on growth regulator-free medium were transferred to MS medium containing 1% sucrose and solidified with 2 g/l Gelgro® in Plant Con® containers where rooting occurred.

Another successful regeneration scheme involved transfer of embryogenic callus to N6 (Chu et al., 1975) medium containing 6% sucrose and no growth regulators (Armstrong & Green, 1985) for two weeks followed by transfer to MS medium without growth regulators as described above. Regeneration was performed at 25° C. under fluorescent lights (250 microeinsteins.m$^{-2}$.s$^{-1}$). After approximately 2 weeks developing plantlets were transferred to a Plant Con® container containing medium 501. When plantlets had developed 3 leaves and 2–3 roots they were transferred to soil, hardened off in a growth chamber (85% relative humidity, 600 ppm $CO_2$, 250 microeinsteins.m$^{-2}$.s$^{-1}$), and grown to maturity either in a growth chamber or the greenhouse.

Regeneration of plants from transformed cells requires careful attention to details of tissue culture techniques. One of the major factors is the choice of tissue culture media. There are many media which will support growth of plant cells in suspension cultures, but some media give better growth than others at different stages of development. Moreover, different cell lines respond to specific media in different ways. A further complication is that treatment of cells from callus initiation through transformation and ultimately to the greenhouse as plants, requires a multivariate approach. A progression consisting of various media types, representing sequential use of different media, is needed to optimize the proportion of transformed plants that result from each cell line. Table 6 illustrates one sequential application of combinations of tissue culture media to cells at different stages of development. Successful progress is ascertained by the total number of plants regenerated.

It can be seen that using the same group of media, cell lines will vary in their success rates (number of plants) (Table 6). There was also variation in overall success rate, line AO1-15 yielding the greatest number of plants overall. (It should be noted, however, that because tissue was limiting not all combinations of media were used on all lines, therefore, overall comparisons are limited.)

A preferred embodiment for use on cell lines SC82 and SC716, at least initially, is the combination shown in the second column under the regeneration media progression (media 227, 171, 101, 501). Media 227 is a good media for the selective part of the experiments, for example, to use for growth of callus in the presence of bialaphos. This media contains the growth regulator dicamba. NAA and 2,4-D are growth regulators in other media. In liquid media, these may be encapsulated for controlled release (Adams, W. et al., in preparation).

Thus, it can be seen from Table 1 that the various media are modified so as to make them particularly applicable to the development of the transformed plant at the various stages of the transformation process. For example, subculture of cells in media 171 after applying the selective agent, yields very small embryos. Moreover, it is believed that the presence of BAP in the media facilitates development of shoots. Myo-inositol is believed to be useful in cell wall synthesis. Shoot elongation and root development proceeds after transfer to media 101. 101 and 501 do not contain the growth regulators that are required for earlier stages of regeneration.

TABLE 6

Plants to Soil From Bombardment of SC716 (Expts 1, 2; Table 6).

REGENERATION MEDIA PROGRESSIONS

| Cell Line | 227b 101 | 227b 171 101 | 227b 201b 171 101 | 227b 52 171 101 | 227b 163 171 101 | 227b 205 171 101 | 227b 173 101 | 227b 201b 173 101 | 227b 205 173 101 | 227b 163 173 101 | 227b 177 101 | 227b 201b 177 101 | # PLANTS TO SOIL |
|---|---|---|---|---|---|---|---|---|---|---|---|---|---|
| CONTROLS | | | | | | | | | | | | | |
| A01C-11 | X | 4 | X | X | X | X | 2 | X | X | X | X | X | 6* |
| A01C-01 | X | 7 | X | X | X | X | 27 | X | X | X | X | X | 34* |
| TOTAL TRANSFORMED | X | 11 | X | X | X | X | 29 | X | X | X | X | X | 40* |
| A01C-11 | X | X | X | 0 | 0 | 0 | X | X | 0 | 0 | X | X | 0 |
| A01C-12 | X | 2 | X | 0 | 0 | 0 | X | X | 0 | 0 | X | X | 2 |

TABLE 6-continued

Plants to Soil From Bombardment of SC716 (Expts 1, 2; Table 6).

REGENERATION MEDIA PROGRESSIONS

| Cell Line | 227b 101 | 227b 201b 171 101 | 227b 201b 52 171 101 | 227b 163 171 101 | 227b 205 171 101 | 227b 171 101 | 227b 173 101 | 227b 201b 173 101 | 227b 205 173 101 | 227b 163 173 101 | 227b 177 101 | 227b 201b 177 101 | # PLANTS TO SOIL |
|---|---|---|---|---|---|---|---|---|---|---|---|---|---|
| A01C-13 | X | 5 | 1 | 4 | 0 | 0 | 1 | 1 | 1 | 1 | X | X | 14* |
| A01C-14 | X | 2 | X | 0 | 0 | 0 | X | X | 1 | 0 | X | X | 3* |
| A01C-15 | X | 28 | 0 | 12 | 7 | 1 | 23 | 13 | 0 | 0 | 0 | 0 | 84* |
| A01C-17 | X | 7 | 0 | 0 | 0 | 0 | 17 | 0 | 0 | 0 | 0 | 0 | 24 |
| A01C-18 | X | 12 | 0 | 0 | X | 0 | 21 | 10 | 0 | X | 2 | 0 | 45* |
| A01C-19 | X | 0 | X | X | 0 | X | 0 | X | X | 0 | X | 0 | 0 |
| A01C-20 | X | 10 | X | 0 | 0 | X | 0 | X | X | 0 | X | 0 | 10* |
| A01C-21 | X | 0 | X | X | X | X | 0 | X | X | X | X | 0 | 0 |
| A01C-24 | 2 | 4 | 0 | 0 | 0 | 0 | 6 | 5 | 0 | 0 | 0 | 0 | 17* |
| A01C-25 | X | 9 | X | X | 0 | 0 | 1 | X | 0 | 0 | X | X | 10 |
| A01C-27 | X | 0 | X | X | X | X | 10 | X | X | X | X | 0 | 10* |
| TOTAL COMBINED | 2 | 79 | 1 | 16 | 7 | 1 | 79 | 29 | 2 | 1 | 2 | 0 | 219* |
| CONTROLS | X | 11 | X | X | X | X | 29 | X | X | X | X | X | 40* |
| TRANSFORMED | 2 | 79 | 1 | 16 | 7 | 1 | 79 | 29 | 2 | 1 | 2 | 0 | 219* |
| TOTAL | 2 | 90 | 1 | 16 | 7 | 1 | 108 | 29 | 2 | 1 | 2 | 0 | 259* |

X = Regeneration not attempted by this route.
201b = 201 with 1 mg/l bialophos.
* = More plants could have been taken to soil.
227b = 227 with 1 mg/l bialophos.

Transfer of regenerating plants is preferably completed in an agar-solidified media adapted from a nutrient solution developed by Clark (1982), media 501. The composition of this media facilitates the hardening of the developing plants so that they can be transferred to the greenhouse for final growth as a plant. The salt concentration of this media is significantly different from that of the three media used in the earlier stages, forcing the plant to develop its own metabolic pathways. These steps toward independent growth are required before plants can be transferred from tissue culture vessels (e.g. petri dishes, plant cans) to the greenhouse.

Approximately 50% of transformed callus lines derived from the initial SC82 and SC716 experiments were regenerable by the routes tested. Transgenic plants were regenerated from four of seven independent SC82 transformants and ten of twenty independent SC716 transformants. Regeneration of thirteen independently, transformed cell lines and two control lines of SC716 was pursued. Regeneration was successful from ten of thirteen transformants. Although a total of 458 plantlets were regenerated, due to time and space constraints only 219 transformed plants (representing approximately 48% of the total number of regenerants) were transferred to a soilless mix (see below). Approximately 185 plants survived. Twelve regeneration protocols were investigated and the number of plants regenerated from each route has been quantified (Table 6). There appeared to be no significant advantage to maturing the tissues on 201, 52, 163, or 205 (see Table 1 for media codes) prior to transfer to medium 171 or 173. The majority of the plants were generated by subculturing embryogenic callus directly from 227 to either 171 or 173. The majority of the plants were generated by subculturing embryogenic callus directly from 227 to either 171 or 173. These plantlets developed roots without addition of exogenous auxins, and plantlets were then transferred to a soilless mix, as was necessary for many of the transformants regenerated from SC82.

The soilless mix employed comprised Pro Mix, Micromax, Osmocote 14-14-14 and vermiculite. Pro Mix is a commercial product used to increase fertility and porosity as well as reduce the weight of the mixture. This is the bulk material in the mixture. Osmocote is another commercial product that is a slow release fertilizer with a nitrogen-phosphorus-potassium ratio of 14:14:14. Micromax is another commercial fertilizer that contains all of the essential micronutrients. The ratio used to prepare the soilless mix was: 3 bales (3 $ft^3$ each) Pro Mix; 10 gallons (vol.) vermiculite; 7 pounds Osmocote: 46 ml Micromax. The soilless mix may be supplemented with one or two applications of soluble Fe to reduce intervenial chlorosis during early seedling and plant growth.

Regeneration of transformed SC82 selected cell lines yielded 76 plants transferred to the soilless mix, and 73 survived. The plants were regenerated from six bialaphos-resistant isolates, representing four of seven clonally independent transformants. Eighteen protocols were used successfully to regenerate the seventy six plants (Table 7). Differences in morphology between cell lines deemed some protocols more suitable than others for regeneration.

TABLE 7

EFFECTS OF PROGRESSION OF MEDIA ON THE NUMBER OF PLANTS REGENERATED (SC82)*

| CELL LINE | 227B 201B 205 227B 142 101 501 | 201B 227B 173 101 501 | 227B 205 171 101 501 | 227B 201B 1 205 101 501 | 227B 201B 52 209 101 501 | 227B 201B 227A # OF 173 101 501 | 227B 227A 173 101 501 | 227B 227A 173 101 501 | 227B 171 101 501 |
|---|---|---|---|---|---|---|---|---|---|
| B3-14-4 |   | 1 | X | 14 | X | X | X | 1 | 1 | X |
| B3-14-9 |   | X | X | 1 | 1 | X | 4 | 1 | X | X |
| B3-14-7 |   | X | X | X | X | X | X | X | X | X |
| B3-14-6 |   | X | X | X | X | 1 | X | X | X | X |
| B3-14-3 |   | X | X | X | X | X | X | X | X | X |
| B3-14-2 |   | X | X | X | X | X | X | X | X | X |
| B3-14-1 |   | X | X | X | X | X | X | X | X | X |
| B3-14-5 |   | X | X | X | X | X | X | X | X | X |
| B3-13-5 |   | X | X | X | X | X | X | X | X | X |
| B3-13-2 |   | X | 1 | 13 | X | X | X | 3 | 2 | 2 |
| B3-13-1 |   | X | 3 | X | 1 | X | X | X | X | 1 |
| TOTAL | 1 | 4 | 28 | 2 | 1 | 4 | 5 | 3 | 3 | 2 |

| | 227B 227A 173 101 501 | 227B 173 101 501 | 171 178 101 501 | 227B 52 171 101 501 | 227B 52 177 101 501 | 227B 52 177 101 501 | 227B 201B 171 178 101 501 | 227B 201B 201B 171 101 | PLANTS |
|---|---|---|---|---|---|---|---|---|---|
| B3-14-4 | 2 | X | X | 5 | X | 5 | X | X | X | 29 |
| B3-14-9 | X | X | X | X | 1 | X | 1 | X | X | 9 |
| B3-14-7 | X | 6 | 2 | X | X | X | X | X | 1 | 9 |
| B3-14-6 | X | X | X | X | X | X | X | X | X | 1 |
| B3-14-3 | X | X | X | X | X | X | X | X | X | 0 |
| B3-14-2 | X | X | X | X | X | X | X | X | X | 0 |
| B3-14-1 | X | X | X | X | X | X | X | X | X | 0 |
| B3-14-5 | X | X | X | X | X | X | X | X | X | 0 |
| B3-13-5 | X | X | X | X | X | X | X | X | X | 0 |
| B3-13-2 | X | X | X | X | X | 1 | X | X | X | 22 |
| B3-13-1 | X | X | X | X | X | X | X | 1 | X | 6 |
| TOTAL | 6 | 2 | 5 | 1 | 6 | 1 | 1 | 1 | 76 | |

* = See table 1 for media codes.
X = This media progression was either attempted and unsuccessful or not attempted.
227A = 227 with $10^{-7}$ M ABA.
227B = 227 with 1 mg/l bialaphos.

Prior to regeneration, the callus was transferred to either a) an N6-based medium containing either dicamba or 2,4-D or b) an MS-based medium containing 2,4-D. These steps allowed further embryoid development prior to maturation. Most of the maturation media contained high BAP levels (5–10 mg/l) to enhance shoot development and cause proliferation. An MS-based medium with low 2,4-D (0.25 mg/l) and high BAP (10 mg/l), as described by Shillito et al., 1989, was found to be quite effective for regeneration.

Likewise, an MS-based medium containing 1 μm NAA, 1 μm IAA, 2 μm 2-IP, and 5 mg/l BAP (modified from Conger et al., 1987) also promoted plant regeneration of these transformants. After plantlets recovered by any of the regenerative protocols had grown to five cm, they were transferred to a nutrient solution described by Clark, 1982, supplemented with 2% sucrose and solidified with Gelgro. Plantlets which were slow to develop roots were treated with 3 μl droplets of 0.3% IBA at the base of the shoot to stimulate rooting. Plants with well developed root systems were transferred to a soilless mix and grown in controlled environmental chambers from 5–10 days, prior to transfer to the greenhouse.

EXAMPLE 31

Regeneration of AT824 Transformants

Transformants were produced as described in examples 19 and 20. For regeneration tissue was first transferred to solid medium 223 and incubated for two weeks. Transformants may be inititally subcultured on any solid culture that supports callus growth, e.g., 223, 425, 409 and so forth. Subsequently transformants were subcultured one to three times, but usually twice on 189 medium (first passage in the dark and second passage in low light) and once or twice on 101 medium in petri dishes before being transferred to 607 medium in Plant Cons©. Variations in the regeneration protocol are normal based on the progress of plant regeneration. Hence some of the transformants were first subcultured once on 425 medium, twice on 189 medium, once or twice on 101 medium followed by transfer to 501 medium in Plant Cons©. As shoots developed on 101 medium, the light intensity was increased slowly adjusting the distance of the plates from the light source located overhead. All subculture intervals were for about 2 weeks at 24° C. Transformants that developed 3 shoots and 2–3 roots were transferred to soil.

Plantlets in soil were incubated in an illuminated growth chamber and conditions were slowly adjusted to adapt or condition the plantlets to the drier and more illuminated conditions of the greenhouse. After adaptation/conditioning in the growth chamber, plants were transplanted individually to 5 gallon pots of soil in the greenhouse.

Figure 8A:
FIG. 8(A). Basta$^R$ resistance in transformed $R_0$ plants. A Basta$^R$ solution was applied to a large area (about 4×8 cm) in the center of leaves of nontransformed A188×B73 plant (left) and a transgenic $R_0$ E3/E4/E6 plant (right).

M. Assay for Integration of Exogenous DNA and Expression of DNA in $R_0$ $R_1$ Plants Studies were undertaken to determine the expression of the transformed gene(s) in transgenic $R_0$ and $R_1$ plants. Functional activity of PAT was assessed by localized application of a commercial herbicide formulation containing PPT to leaves of SC82 $R_0$ and $R_1$ plants. No necrosis was observed on leaves of $R_0$ plants containing either high levels (E2/E5), or low levels (E3/E4) of PAT. Herbicide-treated E3/E4/E6 and control leaves are shown in FIG. 8A. Herbicide was also applied to leaves of E2/E5 progeny segregating for bar. As demonstrated in FIG. 8B, leaves of $R_1$ plants expressing bar exhibited no necrosis six days after application of the herbicide while $R_1$ plants without bar developed necrotic lesions. No necrosis was observed on transformed leaves up to 30 days post-application.

Figure 9:
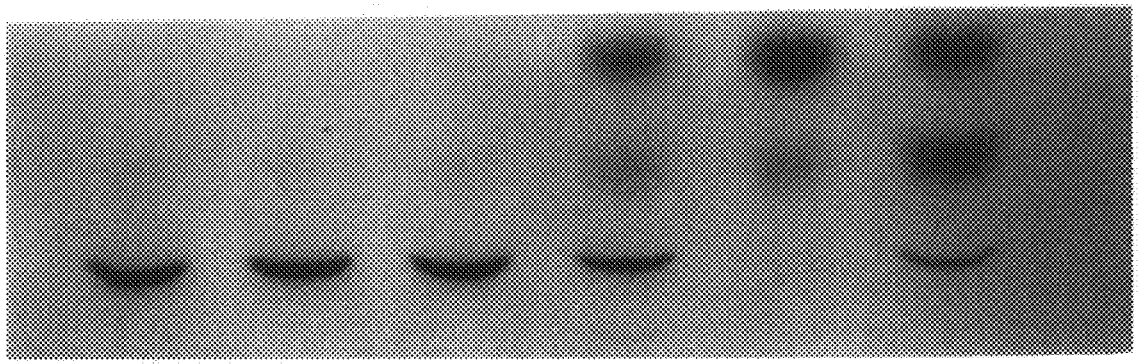
FIG. 9. PAT Activity in Protein Extracts of $R_0$ Plants. Extracts from one plant derived from each of the four transformed regenerable callus lines from a suspension culture of A188×B73, SC82 (E10, E11, E2/E5, and E3/E4/E6) were tested for PAT activity (The designations E2/E5 and E3/E4/E6 represent transformed cell lines with identical DNA gel blot hybridization patterns; the isolates were most likely separated during the culturing and selection process.) Protein extracts from a nontransformed B73 plant and a Black Mexican Sweet (BMS) cell culture bar transformant were included as controls. Approximately 50 micrograms of total protein was used per reaction.

Twenty-one $R_0$ plants, representing each of the four regenerable transformed SC82 callus lines, were also analyzed for expression of the bar gene product, PAT, by thin-layer chromatographic techniques. Protein extracts from the leaves of the plants were tested. PAT activity of one plant regenerated from each callus line is shown in FIG. 9.

All 21 plants tested contained PAT activity. Furthermore, activity levels were comparable to levels in the callus lines from which the plants were regenerated. The nontransformed plant showed no PAT activity (no band is in the expected position for acetylated PPT in the autoradiograph from the PAT chromatogram). A band appears in the BMS lane that is not in lanes containing protein extracts from the plant leaves. This extra band was believed to be an artifact.

Figure 10:
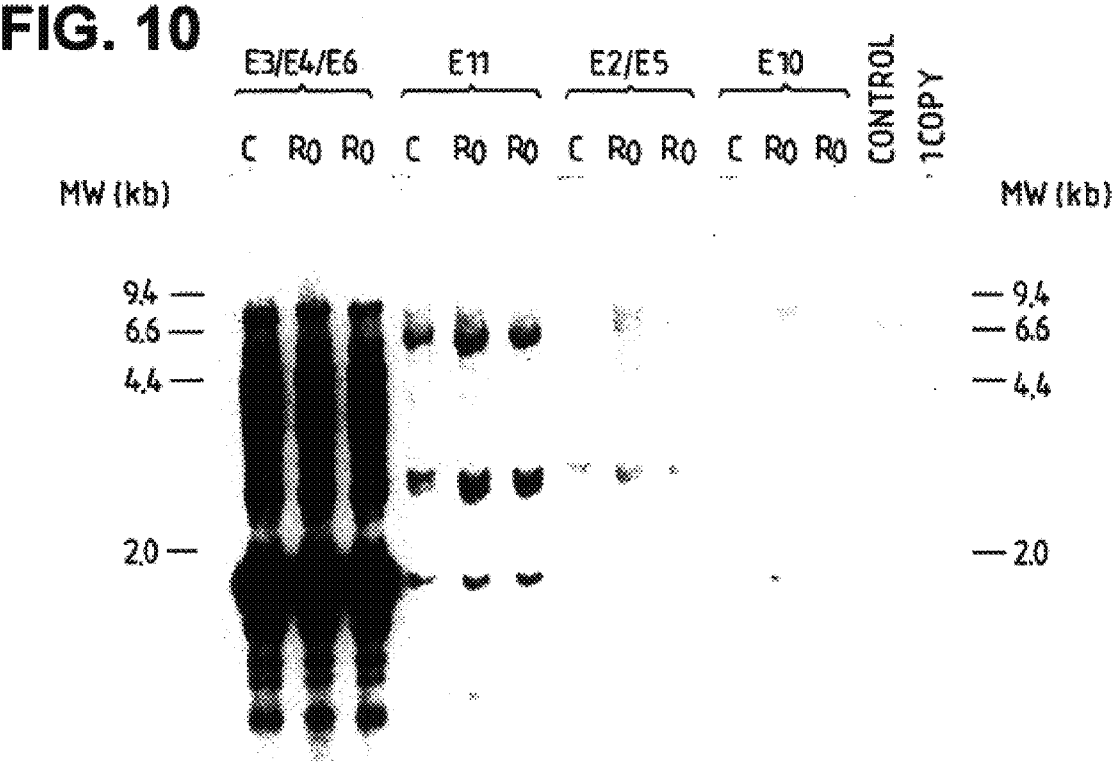
FIG. 10. DNA Gel Blot Analysis of Genomic DNA from Transformed Callus and Corresponding $R_0$ Plants Probed with bar. Genomic DNA was digested with EcoRI and HindIII, which released the 1.9 kb bar expression unit (CaMV 35S promoter-bar-Tr7 3'-end) from pDPG165, the plasmid used for microprojectile bombardment transformation of SC82 cells, and hybridized to bar. The molecular weights in kb are shown on the left and right. Lanes designated E3/E4/E6, E11, E2/E5, and E10 contained 5 $\mu$g of either callus (C) or $R_0$ plant DNA. The control lane contained DNA from a nontransformed A188×B73 plant. The lane designated "1 copy" contained 2.3 pg of the 1.9 kb EcoRI/HindIII fragment from pDPG165 representing one copy per diploid genome.

As another method of confirming that genes had been delivered to cells and integrated, genomic (chromosomal) DNA was isolated from a nontransformed plant, the four regenerable callus lines and from two $R_0$ plants derived from each callus line. FIG. 10 illustrates results of gel blot analysis of genomic DNA from the four transformed calli (C) and the $R_0$ plants derived from them. The transformed callus and all plants regenerated from transformed callus contained sequences that hybridized to the bar probe, indicating the presence of DNA sequences that were complementary to bar. Furthermore, in all instances, hybridization patterns observed in plant DNA were identical in pattern and intensity to the hybridization profiles of the corresponding callus DNA.

DNA from E3/E4/E6 callus and the desired $R_0$ plants contained approximately twenty intact copies of the 1.9 kb bar expression unit (Cauliflower Mosaic Virus 35S promoter-bar-Agrobacterium transcript 7 3'-end) as well as numerous other bar-hybridizing fragments. E11 callus and plant DNA contained 1–2 copies of the intact expression unit and 5–6 additional non-intact hybridizing fragments. E10 callus and plants contained 1–2 copies of the intact bar expression unit. E2/E5 DNA contained a single fragment of approximately 3 kb that hybridized to the probe. To confirm that the hybridizing sequence observed in all plants were integrated into the chromosomal DNA, undigested genomic DNA from one plant derived from each independent transformant was analyzed by DNA gel blot hybridization. Hybridization to bar was observed only in high molecular weight DNA providing evidence for the integration of bar into the maize genome.

Figure 8B:
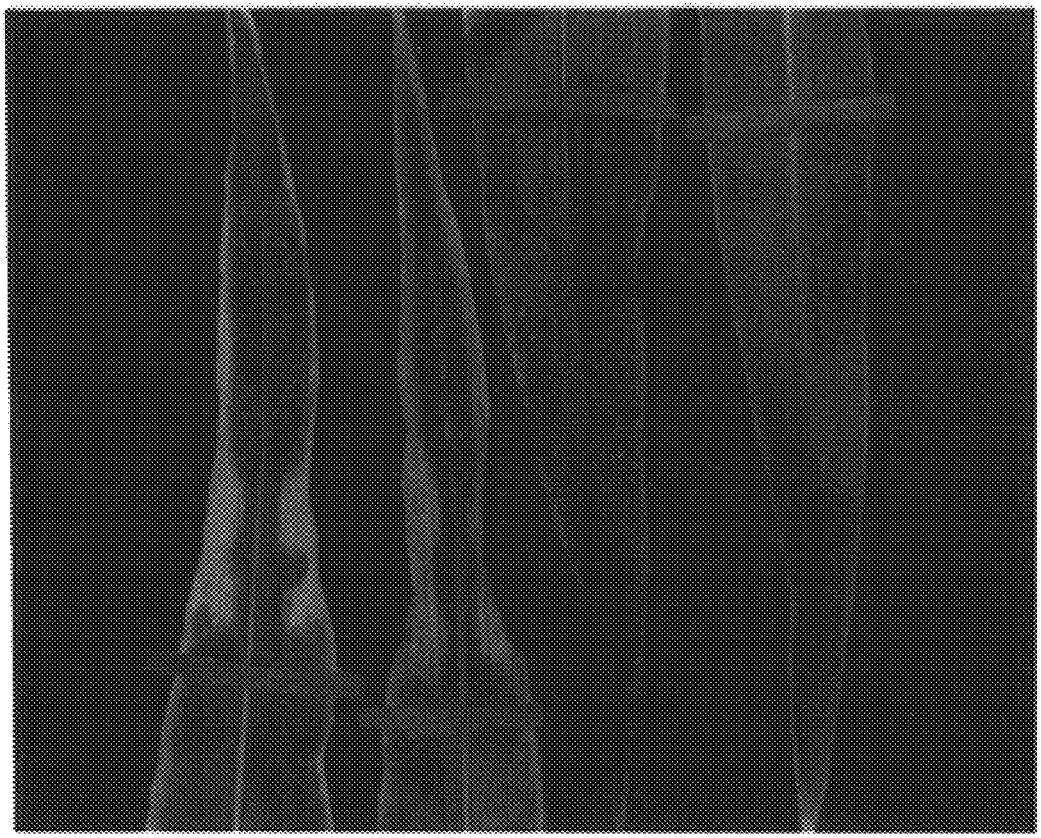
FIG. 8(B). Basta$^R$ resistance in transformed $R_1$ plants; two plants without bar (left) and two plants containing bar (right). The herbicide was applied to $R_1$ plants in 1 cm circles to four locations on each leaf, two on each side of the midrib. Photographs were taken six days after application.
Figure 8C:
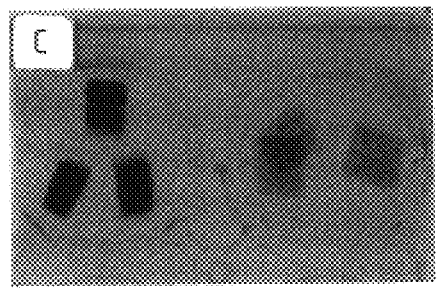
FIG. 8(C). GUS activity in leaf tissue of a transgenic $R_0$ plant. Histochemical determination of GUS activity in leaf tissue of a plant regenerated from cotransformed callus line Y13 (right) and a nontransformed tissue culture derived plant (left). Bar=1 cm.
Figure 8D:
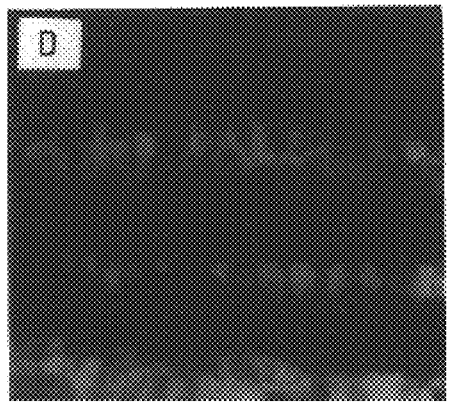
FIG. 8(D). Light micrograph of the leaf segment from a Y13 plant shown in (C), observed in surface view under bright field optics. GUS activity was observed in many cell types throughout the leaf tissue (magnification=230X). (E) Light micrograph as in (D) of control leaf.
Figure 8E:
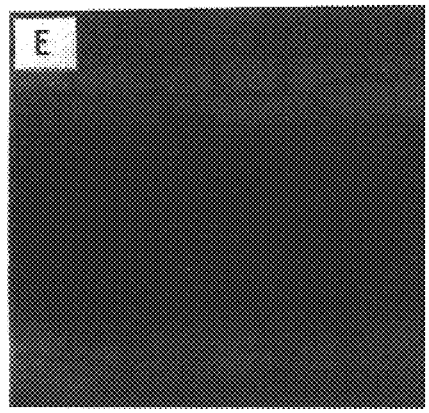
FIG. 8. Functional Expression of Introduced Genes in Transformed $R_0$ and $R_1$ Plants.

Plants were regenerated from the coexpressing callus line, Y13, shown in FIG. 6. Plants regenerated from Y13 (experiment #6, Table 5) were assayed for GUS activity and histochemically stained leaf tissue from one plant is shown in FIGS. 8C, D, E. Numerous cell types including epidermal, guard, mesophyll and bundle sheath cells stained positive for GUS activity. Staining intensity was greatest in the vascular bundles. Although all leaf samples from the regenerated plants tested (5/5) expressed the nonselected gene, some non-expressing leaf sectors were also observed. Leaf tissue extracts from three Y13 and three control plants were also assayed for GUS activity by fluorometric analysis (Jefferson, 1987). Activity detected in two opposing leaves from each of three Y13 plants tested was at least 100-fold higher than that in control leaves.

EXAMPLE 32

General Methods for Assays

A method to detect the presence of phosphinothricin acetyl transferase (PAT) activity is to use an in vitro enzyme reaction followed by thin layer chromatography.

An example of such detection is shown in FIG. 9 wherein various protein extracts prepared from homogenates of potentially transformed cells, and from control cells that have neither been transformed nor exposed to bialaphos selection, are assayed by incubation with PPT and $^{14}$C-Acetyl Coenzyme A followed by thin layer chromatography. 25 µg of protein extract were loaded per lane. The source in lanes E1–E11 were SC82 transformants; B13 is a BMS (Black Mexican Sweet corn nonembryogenic) bar transformant. E0 is a nonselected, nontransformed control.

As can be seen at the position indicated by the arrow (the position expected for the mobility of $^{14}$C-N-AcPPT), all lanes except the nontransformed control exhibit PAT activity by the formation of a compound with the appropriate mobility expected for $^{14}$C-N-Acetyl PPT. Variation in the activity levels among the transformants was approximately 10 fold, as demonstrated by the relative intensity of the bands. The results of this assay provide confirmation of the expression of the bar gene which codes for PAT. For analysis of PAT activity in plant tissue, 100–200 mg of leaf tissue was extracted in sintered glass homogenizers and assayed as described previously.

GUS activity was assessed histochemically as described using 5-bromo-4-chloro-3-indolyl glucuronide (Jefferson, 1987); tissue was scored for blue cells 18–24 h after addition of substrate. Fluorometric analysis was performed as described by Jefferson (1987) using 4-methyl umbelliferyl glucuronide.

DNA analysis was performed as follows. Genomic DNA was isolated using a procedure modified from Shure, et al., 1983. Approximately 1 gm callus tissue was ground to a fine powder in liquid N2 using a mortar and pestle. Powdered tissue was mixed thoroughly with 4 ml extraction buffer (7.0 M urea, 0.35 M NaCl, 0.05 M Tris-HCl pH 8.0, 0.01 M EDTA, 1% sarcosine). Tissue/buffer homogenate was extracted with 4 ml phenol/chloroform. The aqueous phase was separated by centrifugation, passed through Miracloth, and precipitated twice using 1/10 volume of 4.4 M ammonium acetate, pH 5.2 and an equal volume of isopropanol. The precipitate was washed with 70% ethanol and resuspended in 200–500 µl TE (0.01 M Tris-HCl, 0.001 M EDTA, pH 8.0). Plant tissue may also be employed for the isolation of DNA using the foregoing procedure.

The presence of a gene in a transformed cell may be detected through the use of polymerase chain reaction (PCR). Using this technique specific fragments of DNA can be amplified and detected followed agarose gel electrophoresis. For example the bar gene may be detected using PCR. Two hundred to 100 ng genomic DNA is added to a reaction mix containing 10 mM Tris-HCl pH 8.3, 1.5 mM $MgCl_2$, 50 mM KCl, 0.1 mg/ml gelatin, 200 uM each dATP, dCTP, dGTP, dTTP, 0.5 uM each forward and reverse DNA primers, 20% glycerol, and 2.5 units Taq DNA polymerase. The forward primer is CATCGAGACAAGCACGGT-CAACTTC (seq id no:16). The reverse primer is AAGTC-CCTGGAGGCACAGGGCTTCAAGA (seq id no:17). PCR amplification of bar using these primers requires the presence of glycerol, but this component is not needed for most other applications. The reaction is run in a thermal cycling machine as follows: 3 minutes at 94 C, 39 repeats of the cycle 1 minute at 94 C, 1 minute at 50 C, 30 seconds at 72 C, followed by 5 minutes at 72 C. Twenty ul of each reaction mix is run on a 3.5% NuSieve gel in TBE buffer (90 mM Tris-borate, 2 mM EDTA) at 50V for two to four hours. Using these primers a 279 base pair fragment of the bar gene is amplified.

For Southern blot analysis genomic DNA was digested with a 3-fold excess of restriction enzymes, electrophoresed through 0.8% agarose (FMC), and transferred (Southern, 1975) to Nytran (Schleicher and Schuell) using 10×SCP (20×SCP: 2 M NaCl, 0.6 M disodium phosphate, 0.02 M disodium EDTA). Filters were prehybridized at 65° C. in 6×SCP, 10% dextran sulfate, 2% sarcosine, and 500 μg/ml heparin (Chomet et al., 1987) for 15 min. Filters were hybridized overnight at 65° C. in 6×SCP containing 100 μg/ml denatured salmon sperm DNA and $^{32}$P-labeled probe. The 0.6 kb SmaI fragment from pDPg165 and the 1.8 kb BamHI/EcoRI fragment from pCEV5 were used in random priming reactions (Feinberg & Vogelstein, 1983; Boehringer-Mannheim) to generate labeled probes for detecting sequences encoding PAT or GUS, respectively. Filters were washed in 2×SCP, 1% SDS at 65° C. for 30 min. and visualized by autoradiography using Kodak XAR5 film. Prior to rehybridization with a second probe, the filters were boiled for 10 min. in distilled $H_2O$ to remove the first probe and then prehybridized as described above.

N. Fertility of Transgenic Plants

To recover progeny the regenerated, genetically transformed maize plants (designated $R_0$), were backcrossed with pollen collected from nontransformed plants derived from seeds. Alternatively pollen was collected from $R_0$ plants and used to pollinate nontransformed plants. Progeny (designated $R_1$) that contained and expressed bar were recovered from crosses in which the transformant was used as a male or female parent.

An important aspect of this invention is the production for the first time of fertile, genetically transformed maize plants ($R_0$) and progeny ($R_1$). These were regenerated from embryogenic cells that were transformed. $R_1$ plants are those resulting from backcrossing of $R_0$ plants.

Pollination of transgenic $R_0$ ears with non-transformed B73 pollen resulted in kernel development. In addition, kernels developed from pistillate flowers on male inflorescences that were pollinated with non-transformed B73 pollen. Kernels on transformed $R_0$ plants from SC82 developed normally for approximately 10–14 days post-pollination but after this period the kernels ceased development and often collapsed. Most plants exhibited premature senescence at this time. A total of 153 kernels developed sporadically on numerous plants (see Table 8): 8 of 37 E2/E5 plants, 2 of 22 E10 plants, and 3 of 6 E11 plants. Viable progeny were recovered by embryo rescue from 11 E2/E5 plants and one E10 plant.

SC716 $R_0$ plants were also backcrossed with seed-derived B73 plants. To date, from the 35 mature SC716 $R_0$ plants nine plants (representing four independent callus lines) yielded 51 kernels, 31 of which produced vigorous $R_1$ seedlings (Table 8). Most kernels that developed on SC716 plants did not require embryo rescue. Kernels often developed for 30–40 days on the plant and some were germinated in soil. The remaining seed was germinated on MS-based medium to monitor germination and transferred to soil after a few days. In addition to the improved kernel development observed on SC716 $R_0$ plants relative to SC82 $R_0$ plants, pollen dehisced from anthers of several SC716 plants and some of this pollen germinated in vitro (Pfahler, 1967). Transmission of the foreign gene has occurred both through SC716 $R_1$ ears and using SC716 $R_1$-derived pollen on non-transformed ears.

TABLE 8

Regenerated Plants ($R_o$) and Progeny ($R_1$)

| Exp. # | Culture Bombarded | # of Independent bar Transformant Recovered | # of Regenerable Transformed Callus Lines | # of $R_o$ Plants | # Reaching Maturity | # of $R_o$ Producing Kernels | # of Kernels Recovered | # of $R_1$ Plants |
|---|---|---|---|---|---|---|---|---|
| 1, 2 | SC82 | 7 | 4 | 76 | 73 | 23 | 153 | 40 |
| 4, 5 | SC716 | 20 | 10 | 219 | (35) | (9) | (51) | (31) |
| 3 | SC94 | 8 | 2[a] | 11[a] | (0) | (0) | (0) | (0) |
| 6 | SC82 | 19 | 4[a] | 23[a] | (0) | (0) | (0) | (0) |

[a]Regeneration in progress.
( )Experiment still in progress, data still being collected.

To date fertile plants from 267 transgenic lines have produced over 59,577 seed (about 227 $R_1$ seed per transgenic line). Table 2 indicates that these plants were derived from 11 different cell lines. In addition both male and female fertility has been observed in many of these cells lines. Kernels routinely mature on plants for which the transformant is either the male or the female parent. Embryo rescue is only necessary under unusual circumstances.

Figure 7A:
FIG. 7(A). Mature transgenic $R_0$ plant regenerated from an E2/E5 callus.
Figure 7B:
FIG. 7(B). progeny derived from an E2/E5 plant by embryo rescue; segregant bearing the resistance gene on the right, and lacking the gene on the left.
Figure 7C:
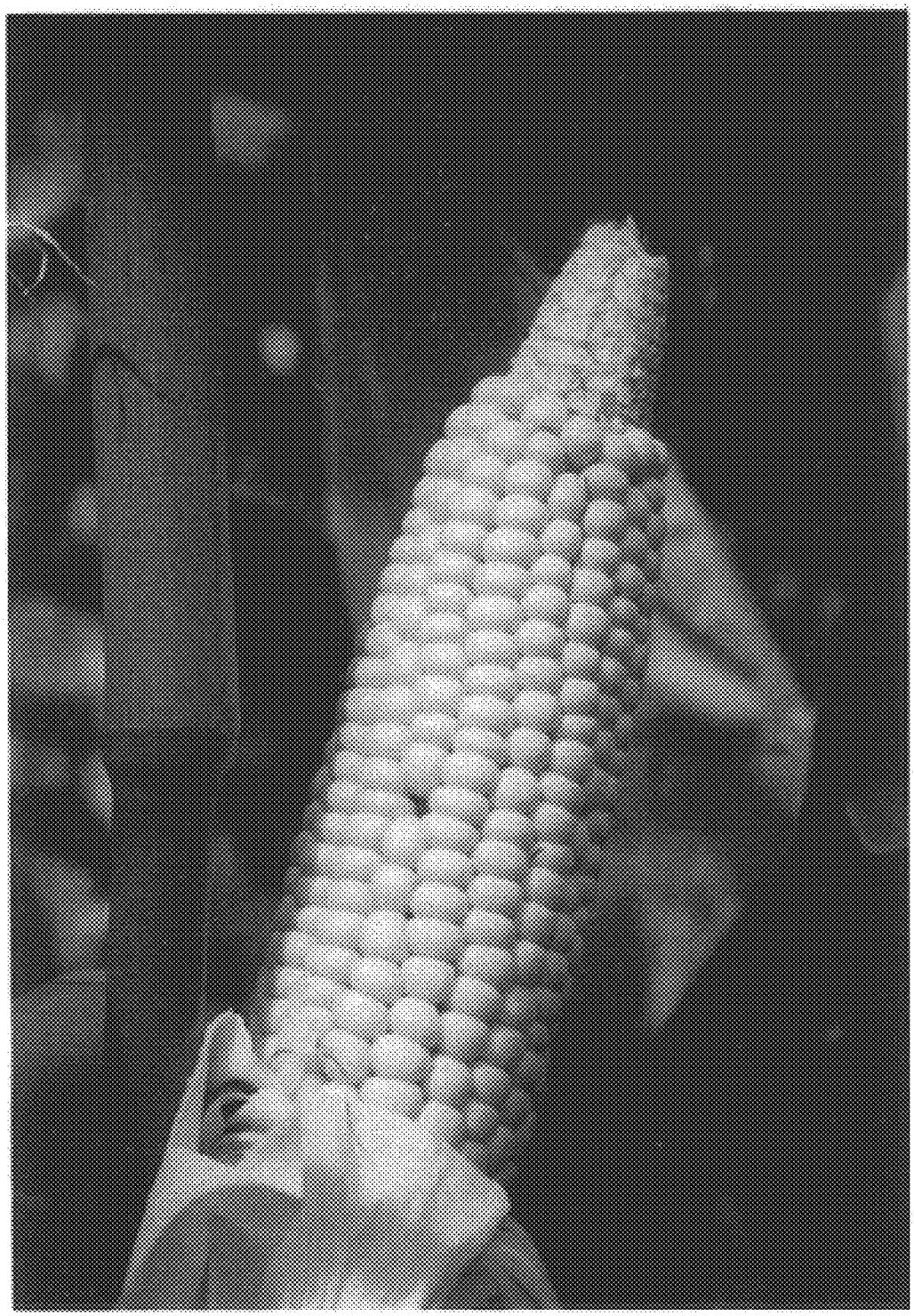
FIG. 7(C). Using pollen from transformed $R_1$ plants to pollinate B73 ears, large numbers of seed have been recovered.
Figure 7D:
FIG. 7(D). A transformed ear from an $R_1$ plant crossed with pollen from a non-transformed inbred plant.

Pollen obtained from transformed $R_1$ plants has been successfully employed to pollinate B73 ears and a large number of seeds have been recovered (see FIG. 7C). Moreover, a transformed ear from an $R_1$ plant crossed with pollen from a non-transformed inbred plant is shown in FIG. 7D. The fertility characteristics of the $R_1$ generation has been confirmed both from a standpoint of the pollen's ability to fertilize non-transformed ears, and the ability of $R_1$ ears to be fertilized by pollen from non-transformed plants.

Fertility of transgenic plants has been maintained for at least 12 generations.

By providing fertile, transgenic offspring, the practice of the invention allows one to subsequently, through a series of breeding manipulations, move a selected gene from one corn line into an entirely different corn line without the need for further recombinant manipulation. Movement of genes between corn lines is a basic tenet of the corn breeding industry, involving simply backcrossing the corn line having the desired gene (trait). Introduced transfers are valuable in that they behave genetically as any other corn gene and can be manipulated by breeding techniques in a manner identical to any other corn gene. Exemplary procedures of this nature have been successfully carried out by the inventors. In these backcrossing studies, the gene for resistance to the herbicide Basta®, bar, has been moved from two transformants derived from cell line SC716 and one transformant derived from cell line SC82 into 18 elite inbred lines by backcrossing. It is possible from these 18 inbreds to make a large number of hybrids of commercial importance. Eleven of the possible hybrids have been made and are being field tested for yield and other agronomic characteristics and herbicide tolerance. Additional backcrossing to a further 68 elite inbred lines is underway.

EXAMPLE 33

Analysis of Progeny ($R_1$) of Transformed $R_0$ Plants for PAT and bar

Figure 11A:
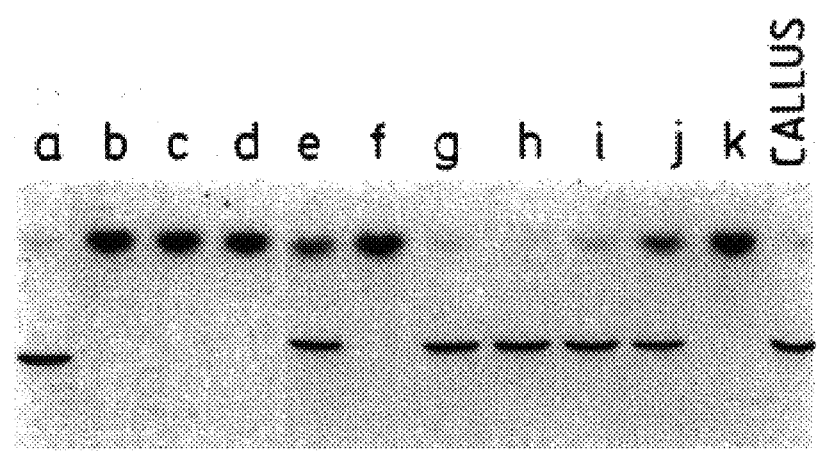
FIG. 11(A). Analysis of PAT activity in ten progeny (lanes a–j) and a nontransformed control plant (lane k). Lanes designated a, b–h, i, and j contained protein extracts from progeny of separate parental $R_0$ plants. The lane designated callus contained protein extract from E2/E5 callus. Approximately 25 micrograms of total protein were used per reaction.
Figure 11B:
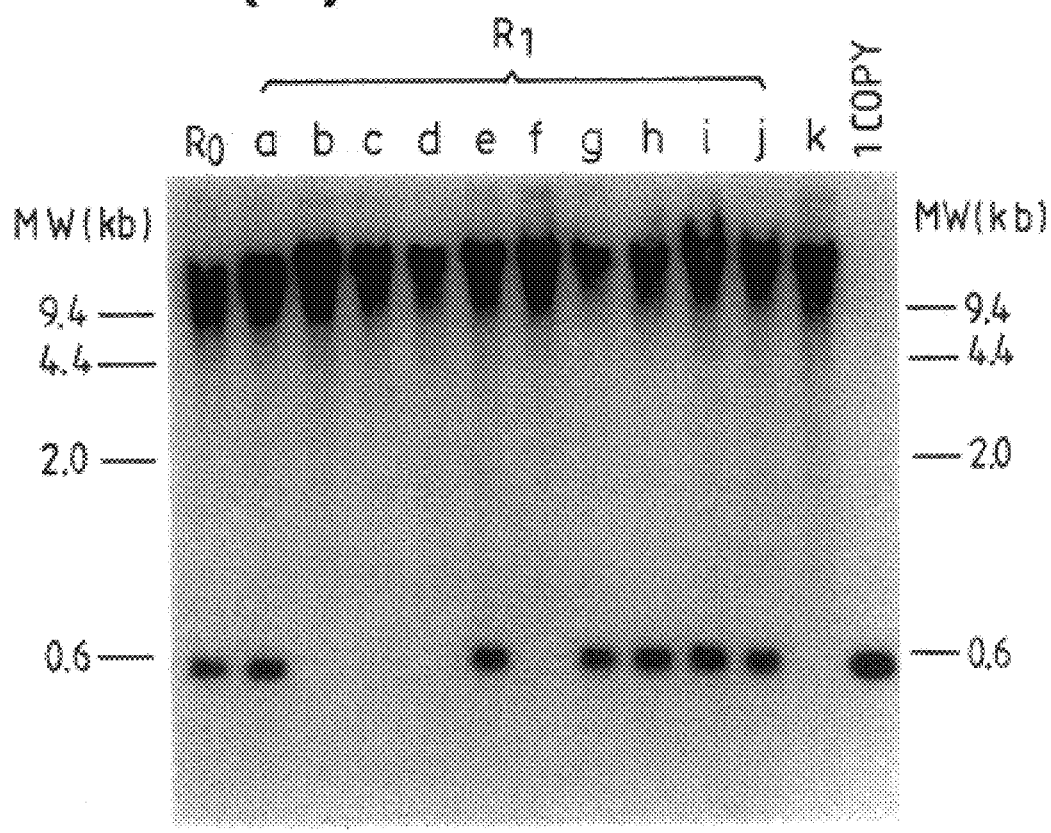
FIG. 11(B). DNA gel blot analysis of genomic DNA isolated from the ten progeny analyzed in A. Genomic DNA (5 μg/lane) was digested with SmaI, which releases a 0.6 kb fragment containing bar from pDPG165, and hybridized with bar probe. The lane designated $R_0$ contained DNA from the $R_0$ parent of progeny a. The lane designated 1 copy contained pDPG165 digested with SmaI to represent approximately 1 copy of the 0.6 kb fragment per diploid genome (0.8 pg).

A total of 40 progeny of E2/E5 $R_0$ plants were analyzed for PAT activity, ten of which are shown in FIG. 11A. Of 36 progeny which were assayed, 18 had PAT activity. Genomic DNA from the same ten progeny analyzed for PAT activity was analyzed by DNA gel blot hybridization for the presence of bar as shown in FIG. 11B. The six progeny tested that expressed PAT contained a single copy of bar identical in mobility to that detected in callus and $R_0$ plants; the four PAT-negative progeny tested did not contain bar-hybridizing sequences. In one series of assays, the presence of the bar gene product in 18 of 36 progeny indicates a 1:1 segregation of the single copy of bar found in E2/E5 $R_0$ plants and is consistent with inheritance of PAT expression as a single dominant trait. A dominant pattern of inheritance would indicate the presence in the plant of at least one copy of the gene coding for PAT. The single progeny recovered from an E10 $R_0$ plant tested positive for PAT activity.

It was determined that the methods disclosed in this invention resulted in transformed $R_0$ and $R_1$ plants that produced functionally active PAT. This was determined by applying Basta (PPT) to the leaves of plants and determining whether necrosis (tissue destruction) resulted from this application. If functionally active PAT is produced by the plants, the leaf tissue is protected from necrosis. No necrosis was observed on $R_0$ plants expressing high levels of PAT (E2/E5) or on plants expressing low levels (E3/E4/E6) (FIG. 8A).

Herbicide was also applied to leaves of $R_1$ progeny segregating for bar. In these studies, no necrosis was observed on $R_1$ plants containing and expressing bar, however, necrosis was observed on those $R_1$ plants lacking the bar gene. This is shown in FIG. 8B.

Segregation of bar did not correlate with the variability in phenotypic characteristics of $R_1$ plants such as plant height and tassel morphology. In FIG. 5B, the plant on the right contains bar, the plant on the left does not. In addition, most plants were more vigorous than the $R_0$ plants.

Of the 23 $R_1$ seedlings recovered in this experiment from the SC716 transformants, ten of 16 had PAT activity. PAT activity was detected in four of ten progeny from $R_0$ plants representing callus line $R_{18}$ and six of six progeny from $R_0$ plants representing callus line R9.

O. Embryo Rescue

In cases where embryo rescue was required, developing embryos were excised from surface disinfected kernels 10–20 days post-pollination and cultured on medium containing MS salts, 2% sucrose and 5.5 g/l Seakem agarose. Large embryos (>3 mm) were germinated directly on the medium described above. Smaller embryos were cultured for approximately 1 week on the above medium containing $10^{-5}$ M abscisic acid and transferred to growth regulator-free medium for germination. Embryos that became bacterially contaminated; these embryos were transferred to medium containing 300 µg/ml cefoxitin. Developing plants were subsequently handled as described for regeneration of $R_0$ plants.

EXAMPLE 34

Embryo Rescue

Viable progeny, recovered from seven SC82 E2/E5 plants and one SC82 E10 plant, were sustained by embryo rescue. This method consisted of excising embryos from kernels that developed on $R_0$ plants. Embryos ranged in size from about 0.5 to 4 mm in length. Small embryos were cultured on maturation medium containing abscisic acid while larger embryos were cultured directly on germination medium. Two of the approximately forty viable progeny recovered from SC82 $R_0$ plants by embryo rescue are shown in FIG. 7B.

P. Phenotype of Transgenic Plants

Most of the $R_0$ plants regenerated from SC82 transformants exhibited on A188 X B73 hybrid phenotype. Plants were similar in height to seed derived A188 plants (3–5 feet) but had B73 traits such as anthocyanin accumulation in stalks and prop roots, and the presence of upright leaves. Many plants, regardless of the callus line from which they were regenerated, exhibited phenotypic abnormalities including leaf splitting, forked leaves, multiple ears per node, and coarse silks. Although many of the phenotypic characteristics were common to all $R_0$ plants, some characteristics were unique to plants regenerated from specific callus lines. Such characteristics were exhibited regardless of regeneration route and the time spent in culture during regeneration.

Nontransformed control plants were not regenerated from this culture and, therefore, cannot be compared phenotypically. Pistillate flowers developed on tassels of one E11 (⅙), several E10 (3/22) and almost one-third of the E2/E5 (12/37) plants with a range of three to approximately twenty ovules per tassel. Primary and secondary ears developed frequently on most E2/E5, E10, and E11 plants; a mature E2/E5 plant is shown in FIG. 7A. Anthers rarely extruded from the tassels of plants regenerated from SC82 transformants and the limited number of anthers which were extruded did not dehisce pollen. Some phenotypic characteristics observed were unique to plants regenerated from a specific callus line such as the lack of ears on E3/E4/E6 plants and a "grassy" phenotype (up to 21 long narrow leaves) exhibited on all E11 plants.

All SC82 plants senesced prematurely; leaf necrosis began approximately two weeks after anthesis. The $R_0$ plants regenerated from SC82 transformed cell lines have tended to senesce prematurely; typically before the developing kernels were mature. This has necessitated the use of embryo rescue to recover progeny ($R_1$ generation). Segregation of bar in the $R_1$ generation does not correlate with the variability in phenotypic characteristics of $R_1$ plants such as plant height and tassel morphology. In FIG. 7B, the plant on the right contains bar, the plant on the left does not. In addition, most of the $R_1$ plants are more vigorous than the $R_0$ plants. Transformed progeny (R1) have produced kernels and progeny testing has now been advanced to the $R_{12}$ generation.

Of 219 plants regenerated from 10 independent SC716 transformants, approximately 35 reached maturity (Table 8). The SC716 plants did not exhibit the phenotypic differences which characterized the plants regenerated from the individual callus lines of SC82. These plants were more uniform and abnormalities less frequent. The phenotype of these plants closely resembled that of control plants regenerated from a SC716 cryopreserved culture which was not bombarded. Plant height ranged from three to six feet with the majority of the plants between five and six feet. Most mature plants produced large, multi-branched tassels and primary and secondary ears. Pistillate flowers also developed on tassels of several SC716 plants. Although anther extrusion occurred at approximately the same low frequency as in the SC82 plants, a small amount of pollen dehisced from some extruded anthers. For most of the SC716 plants that reached maturity, senescence did not commence until at least 30 days after anthesis.

The improved characteristics of SC716 plants over SC82 plants indicate that differences between the suspension cultures may be responsible. This observation has been supported by further experiments in which AT824 plants have been regenerated. These plants are normal in appearance. Plants produce normal tassels and shed viable pollen. In addition plants do not prematurely senesce and seed will mature on the plant. Many plants derived from this cell line and the lines ABT4 and Hi-II are indistinguishable from nontransformed plants.

I. Transformation with Genes for Desirable Traits

One of the distinct advantages provided by the present invention is the ability to transform monocot plants, such as maize, with a gene or genes which imparts a desirable trait to the resultant transgenic plants. These traits include, for example, resistance to insects, herbicides, drought, etc., and the improvement of characteristics such as appearance, yield, nutritional quality, and the like. Certain such genese which are highly desirable in monocot transformation have been discussed as selectable markers, for example, bar and EPSPS. These genes encode proteins which confer herbicide resistance on the plant. Other particularly preferred transgenes include those that have insecticidal activities, such as toxins, proteinase inhibitors and lectins, and those genes that alter the nutritional quality of the grain. The following examples illustrate the use of the present invention in generating advantageous transgenic plants. Table 9 lists all of the genese successfully introduced into maize by the inventors and summarizes the status of analysis for the presence of the introduced DNA and expression. The Table indicates that stable transformants have been recovered containing all genes attempted. Expression has been detected from all structural genese listed in at least one transformed cell line in studies that have progressed to this stage. Detection of expression is dependent on the promotor and enhancers used to drive expression of the structural gene, the structural gene itself, and the limits of the detection system. At this point in time fertile plants containing the uidA, bar, Bt, aroA, dapA, 10 kD zein storage protein and hygromycin resistance genes have been recovered from transformants. Expression of the bar gene has been detected in progeny from all transformants examined (19/19). Expression of the uidA gene has been detected in the progeny of one out of five transformants assayed.

The protocols employed for preparing the transgenic plants described in the foregoing Table were as described above. The preparation of the various vectors, etc, was accomplished through the application of molecular biology techniques as described above and/or using routine laboratory procedures. The numeral designations under "Protocol" represent the following:

1. Tissue (suspension) was plated on filters, bombarded and then filters were transferred to culture medium. After 2–7 days, the filters were transferred to selective medium. Approximately 3 weeks after bombardment, tissue was picked from filters as separate callus clumps onto fresh selective medium.

2. As in 1. above, except after bombardment the suspension was put back into liquid—subjected to liquid selection from 7–14 days and then pipetted at a low density onto fresh selection plates.

3. Callus was bombarded while sitting directly on medium or on filters. Cells were transferred to selective medium 1–14 days after particle bombardment. Tissue was transferred on filters 1–3 times at 2 weeks intervals to fresh selective medium. Callus was then briefly put into liquid to disperse the tissue onto selective plates at a low density.

4. Callus bombardment. The tissue was transferred onto selective plates one to seven days after DNA introduction. Tissue was subcultured as small units of callus on selective plates until transformants were identified.

TABLE 9

| Expression Cassette | Protocol | Gene in Callus | Callus Expression | Gene in Ro Plant | Ro Plant Expression | Gene in Progeny Plant | Progeny Plant Expression |
|---|---|---|---|---|---|---|---|
| uidA (GUS, reporter gene) | 1,2,3,4 | + | + | + | + | + | + |
| bar (bialaphos resistance, selectable marker) | 1,2,3,4 | + | + | + | + | + | + |
| lux (luciferase reporter, gene) | 2 | + | + | + | + | In progress | |
| hyg (hygromycin resistance, selectable marker) | 4 | + | + | + | + | + | + |
| 35S-adh-aroA (Gyphosate tolerance) | 2 | + | + | + | + | + | + |
| α-tubulin-aroA | 2 | + | + | + | + | In | |

TABLE 9-continued

| Expression Cassette | Protocol | Gene in Callus | Callus Expression | Gene in Ro Plant | Ro Plant Expression | Gene in Progeny Plant | Progeny Plant Expression |
|---|---|---|---|---|---|---|---|
| (Glyphosate tolerance) | | | | | | progress | |
| 2xhis-aroA (Glyphosate tolerance) | 2 | + | – | ND | ND | In progress | |
| 35Shis-aroA (Glyphosate tolerance) | 2 | + | – | ND | ND | In progress | |
| R,C1 (anthocyarin pigment synthesis) | 1 | + | + | | | | |
| 35S-IaB6 (Bt) | 2 | + | ND | + | ND | In progress | |
| 35S-HD73 (Bt) | 4 | + | – | + | – | + | ND |
| 35S-1800b (Bt) | 2,4 | + | – | + | + | + | + |
| 2730CS-AdhVI-1800b (Bt) | 2 | + | ND | + | + | In progress | |
| 35S-Adh1-1800b (Bt) | 2,4 | + | ND | + | In progress | | |
| 35S-MZTP-1800b (Bt) | 2,4 | + | In progress | | | | |
| Adh1-adh1-1800b (Bt) | 4 | + | + | + | – | Completed | |
| potato pinII (proteinase inhibitor confers insect resistance) | 2 | + | + | + | ND | In progress | |
| tomato pinII (proteinase inhibitor confers insect resistance) | 2 | + | ND | + | ND | In progress | |
| 35S-dapA (altered lysine production) | 3,4 | + | + | In progress | | | |
| Z27-dapA (altered lysine production in seed) | 3,4 | + | NA | ND | ND | In progress | |
| Z27Z10 (altered storage protein in seed) | 3,4 | + | NA | ND | NA | + | + |
| Z4Z10 (altered storage protein in seed) | 3,4 | + | NA | ND | NA | In progress | |
| Z10Z10 (altered storage protein in seed) | 3,4 | + | NA | ND | NA | In progress | |
| 10Z4ENT (altered storage protein in seed) | 3,4 | + | NA | ND | NA | In progress | |
| 1020P (altered storage protein in seed) | 3,4 | + | NA | ND | NA | In progress | |
| 35S-adhl-mt1D (enhanced stress resistance) | 2 | + | In progress | | | | |
| deh (resistance to dalapon herbicide) | 4 | ND | + | In Progress | | | |

NA indicates not applicable, e.g., gene does not express in that tissue type.
ND indicates not done, but tissue was available.
Blank space indicates experiment has not progressed to this point or was terminated before this point.
The symbol "+" indicates that expression of the gene was detected by RNA, protein, enzyme assay or biological assay.

1. Herbicide Resistance

EXAMPLE 35

Glyphosate Resistance—Transformants Containing the *Salmonella typhimurium* aroA gene This example describes certain methods relating to the use of an aroA gene construct in maize transformation. The herbicide glyphosate acts by inhibiting the enzyme EPSP Synthase. EPSP Synthase is presents in plants and bacteria and the gene used in this example, aroA, was isolated from *Salmonella typhimurium*. Certain mutated versions of the aroA gene are known which encode variant EPSP Synthase enzymes which are insensitive to glyphosate (Comai et al., 1983).

Transformation studies were conducted employing pDPG238, a tandem bar-aroA construct containing a Calgene aroA plant expression cassette. Transformation using the SC716 culture yielded four clones that produced forty-five plants in the greenhouse. Results from PCR analysis demonstrated that three of these four clones contained the aroA gene and one line also expressed the gene at the limit of detection by Western analysis. A plant from this clone was pollinated, two embryos rescued and two $R_1$ plants grown (designated TGB-4 and TGB-5). Both $R_1$ plants contained the aroA gene as determined by PCR analysis and one plant (TGB-5) expressed the gene as determined by Western analysis. Progeny of the aroA expressing plant (TGB-5) were included in field tests.

An experiment was conducted to examine the level of resistance to glyphosate (Roundup®) in crosses of the aroA expressing line TGB-5 produced using pDPG238. This line contains both the bar and aroA genes and hence is expected to confer resistance to both Basta® and Roundup®. A single progeny of TGB-5, designated TGB-56, was crossed to four elite inbreds, representing four different heterotic groups. The progeny were grown and self-pollinated to increase seed, and the resultant seeds were planted in two experiments. The first experiment was sprayed with 1.5 lb/A Basta® to confirm Medlian segregation of the introduced DNA (Table 10). The remaining plants were divided into four blocks and sprayed with application rates of Roundup® of 2 oz/A, 4 oz/A, 8 oz/A, and 16 oz/A. All plants were killed in the 8 oz and 16 oz treatments (normal field application rates for weed control). At 4 oz/A a portion of the transformed plants were killed and a portion were stunted in growth. The ratio of dead plants to slow growing plants was not significantly different from the expected 3:1 ratio in progeny from three of the four self pollinations (Table 11), indicating that there was a low level of expression of the aroA gene providing partial resistance to herbicide application.

TABLE 10

Segregation of Basta ® resistance.
Resistant Susceptible (CD × TGB-56)12856 $\chi^2$ = 1.22
(AW × TGB-56)12952 $\chi^2$ = 1.10
(CN × TGB-56)13648 $\chi^2$ = .075
(AF × TGB-56)10744 $\chi^2$ = 1.17

TABLE 11

Segregation of Roundup ® Resistance.

| | Resistant | Susceptible | |
|---|---|---|---|
| (CD × TGB-56) | 63 | 26 | $\chi^2$ = 0.739 |
| (AW × TGB-56) | 66 | 30 | $\chi^2$ = 1.680 |
| (CN × TGB-56) | 64 | 25 | $\chi^2$ = 0.005 |
| (AF × TGB-56) | 53 | 30 | $\chi^2$ = 4.430 |

Studies involving the E1 cell line yielded nine clones that have produced sixty-five plants in the greenhouse. Results from PCR analysis demonstrated that five of these clones contain aroA, and Western analysis of leaf tissue indicated that certain plants (clone #58) express aroA. No $R_1$ progeny were recovered from E1 plants.

Several tandem bar-aroA vectors were utilized in which aroA expression units had been introduced into pDPG295 and pDPG298, as described earlier (see section E, DNA segments). Briefly, these include vectors with a 35S-histone promoter fusion, in which the genes are placed in convergent, divergent, and colinear orientations (pDPG314, pDPG313, and pDPG317, respectively) with respect to the bar expression cassette; colinear and divergent vectors employing a histone promoter (pDPG315 and pDPG316, respectively); and colinear and divergent vectors employing an α-tubulin promoter (pDPG318 and pDPG319, respectively). DNA of five of these constructs was prepared for bombardment (pDPG313, pDPG314, pDPG315, pDPG317, pDPG319).

It was firstly determined which of the tandem bar-aroA orientation-promoter combinations functioned best under the experimental employed. The 5 DNA constructs, pDPG313, pDPG314, pDPG315, pDPG317, and pDPG319, were bombard into the E1 cell line. Many transformed clones were recovered which revealed that no construct was more useful than any other using bialaphos section. PCR analysis showed that co-transformation frequencies were about identical (75%) regardless of which construct was used. It was therefore concluded that all constructs were functioning, and that no one construct was better than another for transformation. Clones from these studies were cryopreserved for future analysis.

Since all constructs appeared to be functioning similarly, efforts were concentrated on using the 3 divergently constructed tandems pDPG315, pDPG317, and pDPG319 in which the aroA gene is driven by the 2X histone, Camv 35S-histone, and α-tubulin promoters, respectively. Bombardments were initiated using 16 new cell lines (other than E1). These lines include AT824, SC716, E4, ABT4, and various other new A188 × B73 and B73 × A188 cultures. aroA transformants were successfully recovered from cell lines AT824, SC716, and E4 (A1880 cell culture revived from EniMont cryopreservation). Regeneration was begun on aroA confirmed clones of all three lines. Regenerated plants from the AT824 and SC716 clones are in the greenhouse. Four SC716 transformants containing the α-tubulin promoter-aroA expression vector produced $R_1$ seed. AT824 transformants produced $R_1$ seed as follows: five transformants containing the α-tubulin promoter, two transformants containing the CaMV 35S-histone fusion promoter and six transformants containing the 2×histone promoter. These transformants are currently in field tests to determine levels of glyphosate resistance.

EXAMPLE 36

Tissue Specific Expression of aroA in Roots of Transgenic Plants

Transformants were maintained on medium 223 (Table 1). For regeneration cells were transferred to medium 189

(Table 1) and cultured in the dark. Cultures were subcultured two weeks later onto fresh medium 189 (Table 1). Regenerating tissue was transferred to medium 101 (Table 1) in low light, followed by rooting of shoots on medium 607 (Table 1) or 501 (Table 1) and transfer to Plant Cons®. Rooted plants were grown hydroponically to avoid soil and microbial contamination when attempting to assay plants for root specific expression of the EPSPS gene.

Expression of the EPSPS gene, aroA, was assayed by Western blot analysis. Leaf and root samples were harvested from transgenic plants. Approximately 1 gram of tissue was ground in a glass homogenizer with 400 ul RIPA buffer (150 mM NaCl, 1% NP-40, 0.1% SDS, 50 mM Tris-HCl pH 8.0). Extracts were centrifuged at 14,000×g and supernatants collected for protein analysis. Forty ul of each protein extract was run on a 12.5% polyacrylamide denaturing gel (Laemmli, 1970). The gel was run overnight at 50 volts. Following running the gel was electroblotted to nitrocellulose paper and the nitrocellulose dried at 37 C. The blot was washed in 50 ml 5% nonfat dry milk (NFD) in TBS (20 mM Tris-HCl pH 7.5, 0.5M NaCl) for 30–60 minutes followed by incubation overnight in 50 ml 5% NFD, TBS containing 100 ul EPSPS rabbit antiserum. The nitrocellulose blot was washed 3 times for 5 minutes each in TBS and then incubated in 50 ml 5% NFD, TBS containing 100 ul goat anti-rabbit antiserum conjugated to horseradish peroxidase for two hours. The nitrocellulose blot was washed 3 times with TBS for 5 minutes each prior to staining. The blot was stained as follows. Twenty four mg 4-chloro-1-naphthol was dissolved in 8 ml methanol. Forty two ul 3% $H_2O_2$ was added. Thirty minutes after initiation of staining 400 ul of $H_2O_2$ was added. The staining reaction was stopped by adding water and drying the blot. Western blots were stored in the dark.

Expression of EPSPS was detected in roots derived from plants of transformant S10AV13. No expression was observed in leaf tissue. The protein expressed in the root was identical in size to EPSPS protein isolated from *Salmonella typhimurium* and run on the same gel as a positive control. This is the expected expression profile expected, because the α-tubulin promoter is root specific in maize. The aroA expression cassette in pDPG319 also contains a transit peptide of about 130 amino acids to target the EPSPS protein to the plastids. As the protein expressed in maize is identical in molecular weight to the protein isolated from *S. typhimurium* it is apparent that the transit peptide has been correctly cleaved from the EPSPS protein. Hence it is believed that the EPSPS protein was targeted to the plastids as demonstrated in example 7.

EXAMPLE 37

Herbicide Application (Basta®)

The herbicide formulation used, Basta TA$^R$, contains 200 g/l glufosinate, he ammonium salt of phosphinothricin. Young leaves were painted with a 2% Basta solution (v/v) containing 0.1% (v/v) Tween-20. The prescribed application rate for this formulation is 0.5–1%.

In FIG. 8A, Basta$^R$ solution was applied to a large area (about 4×8 cm) in the center of leaves of a nontransformed A188 X B73 plant (left) and a transgenic R$_0$ E3/E4/E6 plant (right). In FIG. 8B, Basta was also applied to leaves of four R$_1$ plants; two plants without bar and two plants containing bar. The herbicide was applied to R$_1$ plants in 1 cm circles to four locations on each leaf, two on each side of the midrib. Photographs were taken six days after application.

EXAMPLE 38

Resistance in the Field to the Herbicide Ignite®/Basta®

Experiments have been undertaken to determine whether transformants containing the bar gene exhibit sufficient levels of herbicide resistance to be useful commercially. Eleven independent bar transformants were evaluated for field levels of resistantce to the herbicide Basta®(a.k.a. Ignite®). The field design used a split-split plot with 2 repetitions. Whole plots were spray rates (1×, 3× and 7×) and subplots were transformant sources. Transformant sources were planted in four-row plots with two rows sprayed with Ignite and two rows sprayed with water. A spray rate of 0.33 lb/A (1×) was used to test for efficacy. This will probably be the field rate for weed control in corn fields.

The range of responses was too narrow and field variation too large for a rating system to be useful for evaluating field levels of resistance. At the normal field application rate of Ignite® all transformant sources demonstrated resistance to the herbicide. Differences were observed between the transformants at an application rate that was three times the normal rate. Each plot was examined by comparing sprayed versus unsprayed rows for 1) leaf-necrosis in the whorl where the herbicide accumulated at spraying; 2) chlorosis of the whorl tissue; 3) abnormal leaf growth in the whorl after spraying; 4) variability and stunting of sprayed planting compared to unsprayed; and 5) overall reduction in plant growth of sprayed versus unsprayed rows.

Differences in herbicide sensitivity were not dramatic, but consistent enough to rank each transformant, i.e. all transformant showed resistance to the herbicide. Transformants could be roughly classified into three major response groups with little difference between sources within the group. Transformants A24, B16 and E29 were most resistant to the herbicide. The sources A24 and B16 were the best, with no phenotypic difference between sprayed and unsprayed plots. Source E29 was also very good, but was somewhat variable or slightly shorter in sprayed plots. Sources A18, V11, and E19 were intermediate in response to Ignite®. The sprayed rows were slightly shorter, but were uniform and did not have any of the phenotypic abnormalities seen in the more sensitive transformants. Transformant sources G18, G20, K20, E14 and E27 were clearly sensitive to the 3× application rate of Ignite®. They were shorter and had plants with necrotic lesions, chlorotic whorls and leaf abnormalities group.

These experiments clearly demonstrate that transformants containing the bar gene are useful for production of herbicide resistant commercial hybrids.

2. Grain Quality

EXAMPLE 39

Elevation of Lysine Levels in Maize Grain

As described in the previous U.S. patent application Ser. No. 07/204,388 (most claims of which have been granted), one approach to enhancing lysine levels in maize grain involves lysine overproduction through deregulation of the lysine biosynthetic pathway. A key reguatory point in the lysine biosynthetic pathway occurs at the condensation reaction in which pyruvuate and aspartyl semialdehyde form dihydrodipicolinic acid. This reaction is catalyzed by the enzyme dihydrodipicolinic acid synthase (DHDPS), which is normally feedback-inhibited by free lysine. In that previous patent application, data were presented which demonstrate that expression of a lysine-tolerant version of DHDPS, encoded by the E. coli dapA gene, in transgenic tobacco plants leads to elevated lysine levels in plant cells. As presented below, we have transferred similar gene constructs to maize cells and have successfully regenerated transgenic plants which contain these dapA gene constructs and express the lysine-tolerant DHDPS in maize seeds.

Plasmid constructs were introduced, in various combinations, into maize cells by particle bombardment as described above. Transgenic cell lines were identified on the basis of resistance to the appropriate selectable agent, either hygromicin (Hyg), phosphoinothricin (Ppt), or bialophos (Blp), included in the growth medium. These lines were then screened at the callus level for presence of appropriate DNA sequences by PCR amplification assays. Several cell lines have been established which are at various stages of plant regeneration. Current status of transformed plants that have been transferred to soil is summarized in the following Table 12:

TABLE 12

| DPG plasmid constructs used for bombardment | Recipient cell line | Selection agent | Transgenic line(s) carried through plant regeneration | Status |
|---|---|---|---|---|
| 334/367 | AB61 | Hyg | HAL | R2 seed |
| 334/366 | AB61 | Hyg | Dap2 | R2 plants |
| 334/371/367 | AB61 | Hyg | Dap3 | R2 plants |
| 335/355 | HAL | Ppt | Dap4 | R1 seed |
| 371/363 | ABT4 | Ppt | ND1-1 ND1-4 | R1 plants |
| 335/372/231 | ABT4 | Blp | dAH03CF-10 dA06CF-10 dA06CF-15 dA09CF-11 | R0 plants |
| 335/372/231 335/372/283 | ABT4 | Blp | dAH04CG-11 dAH07CF-11 dAH07CF-12 dAH07CF-15 dAH07CF-19 dAH07CF-24 dAH07CG-17 | R0 plants |
| 335/165 | HB13-3 | Blp | dAU01CG-10 | R0 plants |

For each of the most recent experiments, where only R0 plants have been generated to date, several additional cell lines are in the plant regeneration process. In these experiments, in which the main objective is to obtain expression of the DSTP/dapA transgene in various tissues, several dozen transformants have been obtained by co-bombardment with multiple plasmids. Only those lines which, when assayed at the callus level, are PCR-positive for the selectable marker transgene and the dapA construct(s) of interest are transferred to the plant regeneration program. In summary, these experiments have yielded the following numbers of bar-positive transformants:

| Genotype by PCR assay | No. transformants |
|---|---|
| DPG 335/372 | 35 |
| DPG 335 | 21 |
| DPG 372 | 26 |
| DPG418 | 20 |

PCR-amplification assays of DNA extracted from callus samples were performed by standard procedures. In each assay, one oligonucleotide primer (primer 1 in the table below) was specific to the promoter present in the transgene, and a second primer (primer 2) corresponded to the dapA coding region or, for pDPG418, the Glb1 3' sequence. Designations of the primers used for the PCR-amplification assays of the dapA constructs, along with the sizes of the amplified fragment products, are provided in the following Table 13:

TABLE 13

| Construct | Primer 1 | Primer 2 | Fragment size |
|---|---|---|---|
| 334 Z10/MZTP/dapA/nos | Z10P965 | dapAPCR1 | 572 bp |
| 335 Z27/DSTP/dapA/35S | Z27mid | DAP6 | 1011 bp |
| 371 35S/MZTP/dapA/nos | 35SPCR1 | dapAPCR1 | 480 bp |
| 372 | 35SPCR1 | DAP6 | 610 bp |
| 35S/DSTP/dapA/nos | 35SPCR1 | dapAPCR1 | 486 bp |
| 418 | 35SPCR1 | DAP6 | 616 bp |
| G1b1/DSTP/dapA/G1b1 | G1b15' | G1b13' | 1300 bp |
| | G1b15' | dapAPCR1 | 464 bp |
| | G1b15' | DAP6 | 594 bp |

Expression of dapA transgenes in transformed plant cells has been analyzed to date primarily by assaying for the presence of lysine-tolerant DHDPS activity essentially as described in U.S. patent application Ser. No. 07/204,388, except that modifications have been made for use of the assay in a qualitative manner in a microtiter plate format as follows: a few milligrams of each tissue sample are placed in the wells of a 96-well plate with 50 ul of 0.225 M tris, 17.3 mM sodium pyruvate, pH 8.2, covered, then transferred to a −20° C. freezer for at least one hour. After the samples are thawed briefly, 50 ul of the reaction mix described by Yugari et al (J. Biol. Chem, 240:4710–4716, 1965), supplemented with L-lysine to 0.45 mM, was added and the reactions were incubated at 37° C. for 1–2 hours. Reactions were quenched by the addition of 175 ul stop buffer, and pink color was allowed to develop at room temperature for 15–60 minutes, at which time the samples were scored as plus or minus lysine-tolerant DHDPS activity on the basis of presence or absence, respectively, of pink color. This assay has been applied in this form to portions of cultured maize callus, portions of immature seeds, fragments of mature dry kernels, and leaf sections from plants at various stages of growth. Results of lysine-tolerant DHDPS expression assays in the transgenic maize lines from which mature plants have been obtained are summarized in the following Table 14:

TABLE 14

| Transgenic line | dapA promoter construct(s) | Callus | Leaf | Immature kernels (20 DAP) | Mature kernels |
|---|---|---|---|---|---|
| HAL | 334 (Z10) | no | nd | nd | nd |
| Dap2 | 334 (Z10) | no | no | yes | yes |
| Dap3 | 334 (Z10) | nd | no | yes | yes |

TABLE 14-continued

| Transgenic line | dapA promoter construct(s) | Callus | Leaf | Immature kernels (20 DAP) | Mature kernels |
|---|---|---|---|---|---|
| Dap4 | 371 (35S) 335 (Z27) | nd | nd | nd | nd |
| ND1-1 | 371 (35S) | yes | nd | nd | n.d. |
| ND1-4 | 371 (35S) | yes | yes | nd | no |

The expression of the dapA transgene in both developing and mature maize kernels from transgenic plants is significant with respect to use of these, and related, gene constructs in development of high-lysine maize types through deregulation of the lysine biosynthetic pathway. This trait is transmitted and expressed at least through the R2 generation, as R2 seeds of both Dap2 and Dap3 contain lysine-tolerant DHDPS activity.

The following additional lines have been assayed for lysine-tolerant DHDPS activity at the callus level. These lines have either produced plants that have recently been transferred to soil or are in the early stages of plant regeneration (Table 15).

TABLE 15

| Cell line | dapA construct(s) | Lys-tolerant DHDPS activity |
|---|---|---|
| dAH03CF-10 | 335/372 | + |
| dAH06CF-10 | | + |
| dAH06CF-15 | | − |
| dAH09CF-11 | | − |
| dAH04CG-11 | 335/372 | − |
| dAH07CF-11 | | − |
| dAH07CF-12 | | + |
| dAH07CF-15 | | − |
| dAH07CF-19 | | − |
| dAH07CF-24 | | − |
| dAH07CG-17 | | + |
| dAU01CG-10 | 335 | + |
| dAR01E1-10 | 418 | − |
| dAR01E1-11 | | + |
| dAR01E1-13 | | + |
| dAR01E1-14 | | + |
| dAR01E1-15 | | − |
| dAR01E1-16 | | + |
| dAR01E1-17 | | − |
| dAR01E1-18 | | + |
| dAR01E1-19 | | + |
| dAR01E1-20 | | + |
| dAR01E1-21 | | + |
| dAR01E1-23 | | − |
| dAR01E1-24 | | − |

Expression of the dapA transgene in seeds of transformed plants as described above is very encouraging with respect to our goal of deregulating lysine biosynthesis in maize kernels. To date, expression of the lysine-tolerant dapA gene product has been accomplished by using the endosperm-specific promoters Z10 and Z27, and it is anticipated that use of the embryo-specific Glb1 promoter will result in expression of the dapA gene product in embryos as well.

EXAMPLE 40

Enhanced Methionine Content of Maize Seeds

The purpose of these experiments is to enhance methionine content of maize kernels for improved poultry feed. This goal is achieved through particle bombardment of maize cells with DNA-coated microprojectiles and subsequent selection of transformed cells, followed by regeneration of stably transformed, fertile transgenic maize plants which transmit the introduced genes to progeny. The gene used for enhanced methionine content encodes a 10 kD zein seed strorage protein which is 23% methionine, and seeds of transformed plants overexpress this gene, leading to increased 10 kD zein and increased methionine content.

The zeins are a large family of related proteins which accounts for more than 50% of the total protein in maize seeds. The α-zeins, which are low in lysine, methionine and tryptophan, are the most abundant of the zeins. Thus, maize seeds are deficient in these amino acids because such a large fraction of the total protein is α-zein. One method to correct for this deficiency, and to substantially increase the seed levels of various amino acids, especially methionine, is to overexpress a gene encoding a 10 kD δ-zein containing 23% methionine.

U.S. patent application 07/636,089, filed Dec. 28, 1990, describes the production of transgenic Zea mays plants and seeds, which have been transformed with recombinant DNA encoding the 10 kD δ-zein. Transgenic plants are obtained by bombardment of friable, embryogenic callus with microprojectiles coated with recombinant DNA encoding the 10 kD zein and a selectable marker gene, followed by selection of transformed callus and regeneration of fertile plants, which transmit the introduced gene to progeny.

A transformed cell line, designated Met1, was obtained by bombarding AB63S cells with the plasmids pDPG367, pDPG338, and pBII221. Selection was on 60 mg/l hygromycin, and the presence of the HPT, GUS and Z27Z10 genes was confirmed by PCR analysis. Additionally, the presence of the HPT coding sequence and the Z27Z10 gene was confirmed by Southern analysis. Met1 exhibited strong resistance to hygromycin, and was only 20% inhibited at 200 mg/l hygromycin. Thirty two additional lines carrying methionine constructs were identified (using selection procedures described elsewhere in this CIP) as shown in Table 16.

TABLE I6

Genotypes of Cell Lines PCR[+] for Methionine Constructs

| Cell Line | Genotype |
|---|---|
| Met1 | Z27Z10 |
| MD 64-1 | Z27Z10, Z10Z10 |
| MD 84-34 | Z27Z10, Z4Z10 |
| MD 84-31 | Z4Z10, Z10Z10 |
| MD 84-2 | Z4Z10 |
| MD 52-8 | Z4Z10, Z10Z10 |
| MD 52-11 | Z27Z10, Z4Z10, Z10Z10 |
| MD 52-10 | Z4Z10 |
| MD 44-2 | Z4Z10, Z10Z10 |
| MD 42-1 | Z27Z10, Z4Z10, Z10Z10 |
| MD 32-2 | Z10Z10 |
| MD 32-1 | Z27Z10, Z10Z10 |
| A6-101 | Z27Z10, Z4Z10, Z10Z10 |

TABLE I6-continued

Genotypes of Cell Lines PCR+ for Methionine Constructs

| Cell Line | Genotype |
| --- | --- |
| A6-115 | Z27Z10, Z4Z10, Z10Z10 |
| A6-181 | Z27Z10, Z10Z10 |
| A6-151 | Z27Z10, Z4Z10, Z10Z10 |
| A6-161 | Z4Z10, Z10Z10 |
| A6-907 | Z27Z10, Z4Z10, Z10Z10 |
| A8-113 | Z10Z10 |
| A8-301 | Z27Z10, Z4Z10, Z10Z10 |
| A10-2 | Z27Z10, Z4Z10, Z10Z10 |
| A10-7 | Z27Z10, Z4Z10, Z10Z10 |
| B1-72 | Z27Z10 |
| B1-82 | Z27Z10 |
| B1-94 | Z27Z10 |
| B1-101 | Z27Z10 |
| B1-401 | Z27Z10 |
| B1-601 | Z27Z10 |
| B1-702 | Z27Z10 |
| B1-703 | Z27Z10 |
| B1-703 | Z27Z10 |
| B1-704 | Z27Z10 |
| B1-705 | Z27Z10 |
| B1-901 | Z27Z10 |

Transformants were identified by PCR analysis. The Z27Z10 chimeric gene was distinguished from endogenous genes by generation of a PCR product which spanned the junction of the Z27 promoter and the Z10 coding sequence. Similarly, the Z10Z10 introduced gene was identified by a PCR product which spanned the junction of the pUC plasmid which carried the construct and the Z10 promoter, and the Z4Z10 construct was identified by a PCR product spanning the junction between the Z4 promoter and the Z10 coding sequence.

Forty five plants were regenerated from Met1 callus. These plants were selfed and reciprocal crosses were made using 6 inbred lines. Immature seed was harvested at 21–24 DAP for Northern analysis, and genotype of the progeny was also examined by PCR. In all cases, the HPT and Z27Z10 gene cosegregated, consistent with Mendelian segregation of a single locus, and indicating linkage of the introduced HPT and chimeric Z27Z10 genes. Additionally, the GUS gene was shown to cosegregate with the HPT and Z27Z10 genes, allowing the use of a GUS assay to be used to identify the Z27Z10 genotype. Northern analysis confirmed that the chimeric Z27Z10 gene was expressed only in seeds PCR+ for the Z27Z10 gene. As with PCR analysis, the presence of the Z27Z10 transcript was confirmed using a probe which spanned the junction between the Z27 and Z10 sequences.

ELISA analysis of Met1 $R_1$ seed using a Z10-specific antibody revealed a trend of increased 10 kD zein levels as compared to controls. Seeds carrying the Z27Z10 gene shoed 2 to 3-fold higher levels of 10 kD zein per unit protein than nontransformed seed. Even more striking results were obtained in ELISA analysis of $R_2$ seeds. In these experiments, embryos were isolated from seeds and germinated, and PCR analysis for the Z27Z10 gene was carried out on the seedlings from the excised embryos, and protein analysis was carried out on the remaining seed tissue. The Z10 gene product accounted for up to 0.6% of the dry seed weight, or 6% of the total protein. An average 7-fold increase in 10 kD zein expression was found. Field test data from 90 bulked $R_3$ seed samples indicated a positive correlation between elevated 10 kD zein levels and the presence of the Z27Z10 construct. For ELISA analysis, zeins were extracted from corn meal samples in 70% ethanol and 2% B-mercaptoethanol at room temperature. Extracts were dried down on 96-well microtiter plates and incubated sequentially with 1% BSA, primary antibody, peroxidase-conjugated secondary antibody, and enzyme substrates (for peroxidase). Absorbances at 490 minus 410 nanometers were collected, and a standard curve using purified 10 kD-specific antibody was used to calibrate each plate. Three extractions were carried out for each sample, and each extraction was assayed in 3 wells. Thus, 9 absorbance measurements were made for each sample.

Protein levels were measured by near infra-red reflectance spectroscopy, and methionine levels were measured by oxidation of meal, followed by acid hydrolysis with detection of the released methionine sulfone by PITC (phenyl-isothiocarbymate) pre-column derivitization and reverse-phase HPLC. The presence of Z27Z10 DNA was confirmed by PCR and/or Southern analysis.

PCR, 10 Kd zein, methionine and protein analyses were carried out on field test samples from 65 ears. Of the three lines analyzed, it was demonstrated that PCR+ ears contained higher levels of 10 Kd zein, regardless of genotype. In addition, a correlation was shown between increased Z10 gene product, as determined by ELISA analysis, and elevated methionine levels in the seed, as determined by amino acid analysis.

EXAMPLE 41

Improved Protein and Starch Content of Maize Seeds by Antisense DNA

The purpose of these experiments is to improve the nutritional content of maize kernels by reducing the expression of α-zeins, with a concomitant increase in the levels of other proteins or starch. The reduction in α-zein expression is to be achieved by particle bombardment of maize cells with microproprojectiles coated with antisense genes to the 19 and 22 kD α-zein families, to reduce translation of α-zein mRNA.

The majority of the zein proteins, which account for over 50% of the total seed protein, are the 19 and 22 kD α-zeins. The high levels of α-zeins, which are low in methionine, lysine and tryptophan, result in seeds low in these amino acids. Maize seed protein levels are inversely correlated with starch, thus reduced α-zein levels would potentially result in increased starch. Increased levels of other proteins are also associated with reduced levels of α-zeins in opaque and floury mutants, which reduce levels of α-zeins.

The α-zeins are encoded by a large multigene family with regions of sequence homology. Consequently, a small number of introduced antisense genes (with transcripts complementary to the conserved regions of homology in α-zein transcripts) would likely be needed. Introduction of antisense genes and selection for reduced α-zein content and increases in starch or other proteins of interest, would be followed by introduction of these selected lines into a breeding program to optimize desirable characteristics. It is believed that, in light of the present disclosure, one of skill in the art would now be able to alter the nutritional content of maize seeds through transformation of maize plants using genes encoding antisense genes to the α-zeins.

Two α-zein antisense genes to the 19 kD zein (A20 gene) and 22 kD zein (Z4 gene) under control of the 10 kD zein promoter have been used to transform maize cells. These two plasmids were chosen from a variety of plasmids containing antisense sequences to α-zeins based on reduction of α-zein protein levels following hybrid arrest of α-zein RNA using antisense transcripts, and in vitro translation of α-zein mRNA not removed by hybridization. In these experiments, in vitro synthesized sense and antisense RNAs were prepared and mixed using a 4:1 ratio of antisense to sense RNA. Annealing conditions were determined by the appearance of sense::antisense hybrids on agarose gels. Although RNAs were successfully translated in both wheat germ and rabbit reticulocyte systems, the rabbit reticulocyte system was shown to be more efficient. Laser densitometry was used to quantitate the results of the in vitro translations. Several plasmids carrying antisense genes or parts of antisense genes were examined, and the plasmids p1020p and pZ4ENT were shown to be the most efficient in these assays.

Stable transformants were obtained by bombarding maize cells with the antisense constructs and selectable marker genes, and selection was carried out as described elsewhere, using Basta, bialaphos or hydromycin. Presumptive transformed calli were screened for antisense constructs by PCR, using primers to the Z10 promoter and the nos 3' sequence. Seven lines were identified which were PCR-positive for pZ4ENT, 15 lines were PCR-positive for p1020P, and 1 line was positive for both constructs. These lines were regenerated and crossed to various inbred lines. Further transformation experiments using pDPG165 as the selectable marker gene, resulted in an additional 13 transformants which carried p1020P, 13 with pZ4ENT, and 42 which were PCR+ for both plasmids. These transformed cell lines are now being regenerated according to standard procedures.

$R_1$ seeds were collected from regenerated plants, and 110 $R_1$ seeds from 6 antisense lines were grown in the greenhouse. Seed was uniform in appearance and synchronous germination occurred at 95%. Plants appeared normal, and selection for Basta resistance was carried out one month after planting by leaf painting with 2% Basta. Twenty four resistant plants were identified in this manner. These plants were selfed and crossed to inbred lines. Immature kernels of selfed plants were harvested at 10, 12 and 16 days after pollination and frozen in liquid nitrogen for future Northern analysis of antisense constructs.

3. Insect Resistance

The yield and efficiency of producing grain from maize throughout the world is affected by the action of a number of insect pests. The insect pests that currently affect the US maize crop include: the European Corn Borer (*Ostrinia nubilalis*;Hbn), Southwestern Corn Borer (*Diatraea grandiosella*), Southern Cornstalk Borer (*Diatraea crambidoides*), Lesser Cornstalk Borer (*Elasmopalpus lignosellus*), the corn rootworm (*Diabrotica spp.*), the corn earworm (*Heliothis zea*), armyworms (*Spodoptera frugiperda; Pseudaletia unipuncta*), cutworms (e.g. black cutworm; *Agrotis ipsilon*), wireworms, assorted grubs, Chinch Bugs (*Blissus leucopterus*), Corn Flea Beetles, Billbugs, Corn Root Aphids, Corn Leaf Aphids, Corn Planthopper. As well as directly affecting growth and yield, insect feeding can also lead to increased damage due to infection by other pathogens, e.g. when the insect serves actively as a vector for the pathogen (maize chlorotic mottle virus) or passively by opening the plant tissue to infection (stalk, root and ear rot fungi). Infection of the ear by fungi can also lead to unacceptible levels of fungal toxins (aflatoxin) in maize grain. Furthermore, grain harvested from maize can also be damaged in storage by a variety of insects (e.g. seed corn maggot, meal moths, worms, beetles and weevils).

The control of insect pests to prevent damage is achieved in the US mainly by adopting good integrated pest management (IPM) procedures that include the use of certain farming (and storage) practices, the use of chemical and biological control measures and the use of maize germplasm that confers resistance or tolerance to insect pests. The use of some of these aspects of IPM are not always compatible with efficient, cost-effective farming or can detrimentally impact the environment through the use of chemical insecticides. Also, while traditional breeding has produced resistance or tolerance to some insect pests, the level of resistance to several important insect pests has either been inadequate to prevent economic levels of damage or is incompatible with maintaining high yield. To circumvent these problems and to reduce the use of chemical insecticide, it would be advantageous to introduce insect resistance genes into maize from a variety of sources.

In the examples described below we have utilized the transformation process to introduce into maize plants two genes from diverse sources that can, or have the potential to, control insect damage. We have demonstrated expression and inheritance of the genes in maize and have also demonstrated that the gene(s) can be used to confer resistance to a major insect pest of maize, the European Corn Borer.

In the first example (see example 42), DNA coding for the endotoxin from a solid bacterium, *Bacillus thuringiensis* (Bt gene), and DNA coding for protease inhibitor II protein from tomato (*Lycopersicum esculentum*) were simultaneously transformed into maize cells and plants were regenerated to produce fertile transgenic maize plants containing one or both of the genes. In the second example (Example 43), a Bt gene alone was introduced. In both examples a selectable marker coding for resistance to the herbicide bialaphos was also introduced and used to initially identify transformants. The close genetic linkage of the herbicide resistance and insect resistance genes may provide some utility by allowing breeders to follow the inheritance of the insect resistance genes by screening for herbicide resistance.

Potential insect resistance genes which can be introduced include the *Bacillus thuringiensis* crystal toxin genes or Bt genes (Watrud et al., 1985). Preferred Bt toxin genes for use in such embodiments include the CryIA(b) and CryIA(c) genes (H. Hofte and H. R. Whiteley, 1989, Microbiol. Revs. 53: 242–255).

The poor expressions of the prokaryotic Bt toxin genes in plants is a well-documented phenomenon, and the use of different promoters, fusion proteins, and leader sequences has not led to sufficient gene expression to produce resistance in several plant species (Perlak et al, 1991). We have previously introduced expression vectors into maize that contain the native coding sequence for the HD73 Bt gene (a representative of the cryIA(C) class of Bt genes). The gene was derived by cloning from the *B.thuringiensis* strain and modified by removing the genetic elements necessary for expression in its original host and replacing them with elements known to be capable of directing the initiation and termination of transcription of other foreign genes in maize. The expression vector produced was transformed into regenerable maize cells that were eventually regenerated into plants. The transformed maize cells and plants that were recovered that contained the Bt expression vector failed to provide resistance to ECB larvae.

To reduce this factor as an influence on Bt gene expression in maize, we have synthesized new DNA sequences for the HD73 and HD1 Bt genes that code for the same amino acid sequences as their native counterparts but which replace codons that are rarely used in actively expressed maize genes (less than 19% of the time) with codons that are most frequently used in highly expressed maize genes. The synthetic DNA sequences coded for the active portion of the Bt genes and contained approximately the first 613 codons of the Bt genes (including the f-met initiation codon; see FIGS. 1 and 2 for sequences). The HD73 Bt endotoxin gene was introduced into a plant expression vector similar to that previously used for the native Bt gene and also into expression vectors with modified expression control elements designed to increase expression. Other examples of modified Bt toxin genes reported by others include the synthetic Bt CryIA(b) gene and CryIA(c) genes (Perlak et al., 1991).

In the current examples, genes coding for protease inhibitors have also been introduced into maize. The use of protease inhibitors to mediate resistance to insect pests has been described before (R. Johnson et al., 1989.; V. A. Hilder et al., 1987) but none of these genes have previously been reported to have been introduced into maize using the transformation process. The use of a protease inhibitor II gene (PIN) from tomato or potato is envisioned to be particularly useful. Even more advantageous is the use of a PIN protein in combination with a Bt toxin protein, the combined effect of which has been discovered by the present inventors to produce synergistic insecticidal activity.

The two examples cited below illustrate the utility and benefits of using the current invention to introduce insect resistance genes into maize.

EXAMPLE 42

Insect Resistance in Transgenic Plants

In this example AT824 cells were bombarded with 10 ug each pDPG165, pDPG354 and pDPG44 as described in example 10.

Transformants were selected similar to example 19. The bombarded cells were removed from the microprojectile gun chamber, incubated on the wet filters in the petri dish for 16–24 hours, scraped from the filter and placed in liquid 409 medium (10 ml medium in a 125 ml conical flask). Flasks were incubated at ambient temperature (20–25° C.) in an orbital shaker (New Brunswick Scientific, controlled environment, incubator shaker; 125–150 rpm). Cells were subcultured (2 ml PCV into 20 ml medium) every 3.5 days for one week without herbicide then subcultured in fresh 409 medium plus 1 mg/L bialaphos (medium 434) every 3.5 days for 2 weeks. Cells were the dispensed onto solid 425 medium (3 mg/L bialaphos) at a density of 0.1 ml PCV per plate and incubated in the dark at ambient temperature. Approximately 250 plates were generated per original bombarded filter and 3–5 weeks post plating colonies of cells potentially resistant to the herbicide were identified.

Bialaphos resistant transformants were transferred to fresh solid 425 medium and subcultured twice (once every two weeks) before selected samples were taken for analysis by polymerase chain reaction (PCR) to detect the presence of the Bt and/or protease inhibitor (PIN) genes For PCR analysis, standard protocols were followed using the following primers:

PCR primers for PIN gene were:

```
PIN-1     5'- GCT TAC CTA CTA ATT GTT CTT GG -3'
(MD-1):

PIN-4:    5'- CAG GGT ACA TAT TTG CCT TGG G - 3'
(MD-4):
```

PCR primers for Bt gene were:

```
BTSN64:   5'- AAC CCT GAA TGG AAG TGC - 3'

BTASN506: 5'- ACG GAC AGA TGC AGA TTG G - 3'.
```

Forty-two of the putative transformants (Table 17) were analyzed by PCR for the Bt gene and in most cases also for the PIN gene; A number were positive for Bt or PIN alone and a majority of PCR positive transformants were positive for both genes.

Regeneration of plants was similar to example 31. To regenerate the transformed maize cells, the bialaphos resistant maize clones were passaged (every two weeks; 24° C.) on the following media at 24° C.:

(i) On solid 223 medium or 425 medium and maintained for 1–10 passages (2–3 weeks per passage).

(ii) Passaged one to three times on 189 medium (first passage in the dark; later passages in low light; 16 hours light; 8 hours dark), (iii) Passaged one to four times on 101 medium in higher light.

(iv) Passaged one to four times on 607 or 501 medium in Plant Con® containers in higher light.

Once shoots were observed in tissue incubated on 101 medium, the light intensity (fluorescent light: 25–250 $mE.M^{-2}.S^{-1}$) was increased by slowly adjusting the distance of the plates from the light source located overhead. Transformants that developed 3 leaves and 2–3 roots were then transferred to a soilless plant growth mix. In some cases indolebutyric acid (3 ml of 0.3% w/v solution) was applied to the base of rootless plants to stimulate root development.

Plantlets in soil were introduced in an illuminated growth chamber and conditions were slowly adjusted to adapt or condition the plantlets to the drier and more illuminated conditions of the greenhouse. After adaptation/conditioning in the growth incubator, plants (R0 generation) were transplanted individually to large (5 gal) pots of soil and transferred to the greenhouse.

Genotypic Analysis

The genotype of several of the R0 plants was further analyzed by Southern blot to determine if the transformants were independent and had Bt DNA inserted in variable locations within the maize genome. This was achieved by: (i) cutting DNA isolated from the transformants with a restriction endonuclease (e.g. Kpn I) which cleaves to the 3' terminus of the Bt coding sequence and does not cleave the DNA sequence 5' to the Bt gene in the vector and (ii) carrying out a Southern blot probing the DNA with a radioactively labeled DNA probe specific to the Bt gene. The size and number of the resulting bands detected by autoradiography were indicative of the location of the nearest restriction endonuclease site located in the maize genome 5' to the inserted Bt DNA sequence. These varied in size for different independent insertion events. The results showed that, for most of the transformants analyzed, the Bt DNA inserted into different sites in the maize genome and most of the transformants were independent transformants (i.e. not clonaly related to each other).

Demonstration of expression of Bt endotoxin and PIN genes

Insect Bioassay (resistance to European corn borer)

The regenerated (R0) plants were grown to early whorl stage (18"–26" extended leaf height with 5–6 leaves) and infested with neonate European corn border larvae. A 'Davis' inoculator (BIO-SERV, Frenchtown, N.J.) was used to reproducibly introduce a fixed number (80–120) of newly hatched European corn borer larvae (dispersed with corn cob grits.) into the whorl of the plants. Following inoculation, the larvae were allowed to feed on the plants for 2 weeks before they were evaluated for leaf damage. This infestation provided a simulation of an infestation with first brood (first generation) European corn borer larvae.

As shown in Table 18, high levels of resistance to ECB were seen in several transformants containing the Bt gene. Since DNA, introduced into plants by a variety of methods, can insert into a wide variety of locations within the maize genome, the level of expression of any inserted gene is variable and partly dependant on the location of insertion into the genomes. The average level and pattern (developmental or temporal) of expression is also dependent on the composition of the inserted DNA. This also appears to be the case for the current example, since while several of the individual transformants showed high levels of resistance to insect feeding although a lower number containing the Bt gene did not. Depending on the composition of the introduced DNA it would usually be appropriate to evaluate a number of transformants to obtain transformants with the optimum level of expression of the introduced DNA.

Demonstration of transcription of Bt and protease inhibitor genes

The transgenic R0 plants were further analyzed to determine whether transcription (production of gene-specific RNA) of the introduced genes could be detected. Total RNA was isolated from leaf tissue excised from the transgenic maize plants and suitable negative controls and analysed by northern blotting procedures. The RNA was first separated according to size by electrophoresis into an agarose gel (under denaturing conditions), transferred and bound to a membrane support and then hybridized with gene specific, radio-labelled probes. The probes used were:

Bt gene: A fragment of DNA containing the first 1364 bp of the coding sequence of the synthetic Bt gene (approximately from the Nco I site at the 5' terminus of the Bt gene to the Bam HI site 1364 bp into the Bt gene).

Tom PIN gene: The Xba I-Bam HI fragment of pDPG344 containing the cDNA coding sequence of the tomato protease inhibitor I gene.

barR gene: The Bam HI - Kpn I fragment from pDPG165 comprising the coding sequence of the barR gene.

After hybridization and washing to remove non-specifically bound probes, the membranes were exposed to X-ray film and analyzed. The appearance of bands representing probe hybridizations to specific species of RNA demonstrated the transcription of the introduced genes in the transgenic maize plants. The presence of Bt RNA correlated well with the appearance of resistance to the ECB larvae. In this case since expression of the Tom PIN gene was also detected the contribution of this gene to the resistance could not be determined. Other transformants that are resistant and contain only the Bt gene, with no PIN gene present, indicate that the Bt gene can significantly increase the resistance of maize to ECB larvae (see Example 43 below).

Sexual competency of R0 transgenic plants containing insect resistance genes

The S23BI3602 and S23BI2702 R0 plants, containing the introduced insect resistance genes, were grown to sexual maturity and crossed to non-transgenic inbred maize lines (e.g. inbreds "CN" and "AW") either by fertilizing the non-transgenic inbred maize plants with pollen derived from transgenic maize or fertilizing the transgenic plants with pollen from non-transgenic inbreds. The techniques used to cross and self-pollinate transgenic maize plants were described in the CIP (filed Apr. 11, 1990) of U.S. patent application Ser. No. 07/467983 (filed Jan. 22, 1990). The yield of progeny was variable and depended on the inbred parent used, but sufficient seed was recovered to demonstrate that the transgenic plants were fertile.

Sexual transmission, segregation and expression of insect resistance genes in progeny The harvested seed (R1 generation) was harvested, planted in soil in 5 gal pots and grown in the greenhouse. When the plants had grown so they had at least one true leaf extended, a 2%(w/v) solution of a commercial formulation of bialaphos (BASTA®, Hoechst TX100) was painted on a small circle of leaf tissue and after one week the plants were evaluated for herbicide resistance. Resistance to the herbicide was identified by the lack of a browning reaction (necrosis) in the area treated with herbicide (tissue browning=sensitivity, no browning=resistance).

Following this assay, samples were taken to determine the genotype of the segregants (by PCR assay) and the plants were infested with ECB larvae to determine insect resistance phenotype. The results (Table 19) showed that the progeny inherited the Bt and PIN genes together with the resistance to bialaphos and ECB larvae. The low insect damage rating number (high insect resistance) correlated with the presence of the Bt. No significant resistance to ECB larvae above the no-Bt control was ever been detected in transgenic maize with only the BarR gene present. Furthermore, in a separate experiment when only the pDPG354 and pDPG165 expression cassettes were maintained in the transformed cells, R0 and R1 plants (transformant S25BJ18) the insect resistance phenotype was still inherited, suggesting that the Bt gene (without PIN gene) is capable of confering resistance to ECB larvae.

There was no independent assortment of the introduced genes, indicating that the Bt, PIN and bialaphos resistance genes in transformants S23BI36 or S23BI37 were closely linked. Resistance was inherited independent of the inbred used. Close linkage of the herbicide resistance and insect resistance will provide an advantage for the production of commercial maize seed containing the insect resistance gene, since the presence of the Bt gene in subsequent generations can be detected and followed by screening for herbicide resistance. This will allow for screening for the Bt gene to take place in locations and times when infestation with insects is impossible or difficult (e.g. in winter nurseries).

TABLE 17

PCR Analysis of transgenic maize cells (S23BI31 clones) containing Bt and/or Tom PIN genes.

| Clone | PIN PCR | Bt PCR | Clone | PIN PCR | Bt PCR |
|---|---|---|---|---|---|
| 01 | — | + | 25 | ND | ND |
| 02 | — | ND | 26 | — | ND |
| 03 | — | ND | 27 | ND | ND |
| 04 | — | ND | 28 | — | — |
| 05 | + | + | 29 | + | + |
| 06 | — | ND | 30 | + | + |
| 07 | + | + | 31 | + | + |
| 08 | — | + | 32 | + | + |
| 09 | SG | SG | 33 | + | + |
| 10 | + | — | 34 | — | — |
| 11 | + | + | 35 | + | — |
| 12 | + | + | 36 | + | + |
| 13 | + | + | 37 | + | + |
| 14 | + | + | 38 | + | + |
| 15 | SG | SG | 39 | — | + |
| 16 | + | — | 40 | — | + |
| 17 | SG | SG | 41 | — | + |
| 18 | — | ND | 42 | + | + |
| 19 | — | ND | 43 | + | + |
| 20 | — | ND | 44 | + | + |
| 21 | SG | SG | 45 | + | + |
| 22 | + | + | 46 | — | — |
| 23 | + | + | 47 | — | — |
| 24 | + | + | 48 | — | — |

Key:
+ = target DNA present
— = target DNA not present
ND = not determined
SG = tissue stopped growing.

TABLE 18

Expression of Bt gene in transgenic maize plants.

| RO plant | Bt RNA | Resistance Rating | PIN RNA | bar RNA |
|---|---|---|---|---|
| S23BI3015 | +++ | 1 | + | ++ |
| S23BI3016 | +++ | 1 | + | ++ |
| S23BI3119 | +++ | 1 | + | ++ |
| S23BI3128 | +++ | 1 | + | ++ |
| S23BI3203 | — | 5 | — | + |
| S23BI3202 | — | 8 | — | + |
| S23BI3204 | — | 8 | — | + |
| S23BI3704 | +++ | ND | + | ++ |
| S23BI3708 | +++ | 2 | ++ | +++ |
| S23BI3709 | +++ | 1 | ++ | +++ |
| S23BI3712 | +++ | 1 | ++ | +++ |
| S23BI3715 | +++ | 1 | ++ | +++ |
| S23BI3716 | +++ | 2 | ++ | + |
| S23BI3720 | + | 3 | ND | ND |
| No-Bt control | — | 5–9 | — | — |

Key:
— = no RNA detected resistant
+ = low level Bt RNA susceptible
++ = intermediate level of Bt RNA
+++ = higher level of Bt RNA
ND = not determined Resistance ratings:
1 = highly
9 = highly

TABLE 19

Inheritance and expression of insect resistance in progeny from Example 42.

| Transformant {R:S RATIO} | Plant Number | Bt PCR | PIN PCR | BAR resistance | ECB resistance |
|---|---|---|---|---|---|
| S23BI3602(CN) {4R:6S} | 02 | — | — | S | 6 |
| | 05 | — | — | S | 6 |
| | 07 | ND | ND | S | ND |
| | 08 | + | + | R | 1 |
| | 09 | — | — | S | 6 |
| | 10 | + | + | R | 1 |
| | 11 | ND | ND | S | 9 |
| | 13 | — | — | S | 3 |
| | 14 | + | + | R | 1 |
| | 15 | + | + | R | 1 |
| S23BI3604(AW) {6R:9S} | 01 | — | — | S | 5 |
| | 02 | + | + | R | 1 |
| | 03 | ND | ND | S | 9 |
| | 04 | — | — | S | 7 |
| | 05 | ND | ND | S | ND |
| | 06 | — | ND | S | 6 |
| | 07 | + | + | R | 1 |
| | 08 | + | + | R | 1 |
| | 09 | + | + | R | 1 |
| | 10 | — | — | S | 7 |
| | 11 | + | + | R | 1 |
| | 12 | ND | ND | S | 9 |
| | 13 | ND | ND | S | 9 |
| | 14 | ND | ND | S | ND |
| | 15 | + | + | R | 1 |
| S23BI3702(bk) {6R:5S} | 01 | ND | ND | S | 9 |
| | 02 | + | ND | R | 1 |
| | 03 | + | + | R | 1 |
| | 05 | + | + | R | 1 |
| | 06 | + | + | R | 1 |
| | 07 | + | + | R | 1 |
| | 08 | ND | ND | S | 6 |
| | 09 | ND | ND | S | 9 |
| | 10 | ND | ND | S | 9 |
| | 12 | + | ND | R | 1 |
| | 13 | — | — | S | 6 |
| | 15 | ND | ND | S | 9 |
| S25BJ1801(AW) {5R:2S} | 05 | + | ND | R | 1 |
| | 08 | + | ND | R | 1 |
| | 10 | + | ND | R | 1 |
| | 11 | ND | ND | S | 9 |
| | 13 | ND | ND | R | 3 |
| | 14 | — | ND | R | 1 |
| | 15 | ND | ND | S | 9 |

Key for Table 19:
+ = DNA present
— = DNA not present
S = susceptible to bialaphos
R = resistant to bialaphos
ND = Not determined ECB resistance:
1 = Highly resistant
9 = highly suceptible

EXAMPLE 43

Insect Resistant Transgenic Plants

Microprojectiles were coated with DNA as described in Example 10 except 14 ul of pDPG165 and 14 ul of pDPG337 DNA were used. The bombarded cells were transferred (on the filter) onto solid 409 medium and moistened with 0.5 ml of liquid 409 medium. Tissue was returned to liquid 401 plus coconut water one day after bombardment. Selection in liquid 409 plus 1 mg/L bialaphos (434 medium) began 8 days post-bombardment and the cells were then treated as described in Example 42.

Genotype analysis

The data obtained using the Bt PCR primers and techniques described in Example 42 above showed that 5 out of 7 clones tested contained the Bt gene.

Regeneration of transformants

Clones positive for Bt were subcultured on 425 medium for 2–5 months and depending on the clone either:
  (i) passaged on 409 solid medium (1 st passage about 2 months and second passage about 2 weeks) or passaged on solid 223 medium for about 19 days before:
  (ii) two passages on 189 solid medium (1st for about 14–19 days and second for about 10–14 days) followed by:
  (iii) three passages on 101 solid media and;
  (iv) one to two passages on 501 solid medium (about 2 weeks per passage) in Plant Con® containers.

Bioassay of R0 plants

Clones developing shoots and roots on 501 medium in Plant Con® containers were transferred to a soilless m 4. Biological peptides Genes controlling the production of large or small polypeptides active against insects when introduced into the insect pests, such as (i) lytic peptides (Westerhoff et al., 1989), (ii) peptide hormones (Kattaoka, H. et al., 1989; Keeley, L. L. and Hayes, T. K., 1987) and (iii) toxines and venoms (Zlotkin, E., 1985; Dee, A. et al., 1990). Such polypeptides could be synthesized in the plant as mono- or oligomers, as fusion proteins fused to carrier proteins, such as Bt, or delivered to the insects in the presence of other agents, e.g. lectins, that may stimulate uptake or activity. Biological peptides may include peptides designed by molecular modeling to interact with components in or on insects to affect growth, development, viability and/or behaviour.

5. Lipoxygenases

These naturally occuring plant enzymes have been shown to have antinutritional effects on insects and to reduce the nutritional quality of their diet. Plants with enhanced lipoxygenase activity may be resistant to insect feeding (S. S. Duffey and G. W. Felton, 1991).

6. Production of inadequate nutrients or removal of essential nutrients

Genes that code for enzymes that facilitate the production of compounds that reduce the nutritional quality of the host plant to insect pests. Examples include: (i) genes that alter the sterol composition of plants may have a negative effect on insect growth and/or development and hence provide the plant with insecticidal activity. Essential sterols could be converted to undesirable sterols or undesirable sterols could be produced directly; (ii) increasing levels or the characteristics of polyphenol oxidases and/or its substrate thereby increasing the production of toxic products or conversion of protein nutrients to undesirable by-products (Duffey, S. S. and Felton, G. W., 1991).

7. Qualitative or quantitative changes in plant secondary metabolites

DIMBOA: It has been demonstrated that some lines of maize show resistance to first brood European Corn borer larvae due to the production of DIMBOA (Klun, J. A. et al., 1967) in the plant. There are also suggestions that DIMBOA production could have an impact on rootworm damage. The introduction of DNA that changes quantity, timing or/and location of DIMBOA production may lead to improved resistance to several maize insect pests. Candidate genes for consideration would include those involved in the pathway for production of DIMBOA, e.g. genes at the bx locus (Dunn, G. M. et al., 1981)

Maysin: Since maysin has been implicated in the resistance of maize to earworm (Guildner, R. C., et al., 1991) the introduction of genes that can regulate the production of maysin may be beneficial to the production of insect resistant maize. Since the current invention allows for the transfer of genes from diverse sources into maize, the invention could also make possible the transfer of the capability to produce any other secondary metabolite from any biological source into maize provided the genes needed to control the production of the metabolite are available.

Dhurrin: genes involved in the production of dhurrin in sorghum (Branson, T. F., et al., 1969) which could be transferred to maize and facilitate resistance to corn rootworms.

8. Genes transferred from native grasses

There are a number of native grasses that are resistant to some of the insect pests of commercial inbred maize are susceptible to. Selected landraces of *Tripsacum dactyloides* have been reported to be resistant to corn rootworms (Branson, T. F., 1971). Genes coding for the resistance trait in this species could be isolated and transformed into maize to produce rootworm resistant maize.

9. Cuticle degradating enzymes

Genes that code for enzymes that affect the integrity of the insect cuticle such as chitinase, protease and lipase (M. S. Goettel et al., 1989; J. D. G. Jones et al., 1988) could be introduced into maize to produce insect resistant plants. Including with these genes would be genes that code for activities that affect insect molting such those affecting the production of ecdysteroid UDP-glucosyl transferase (D. R. O'Reilly and L. K. Miller, 1989).

10. Antibiotics

Genes that control the production of antibiotics that affect insect viability, growth or development, e.g. genes for the production of nikkomycin—a compound that inhibits chitin synthesis (U. Schluter and G. Serfert, 1989) and avermectin and abamectin (Campbell, W. C., Ed., 1989; Ikeda et al., 1987) and insecticides from fungi (P. F. Dowd and O. K. Miller, 1990).

11. Antibodies

Genes that can control the production of antibodies that can inhibit insects. Antibodies have been produced in transgenic plants (Hiatt, A. et al., 1989). The genes coding for the antibodies to insect targets could be cloned, engineered and transferred to maize using the current invention.

12. Pro-insecticides

Another approach that can use genes introduced into maize is the introduction of genes that code for enzymes that can covert a non-toxic insecticide (pro-insecticide) applied to the outside of the plant into an insecticide inside the plant. The benefits would be to: (i) reduce the levels of toxic insecticides applied to crops and (ii) make the insecticide very selective since it would only be converted to the insecticide inside the transgenic plants. Plants could further be engineered to degrade residual insecticide in plants parts destined for consumption by introducing genes coding for degradative enzymes that are expressed temporally or spacially to degrade the insecticide in selected tissues.

13. Others

There are numerous other genes that have the potential to facilitate resistance to insects if introduced and expressed in maize. These include: ribosome inactivating proteins (A. M. R. Gatehouse et al., 1990) genes controlling expression of juvenile hormones (Hammock et al., 1990), genes that regulate plant structures (e.g. thickness of leaves and stalks, presence of trichomes, size of root system), the production of chemicals that can deter insect pests, act as feeding deterrents or reduce the immunity of the insect pest to disease (D. W. Stanley-Samuelson et al., 1991).

In the above examples, depending on the source of the DNA, the DNA to be introduced and expressed in maize may need to be modified to obtain optimum expression (level, timing and location of expression) by changing the genetic elements that regulate expression (promoters, introns, etc.) and the coding sequence (to improve translation, RNA stability and/or gene product activity).

The main element required for expression of an introduced gene is the structural gene for the protein that mediates the resistance either directly as in the case of the insecticidal Bt protein, or indirectly such as in the case of an enzyme that might degrade nutrients essential for insect growth. In practices, most expression vectors will contain: (i) a promoter, located 5' to the coding sequence, to initiate transcription of the introduced gene; (ii) the DNA sequence of the gene coding for the insect resistance factor and (iii) a sequence located 3' to the coding sequence to stimulate termination of transcription. Additional sequences (enhancers, introns, leader sequences, transit or signal sequences and 3' elements (transcription terminators or poly-adenylation sites) may be used to increase expression or accummulation of the gene product.

Promoters

Promoters that could be used include promoters from:
(a) the maize Adh I (Walker et al., 1987), cab (T. Sullivan et al., 1989.) rbcs (Lebrun et al., 1987), PEPCase (R. L. Hudspeth and J. W. Grula. 1989) genes;
(b) genes that express in pollen (e.g., Hansen et al., 1989)
(c) genes isolated from tissue-specific libraries;
(d) any gene that is functional in maize;
(e) pathogens that replicate in plants, especially; monocotyledonous plants;
(f) synthetic promoters that utilize elements from various plant genes or gene from pathogens that replicate in plants;
(g) genes that are expressed in leaves, stalks, earshanks, collar sheaths or roots;
(h) genes that are expressed in leaves, stalks, earshanks, collar sheaths or roots but are not expressed in developing kernels.

In addition to promoters that produce adequate levels of the insect resistance gene product in the tissues eaten by the insect pest, it may sometimes be required to construct vectors that express the anti-sense mRNA of an insect resistance gene in the kernel, or other parts of the plant, in order to inhibit accumulation of the gene product in locations where it may be undesirable.

Enhancers

Transcription enhancers or duplications of enhancers could be used to increase expression. These enhancers are often found 5' to the start of transcription in a promoter that functions in eukaryotic cells, but can often be inserted in the forward or reverse orientation 5' or 3' to the coding sequence. Example of enhancers include elements from the CamV 35S promoter and octopine synthase gene (Ellis et al., 1987). and even promoters from non-plant enkayotes (e.g. yeast; J. MA et al., 1988 Nature 334:631–633).

Leader sequences

The DNA sequence between the transcription initiation site and the start of the coding sequence is termed the untranslated leader sequence. The leader sequence can influence gene expression and compilations of leader sequences have been made to predict optimum or sub-optimum sequences and generate "consensus" and preferred leader sequences (C. P. Joshi, 1987). The sequences may increase or maintain mRNA stability and prevent inappropriate initiation of translation. Sequences that are derived from genes that are highly expressed in plants, and in maize in particular, would be preferred. The leader sequence from the soybean rbcs (RuBISCO) gene was used in pDPG337.

Transit or signal peptides

Sequences that are joined to the coding sequence of the resistance gene, which are removed post-translationally from the initial translation product and which facilitate the transport of the protein into or through intracellular or extracellular membranes are termed transit (usually into vacuoles, vesicles, plastids and other intracellular organelles) and signal sequences (usually to the outside of the cellular membrane). By facilitating the transport of the protein into compartments inside and outside the cell these sequences may increase the accummulation of gene product protecting them from proteaolytic degradation. These sequences also allow for additional mRNA sequences from highly expressed genes to be attached to the coding sequence of the insect resistance genes. Since mRNA being translated by ribosomes is more stable than naked mRNA, the presence of translatable mRNA in front of the gene may increase the overall stability of the mRNA transcript from the insect resistance gene and thereby increase synthesis of the gene product. Since transit and signal sequences are usually post-translationally removed from the initial translation product, the use of these sequences allows for the addition of extra translated sequences that may not appear on the final polypeptide.

In two examples (see section entitled "Examples of other expression vectors." above) listed above, the transit peptide sequence for the maize RUBISCO gene was fused to the Bt gene and transformed into regenerable maize cells.

3' Elements

The most commonly used 3' elements include a sequence of DNA that acts as a signal to terminal transcription and allow for the poly-adenylation of the 3' end of the mRNA coding for the gene product. These sequences can be obtained from a number of genes that are transcribed in maize and often can be isolated from genes that expressed in other plants or pathogens that infect plants. The most commonly used 3' elements are the 3' elements from: (i) the nopaline synthase gene from *Agrobacterium tumefasciens* (M. Bevan et al., 1983. Nucleic Acids Res. 11:369–385), (ii) the terminator for the T7 transcript from the octopine synthase gene of *Agrobacterium tumefasciens* (and the 3' end of the protease inhibitor I or II genes from potato or tomato.

Conclusions

The examples described above show that the invention can be used to introduce insect resistance genes into maize and that functional genes can be successfully inherited. Thus the invention shows great utility in producing transgenic maize plants of significant commercial value and benefit, allowing for improved resistance to insect pests, improved productivity to the farmer and improved quality of the environment by reducing the dependency on chemical insecticides.

While the invention is susceptible to various modifications and alternative forms, specific embodiments thereof have been shown by way of example in the drawings and herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

REFERENCES

The references listed below are incorporated herein by reference to the extent that they supplement, explain, provide a background for, or teach methodology, techniques, and/or compositions employed herein.

Abe, K. et al., (1987) J.Biol.Chem. 262: 16793–16797

Abel, P. P., Nelson, R. S., De, B., Hoffman, N., Rogers, S. G., Fraley, R. T. and Beachy, R. N. 1986. Science 232:738–743.

Adams, W. R., Adams, T. R., Wilston, H. M., Krueger, R. W., and Kausch, A. P., Silicone Capsules for Controlled Auxin Release, in preparation.

Adang, M. J. et al. (1985) Gene 289–300.

An, G. et al., (1989) Plant Cell 1: 115–122.

Armaleo et al. (1990) Current Genetics 17:97–103.

Armstrong C. L., Green C. E. (1985). Planta 164:207–214.

Armstrong, C. L., Green, C. E., and Phillips, R. L. 1991. Maize Genetics Coop Newsletter 65:92–93.

Barkai-Golan, R., Mirelman, D., Sharon, N. (1978) Arch. Microbiol 116:119–124.

Barton, K. A., Whiteley, H. R. & Yang, K. S. (1987) Plant Physiol. 85, 1103–1109.

Beck, E., Ludwig, G., Auerswald, E. A., Reiss, B., Schaller, H. 1982. Gene 19:327–336.

Belanger and Kriz Genetics 129:863–872. 1991

Benfey, P. N., Ren, L. & Chua, N. H. (1989) EMBO Journal, 8(8):2195–2202.

Berg, D. E., Egner, C., Hirschel, B. J., Howard, J., Jorgensen, R., and Tisty, T. D. (1980) Cold Spring Harbor Symposium 45:448–465.

Bernal-Lugo, I. and Leopold, A. C. 1992. Plant Physiol. 98:1207–1210.

Berry-Lowe, S. L. et al., 1982. J.Mol.Appl.Genet 1:483–498

Bevan, M., 1984. Nucleic Acid Research 12: 8711–8721.

Bevan, M., Barnes, W. M., Chilton, M. D., 1983. Nucleic Acid Research. 11:369–385.

Blackman, S. A., Obendorf, R. L., Leopold, A. C. 1992. Plant Physiol. 100:225–230.

Bol, J. F., Linthorst, H. J. M., Cornelissen, B. J. C. 1990. Annu. Rev. Phytopath. 28:113–138.

Bottino P. J., (1975). Botany 15:1–16.

Bouchez D., Tokuhisa J. G., Llewellyn D. J., Dennis E. S. and Ellis J. G., (1989) EMBO Journal 8(13):4197–4204.

Bowler, C., Van Montagu, M., and Inze, D. 1992. Ann Rev. Plant Physiol. 43:83–116.

Branson, T. F. et al., (1969) J. Econ.Entom. 62: 1375–1378.

Branson, T. F. (1971) Annals of Am. Soc of Entomol. 64:861–863.

Branson, T. F. and Guss, P. L. 1972. Proceedings North Central Branch Entomological Soceity of America 27:91–95.

Broakaert, W. F., Parijs, J., Leyns, F., Joos, H., Peumans, W. J. (1989) Science 245:1100–1102.

Buchanan-Wollaston, V., Snape, A., and Cannon, F. 1992. Plant Cell Reports 11:627–631.

Callis, J., Fromm, M., Walbot, V. (1987), Genes and Develop. 1:1183–1200.

W. C. Campbell, ed. 1989. Avermectin and Abamectin.

Cao et al., Plant Cell Rep (1992) 11:586–591.

Carlsson J., Drevin H., Axen R. (1978). Biochem J. 173:723.

Cavener & Ray (1991). Nucl Acids Res 19:3185–3192.

Chauboute, H. E., Chambet, N., Philipps, G., Ehung, M. and Grigot, C. 1987. Plant Mol. Biol. 8: 179–191.

Chaubet, N., Clement, B., Philipps, G. and Gigot, C. 1991. Plant Molecular Biology 17: 935–940.

Chandler, V. L., Radicella, J. P., Robbins, P. P., Chen, J., Turks, D. (1989), The Plant Cell 1:1175–1183

Chomet P. S., Wessler S., Dellaporta S. L. (1978). EMBO J 6:295–302.

Chrispiels, M. A. et al., (1991) The Plant Cell 3:1–9

Chu C. C., Wang C. C., Sun C. S., Hsu C., Yin K. C., Chu C. Y., Bi F. Y. (1975). Scientia Sinica 18:659–668.

Clark, R. (1982). J. of Plant Nutrition 5:1039.

Coe, E. H., Neuffer, M. G., and Hoisington, D. A. (1988), in Corn and Corn Improvement, Sprague, G. F. and Dudley, J. W., eds., pp. 81–258

Comai, L., U.S. Pat. No. 4,535,060; and ATCC deposit 39256.

Comai L., Gacciotti D., Hiatt W. R., Thompson G., Rose R. E., Stalker D. (1985). Nature 317:741–744

Comai, L., Sen, L. C., Stalker, D. M. 1983. Science 221:370–371.

Conger, B. V., Novak, F. J., Afza, R., Erdelsky, K. (1987), Plant Cell Rep 6:345–347

Conkling, M. A., Cheng, C. L., Yamamoto, Y. T., Goodman, H. M. (1990), Plant Physiol. 93:1203–1211.

Coxson, D. S., McIntyre, D. D., and Vogel, H. J. 1992. Biotropica 24: 121–133.

Cristou P., McCabe D. E., Swain W. F. (1988). Plant Physiol 87:671–674.

Cuozzo, M., O'Connell, K. M., Kaniewski, W., Fang, R. X., Chua, N. and Turner, N. 1988. Bio/Technology 6:549–553.

Cutler, A. J., Saleem, M., Kendell, E., Gusta, L. V., Georges, F., Fletcher, G. L. (1989), *J Plant Physiol* 135:351–354.

Czapla and Lang (1990), J. Econ. Entomol. 83:2480–2485.

Davies, T. G. E., Thomas, H., Thomas, B., Rogers, L. J. 1990. Plant Physiol. 93:588–595.

De Block, M., Botterman J., Vandiwiele M., Dockx J., Thoen C., Gossele V, Movva N. R., Thompson C., Van Montagu M., Leemans J. (1987). EMBO J. 6:2513–2518; see also PCT Publication number WO 87/05629, published Sep. 24, 1987.

De Block, H., Botterman J., Vandiwiele M., Dockx J., Thoen C., Gossele V, Movva N. R., Thompson C., Van Montagu M., Leemans J. (1989). Plant Physiol 91:694–701.

DE 3 642 B29 A.

Dee. A., R. M. Belagaje, K. Ward, E. Chio and Mei-Huei T. Lai (1990) BioTechnology 8:339–342.

Dekeyser R., Claes B., Marichal M., Van Montagu M., Caplan A. (1989). Plant Physiol 90:217–223.

Dekeyser et al. (1990), Plant Cell, 2:591–602.

Delannay X., LaVallee B. J., Proksch R. K., Fuchs R. L., Sims S. R., Greenplate J. R., Marrone P. G., Dodson R. B., Augustine J. J., Layton J. G., Fischhoff D. A. (1989). Bio/Technol 7:1265–1269.

Dellaporta, S., Greenblatt, I., Kermicle, J., Hicks, J. B., Wessler, S. (1988) in Chromosome Structure and Function: Impact of New Concepts, 18th Stadler Genetics Symposium, J. P. Gustafson and R. Appels, eds (New York: Plenum Press), pp. 263–282.

Dellaporta, S. L., Greenblatt, I. M., Kermicle, J., Hicks, J. B., and Wessler, S. (1988), Stadler Symposium 11:263–282.

Depicker, A. G., Jacobs, A. M., and Van Montagu, M. C. 1988. Plant Cell Reports 7:63–66.

DeWet, J. R., Wood, K. V., DeLuca, N., Helinski, D. R., Subramani, S. 1987. Mol. Cell Biol. 7:725–737.

Dhaese, P. et al., 1983, EMBO J. 2, 419–426.

D'Halluin, K., Bonne, E., Bossut, M. De Beuckeleer, M., and Leemans, J. The Plant Cell 4:1495–1505.

Doring, H. P. and Starlinger (1986), Ann. Rev. Genet. 20:175–200.

Dowd, P. F. and O. K. Miller (1990) Entomol. exp. appl. 57: 23–28.

Duffey, S. S. and G. W. Felton, 1991. "Bioregulators," P. A. Hedin, Ed., ACS Symp.Series #449).

Dunn, G. M. et al., (1981) Can.J. Plant Sci., 61:583–593).

Dure, L., Crouch, N., Harada, J., Ho, T. -H. D., Mundy, J., Quatrano, R., Thomas, T., and Sung, Z. R. 1989. Plant Molecular Biology 12:475–486.

Ebert, P. R., Ha, S. B., An. C. (1987), PNAS 84:5745–5749.

Eichholtz, D. A., Rogers, S. G., Horsch, R. B., Klee, H. J., Hayford, N., Hoffman, N. L., Bradford, S. B., Fink, C., Flick, J., O'Connell, K. M., Frayley, R. T. 1987. Somatic Cell Mol. Genet. 13: 67–76.

Ellis J. G., Llewellyn D. J., Walker J. C., Dennis E. S., and Peacock W. J., (1987) EMBO Journal 6(11):3203–3208.

Erdmann, N., Fulda, S., and Hagemann, M. 1992. J. Gen. Microbiology 138:363–368.

European Patent Application 154,204 (Sept. 11, 1985).

European Patent Application publication number 0218571 A2, published Apr. 15, 1987.

Farrell & Beachy, (1990), Plant Mol. Biol. 15:821.

Federoff, N. (1989), "Maize Transposable Eleinents", in Mobile DNA. Wowe, N. M. and Berg, D. E., eds., Amer. Soc. Microbiol., Wash., D.C., pp. 377–411.

Feinberg A. P., Vogelstein B. (1983). Anal Biochem 132:6–13.

Finkle B. J., Ulrich J. M., Rains W., Savarek S. J. (1985). Plant Sci 42:133–140.

Fischhoff D. A., Bowdish K. S., Perlak F. J., Marrone P. G., McCormick S. M., Niedermeyer J. G., Dean D. A., Kusano-Kretzmer K., Mayer E. M., Rochester D. E., Rogers S. C., Fraley R. T. Bio/Technol 5:807–813.

Fitzpatrick, T. 1993. Gen. Engineering News 22 (March 7): 7.

Fluhr, R., Moses, P., MOrelli, G., Coruzzi, C., Chua, N. -H. 1986. EMBO J. 5: 2063–2071.

Fransz, P. F., de Ruijter, N. C. A., Schel, J. H. N. (1989), Plant Cell Rep 8:67–70

Frisch et al. Mol. Gen. Genet. 228:287–293, 1991

Fromm N. E., Taylor L. P., Walbot V. (1986). Nature 312:791–793.

Fromm, H., Katagiri, F., Chua, N. H. (1989), The Plant Cell 1:977–984.

Gallie, D. R., Lucas, W. J., Walbot, V. (1989), The Plant Cell 1:301–311.

Gatehouse, A. M., Dewey, F. M., Dove, J., Fenton, K. A., Dusztai, A. (1984), J Sci Food Agric 35:373–380.

Gatehouse, A. M. R., Barbieri, L., Stirpe, F. and Croy, R. R. D. 1990. Entomol. Exp. Appl. 54:43–51.

Gelvin, S. B., Schilperoort, R. A., Varma, D. P. S., eds. Plant Molecular Biology Manual (1990).

Goettel, M. S., R. J. St. Leger, N. W. RIZZO, R. C. Staples, and D. W. Roberts (1989) J.Gen. Microbiol. 135:2233–2239.

Goff, S., Klein, T., Ruth, B., Fromm, M., Cone, K., Radicella, J., Chandler, V. 1990. EMBO J.: 2517–2522.

Graham, J. S., Hall, G., Pearce, G., Ryan, C. A. 1986 Mol. Cell. Biol. 2:1044–1051.

Graham, J. S. et al., 1985, J Biol Chem 260: 6561–6564

Guerrero, F. D., Jones, J. T., Mullet, J. E. 1990. Plant Molecular Biology 15: 11–26.

Guildner, R. C. et al., 1991, in "Naturally Occuring Pest Bioregulators." ed. P. A. Hedin. ACS Sympos. Series #449)

Gupta, A. S., Heinen, J. L., Holaday, A. S., Burke, J. J., and Allen, R. D. 1993. Proc. Natl. Acad. Sci USA 90:1629–1633.

Goring, D. R., Thomson, L., Rothstein, S. J. 1991. Proc. Natl. Acad Sci. USA 88:1770–1774.

Guilley, H. et al., 1982 Cell 30:763–773.

Hammock, B. D., Bonning, B. C., Possee, R. D., Hanzlik, T. N., and Maeda, S. (1990), Nature 344:458–461.

Hansen, D. D. et al 1989. Plant Cell 1:173–179

Haughn G. W., Smith J., Mazur B., Somerville, C. (1988). Mol Gen Genet 211:266–271.

Hauptmann R. M., Vasil V., Ozias-Aikins P., Tabaeizadeh Z., Rogers S. C., Fraley R. T., Horsch R. B., Vasil I. K. (1988). Plant Physiol 86:602–606.

Heidecker & Messing (1986). Ann Rev Plant Physiol, 37:439–466.

Hemenway, C., Fang, R., Kaniewski, W. K., Chua, N. and Turner, N. E. 1988. The EMBO J. 7:1273–1280.

Hiatt. A., R. Caffetterkey and K. Bowdish (1989) Nature 342:76–78.

Hilder, V. A., Gatehouse, A. M. R., Sheerman, S. E., Barker, R. F., Boulter, D. (1987) Nature 330:160–163.

Hinchee, M. A. W., Connor-Ward, D. V., Newell, C. A., McDonell, R. E., Sato, S. J., Casser, C. S., Fischhoft, D. A., Re, C. B., Fraley, R. T., Horsch, R. B. (1988) Bio/technol 6:915–922.

Höfte, H. and Whiteley, H. R., 1989. Microbiological Reviews. 53: 242–255.

Hudspeth, R. L. and J. W. Grula. 1989. Plant Mol. Biol. 12:579–589.

Ikuta, N., Souza, M. B. N., Valencia, F. F., Castro, M. E. B., Schenberg, A. C. G., Pizzirani-Kleiner, A., Astolfi-Filho, S. (1990), Bio/technol 8:241–242.

Ikeda, H., Kotaki, H., Omura, S. (1987), J Bacteriol 169:5615–5621.

Ingelbrecht, I. L. W., Herman, L. M. F., Dekeyser, R. A., Van Montagu, M. C., Depicker, A. G. (1989), The Plant Cell 1:671–680.

IPRF European Patent Application No. 90033A.

Iturraga, G et al. (1989), Plant Cell 1:8447.

Jefferson R. A. (1987). P1 Mol Biol Repr 5:387–405.

Jefferson, R. A., Kavanagh, T. A., and Bevan, M. W. 1987. EMBO J. 6: 3901–3907.

Jones, J. D. G., C. Dean, D. Gidoni, D. Gilbert, D. Bond-Nutter, R. Lee, J. Bedbrook, and P Dunsmuir. (1988) Mol. Gen.Genet. 212: 536–542.

Johnson, R., Norvdez, J., An, G, and Ryan, C. (1989), Proc. Natl. Acad. Sci. USA 86:9871–9875.

Joshi, C. P. (1987) Nucleic Acids Res., 15:6643–6653.

Kaasen, I., Falkenberg, P., Styrvold, O. B., Strom, A. R. 1992. J. Bacteriology 174:889–898.

Kaeppler et al. (1990) Plant Cell Reports 9: 415–418.

Karsten, U., West, J. A. and Zuccarello, G. 1992. Botanica Marina 35:11–19.

Kattaoka, H., R. G. Troetschler, J. P. Li, S. J. Kramer, R. L. Carney and D. A. Schooley. (1989) PNAS 86:2976–2980.

Katz et al. (1983) J. Gen. Microbiol. 129:2703–2714.

Kay, R. et al. (1987) Science 236, 1299–1302

Keeley, L. L. and T. K. Hayes (1987). Insect Biochem 17:639–651.

Keller et al. (1989), EMBO J., 8(5):1309–1314.

Kirihara, J. A., Petri, J. B., and Messing, J. 1988. Gene 71:359–370,

Kirihara, J. A., Hunsperger, J. P., Mahoney, W. C., Messing, J. 1988. Mol. Gen. Genet. 211: 477–484.

Klein, T. M., Gradziel, T., Fromm, M. E., Sanford, J. C. 1988. Bio/Technology 6:559–563.

Klein T. M., Kornstein L., Sanford J. C., Fromm M. E. (1987). Nature 327:70–73.

Klein T. M., Kornstein L., Sanford J. C., Fromm M. E. (1989). Plant Physiol 91:440–444.

Klun, J. A. et al., (1967) J. Econ. Entom. 60:1529–1533)

Koster, K. L. and Leopold, A. C. 1988. Plant Physiol. 88:829–832.

Kozak M. (1984). Nucl Acids Res 12:857–872.

Krzyzek, R., and Laursen, C. PCT Publication WO 92/12250.

Krzyzek et al. (1990), U.S. patent application Ser. No. 07/635,279, filed Dec. 28, 1990.

Laemmli, U. K. 1970. Nature 227:280.

Laufs, J., Wirtz, U., Kammann, M., Matzeit, V., Schaefer, S., Schell, J., Czernilofsky, A. P., Baker, B., and Gronenborn, B. 1990. Proc. Natl. Acad. Sci: 7752–7756.

Laursen, C. M., Krzyzek, R. A., Flick, E. E., Anderson, P. C., Spencer, T. M. 1993. Plant Molecular Biology. Submitted.

Lawton, M. A., Tierney, M. A., Nakamura, I., Anderson, E., Komeda, Y., Dube, P., Hoffman, N., Fraley, R. T., Beachy, R. N. (1987), Plant Mol. Biol. 9:315–324.

Lebrun, M., Waksman, G., and Freyssinet, G. 1987. Nucl. Acid. Res. 15:4360

Lee et al. (1991), PNAS, 88:6389–6393.

Lee and Saier, 1983. J. of Bacteriol. 153–685.

Levings, C. S., III. 1990. Science 250: 942–947.

Lindsey and Jones (1987a), Planta, 172:346–355.

Lindsey and Jones (1987b), Plant Mol. Biol., 10:43–52.

Lindsey and Jones (1990), Physiol. Plant, 79:168–172.

Lorz H., Baker B., Schell J. (1985). Mol Gen Genet 199:178–182.

Loomis, S. H., Carpenter, J. F., Anchordoguy, T. J., Crowe, J. H., and Branchini, B. R. 1989. J. Expt. Zoology 252:9–15.

Lyznik L. A., Ryan R. D., Ritchie S. W., Hodges T. K. (1989). Plant Mol Biol 13:151–16.

MA, J. et al., 1988 Nature 334:631–633).

Maniatis, T., E. F. Fritsch and J. Sambrook (1982) Molecular Cloning. Cold Spring Harbor Laboratory. First Ed.

Mariani, C., De Beuckeleer, M., Truettner, J., Leemans, J. and Goldberg, R. B. 1990. Nature 347:737–741.

McCabe D. E., Swain W. F., Martinell B. J., Cristou P. (1988). Bio/Technol 6:923–926.

McDaniel C. N., Poethig R. S. (1988). Planta 175:13–22.

Mundy, J. and J. C. Rogers (1986) Planta 169:51–63

Mundy, J. and Chua, N. -H. 1988. The EMBO J. 7: 2279–2286.

Murdock et al., (1990) Phytochemistry 29:85–89.

Murakami T., Anzai H., Imai S., Satoh A., Nagaoka K., Thompson C. J. (1986). Mol Gen Genet 205:42–50.

Murashige T., Skoog F. (1962). Physiol Plant 15:473–497.

Napoli, C., Lenieux, C., Jorgense, R. 1990. Plant Cell 2:279–289.

Nelson R. S., McCormick S. M., Delannay X., Dube P., Layton J., Anderson E. J., Kaniewska M., Proksch R. K., Horsch R. B., Rogers S. C., Fraley R. T. Beachy R. N. (1988). Bio/Technol 6:403–409.

Nester, E. W. et al., (1984). Ann. Rev. Plant Physiol 35:387–413.

Odell, J. T., Nagy, F., Chua, N. H. (1985) Nature 313:810–812.

Ogawa, Y. et al (1973). Sci. Rep., Meija Seika 13:42–48.

Omirulleh, S, Abraham, M., Golovkin, M., Stefanov, I., Karabaev, M. K., Mustardy, L., Morocz, S., Dudits, D. Plant Molecular Biology 21:415–428.

O'Reilly, D. R. and L. K. Miller (1989) Science 245: 1110–1112.

Ow, D. W., Wood, K. V., DeLuca, M., dewet, J. R., Helinski, D. R., Howell, S. H. (1986) Science 234:856–859.

PCT No. WO 87/-00141.

Pearce, G., Strydom, D., Johnson, S., Ryan, C. A. 1991. Science 253: 895–898.

Perlak F. J., Fuchs R. L., Dean D. A., McPherson S. L., and Fischhoff D. A., (1991) Proc. Natl. Acad. Sci. USA 88:3324–3328.

Pfahler P. L. (1967). Can J. Bot 45:836–845.

Phi-Van, L., Kries, J. P., Ostertag, W., Stratling, W. H. (1990), Mol Cell Biol 10:2302–2307.

Piatkowski, D., Schneider, K., Salamini, F. and Bartels, D. 1990. Plant Physiol. 94:1682–1688.

Potrykus, I., Saul, M. W., Petruska, J., Paszkowski, J., Shillito, R. D. (1985), Mol Gen Genet 199:183–188

Potrykus I. (1989) Trends Biotechnol 7:269–273.

Prasher, et al. (1985) Biochem. Biophys. Res. Commun., 126(3):1259–1268.

Prioli L. M., Sondahl M. R. (1989). Bio/Technol 7:589–594.

Puite et al. (1985) Plant Cell Rep. 4:274–276.

Raikhol, N. V. and T. A. Wilkins, 1987, PNAS 84:6745–6749.

Reed, R. H., Richardson, D. L., Warr, S. R. C., Stewart, W. D. P. 1984. J. Gen. Microbiology 130:1–4.

Rhodes C. A., Pierce D. A., Mettler I. J., Mascarenhas D., Detmer J. J. (1988). Science 240:204–207.

Richaud, R., Richaud, C., Rafet, P. and Patte, J. C. 1986. J. Bacteriol. 166: 297–300.

Ryan, C. A. (1981) Biochemistry of Plants 6: ch. 6, Acad.Press

Ryan, C. A. (1989) BioEssays 10:20–24.

Sambrook, J., Fritsch, E. F., and Maniatus, T. (1989), Molecular Cloning, A Laboratory Manual 2nd ed.

Schluter, U. and Seifert, G. 1989. J. Inver. Pathol. 53:387–391.

Schmidt, R. J., Ketudat, M., Ankerman, M. J. and Hoschek, G. 1992. Plant Cell 4: 689–700.

Shagan, T., Bar-Zvi, D. 1993. Plant Physiol. 101:1397–1398.

Shah D. M., Horsch R. B., Klee H. J., Kishore G. M., Winter J. A., Tumer N. E., Hironaka C. M., Sanders P. R., Gasser C. S., Aykent S., Siegel N. R., Rogers S. G., Fraley R. T. (1986). Science 233:478–481.

Shapiro, J. A. (1983), Mobile Genetic Elements, Academic Press, N.Y.

Shillito R. D., Carswell G. K., Johnson C. M., DiMaio J. J., Harms C. T. (1989). Bio/Technol 7:581–587.

Shimamoto K., Terada R., Izawa T., Fujimoto H. (1989). Nature 338:274–276.

Shure M., Wesler S., Federoff, N. (1983). Cell 35:225–233.

Skriver, K. and Mundy, J. 1990. Plant Cell 2:503–512.

Smith, J. J., Raikhel, N. V. 1989. Plant Mol. Biology 13: 601–603.

Smith, C. J. S., Watson, C. F., Bird, C. R., Ray, J., Schuch, W. and Grierson, D. 1990. Mol. Gen. Genet. 224:447–481.

Southern E. M. (1975). J Mol Biol 98:503–517.

Spencer, T. M., Gordon-Kamm, W., Daines, R., Start, W., Lemaux, P. 1990. Theor. Appl. Genet. 79: 625–631.

Spencer, T. M., O'Brien, J. V., Start, W. G., Adams, T. R., Gordon-Kamm, W. J. and Lemaux, P. G. 1992. Plant Molecular Biology 18:201–210.

Spencer, T. M., Laursen, C. M., Krzyzek, R. A., Anderson, P. C. and Flick, C. E. 1993. Proceedings of the NATO Advanced Study Institute on Plant Molecular Biology. In press.

Stalker, D. M., McBride, K. E., and Malyj, L. Science 242: 419–422, 1988.

Stalker, D. M., Malyj, L. D., McBride, K. E. (1988), J Biol Chem 263:6310–6314.

Stanley-Samuelson. D. W., E. Jensen, K. W. Nickerson, K. Tiebel, C. L. Ogg and R. W. Howard (1991) PNAS 88: 1064–1068.

Stief, A., Winter, D., Stratling, W. H., and Sippel, A. E. (1989), Nature 341:343.

Stiefel et al. (1990), The Plant Cell, 2:785–793.

Stougaard, J. 1993. The Plant Journal 3:755–761.

Sullivan, T. et al., 1989. Mol. Gen. Genet 215:431–440)

Sutcliffe, J. G. (1978), Proc Natl Acad Sci USA 75:3737–3741.

Szoka, U.S. Pat. No. 4,394,448.

Tarczynski, M. C., Jensen, R. G., and Bohnert, H. J. (1992), Proc. Natl. Acad. Sci. USA, 89: 2600

Tarczynski, M. C., Jensen, R. G., and Bohnert, H. J. 1993. Science 259:508–510.

Thillet, J., Absil, J., Stone, S. R., Pictet, R. (1988), J Biol Chem 263:12500–12508.

Thompson C. K., Movva N. R., Tizard R., Crameri R., Davies J. E., Lauwereys M., Botterman J. (1987). EMBO J 6:2519–2623.

Timmermans, M. C. P., Maliga, P., Maliga, P., Vieiera, J. and Messing, J. 1990. J. Biotechnol. 14: 333–344.

Tomes D. (1990). Annual Meting Proceedings, 26th Annual Corn Breeders School, University of Illinois, February 26–27, pp. 7–9.

Topfer et al. (1989), Plant Cell, 1:133–139.

Topfer et al. (1990), Physiol. Plant, 79:158–162.

Twell D., Klein T. M., Fromm M. E., McCormick S. (1989). Plant Physiol 91:1270–1274.

Ueda, T. and Messing, J. 1991. Theor. Appl. Genet. 82: 93–100.

Ugaki et al., (1991). Nucl Acid Res, 19:371–377.

U.S. Pat. No. 4,535,060.

Vaeck M., Reynaerts A., Hofte H., Jansens S., De Beuckeleer M., Dean C., Zabeau M., Van Montagu M., Leemans J. (1987). Nature 328:33–37.

Vain, P., Yean, H., and Flament, P. 1989. Plant Cell, Tissue and Organ Culture 18: 143–151.

van der Krol, A. R., Mur, L. A., Beld, M., Mol, J. N. M. 1990. Plant Cell 2:291–299.

van Rensburg, L., Kruger, G. H. J., and Kruger, H. 1993. J. Plant Physiol. 141:188–194.

Vasil, V., Clancy, M., Ferl, R. J., Vasil, I. K., Hannah, L. C. (1989), Plant Physiol. 91:1575–1579.

Vernon, D. M. and Bohnert, H. J. 1992. The EMBO J.11:2077–2085.

Waldron, C., Murphy, E. B., Roberts, J. L., Gustatson, G. D., Armour, S. L., and Malcolm, S. K. Plant Molecular Biology 5: 103–108, 1985.

Walker, J. C., Howard, E. A., Dennis, E. S., Peacock, W. J. (1987), PNAS 84:6624–6628.

Walters, D. A., Vetsch, C. S., Potts, D. E., and Lundquist, R. C. Plant Mol Biol. 18:189–200, 1992.

Wang, Y., Klein, T., Fromm, M., Cao, J., Sanford, J., Wu, R. 1988. Plant Molecular Biology 11:433–439.

Wang, Y., Zhang, W., Cao, J., McEhoy, D. and Ray Wu. 1992. Molecular and Cellular Biology 12: 3399–3406.

Watrud, L. S., Perlak, F. J., Tran, M. -T., Kusano, K., Mayer, E. J., Miller-Widemann, M. A., Obukowicz, M. G., Nelson, D. R., Kreitinger, J. P., and Kaufman, R. J. (1985), in *Engineered Organisms and the Environment*, H. O. Halvorson et al., eds., Am. Soc. Microbiol., Washington, D.C.

Westerhoff, H. V., D. Juretic, R. W. hendler and M. Zasloff. (1989) PNAS 86: 6597–6601.

White, J., Chang, S. P., Bibb, M. J., Bibb, M. J. (1990), Nucl Acids Res, 18:1062.

Withers L. A., King P. J. (1979). Plant Physiol 64:675–678.

Wolter, F., Schmidt, R., and Heinz, E. 1992. The EMBO J. 4685–4692.

Wong, Y. C. et al. (1988). Plant Mol Biol 11:433–439.

Wyn Jones, R. G., and Storey, R. 1981. *Physiology and Biochemistry of Drought Resistance in Plants:* 171–204.

Xiang, C. and Guerra, D. J. 1993. Plant Physiol. 102:287–293.

Yamaguchi-Shinozaki, K., Koizumi, M., Urao, S., Shinozaki, K. 1992. Plant Cell Physiol. 33:217–224.

Yang, N. S., Russell, D. (1990), PNAS 87:4144–4148.

Yang H., Zhang M. H., Davey M. R., Mulligan B. J., Cocking E. C. (1988). Plant Cell Rep 7:421–425.

Yang, L. Y., Gross, P. R., Chen, C. H., Lissis, M. 1992. Plant Molecular Biology 18: 1185–1187.

Yugari et al J. Biol. Chem 240:4710–4716, 1965.

Zhang M. H., Yang H., Rech E. L., Golds T. J., David A. S., Mulligan B. J., Cocking E. C., Davey E. R. (1988). Plant Cell Rep 7:379–384.

Zlotkin, E. 1985. Comprehensive Insect Physiol. Biochem. Parmacol. vol 10, chapter 15:499–541

Zukowsky et al. (1983), Proc. Natl. Acad. Sci. USA 80:1101–1105.

What is claimed is:

1. A fertile transgenic *Zea mays* plant comprising isolated DNA comprising a tissue-specific promoter operably linked to a first non-plant DNA sequence encoding a dihydrodipicolinic acid synthase (DHDPS) which DHDPS is substantially resistant to feedback inhibition by endogenously produced free L-lysine and wherein said DNA further comprises a second sequence attached to the 5' terminus of the DHDPS encoding sequence which encodes a plant DHDPS chloroplast transit peptide (CTP) which localizes the DHDPS in the chloroplasts of the cells of said plant, wherein said DNA is expressed so that the transgenic *Zea mays* plant exhibits an increased level of lysine in its seed over a plant which does not comprise said DNA, and wherein said DNA is heritable.

2. The transgenic *Zea mays* plant of claim 1 wherein said first sequence comprises an *E. coli* dap A gene.

3. The transgenic Zea mays plant of claim 1 wherein the tissue-specific promoter comprises a maize endosperm-specific promoter or a maize embryo-specific promoter.

4. The transgenic Zea mays plant of claim 1 which is an inbred plant.

5. The transgenic Zea mays plant of claim 1 which is a hybrid plant.

6. The transgenic Zea mays plant of claim 1 wherein said isolated DNA further comprises and expresses a selectable marker gene or a screenable marker gene.

7. The transgenic Zea mays plant of claim 6 wherein the selectable marker gene confers resistance or tolerance to a compound selected from the group consisting of hygromycin, glyphosate, methotrexate, imidazoline, sulfonylurea, bromoxynil, phosphinothricin, kanamycin, G418, 2,2-dichloropropionic acid and neomycin.

8. A fertile transgenic Zea mays plant comprising isolated heritable DNA comprising a tissue-specific promoter operably linked to a DNA sequence encoding a non-plant dihydrodipicolinic acid synthase (DHDPS) which DHDPS is substantially resistant to feedback inhibition by endogenously produced free L-lysine, and wherein said isolated DNA further comprises a DNA sequence attached to the 5' terminus of the DHDPS DNA sequence which encodes a plant DHDPS chloroplast transit peptide (CTP) which localizes the DHDPS in the chloroplasts of the cells of said plant, wherein the isolated DNA is expressed so that the transgenic Zea mays plant exhibits an increased level of lysine, and wherein the plant further comprises isolated heritable DNA encoding a protein that contains a high level of an essential amino acid that is expressed so that the level of the amino acid in said transgenic plant is increased above the level in said plant not containing said isolated DNA.

9. A fertile transgenic Zea mays plant comprising isolated heritable DNA comprising a tissue-specific promoter operably linked to a DNA sequence encoding a non-plant dihydrodipicolinic acid synthase (DHDPS) which DHDPS is substantially resistant to feedback inhibition by endogenously produced free L-lysine, and wherein said isolated DNA further comprises a DNA sequence attached to the 5' terminus of the DHDPS DNA sequence which encodes a plant chloroplast transit peptide (CTP) which localizes the DHDPS in the chloroplasts of the cells of said plant, wherein the isolated DNA is expressed so that the transgenic Zea mays plant exhibits an increased level of lysine and wherein the plant further comprises isolated heritable DNA encoding a B. thuringiensis polypeptide or a subunit thereof that is expressed so that the transgenic plant is insect resistant.

10. A fertile transgenic Zea mays plant comprising isolated heritable DNA comprising a tissue-specific promoter operably linked to a DNA sequence encoding a non-plant dihydrodipicolinic acid synthase (DHDPS) which DHDPS is substantially resistant to feedback inhibition by endogenously produced free L-lysine, and wherein said isolated DNA further comprises a DNA sequence attached to the 5' terminus of the DHDPS DNA sequence which encodes a plant DHDPS chloroplast transit peptide (CTP) which localizes the DHDPS in the chloroplasts of the cells of said plant, wherein the isolated DNA is expressed so that the transgenic Zea mays plant exhibits an increased level of lysine, and wherein the plant further comprises isolated heritable DNA encoding a B. thuringiensis polypeptide or a subunit thereof that is expressed so that the transgenic plant is insect resistant, and wherein the plant also comprises isolated heritable DNA encoding a protein that contains a high level of an essential amino acid that is expressed so that the level of the amino acid in said transgenic plant is increased above the level in said plant not containing said isolated DNA.

11. The transgenic plant of claim 8, 9 or 10 wherein the dihydrodipicolinic acid synthase is encoded by an E. coli dap A gene.

12. The transgenic Zea mays plant of claim 8 or 10 wherein the isolated heritable DNA encoding a protein that contains a high level of an essential amino acid further comprises a promoter.

13. The transgenic Zea mays plant of claim 12 wherein the isolated heritable DNA further comprises a seed-specific promoter or control element.

14. The transgenic Zea mays plant of claim 9 or 10 wherein the isolated heritable DNA encoding a B. thuringiensis polypeptide or a subunit thereof further comprises a promoter.

15. The transgenic Zea mays plant of claim 8, 9 or 10 which is an inbred plant.

16. The transgenic Zea mays plant of claim 8, 9 or 10 which is a hybrid plant.

17. The transgenic Zea mays plant of claim 8, 9 or 10 wherein the isolated heritable DNA encoding the DHDPS further comprises and expresses a selectable marker gene or a reporter gene.

18. The transgenic Zea mays plant of claim 17 wherein the selectable marker gene confers resistance or tolerance to a compound selected from the group consisting of hygromycin, glyphosate, methotrexate, imidazoline, sulfonylurea, bromoxynil, phosphinothricin, kanamycin, G418, 2,2-dichloropropionic acid and neomycin.

19. The transgenic Zea mays plant of claim 8 or 10 wherein the isolated heritable DNA encoding a protein that contains a high level of an essential amino acid further comprises and expresses a selectable marker gene or a reporter gene.

20. The transgenic Zea mays plant of claim 19 wherein the selectable marker gene confers resistance or tolerance to a compound selected from the group consisting of hygromycin, glyphosate, methotrexate, imidazoline, sulfonylurea, bromoxynil, phosphinothricin, kanamycin, G418, 2,2-dichloropropionic acid and neomycin.

21. The transgenic Zea mays plant of claim 9 or 10 wherein the isolated heritable DNA encoding a B. thuringiensis polypeptide or a subunit thereof further comprises and expresses a selectable marker gene or a reporter gene.

22. The transgenic Zea mays plant of claim 21 wherein the selectable marker gene confers resistance or tolerance to a compound selected from the group consisting of hygromycin, glyphosate, methotrexate, imidazoline, sulfonylurea, bromoxynil, phosphinothricin, kanamycin, G418, 2,2-dichloropropionic acid and neomycin.

23. The transgenic Zea mays plant of claim 8 or 10 wherein the amino acid is selected from the group consisting of lysine, methionine and threonine.

24. The transgenic Zea mays plant of claim 8 or 10 wherein the amino acid is methionine.

25. The transgenic Zea mays plant of claim 8 or 10 wherein the amino acid is lysine.

26. The transgenic Zea mays plant of claim 9 or 10 wherein the DNA encodes the HD73 or HD1 B. thuringiensis polypeptide.

27. The transgenic Zea mays plant of claim 9 or 10 wherein the DNA further encodes a protease inhibitor.

28. The transgenic Zea mays plant of claim 9 or 10 wherein the DNA encoding the B. thuringiensis polypeptide or said subunit thereof has been modified to increase the number of maize preferred codons over that present in a B. thuringiensis gene encoding said polypeptide or subunit thereof.

29. The transgenic *Zea mays* plant of claim 8 or 10 wherein the protein that encodes a high level of an essential amino acid is a seed storage protein.

30. The transgenic *Zea mays* plant of claim 29 wherein the seed storage protein is a maize seed storage protein.

31. A *Zea mays* seed obtained from a fertile transgenic *Zea mays* plant comprising isolated heritable DNA comprising a tissue-specific promoter operably linked to a first non-plant DNA sequence encoding a dihydrodipicolinic acid synthase (DHDPS) which DHDPS is substantially resistant to feedback inhibition by endogenously produced free L-lysine and wherein said isolated DNA further comprises a second sequence attached to the 5' terminus of the DHDPS encoding sequence which encodes a plant DHDPS chloroplast transit peptide (CTP) which localizes the DHDPS in the chloroplasts of the cells of said plant, wherein the isolated heritable DNA is expressed so that the seed exhibits an increased level of lysine, wherein said increased level of lysine is not present in a seed from said plant not containing said isolated DNA.

32. A *Zea mays* seed obtained from a fertile transgenic *Zea mays* plant comprising isolated heritable DNA comprising a tissue-specific promoter operably linked to a first non-plant DNA sequence encoding a dihydrodipicolinic acid synthase (DHDPS) which DHDPS is substantially resistant to feedback inhibition by endogenously produced free L-lysine, and wherein said isolated DNA further comprises a DNA sequence attached to the 5' terminus of the DHDPS encoding sequence which encodes a plant DHDPS chloroplast transit peptide (CTP) which localizes the DHDPS in the chloroplasts of the cells of said plant, which sequence is expressed so that the seed exhibits an increased level of lysine, wherein said increased level of lysine is not present in a seed from said plant not containing said isolated DNA, and wherein the transgenic plant further comprises isolated heritable DNA encoding a protein that contains a high level of an essential amino acid that is expressed so that the level of the amino acid in said seed is increased above the level in a seed from said plant not containing said isolated DNA.

33. A *Zea mays* seed obtained from a fertile transgenic *Zea mays* plant comprising isolated heritable DNA comprising a tissue-specific promoter operably linked to a first non-plant DNA sequence encoding a dihydrodipicolinic acid synthase (DHDPS) which DHDPS is substantially resistant to feedback inhibition by endogenously produced free L-lysine, and wherein said isolated DNA further comprises a second sequence attached to the 5' terminus of the DHDPS encoding sequence which encodes a *Zea mays* DHDPS chloroplast transit peptide (CTP) which localizes the DHDPS in the chloroplasts of the cells of said plant, which sequence is expressed so that the seed exhibits an increased level of lysine, wherein said increased level of lysine is not present in a seed from said plant not containing said isolated DNA, and wherein the transgenic plant further comprises isolated heritable DNA encoding a *B. thuringiensis* polypeptide or a subunit thereof that is expressed so that the transgenic plant is insect resistant.

34. A *Zea mays* seed obtained from a fertile transgenic *Zea mays* plant comprising isolated heritable DNA comprising a tissue-specific promoter operably linked to a first non-plant DNA sequence encoding a dihydrodipicolinic acid synthase (DHDPS) which DHDPS is substantially resistant to feedback inhibition by endogenously produced free L-lysine, and wherein said isolated DNA further comprises a second sequence attached to the 5' terminus of the DHDPS encoding sequence which encodes a *Zea mays* DHDPS chloroplast transit peptide (CTP) which localizes the DHDPS in the chloroplasts of the cells of said plant, which sequence is expressed so that the seed exhibits an increased level of lysine, wherein said increased level of lysine is not present in a seed from said plant not containing said isolated DNA, and wherein the transgenic plant further comprises isolated heritable DNA encoding a *B. thuringiensis* polypeptide or a subunit thereof that is expressed so that the transgenic plant is insect resistant, and wherein the transgenic plant also comprises isolated heritable DNA encoding a protein that contains a high level of an essential amino acid that is expressed so that the level of the amino acid in said seed is increased above the level in a seed from said plant not containing said isolated DNA.

35. Food or feed produced from a *Zea mays* seed obtained from a fertile transgenic *Zea mays* plant comprising isolated heritable DNA comprising a tissue-specific promoter operably linked to a first non-plant DNA sequence encoding a dihydrodipicolinic acid synthase (DHDPS) which DHDPS is substantially resistant to feedback inhibition by endogenously produced free L-lysine, and wherein said DNA further comprises a second sequence attached to the 5' terminus of the DHDPS encoding sequence which encodes a plant DHDPS chloroplast transit peptide (CTP) which localizes the DHDPS in the chloroplasts of the cells of said plant, wherein the isolated heritable DNA is expressed so that the seed exhibits an increased level of lysine, wherein said increased level of lysine is not present in a seed from said plant not containing said isolated DNA.

36. Food or feed produced from a *Zea mays* seed obtained from a fertile transgenic *Zea mays* plant comprising isolated heritable DNA comprising a tissue-specific promoter operably linked to a sequence encoding a dihydrodipicolinic acid synthase (DHDPS) which DHDPS is substantially resistant to feedback inhibition by endogenously produced free L-lysine, and wherein said isolated encoding further comprises a second sequence attached to the 5' terminus of the DHDPS encoding sequence which encodes a plant DHDPS chloroplast transit peptide (CTP) which localizes the DHDPS in the chloroplasts of the cells of said plant, wherein the isolated heritable DNA is expressed so that the seed exhibits an increased level of lysine, wherein said increased level of lysine is not present in a seed from said plant not containing said isolated DNA, and wherein the transgenic plant further comprises isolated heritable DNA encoding a protein that contains a high level of an essential amino acid that is expressed so that the level of the amino acid in said seed is increased above the level in a seed from said plant not containing said isolated DNA.

37. Food or feed produced from a *Zea mays* seed obtained from a fertile transgenic *Zea mays* comprising isolated heritable DNA comprising a tissue-specific promoter operably linked to a sequence encoding a dihydrodipicolinic acid synthase (DHDPS) which DHDPS is substantially resistant to feedback inhibition by endogenously produced free L-lysine, and wherein said isolated encoding further comprises a second sequence attached to the 5' terminus of the DHDPS encoding sequence which encodes a plant DHDPS chloroplast transit peptide (CTP) which localizes the DHDPS in the chloroplasts of the cells of said plant, wherein the isolated heritable DNA is expressed so that the seed exhibits an increased level of lysine, wherein said increased level of lysine is not present in a seed from said plant not containing said isolated heritable DNA, and wherein the transgenic plant further comprises isolated heritable DNA encoding a *B. thuringiensis* polypeptide or a subunit thereof that is expressed so that the plant is insect resistant.

38. Food or feed produced from a *Zea mays* seed obtained from a fertile transgenic *Zea mays* plant comprising isolated heritable DNA comprising a tissue-specific promoter operably linked to a first non-plant DNA sequence encoding a dihydrodipicolinic acid synthase (DHDPS) which DHDPS is substantially resistant to feedback inhibition by endogenously produced free L-lysine, and wherein said isolated DNA further comprises a second sequence attached to the 5' terminus of the DHDPS encoding sequence which encodes a plant DHDPS chloroplast transit peptide (CTP) which localizes the DHDPS in the chloroplasts of the cells of said plant, wherein the isolated heritable DNA is expressed so that the seed exhibits an increased level of lysine, wherein said increased level of lysine is not present in a seed from said plant not containing said isolated DNA, and wherein the transgenic plant further comprises isolated heritable DNA encoding a *B. thuringiensis* polypeptide or a subunit that is expressed so that the plant is insect resistant, and wherein the transgenic plant also comprises isolated heritable DNA encoding a protein that contains a high level of an essential amino acid that is expressed so that the level of the amino acid in a seed from said plant is increased above the level in a seed from said plant not containing said isolated DNA.

39. The plant of claim 1, wherein the first DNA sequence is a bacterial DNA sequence.

40. The plant of claim 1 wherein the DNA sequence encodes a *Zea mays* DHDPS CTP.

41. The plant of claim 1 wherein said CTP is a maize CTP.

* * * * *

UNITED STATES PATENT AND TRADEMARK OFFICE
CERTIFICATE OF CORRECTION

PATENT NO. : 6,329,574 B1
DATED : December 11, 2001
INVENTOR(S) : Ronald C. Lundquist, David A. Walters and Julie A Kirihara It is certified that error appears in the above-identified patent and that said Letters Patent is hereby corrected as shown below:

Column 68,
Line 3, insert -- (seq id no: 11) -- between "target sequence" and ":".
Line 5, insert -- (seq id no: 13) -- after "pDSTP119".
Line 7, insert -- (seq id no: 12) -- between "modifying to" and ":".

Column 72,
Line 35, delete "in" and insert -- In --, therefor.

Column 126,
Line 12, insert -- (seq id no: 18) -- between "(MD-1)" and ":".
Line 14, insert -- (seq id no: 19) -- between "(MD-4)" and ":".
Line 18, insert -- (seq id no: 20) -- between "BTSN64" and ":".
Line 20, insert -- (seq id no: 21) -- between "BTASN506" and ":".

Column 165,
Lines 61-62, insert -- heritable -- between "isolated" and "DNA".
Line 65, insert -- isolated -- between "said" and "DNA".
Line 66, insert -- DNA -- between "second" and "sequence".

Column 167,
Line 18, insert -- first non-plant -- between "to a" and "DNA". and delete "non-plant" before "dihydrodipicolinic".
Line 22, insert -- second -- between "comprises a" and "DNA".
Line 23, delete "DNA" after "DHDPS" and insert -- encoding --, therefor.
Line 35, insert -- first non-plant-- between "to a" and "DNA" and delete "non-plant" before "dihydrodipicolinic".
Line 39, insert -- second -- between "comprises a" and "DNA".
Line 40, delete "DNA" after "DHDPS" and insert -- encoding --, therefor..
Line 50, insert -- first non-plant -- between "to a" and "DNA" and delete "non-plant" before "dihydrodipicolinic".
Line 54, insert -- second -- between "comprises a" and "DNA".
Line 55, delete "DNA" after "DHDPS" and insert -- encoding --, therefor.

UNITED STATES PATENT AND TRADEMARK OFFICE
CERTIFICATE OF CORRECTION

PATENT NO. : 6,329,574 B1
DATED : December 11, 2001
INVENTOR(S) : Ronald C. Lundquist, David A. Walters and Julie A. Kirihara It is certified that error appears in the above-identified patent and that said Letters Patent is hereby corrected as shown below:

Column 169,
Line 13, insert -- DNA -- between "second" and "sequence".
Line 28, insert -- second -- between "comprises a" and "DNA".
Line 47, insert -- DNA -- between "second" and "sequence".
Line 48, delete -- *Zea mays* -- between "encodes a" and " DHDPS" and insert -- plant --, therefor.
Line 65, insert -- DNA -- between "second" and "sequence".
Line 66, delete "*Zea mays* " between "encodes a" and "DHDPS" and insert -- plant --, therefor.

Column 170,
Line 20, insert -- DNA -- between "second" and "sequence".
Line 31, insert -- first non-plant DNA -- between "to a" and "sequence".
Line 34, delete "encoding" between "isolated" and "further comprises" and insert -- DNA --, therefor.
Line 35, insert -- DNA -- between "second" and "sequence".
Line 51, insert -- first non-plant DNA -- between "to a" and "sequence".
Line 54, delete "encoding" between "isolated" and "further comprises" and insert -- DNA --, therefor.
Line 55, insert -- DNA -- between "second" and "sequence".

Column 171,
Line 6, insert -- DNA -- between "second" and "sequence".

Signed and Sealed this

Twenty first Day of May, 2002

*Attest:*

*Attesting Officer*

JAMES E. ROGAN
*Director of the United States Patent and Trademark Office*

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:1:

Met Ala Thr Val Pro Glu Leu Asn Cys Glu Met Pro Pro Ser Asp
1               5                   10                  15

(2) INFORMATION FOR SEQ ID NO:2:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:2:

GAGGATCCGT CGACATGGTA AGCTTAGCGG GCCCC                         35

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:3:

GATCCGTCGA CCATGGCGCT TCAAGCTTC                                29

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:4:

GCAGCTGGTA CCGCGAAGTT CGAAGGGCT                                29

(2) INFORMATION FOR SEQ ID NO:5:

(i) SEQUENCE CHARACTERISTICS:
        (A) LENGTH: 1845 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1839

(xi) SEQUENCE DESCRIPTION: SEQ ID NO:5:

ATG GAT AAC AAT CCG AAC ATC AAT GAA TGC ATT CCT TAC AAT TGC CTC    48
Met Asp Asn Asn Pro Asn Ile Asn Glu Cys Ile Pro Tyr Asn Cys Leu

|  1 | | | 5 | | | | 10 | | | | 15 | | | | |
|---|---|---|---|---|---|---|---|---|---|---|---|---|---|---|---|
| AGC | AAC | CCT | GAA | GTG | GAA | GTG | CTG | GGT | GGC | GAA | CGC | ATC | GAA | ACC | GGT | 96
| Ser | Asn | Pro | Glu | Val | Glu | Val | Leu | Gly | Gly | Glu | Arg | Ile | Glu | Thr | Gly |
| | | | 20 | | | | 25 | | | | 30 | | | | |

TAC ACC CCA ATC GAT ATT TCC CTG TCC CTG ACC CAA TTT CTG CTG AGC   144
Tyr Thr Pro Ile Asp Ile Ser Leu Ser Leu Thr Gln Phe Leu Leu Ser
         35              40              45

GAA TTT GTG CCC GGT GCT GGC TTT GTG CTG GGC CTG GTG GAT ATC ATC   192
Glu Phe Val Pro Gly Ala Gly Phe Val Leu Gly Leu Val Asp Ile Ile
 50              55              60

TGG GGC ATT TTT GGT CCC TCC CAA TGG GAC GCC TTT CTG GTG CAA ATT   240
Trp Gly Ile Phe Gly Pro Ser Gln Trp Asp Ala Phe Leu Val Gln Ile
 65              70              75              80

GAA CAG CTG ATT AAC CAA CGC ATC GAA GAA TTC GCT AGG AAC CAA GCC   288
Glu Gln Leu Ile Asn Gln Arg Ile Glu Glu Phe Ala Arg Asn Gln Ala
             85              90              95

ATT TCC CGC CTG GAA GGC CTG AGC AAT CTG TAC CAA ATT TAC GCC GAA   336
Ile Ser Arg Leu Glu Gly Leu Ser Asn Leu Tyr Gln Ile Tyr Ala Glu
         100             105             110

TCC TTT CGC GAG TGG GAA GCC GAT CCT ACC AAT CCA GCC CTG CGC GAA   384
Ser Phe Arg Glu Trp Glu Ala Asp Pro Thr Asn Pro Ala Leu Arg Glu
     115             120             125

GAG ATG CGC ATT CAA TTC AAT GAC ATG AAC AGC GCC CTG ACC ACC GCT   432
Glu Met Arg Ile Gln Phe Asn Asp Met Asn Ser Ala Leu Thr Thr Ala
 130             135             140

ATT CCT CTG TTT GCC GTG CAA AAT TAC CAA GTG CCT CTG CTG TCC GTG   480
Ile Pro Leu Phe Ala Val Gln Asn Tyr Gln Val Pro Leu Leu Ser Val
145             150             155             160

TAC GTG CAA GCT GCC AAT CTG CAT CTG TCC GTG CTG CGC GAT GTG TCC   528
Tyr Val Gln Ala Ala Asn Leu His Leu Ser Val Leu Arg Asp Val Ser
             165             170             175

GTG TTT GGC CAA AGG TGG GGC TTT GAT GCC GCC ACC ATC AAT AGC CGC   576
Val Phe Gly Gln Arg Trp Gly Phe Asp Ala Ala Thr Ile Asn Ser Arg
         180             185             190

TAC AAT GAT CTG ACC AGG CTG ATT GGC AAC TAC ACC GAT TAC GCT GTG   624
Tyr Asn Asp Leu Thr Arg Leu Ile Gly Asn Tyr Thr Asp Tyr Ala Val
     195             200             205

CGC TGG TAC AAT ACC GGC CTG GAA CGC GTG TGG GGC CCA GAT TCC CGC   672
Arg Trp Tyr Asn Thr Gly Leu Glu Arg Val Trp Gly Pro Asp Ser Arg
 210             215             220

GAT TGG GTG AGG TAC AAT CAA TTT CGC CGC GAA CTG ACC CTG ACC GTG   720
Asp Trp Val Arg Tyr Asn Gln Phe Arg Arg Glu Leu Thr Leu Thr Val
225             230             235             240

CTC GAT ATC GTG GCT CTG TTC CCA AAT TAC GAT AGC CGC CGC TAC CCA   768
Leu Asp Ile Val Ala Leu Phe Pro Asn Tyr Asp Ser Arg Arg Tyr Pro
             245             250             255

ATT CGA ACC GTG TCC CAA CTG ACC CGC GAA ATT TAC ACC AAC CCA GTG   816
Ile Arg Thr Val Ser Gln Leu Thr Arg Glu Ile Tyr Thr Asn Pro Val
         260             265             270

CTG GAA AAT TTT GAT GGT AGC TTT CGC GGC TCC GCT CAG GGC ATC GAA   864
Leu Glu Asn Phe Asp Gly Ser Phe Arg Gly Ser Ala Gln Gly Ile Glu
     275             280             285

CGC AGC ATT AGG AGC CCA CAT CTG ATG GAT ATC CTG AAC AGC ATC ACC   912
Arg Ser Ile Arg Ser Pro His Leu Met Asp Ile Leu Asn Ser Ile Thr
 290             295             300

ATC TAC ACC GAT GCT CAT AGG GGT TAC TAC TAC TGG TCC GGC CAT CAA   960
Ile Tyr Thr Asp Ala His Arg Gly Tyr Tyr Tyr Trp Ser Gly His Gln
305             310             315             320

ATC ATG GCT TCC CCT GTG GGC TTT TCC GGG CCA GAA TTC ACC TTT CCA  1008

```
Ile Met Ala Ser Pro Val Gly Phe Ser Gly Pro Glu Phe Thr Phe Pro
            325                     330                 335

CTG TAC GGC ACG ATG GGC AAT GCC GCT CCA CAA CAA CGC ATT GTG GCT      1056
Leu Tyr Gly Thr Met Gly Asn Ala Ala Pro Gln Gln Arg Ile Val Ala
            340                 345                 350

CAA CTG GGT CAG GGC GTG TAC CGC ACC CTG TCC TCC ACC CTG TAC CGC      1104
Gln Leu Gly Gln Gly Val Tyr Arg Thr Leu Ser Ser Thr Leu Tyr Arg
            355                 360                 365

CGC CCT TTT AAT ATC GGC ATC AAC AAC CAG CAA CTG TCC GTG CTG GAC      1152
Arg Pro Phe Asn Ile Gly Ile Asn Asn Gln Gln Leu Ser Val Leu Asp
        370                 375                 380

GGC ACC GAA TTT GCT TAC GGC ACC TCC TCC AAT CTG CCA TCC GCT GTA      1200
Gly Thr Glu Phe Ala Tyr Gly Thr Ser Ser Asn Leu Pro Ser Ala Val
385                 390                 395                 400

TAC CGC AAG AGC GGC ACC GTG GAT TCC CTG GAT GAA ATC CCA CCA CAG      1248
Tyr Arg Lys Ser Gly Thr Val Asp Ser Leu Asp Glu Ile Pro Pro Gln
                405                 410                 415

AAT AAC AAC GTG CCA CCT AGG CAA GGC TTT AGC CAT CGC CTG AGC CAT      1296
Asn Asn Asn Val Pro Pro Arg Gln Gly Phe Ser His Arg Leu Ser His
            420                 425                 430

GTG TCC ATG TTT CGC TCC GGC TTT AGC AAT AGC AGC GTG AGC ATC ATC      1344
Val Ser Met Phe Arg Ser Gly Phe Ser Asn Ser Ser Val Ser Ile Ile
            435                 440                 445

CGC GCT CCT ATG TTC TCC TGG ATC CAT CGC AGC GCT GAA TTT AAC AAC      1392
Arg Ala Pro Met Phe Ser Trp Ile His Arg Ser Ala Glu Phe Asn Asn
        450                 455                 460

ATC ATT GCC TCC GAT AGC ATT ACC CAA ATC CCT GCC GTG AAG GGC AAC      1440
Ile Ile Ala Ser Asp Ser Ile Thr Gln Ile Pro Ala Val Lys Gly Asn
465                 470                 475                 480

TTT CTG TTT AAT GGT TCC GTG ATT TCC GGC CCA GGC TTT ACC GGT GGC      1488
Phe Leu Phe Asn Gly Ser Val Ile Ser Gly Pro Gly Phe Thr Gly Gly
                485                 490                 495

GAC CTG GTG CGC CTG AAT AGC AGC GGC AAT AAC ATT CAG AAT CGC GGC      1536
Asp Leu Val Arg Leu Asn Ser Ser Gly Asn Asn Ile Gln Asn Arg Gly
            500                 505                 510

TAC ATT GAA GTG CCA ATT CAC TTC CCA TCC ACC TCC ACC CGC TAC CGC      1584
Tyr Ile Glu Val Pro Ile His Phe Pro Ser Thr Ser Thr Arg Tyr Arg
            515                 520                 525

GTG CGC GTG CGC TAC GCT TCC GTG ACC CCA ATT CAC CTC AAC GTT AAC      1632
Val Arg Val Arg Tyr Ala Ser Val Thr Pro Ile His Leu Asn Val Asn
        530                 535                 540

TGG GGC AAT TCC TCC ATT TTT TCC AAT ACC GTG CCA GCT ACC GCT ACC      1680
Trp Gly Asn Ser Ser Ile Phe Ser Asn Thr Val Pro Ala Thr Ala Thr
545                 550                 555                 560

TCC CTG GAT AAT CTG CAA TCC AGC GAT TTT GGT TAC TTT GAA AGC GCC      1728
Ser Leu Asp Asn Leu Gln Ser Ser Asp Phe Gly Tyr Phe Glu Ser Ala
                565                 570                 575

AAT GCT TTT ACC TCC TCC CTG GGT AAT ATC GTG GGT GTG CGC AAT TTT      1776
Asn Ala Phe Thr Ser Ser Leu Gly Asn Ile Val Gly Val Arg Asn Phe
            580                 585                 590

AGC GGC ACC GCC GGC GTG ATC ATC GAC CGC TTT GAA TTT ATT CCA GTG      1824
Ser Gly Thr Ala Gly Val Ile Ile Asp Arg Phe Glu Phe Ile Pro Val
            595                 600                 605

ACC GCC ACC CTC GAG TAGGTA                                            1845
Thr Ala Thr Leu Glu
        610
```

(2) INFORMATION FOR SEQ ID NO:6:

(i) SEQUENCE CHARACTERISTICS:

(A) LENGTH: 613 amino acids
(B) TYPE: amino acid
(D) TOPOLOGY: linear (ii) MOLECULE TYPE: protein (xi) SEQUENCE DESCRIPTION: SEQ ID NO:6:

```
Met Asp Asn Asn Pro Asn Ile Asn Glu Cys Ile Pro Tyr Asn Cys Leu
  1               5                  10                  15

Ser Asn Pro Glu Val Glu Val Leu Gly Gly Glu Arg Ile Glu Thr Gly
             20                  25                  30

Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
        340                 345                 350

Gln Leu Gly Gln Gly Val Tyr Arg Thr Leu Ser Ser Thr Leu Tyr Arg
    355                 360                 365

Arg Pro Phe Asn Ile Gly Ile Asn Asn Gln Gln Leu Ser Val Leu Asp
370                 375                 380
```

-continued

```
Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
            405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu
        610
```

(2) INFORMATION FOR SEQ ID NO:7:

(i) SEQUENCE CHARACTERISTICS:
        (A) LENGTH: 1848 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1842

(xi) SEQUENCE DESCRIPTION: SEQ ID NO:7:

```
ATG GAT AAC AAT CCG AAC ATC AAT GAA TGC ATT CCT TAC AAT TGC CTC    48
Met Asp Asn Asn Pro Asn Ile Asn Glu Cys Ile Pro Tyr Asn Cys Leu
1               5                   10                  15

AGC AAC CCT GAA GTG GAA GTG CTG GGT GGC GAA CGC ATC GAA ACC GGT    96
Ser Asn Pro Glu Val Glu Val Leu Gly Gly Glu Arg Ile Glu Thr Gly
                20                  25                  30

TAC ACC CCA ATC GAT ATT TCC CTG TCC CTG ACC CAA TTT CTG CTG AGC   144
Tyr Thr Pro Ile Asp Ile Ser Leu Ser Leu Thr Gln Phe Leu Leu Ser
            35                  40                  45

GAA TTT GTG CCC GGT GCT GGC TTT GTG CTG GGC CTG GTG GAT ATC ATC   192
Glu Phe Val Pro Gly Ala Gly Phe Val Leu Gly Leu Val Asp Ile Ile
        50                  55                  60
```

-continued

```
TGG GGC ATT TTT GGT CCC TCC CAA TGG GAC GCC TTT CTG GTG CAA ATT        240
Trp Gly Ile Phe Gly Pro Ser Gln Trp Asp Ala Phe Leu Val Gln Ile
 65              70                  75                  80

GAA CAG CTG ATT AAC CAA CGC ATC GAA GAA TTC GCT AGG AAC CAA GCC        288
Glu Gln Leu Ile Asn Gln Arg Ile Glu Glu Phe Ala Arg Asn Gln Ala
                 85                  90                  95

ATT TCC CGC CTG GAA GGC CTG AGC AAT CTG TAC CAA ATT TAC GCC GAA        336
Ile Ser Arg Leu Glu Gly Leu Ser Asn Leu Tyr Gln Ile Tyr Ala Glu
             100                 105                 110

TCC TTT CGC GAG TGG GAA GCC GAT CCT ACC AAT CCA GCC CTG CGC GAA        384
Ser Phe Arg Glu Trp Glu Ala Asp Pro Thr Asn Pro Ala Leu Arg Glu
         115                 120                 125

GAG ATG CGC ATT CAA TTC AAT GAC ATG AAC AGC GCC CTG ACC ACC GCT        432
Glu Met Arg Ile Gln Phe Asn Asp Met Asn Ser Ala Leu Thr Thr Ala
     130                 135                 140

ATT CCT CTG TTT GCC GTG CAA AAT TAC CAA GTG CCT CTG CTG TCC GTG        480
Ile Pro Leu Phe Ala Val Gln Asn Tyr Gln Val Pro Leu Leu Ser Val
145                 150                 155                 160

TAC GTG CAA GCT GCC AAT CTG CAT CTG TCC GTG CTG CGC GAT GTG TCC        528
Tyr Val Gln Ala Ala Asn Leu His Leu Ser Val Leu Arg Asp Val Ser
                 165                 170                 175

GTG TTT GGC CAA AGG TGG GGC TTT GAT GCC GCC ACC ATC AAT AGC CGC        576
Val Phe Gly Gln Arg Trp Gly Phe Asp Ala Ala Thr Ile Asn Ser Arg
             180                 185                 190

TAC AAT GAT CTG ACC AGG CTG ATT GGC AAC TAC ACC GAT TAC GCT GTG        624
Tyr Asn Asp Leu Thr Arg Leu Ile Gly Asn Tyr Thr Asp Tyr Ala Val
         195                 200                 205

CGC TGG TAC AAT ACC GGC CTG GAA CGC GTG TGG GGC CCA GAT TCC CGC        672
Arg Trp Tyr Asn Thr Gly Leu Glu Arg Val Trp Gly Pro Asp Ser Arg
     210                 215                 220

GAT TGG GTG AGG TAC AAT CAA TTT CGC CGC GAA CTG ACC CTG ACC GTG        720
Asp Trp Val Arg Tyr Asn Gln Phe Arg Arg Glu Leu Thr Leu Thr Val
225                 230                 235                 240

CTC GAT ATC GTG GCT CTG TTC CCA AAT TAC GAT AGC CGC CGC TAC CCA        768
Leu Asp Ile Val Ala Leu Phe Pro Asn Tyr Asp Ser Arg Arg Tyr Pro
                 245                 250                 255

ATT CGA ACC GTG TCC CAA CTG ACC CGC GAA ATT TAC ACC AAC CCA GTG        816
Ile Arg Thr Val Ser Gln Leu Thr Arg Glu Ile Tyr Thr Asn Pro Val
             260                 265                 270

CTG GAA AAT TTT GAT GGT AGC TTT CGC GGC TCC GCT CAG GGC ATC GAA        864
Leu Glu Asn Phe Asp Gly Ser Phe Arg Gly Ser Ala Gln Gly Ile Glu
         275                 280                 285

CGC AGC ATT AGG AGC CCA CAT CTG ATG GAT ATC CTG AAC AGC ATC ACC        912
Arg Ser Ile Arg Ser Pro His Leu Met Asp Ile Leu Asn Ser Ile Thr
     290                 295                 300

ATC TAC ACC GAT GCT CAT AGG GGT TAC TAC TAC TGG TCC GGC CAT CAA        960
Ile Tyr Thr Asp Ala His Arg Gly Tyr Tyr Tyr Trp Ser Gly His Gln
305                 310                 315                 320

ATC ATG GCT TCC CCT GTG GGC TTT TCC GGG CCA GAA TTC ACC TTT CCA       1008
Ile Met Ala Ser Pro Val Gly Phe Ser Gly Pro Glu Phe Thr Phe Pro
                 325                 330                 335

CTG TAC GGC ACG ATG GGC AAT GCC GCT CCA CAA CAA CGC ATT GTG GCT       1056
Leu Tyr Gly Thr Met Gly Asn Ala Ala Pro Gln Gln Arg Ile Val Ala
             340                 345                 350

CAA CTG GGT CAG GGC GTG TAC CGC ACC CTG TCC TCC ACC CTG TAC CGC       1104
Gln Leu Gly Gln Gly Val Tyr Arg Thr Leu Ser Ser Thr Leu Tyr Arg
         355                 360                 365

CGC CCT TTT AAT ATC GGC ATC AAC AAC CAG CAA CTG TCC GTG CTG GAC       1152
Arg Pro Phe Asn Ile Gly Ile Asn Asn Gln Gln Leu Ser Val Leu Asp
     370                 375                 380
```

-continued

```
GGC ACC GAA TTT GCT TAC GGC ACC TCC TCC AAT CTG CCA TCC GCT GTA    1200
Gly Thr Glu Phe Ala Tyr Gly Thr Ser Ser Asn Leu Pro Ser Ala Val
385                 390                 395                 400

TAC CGC AAG AGC GGC ACC GTG GAT TCC CTG GAT GAA ATC CCA CCA CAG    1248
Tyr Arg Lys Ser Gly Thr Val Asp Ser Leu Asp Glu Ile Pro Pro Gln
                405                 410                 415

AAT AAC AAC GTG CCA CCT AGG CAA GGC TTT AGC CAT CGC CTG AGC CAT    1296
Asn Asn Asn Val Pro Pro Arg Gln Gly Phe Ser His Arg Leu Ser His
                420                 425                 430

GTG TCC ATG TTT CGC TCC GGC TTT AGC AAT AGC AGC GTG AGC ATC ATC    1344
Val Ser Met Phe Arg Ser Gly Phe Ser Asn Ser Ser Val Ser Ile Ile
            435                 440                 445

CGC GCT CCT ATG TTC TCC TGG ATC CAC CGC TCC GCT GAG TTC AAC AAC    1392
Arg Ala Pro Met Phe Ser Trp Ile His Arg Ser Ala Glu Phe Asn Asn
450                 455                 460

ATC ATC CCG TCC TCC CAA ATC ACC CAA ATC CCG CTC ACC AAG TCC ACG    1440
Ile Ile Pro Ser Ser Gln Ile Thr Gln Ile Pro Leu Thr Lys Ser Thr
465                 470                 475                 480

AAC CTC GGC TCC GGC ACG TCC GTC GTC AAG GGC CCG GGC TTC ACC GGC    1488
Asn Leu Gly Ser Gly Thr Ser Val Val Lys Gly Pro Gly Phe Thr Gly
                485                 490                 495

GGC GAC ATC CTC CGC CGC ACG TCC CCG GGC CAG ATC TCC ACC CTC CGC    1536
Gly Asp Ile Leu Arg Arg Thr Ser Pro Gly Gln Ile Ser Thr Leu Arg
                500                 505                 510

GTC AAC ATC ACG GCT CCG CTG AGC CAG CGC TAC AGG GTG CGC ATC AGA    1584
Val Asn Ile Thr Ala Pro Leu Ser Gln Arg Tyr Arg Val Arg Ile Arg
            515                 520                 525

TAC GCT AGC ACG ACC AAC CTG CAA TTC CAC ACG TCC ATC GAC GGC AGA    1632
Tyr Ala Ser Thr Thr Asn Leu Gln Phe His Thr Ser Ile Asp Gly Arg
530                 535                 540

CCG ATC AAC CAG GGC AAC TTC AGC GCG ACG ATG AGC TCC GGG TCC AAC    1680
Pro Ile Asn Gln Gly Asn Phe Ser Ala Thr Met Ser Ser Gly Ser Asn
545                 550                 555                 560

CTC CAG TCC GGC TCC TTC CGC ACG GTC GGT TTC ACC ACG CCG TTC AAC    1728
Leu Gln Ser Gly Ser Phe Arg Thr Val Gly Phe Thr Thr Pro Phe Asn
                565                 570                 575

TTC TCC AAC GGC TCC TCC GTC TTC ACG CTC TCC GCT CAC GTC TTC AAC    1776
Phe Ser Asn Gly Ser Ser Val Phe Thr Leu Ser Ala His Val Phe Asn
                580                 585                 590

TCC GGC AAC GAG GTG TAC ATC GAC CGC ATC GAG TTC GTC CCG GCC GAG    1824
Ser Gly Asn Glu Val Tyr Ile Asp Arg Ile Glu Phe Val Pro Ala Glu
                595                 600                 605

GTC ACC TTC GAG CTC GAG TAGGTA                                    1848
Val Thr Phe Glu Leu Glu
        610
```

(2) INFORMATION FOR SEQ ID NO:8:

(i) SEQUENCE CHARACTERISTICS:
        (A) LENGTH: 614 amino acids
        (B) TYPE: amino acid
        (D) TOPOLOGY: linear (ii) MOLECULE TYPE: protein (xi) SEQUENCE DESCRIPTION: SEQ ID NO:8:

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
                20                  25                  30
```

-continued

```
Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
         50                  55                  60

Trp Gly Ile Phe Gly Pro Ser Gln Trp Asp Ala Phe Leu Val Gln Ile
 65              70                  75                      80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
                100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
        130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
                180                 185                 190

Tyr Asn Asp Leu Thr Arg Leu Ile Gly Asn Tyr Thr Asp Tyr Ala Val
                195                 200                 205

Arg Trp Tyr Asn Thr Gly Leu Glu Arg Val Trp Gly Pro Asp Ser Arg
        210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
                260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
        290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
                340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
        370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
```

```
                450           455           460
Ile Ile Pro Ser Ser Gln Ile Thr Gln Ile Pro Leu Thr Lys Ser Thr
465               470              475              480

Asn Leu Gly Ser Gly Thr Ser Val Val Lys Gly Pro Gly Phe Thr Gly
                485              490              495

Gly Asp Ile Leu Arg Arg Thr Ser Pro Gly Gln Ile Ser Thr Leu Arg
                500              505              510

Val Asn Ile Thr Ala Pro Leu Ser Gln Arg Tyr Arg Val Arg Ile Arg
            515              520              525

Tyr Ala Ser Thr Thr Asn Leu Gln Phe His Thr Ser Ile Asp Gly Arg
            530              535              540

Pro Ile Asn Gln Gly Asn Phe Ser Ala Thr Met Ser Ser Gly Ser Asn
545              550              555              560

Leu Gln Ser Gly Ser Phe Arg Thr Val Gly Phe Thr Thr Pro Phe Asn
                565              570              575

Phe Ser Asn Gly Ser Ser Val Phe Thr Leu Ser Ala His Val Phe Asn
                580              585              590

Ser Gly Asn Glu Val Tyr Ile Asp Arg Ile Glu Phe Val Pro Ala Glu
            595              600              605

Val Thr Phe Glu Leu Glu
    610

(2) INFORMATION FOR SEQ ID NO:9:

(i) SEQUENCE CHARACTERISTICS:
        (A) LENGTH: 195 base pairs
        (B) TYPE: nucleic acid
        (C) STRANDEDNESS: single
        (D) TOPOLOGY: linear (xi) SEQUENCE DESCRIPTION: SEQ ID NO:9:

AGCTTGCAGC GAGTACATAC ATACTAGGCA GCCAGGCAGC CATGGCGCCC ACCGTGATGA      60

ACCGTGATGA TGGCCTCGTC GGCCACCGCC GTCGCTCCGT TCCAGGGGCT CAAGTCCACC     120

GCCAGCCTCC CCGTCGCCCG CCGGTCCTCC AGAAGCCTCG GCAACGTCAG CAACGGCGGA     180

AGGATCCGGT GCATG                                                     195

(2) INFORMATION FOR SEQ ID NO:10:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (xi) SEQUENCE DESCRIPTION: SEQ ID NO:10:

ACGTCGCTCA TGTATGTATG ATCCGTCGGT CCGTCGGTAC CGCGGGTGGC ACTACTACCG      60

GAGCAGCCGG TGGCGGCAGC GAGGCAAGGT CCCCGAGTTC AGGTGGCGGT CGGAGGGGCA     120

GCGGGCGGCC AGGAGGTCTT CGGAGCCGTT GCAGTCGTTG CCGCCTTCCT AGGCCAC       177

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:11:
```

```
ATCACTTTCA CGGGA                                              15
```

(2) INFORMATION FOR SEQ ID NO:12:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:12:

```
ATCACGTTCA CGGCA                                              15
```

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:13:

```
Ile Thr Phe Thr Gly
1               5
```

(2) INFORMATION FOR SEQ ID NO:14:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:14:

```
CCTTGGCAGC CATCACGTTC ACGGGAAGTA TTGTC                         35
```

(2) INFORMATION FOR SEQ ID NO:15:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:15:

```
ATCTGGCAGC AGAAAAACAA GTAGTTGAGA ACTAAGAAGA AGAAA              45
```

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:16:

```
CATCGAGACA AGCACGGTCA ACTTC                                   25
```

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:17:

```
AAGTCCCTGG AGGCACAGGG CTTCAAGA                                              28

(2) INFORMATION FOR SEQ ID NO:18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:18:

GCTTACCTAC TAATTGTTCT TGG                                                   23

(2) INFORMATION FOR SEQ ID NO:19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:19:

CAGGGTACAT ATTTGCCTTG GG                                                    22

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:20:

AACCCTGAAT GGAAGTGC                                                         18

(2) INFORMATION FOR SEQ ID NO:21:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:21:

ACGGACAGAT GCAGATTGG                                                        19

(2) INFORMATION FOR SEQ ID NO:22:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:22:

Pro Arg Gly Ser Thr
1               5
```